(12) United States Patent
Bacon et al.

(10) Patent No.: US 8,354,414 B2
(45) Date of Patent: Jan. 15, 2013

(54) SUBSTITUTED BICYCLIC PYRIMIDINES

(75) Inventors: Edward R. Bacon, Audubon, PA (US); Thomas Bailey, Phoenixville, PA (US); Nadine C. Becknell, Coatesville, PA (US); Diane E. Gingrich, Downingtown, PA (US); Greg A. Hostetler, Newark, DE (US); Robert L. Hudkins, Chester Springs, PA (US); Keith S. Learn, Perkiomenville, PA (US); Jason C. Wagner, Coatesville, PA (US)

(73) Assignee: Cephalon, Inc, Frazer, PA (US)

( * ) Notice: Subject to any disclaimer, the term of this patent is extended or adjusted under 35 U.S.C. 154(b) by 138 days.

(21) Appl. No.: 12/939,527

(22) Filed: Nov. 4, 2010

(65) Prior Publication Data

US 2011/0053920 A1 Mar. 3, 2011

Related U.S. Application Data

(62) Division of application No. 11/803,320, filed on May 14, 2007, now Pat. No. 7,851,468.

(60) Provisional application No. 60/800,375, filed on May 15, 2006.

(51) Int. Cl.
| | |
|---|---|
| *C07D 239/70* | (2006.01) |
| *C07D 471/04* | (2006.01) |
| *A61K 31/517* | (2006.01) |
| *A61K 31/519* | (2006.01) |
| *C07D 239/72* | (2006.01) |
| *C07D 239/84* | (2006.01) |
| *C07D 239/78* | (2006.01) |
| *C07D 487/04* | (2006.01) |

(52) U.S. Cl. ............. 514/258.1; 514/261.1; 514/264.11; 514/264.1; 514/266.2; 544/253; 544/254; 544/279; 544/284

(58) Field of Classification Search ................... 544/253; 514/258.1
See application file for complete search history.

(56) References Cited

U.S. PATENT DOCUMENTS

| | | | |
|---|---|---|---|
| 5,294,612 A | 3/1994 | Bacon et al. | |
| 6,162,804 A | 12/2000 | Bilodeau et al. | |
| 6,552,042 B2 | 4/2003 | Han et al. | |
| 6,552,192 B1 | 4/2003 | Hanus et al. | |
| 6,582,351 B1 | 6/2003 | Sawada et al. | |

FOREIGN PATENT DOCUMENTS

| | | |
|---|---|---|
| WO | 97/42187 | 11/1997 |
| WO | 99/10349 | 3/1999 |
| WO | 99/65875 | 12/1999 |
| WO | 03/053330 | 7/2003 |
| WO | 03/055877 | 7/2003 |
| WO | 2005/047289 | 5/2005 |

OTHER PUBLICATIONS

Chu, Ih et al., Journal of Medicinal Chemistry, Synthesis and Biological Evaluation of Xanthine Oxidase Inhibitors, Pyrazolo[3,4-d]pyrimidines and Pyrazolo[3,4-b]pyridines, 1975, 18(2), 161-165.
Banker, G.S. et al., "Modern Pharmaceutics, 3ed.", Marcel Dekker, New York, 1996, p. 596.
Wolff, Manfred E., "Burger's Medicinal Chemistry, 5ed., Part I", John Wiley & Sons, pp. 975-977, (1995).

*Primary Examiner* — Susanna Moore

(57) ABSTRACT

The present invention is related to chemical compositions, processes for the preparation thereof and uses of the composition. Particularly, the present invention relates to compositions that include substituted heterobicyclic pyrimidines of Formula (I):

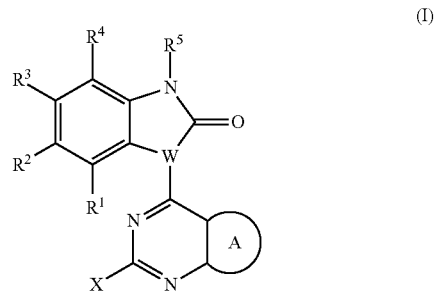

wherein $R^1$, $R^2$, $R^3$, $R^4$, $R^5$, X, W, and ring A are as defined herein; pharmaceutical compositions of substituted heterobicyclic pyrimidines of Formula (I); and their use in the treatment of chronic neurodegenerative diseases, neurotraumatic diseases, depression and/or diabetes. More particularly, the present invention relates to substituted pyrazolopyrimidines of Formula (I).

18 Claims, No Drawings

SUBSTITUTED BICYCLIC PYRIMIDINES

This application is a divisional application of U.S. application Ser. No. 11/803,320, filed May 14, 2007, which, in turn, claims the benefit, under 35 USC 119(e) to U.S. Provisional Application 60/800,375, filed May 15, 2006.

FIELD OF THE INVENTION

The present invention is related to chemical compositions, processes for the preparation thereof and uses of the composition. Particularly, the present invention relates to compositions that include substituted heterobicyclic pyrimidines of Formula (I):

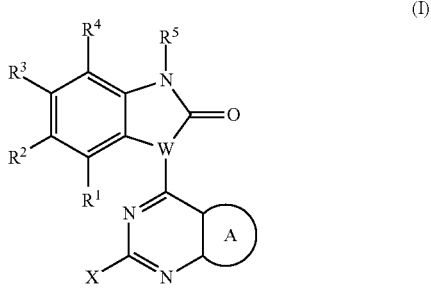

wherein $R^1$, $R^2$, $R^3$, $R^4$, $R^5$, X, W, and ring A are as defined herein; pharmaceutical compositions of substituted heterobicyclic pyrimidines of Formula (I); and their use in the treatment of chronic neurodegenerative diseases, neurotraumatic diseases, depression and/or diabetes. More particularly, the present invention relates to substituted pyrazolopyrimidines of Formula (I).

BACKGROUND OF THE INVENTION

This invention relates to novel substituted heterobicyclic pyrimidine compounds, in particular substituted pyrazolopyrimidine oxindoles, that act as inhibitors of glycogen synthase kinase 3 and cyclin dependant kinase 5.

Glycogen synthase kinase 3 (GSK3) is a serine/threonine protein kinase composed of two isoforms (α and β) encoded by different genes. GSK3 is highly expressed in the central and peripheral nervous system, with GSK3β predominating in the brain. Both isoforms of GSK3 phosphorylate and regulate the activity of several protein substrates, including glycogen synthase, β-catenin, pyruvate dehydrogenase, elongation initiation factor 2b, and tau. GSK3 is regulated by insulin, which stimulates glycogen synthesis via receptor activation of PI3 kinase and protein kinase B. PKB phosphorylates GSK3β on serine 9, resulting in its inactivation. Insulin also activates protein phosphatase 1. Both of these actions of insulin lead to dephosphorylation and activation of glycogen synthase (Srivastava and Pandey, Mol Cell Biochem. 182: 135-141, 1998; Cohen, Biochem Soc Trans., 21:555-567, 1993), and production of glycogen from glucose. β-catenin degradation is increased following phosphorylation by GSK3 (Ikeda, et al., EMBO, 17:1371-1384, 1998). The reduction in available β-catenin may increase the sensitivity of neurons to amyloid β (Aβ) toxicity (Zhang, et al., Nature, 395:698-702, 1998). GSK3β also phosphorylates pyruvate dehydrogenase and prevents the conversion of pyruvate to acetyl CoA (Hoshi, et al., PNAS, 93:2719-2723, 1996). This acetyl CoA is critical for the synthesis of acetylcholine, the loss of which is implicated in the cognitive decline in Alzheimer's Disease (AD). GSK3α regulates production of Aβ from the amyloid precursor protein (Phiel, et al., Nature. 423:435-9, 2003). Two proteases, β- and γ-secreatase liberate the amino and carboxy terminus (respectively) of Aβ. In a concentration dependant manner, Aβ precipitates into toxic, fibrillary species in the AD brain and is thought to lead to additional sequalae of the disease. Phosphorylation of eIF2B by GSK-3β reduces protein translation. eIF2B activation by IGF1 is mediated by the inactivation of GSK3β (Welsh, et al., FEBS Letts, 421:125-130, 1997). The role of tau phosphorylation by GSK3 will be discussed following description of CDK5.

Cyclin Dependant Kinase 5 (CDK5) is also a serine/threonine protein kinase, and is structurally related to GSK3. CDK5 activation predominates in the nervous system due to expression of p35, an accessory protein related to cyclins and necessary for CDK5 activity (Dhavan and Tsai, Nat Rev Mol Cell Biol, 2:749-759, 2001). Unlike CDK1, 2, 4, and 6 which are active in the cell cycle, CDK5 is activated in neurons after cell division has ended, following differentiation and expression of p35. CDK5 activity is regulated by expression of p35 and a calpain-cleaved form of p35, known as p25 (Patzke and Tsai, J Biol Chem, 277:8054-8060, 2002). The generation of p25 leads to increased and mislocalized CDK5 activity since 1) p25 is missing the membrane localizing portion found in p35, and 2) p25 has a longer resident half life in the cytoplasm. CDK5 phosphorylates a number of substrates including DARPP-32, NR2a (NMDA receptor subunit), MEF-2, PSD-95, synaptojanin-1, CRMP2, and tau. DARPP-32 phosphorylation by CDK5 at thr75 leads to the inhibition of PKA in the dopamine 1 receptor (D1) signaling cascade, thereby inhibiting D1 signaling (Bibb, et al., Nature, 402:669-671 1997). Facilitation of D1 signaling may be useful for the treatment of depression or Parkinson's Disease (Chergui, et al., PNAS, 10:2191-2196, 2004). NR2a phosphorylation by CDK5 modulates long term potentiation and may induce apoptotic cell death following ischemia (Wang, et al., Nat. Neurosci., 6:1039-47, 2003). CDK5-dependent phosphorylation of PSD-95 dynamically regulates the clustering of PSD-95/NMDA receptors at synapses, providing a possible mechanism for rapid changes in density and/or number of synaptic receptors (Morabito, et. al., J. Neurosci., 24:865-876, 2004). CDK5 also phosphorylates the presynaptic phosphatase synaptojanin 1 and regulates its function both in vitro and in intact synaptosomes (Lee, et. al., PNAS, 101:546-551, 2004). CRMP2 is also phosphorylated by CDK5, leading to a reduction in CRMP-tubulin binding affinity and modulating growth cone collapse. CDK5 primarily phosphorylates CRMP2 at Ser522 and GSK3β secondarily phosphorylates at Thr509. Dual-phosphorylated CRMP2 is recognized with the antibody 3F4, highly reactive with the neurofibrillary tangles (NFT) of AD brain (Uchida, et al., Genes Cells, 10:165-179, 2005). Overall, the role of CDK5 in synaptic formation and function is well substantiated.

Experimental evidence supports a role for both GSK3 and CDK5 in the tangle and plaque pathology of AD, namely in the tau hyperphosphorylation that leads to NFT formation. AD brain is characterized by intracellular NFTs and extracellular senile plaques consisting of Aβ deposits. Both of these protein aggregates are thought to precipitate the neuronal and synaptic loss, leading to the memory loss and cognitive decline of AD (Hardy, J Mol Neurosci, 20:203-6, 2003).

NFTs are composed of hyperphosphorylated, aggregated forms of the neuron specific, cytoskeletal protein tau (Cairns, et. al., J Pathol, 204:438-449, 2004). The primary function of tau is to stabilize neuronal microtubules, to maintain axonal architecture, and to allow transport of materials both from the cell body to the synapse, and from the synapse back to the cell body. In AD, tau is hyperphosphorylated at many serine/threonine residues, leading to poor binding of tau to the microtubule and loss of trophic interplay between the cell body and the synapse. NFTs represent one of the characteristic features of the AD brain, and are also present in the brains of individuals with progressive supranuclear palsy, frontotemporal dementia with parkinsonism-17, Neimann-Pick's disease, corticobasal degeneration, amyotrophic lateral sclerosis, dementia puglistica, etc.

NFTs are composed of insoluble aggregates of tau protein, hyperphosphorylated on many serine and threonine residues and formed into paired helical filaments. The hyperphosphorylation of tau results in a lower affinity for the microtubule and may represent the first step toward aggregate formation. Both CDK5 and GSK3 phosphorylate tau in both cell-free and cell-based in vitro systems at many of the same sites present in the AD brain. Antibodies directed against both GSK3 (Pei, et. al., J. Neuropath. Exp. Neurol., 58:1010-1019, 1999) and CDK5 (Pei, et. al., Brain Res, 797:267-277, 1998) decorate the NFTs in the AD brain, demonstrating the close association between these kinases and the hyperphosphorylated tau that comprises the tangles. Overexpression of either kinase activity in transgenic animal models (Lucas, et al., EMBO J., 20:27-39, 2001; Cruz, et al., Neuron, 40:471-83, 2003) also demonstrates their ability to hyperphosphorylate tau (both CDK5 and GSK3) and cause the formation of mature NFTs and neuronal loss (CDK5). Phosphorylation by GSK3 at many epitopes requires prior phosphorylation by a so called "priming" kinase C-terminal to the GSK3 phosphorylation site (Cohen and Goedert, Nat Rev Drug Discov, 3:479-487, 2004). Interestingly, CDK5 has been implicated as a priming kinase (at phosphoserine 235) for GSK3, which acts to phosphorylate threonine 231, a site that is phosphorylated early in the progression of AD NFT pathology (Augustinack, et. al., Acta Neuropathol (Berl). 103:26-35, 2002; Li T, Hawkes C, Qureshi H Y, Kar S, Paudel H K, Biochemistry, 45:3145-4154, 2006).

Other disease states in which GSK3 is thought to play a role include cerebral ischemia. GSK3 activity is increased in cellular and animal models of both neurodegeneration and apoptosis, such as cerebral ischemia (Bhat, et al., PNAS, 97:11074-11079, 2000). Lithium, as a representative GSK3 inhibitor, is neuroprotective in these models (Ren, et al., PNAS, USA, 100:6210-6215, 2003). Lithium inhibits GSK3 at concentrations also known to be therapeutic in bipolar disorder (Gould, et al., J Clin Psychiatry, 65:10-21, 2004), implicating GSK3 inhibition as a therapeutic avenue in this disease.

GSK3 activity is increased in peripheral lymphocytes and brains of patients with schizophrenia, as evidenced by reduced levels of both the upstream inhibiting kinase AKT1, and the inhibitory ser9 phosphorylation of GSK3β (Emamian, et al., Nat Genet, 36:131-137, 2004) Clinical treatment leads to normalization of this pathway.

Diabetes mellitus type 2 is characterized by reduced insulin production due to loss of pancreatic beta cells following a period of reduced insulin sensitivity. With the insulin receptor signaling dysfunction that is also present in the disease, direct inhibition of GSK3 has been hypothesized to relieve the hyperglycemia and allow for normal glycogen synthesis and glucose utilization (Wagman, et al., Curr Pharm Des., 10:1105-1137, 2004).

These compounds as GSK3 inhibitors are indicated to be useful for the treatment and/or prophylaxis of conditions in which there is a need for inhibition of GSK3, such as diabetes, conditions associated with diabetes, chronic neurodegenerative diseases such as Alzheimer's Disease, Parkinson's Disease, progressive supranuclear palsy, subacute panencephalitic parkinsonism, postencephalitic parkinsonism, dementia puglistica, guan parkinsonial dementia complex, Pick's disease, corticobasal degeneration, frontotemporal dementia with parkinsonism, Huntington's disease, AIDS associated dementia, amyotrophic lateral sclerosis, multiple sclerosis, and neurotraumatic diseases such as acute stroke, mood disorders such as schizophrenia and bipolar disorders, promotion of functional recovery post stroke, cerebral bleeding (solitary cerebral amyloid angiopathy), hair loss, obesity, atherosclerotic cardiovascular disease, hypertension, polycystic ovary syndrome, syndrome X, ischemia, traumatic brain injury, cancer, leukopenia, Down's syndrome, Lewy body disease, inflammation and immunodeficiency.

These compounds as CDK5 inhibitors are indicated to be useful for the treatment and/or prophylaxis of conditions in which there is a need for inhibition of CDK5 such as the chronic neurodegenerative diseases Alzheimer's disease, Parkinson's Disease, progressive supranuclear palsy, subacute panencephalitic parkinsonism, postencephalitic parkinsonism, dementia puglistica, guan-parkinsonial dementia complex, Pick's disease, corticobasal degeneration, frontotemporal dementia with parkinsonism, Huntington's disease, AIDS-associated dementia, amyotrophic lateral sclerosis and mood disorders such as depression.

Thus, there is a need for novel classes of compounds that possess the beneficial properties. It has been discovered that a class of compounds, referred to herein as substituted heterobicyclic pyrimidine compounds, in particular substituted pyrazolopyrimidine oxindoles, are useful as agents for treating or preventing various diseases or disorders disclosed herein.

SUMMARY OF THE INVENTION

The present invention in one aspect is directed to various novel compounds of structure:

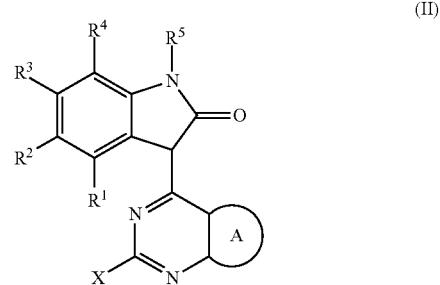

wherein $R^1$, $R^2$, $R^3$, $R^4$, $R^5$, X and ring A are as defined herein; and its stereoisomeric forms, mixtures of stereoisomeric forms, tautomeric forms, or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt or ester form thereof.

Another object of the present invention is to provide methods of treating or preventing diseases or disorders, including chronic neurodegenerative diseases is selected from Alzheimer's Disease, Parkinson's Disease, progressive supranuclear palsy, subacute panencephalitic parkinsonism, postencephalitic parkinsonism, dementia puglistica, guan-parkinsonial dementia complex, Pick's disease, corticobasal degeneration, frontotemporal dementia with parkinsonism, Huntington's disease, AIDS associated dementia, amyotrophic lateral sclerosis, and multiple sclerosis.

Another object of the present invention is to provide methods of treating or preventing diseases or disorders, including neurotraumatic disease selected from acute stroke, mood disorders such as schizophrenia and bipolar disorders, promotion of functional recovery post stroke, cerebral bleeding (solitary cerebral amyloid angiopathy), hair loss, obesity, atherosclerotic cardiovascular disease, hypertension, polycystic ovary syndrome, syndrome X, ischemia, traumatic brain injury, cancer, leukopenia, Down's syndrome, Lewy body disease, inflammation and immunodeficiency.

Another object of the present invention is to provide methods of treating depression.

Another object of the present invention is to provide methods of treating diabetes.

These and other objects, features and advantages of the substituted pyrazolopyrimidines will be disclosed in the following detailed description of the patent disclosure.

DETAILED DESCRIPTION OF THE INVENTION

In a first embodiment, the present invention provides novel compounds of Formula (I):

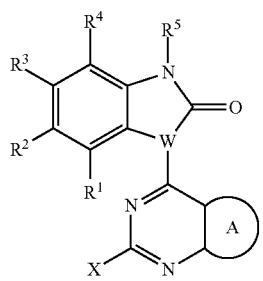

and stereoisomeric forms, mixtures of stereoisomeric forms, tautomeric forms, prodrugs, or pharmaceutically acceptable salt forms thereof, wherein:

W is CH or N;
ring A is

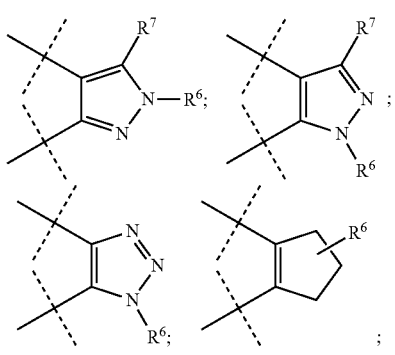

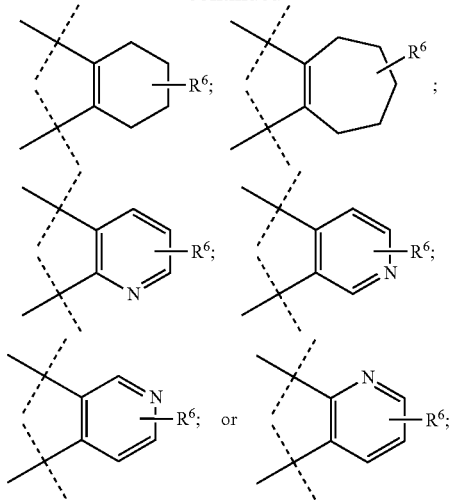

$R^1$, $R^2$, $R^3$, and $R^4$ at each occurrence are independently selected from H, halo, —$OR^{11}$, —$NO_2$, —CN, —$CF_3$, —$CHF_2$, $C_2$-$C_4$ alkenyl, $C_2$-$C_4$ alkynyl, $C_1$-$C_4$ haloalkyl, —$NR^{13}R^{14}$, —$NHOR^{13a}$, —$C(=O)R^{15}$, —$C(=O)OR^{15}$, —$OC(=O)R^{15}$, —$C(=O)NR^{13}R^{14}$, —$NR^{13a}C(=O)R^{15}$, —$NR^{13a}CO_2R^{15}$, —$OC(=O)NR^{13}R^{14}$, —$NR^{13a}C(=S)R^{15}$, —$SR^{15}$, —$S(=O)R^{15}$, —$S(=O)_2R^{15}$, —$S(=O)_2NR^{13}R^{14}$, and $C_1$-$C_4$ alkyl substituted with 0-1 $R^{19}$;

$R^5$ is H, $C_1$-$C_6$ alkyl or a prodrug of an amino group;

$R^6$ is selected from H;
  $C_1$-$C_6$ alkyl substituted by 0-2 $R^{22}$;
  $C_2$-$C_6$ alkenyl substituted by 0-2 $R^{22}$;
  $C_2$-$C_6$ alkynyl substituted by 0-2 $R^{22}$; and
  $C_3$-$C_7$ cycloalkyl substituted by 0-3 $R^{22}$;

$R^7$ is H, —$NO_2$, halo, $C_1$-$C_4$ alkyl or —$NR^{23}R^{24}$;

X is selected from H, —$NR^9R^{10}$, halo, $OR^{12}$, —$NO_2$, —CN, —$CF_3$, —$CHF_2$, $C_1$-$C_4$ alkyl, $C_2$-$C_4$ alkenyl, $C_2$-$C_4$ alkynyl, $C_1$-$C_4$ haloalkyl, —$CH_2NR^9R^{10}$, —$CH_2OR^{12}$, —$NHOR^{16}$, —$C(=O)R^{18}$, —$C(=O)OR^{18}$, —$OC(=O)R^{18}$, —$C(=O)NR^9R^{10}$, —$NR^{16}C(=O)R^{18}$, —$NR^{16}CO_2R^{18}$, —$OC(=O)NR^9R^{10}$, —$NR^{16}C(=S)R^{18}$, —$SR^{18}$, —$S(=O)R^{18}$, —$S(=O)_2R^{18}$, —$S(=O)_2NR^9R^{10}$, and —$NR^{16}S(=O)_2R^{18}$;

$R^9$ and $R^{10}$ at each occurrence are each independently selected from H, —$NH_2$;
  $C_1$-$C_6$ alkyl substituted by 0-1 $R^{19}$;
  $C_2$-$C_6$ alkenyl substituted by 0-1 $R^{19}$;
  $C_2$-$C_6$ alkynyl substituted by 0-1 $R^{19}$;
  $C_6$-$C_{10}$ aryl substituted by 0-5 $R^{19}$;
  $C_3$-$C_7$ carbocyclyl substituted by 0-5 $R^{19}$; and
  5 to 14 membered heterocyclyl group substituted by 0-5 $R^{19}$, wherein said heterocyclyl group comprises one, two, or three heteroatoms selected from N, O, and S;
  5 to 14 membered heteroaryl group substituted by 0-5 $R^{19}$, wherein said heteroaryl group comprises one, two, or three heteroatoms selected from N, O, and S;

alternatively, $R^9$ and $R^{10}$, together with the nitrogen to which they are attached, form a 3-7 membered heterocyclic ring, wherein said 3-7 membered heterocyclic ring contains a nitrogen atom and optionally a second atom selected from N, O, S, S(=O), and S(=O)$_2$, wherein said 3-7 membered heterocyclic ring is substituted with 0-1 $R^{17}$;

$R^{11}$ at each occurrence is independently selected from H, $C_1$-$C_4$ alkyl, and $C_1$-$C_4$ haloalkyl;

$R^{12}$ at each occurrence is independently selected from H, $C_1$-$C_4$ haloalkyl and $C_1$-$C_4$ alkyl substituted with 0-1 $R^{19}$;

$R^{13}$ and $R^{14}$, at each occurrence, are independently selected from H, $C_1$-$C_4$ alkyl substituted with 0-3 $R^{30}$; and $C_6$-$C_{10}$ aryl substituted with 0-5 $R^{30}$;

$R^{13a}$ at each occurrence is independently selected from H, $C_1$-$C_4$ alkyl, and $C_6$-$C_{10}$ aryl;

$R^{15}$ at each occurrence is independently selected from H,
  $C_1$-$C_6$ alkyl substituted by 0-1 $R^{30}$;
  $C_2$-$C_6$ alkenyl substituted by 0-1 $R^{30}$;
  $C_2$-$C_6$ alkynyl substituted by 0-1 $R^{30}$;
  $C_6$-$C_{10}$ aryl substituted by 0-5 $R^{30}$;
  $C_3$-$C_7$ carbocyclyl substituted by 0-5 $R^{30}$; and
  5 to 14 membered heterocyclyl group substituted by 0-5 $R^{30}$, wherein said heterocyclyl group comprises one, two, or three heteroatoms selected from N, O, and S;
  5 to 14 membered heteroaryl group substituted by 0-5 $R^{30}$, wherein said heteroaryl group comprises one, two, or three heteroatoms selected from N, O, and S;

$R^{16}$ at each occurrence is independently selected from H and $C_1$-$C_4$ alkyl;

$R^{17}$ is H, —$NR^{23}R^{24}$, halo, —$NO_2$, —CN, —$CF_3$, $C_1$-$C_4$ haloalkyl, —NHOH, $OR^{25}$, $C(\!=\!O)R^{25}$, $C(\!=\!O)OR^{25}$, $OC(\!=\!O)R^{25}$, $C(\!=\!O)NR^{23}R^{24}$, $NR^{23a}C(\!=\!O)R^{25}$, $NR^{23a}CO_2R^{25}$, $OC(\!=\!O)NR^{23}R^{24}$, $NR^{23a}C(\!=\!S)R^{25}$, $SR^{25}$, $S(\!=\!O)R^{25}$, $S(\!=\!O)_2R^{25}$, $S(\!=\!O)_2NR^{23}R^{24}$, —$NR^{23a}S(\!=\!O)_2R^{25}$, or $C_1$-$C_4$ alkyl substituted by 0-1 $R^{19}$;

$R^{18}$ at each occurrence is independently selected from H;
  $C_1$-$C_6$ alkyl substituted by 0-1 $R^{30}$;
  $C_2$-$C_6$ alkenyl substituted by 0-1 $R^{30}$;
  $C_2$-$C_6$ alkynyl substituted by 0-1 $R^{30}$;
  $C_6$-$C_{10}$ aryl substituted by 0-5 $R^{30}$;
  $C_3$-$C_7$ carbocyclyl substituted by 0-5 $R^{30}$; and
  5 to 14 membered heterocyclyl group substituted by 0-5 $R^{30}$, wherein said heterocyclyl group comprises one, two, or three heteroatoms selected from N, O, and S;
  5 to 14 membered heteroaryl group substituted by 0-5 $R^{30}$, wherein said heteroaryl group comprises one, two, or three heteroatoms selected from N, O, and S;

$R^{19}$ at each occurrence is independently selected from H, —$NR^{23}R^{24}$, halo, —$NO_2$, —CN, —$CF_3$, $C_1$-$C_4$ haloalkyl, —NHOH, $OR^{25}$, $C(\!=\!O)R^{25}$, $C(\!=\!O)OR^{25}$, $OC(\!=\!O)R^{25}$, $C(\!=\!O)NR^{23}R^{24}$, $NR^{23a}C(\!=\!O)R^{25}$, $NR^{23a}CO_2R^{25}$, $OC(\!=\!O)NR^{23}R^{24}$, $NR^{23a}C(\!=\!S)R^{25}$, $SR^{25}$, $S(\!=\!O)R^{25}$, $S(\!=\!O)_2R^{25}$; $S(\!=\!O)_2NR^{23}R^{24}$, —NR
  $C_1$-$C_4$ alkyl substituted by 0-1 $R^{30}$;
  $C_2$-$C_4$ alkenyl substituted by 0-1 $R^{30}$;
  $C_2$-$C_4$ alkynyl substituted by 0-1 $R^{30}$;
  $C_6$-$C_{10}$ aryl substituted by 0-5 $R^{30}$;
  $C_3$-$C_7$ carbocyclyl substituted by 0-5 $R^{30}$; and
  5 to 14 membered heterocyclyl group substituted by 0-5 $R^{30}$, wherein said heterocyclyl group comprises one, two, or three heteroatoms selected from N, O, and S;
  5 to 14 membered heteroaryl group substituted by 0-5 $R^{30}$, wherein said heteroaryl group comprises one, two, or three heteroatoms selected from N, O, and S;

$R^{22}$ is H, —$NR^{23}R^{24}$, —$N_3$, halo, —$NO_2$, —CN, —$CF_3$, $C_1$-$C_4$ alkyl, $C_2$-$C_4$ alkenyl, $C_2$-$C_4$ alkynyl, $C_1$-$C_4$ haloalkyl, $C_3$-$C_7$ carbocyclyl, phenyl, —NHOH, $OR^{25}$, —$CH_2OR^{25}$, $C(\!=\!O)R^{25}$, $C(\!=\!O)OR^{25}$, $OC(\!=\!O)R^{25}$, $C(\!=\!O)NR^{23}R^{24}$, $NR^{23a}C(\!=\!O)R^{25}$, $NR^{23a}CO_2R^{25}$, $OC(\!=\!O)NR^{23}R^{24}$, $NR^{23a}C(\!=\!S)R^{25}$, $SR^{25}$, $S(\!=\!O)R^{25}$, $S(\!=\!O)_2R^{25}$; $S(\!=\!O)_2NR^{23}R^{24}$, or —$NR^{23a}S(\!=\!O)_2R^{25}$;

$R^{23}$ and $R^{24}$ at each occurrence are each independently selected from H or $C_1$-$C_6$ alkyl;

alternatively, $R^{23}$ and $R^{24}$, together with the nitrogen to which they are attached, form a 3-7 membered heterocyclic ring, wherein said 3-7 membered heterocyclic ring contains a nitrogen atom and optionally a second atom selected from N, O and S; wherein said 3-7 membered heterocyclic ring is substituted with 0-1 $C_1$-$C_4$ alkyl;

$R^{23a}$ at each occurrence is each independently selected from H or $C_1$-$C_4$ alkyl;

$R^{25}$ at each occurrence is each independently selected from H or $C_1$-$C_6$ alkyl; and $R^{30}$ is H, F, Cl, Br, —$CF_3$, $C_1$-$C_6$ alkyl, and $C_1$-$C_6$ alkoxy;

provided when ring A is

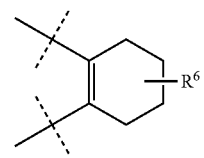

then X is —$NR^9R^{10}$.

In a preferred embodiment, W is CH.

In a preferred embodiment, ring A is

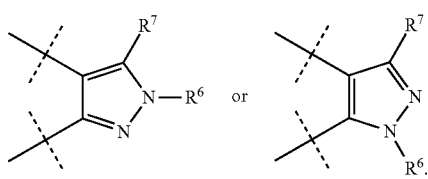

In a preferred embodiment, ring A is

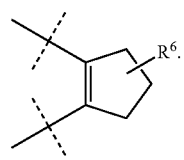

In a preferred embodiment, ring A is

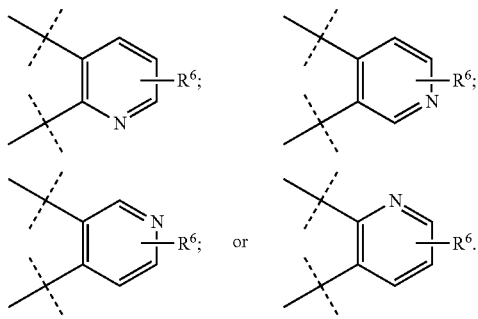

In a preferred embodiment, ring A is

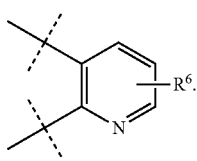

In a preferred embodiment, $R^1$, $R^2$, $R^3$, and $R^4$ at each occurrence are independently selected from H, halo, —$OR^{11}$, —$NO_2$, —CN, and —$CF_3$.

In a preferred embodiment, $R^1$ is H and $R^2$, $R^3$, and $R^4$ at each occurrence are independently selected from H, halo, —$OR^{11}$, —$NO_2$, —CN, and —$CF_3$.

In a preferred embodiment, $R^1$, $R^3$, and $R^4$ are each H and $R^2$ is selected from H, F, Cl, Br, —$OCH_3$, —$NO_2$, —CN, and —$CF_3$.

In a preferred embodiment, X is H, —$NR^9R^{10}$, halo, $C_1$-$C_4$ alkyl, or $OR^{12}$.

In a preferred embodiment, X is —$NR^9R^{10}$.

In a preferred embodiment, X is —$NHR^9$.

In a preferred embodiment, $R^5$ is H.

In another first embodiment, the present invention provides novel compounds of Formula (II):

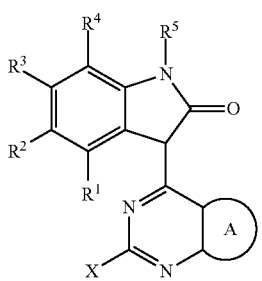

(II)

and stereoisomeric forms, mixtures of stereoisomeric forms, tautomeric forms, prodrugs, or pharmaceutically acceptable salt forms thereof, wherein:

ring A is

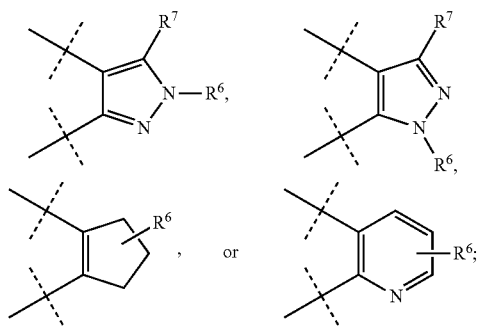

$R^1$, $R^2$, $R^3$, and $R^4$ at each occurrence are independently selected from
  H, halo, —$OR^{11}$, —$NO_2$, —CN, —$CF_3$, —$CHF_2$, $C_2$-$C_4$ alkenyl, $C_2$-$C_4$ alkynyl, $C_1$-$C_4$ haloalkyl, and $C_1$-$C_4$ alkyl;
$R^5$ is H, $C_1$-$C_6$ alkyl or a prodrug of an amino group;
$R^6$ is selected from H;

$C_1$-$C_6$ alkyl substituted by 0-2 $R^{22}$;
  $C_2$-$C_6$ alkenyl substituted by 0-2 $R^{22}$;
  $C_2$-$C_6$ alkynyl substituted by 0-2 $R^{22}$; and
  $C_3$-$C_7$ cycloalkyl substituted by 0-2 $R^{22}$;
$R^7$ is H, —$NO_2$, halo, $C_1$-$C_4$ alkyl or —$NR^{23}R^{24}$;
X is H, —$NR^9R^{10}$, halo, $OR^{12}$, $C_1$-$C_4$ alkyl, or $C_2$-$C_4$ alkenyl;
$R^9$ and $R^{10}$ at each occurrence are each independently selected from H, —$NH_2$;
  $C_1$-$C_6$ alkyl substituted by 0-1 $R^{19}$;
  $C_2$-$C_6$ alkenyl substituted by 0-1 $R^{19}$;
  $C_2$-$C_6$ alkynyl substituted by 0-1 $R^{19}$;
  $C_6$-$C_{10}$ aryl substituted by 0-5 $R^{19}$;
  $C_3$-$C_7$ carbocyclyl substituted by 0-5 $R^{19}$; and
  5 to 14 membered heterocyclyl group substituted by 0-5 $R^{19}$, wherein said heterocyclyl group comprises one, two, or three heteroatoms selected from N, O, and S;
  5 to 14 membered heteroaryl group substituted by 0-5 $R^{19}$, wherein said heteroaryl group comprises one, two, or three heteroatoms selected from N, O, and S;
alternatively, $R^9$ and $R^{10}$, together with the nitrogen to which they are attached, form a 3-7 membered heterocyclic ring, wherein said 3-7 membered heterocyclic ring contains a nitrogen atom and optionally a second atom selected from N, O, S, S(=O), and S(=O)$_2$, wherein said 3-7 membered heterocyclic ring is substituted with 0-1 $R^{17}$;
$R^{11}$ at each occurrence is independently selected from H, $C_1$-$C_4$ alkyl, and $C_1$-$C_4$ haloalkyl;
$R^{12}$ at each occurrence is independently selected from H, $C_1$-$C_4$ haloalkyl and $C_1$-$C_4$ alkyl substituted with 0-1 $R^{19}$;
$R^{17}$ is H or $C_1$-$C_4$ alkyl substituted by 0-1 $R^{19}$;
$R^{19}$ at each occurrence is independently selected from H, —$NR^{23}R^{24}$, halo, —$NO_2$, —CN, —$CF_3$, $C_1$-$C_4$ haloalkyl, —NHOH, $OR^{25}$, C(=O)$R^{25}$, C(=O)O$R^{25}$, OC(=O)$R^{25}$, C(=O)$NR^{23}R^{24}$, $NR^{23a}$C(=O)$R^{25}$, $NR^{23a}CO_2R^{25}$, C(=O)$NR^{23}R^{24}$, $NR^{23a}$C(=S)$R^{25}$, $SR^{25}$, S(=O)$R^{25}$, S(=O)$_2R^{25}$; S(=O)$_2NR^{23}R^{24}$, —$NR^{23a}$S(=O)$_2R^{25}$,
  $C_1$-$C_4$ alkyl substituted by 0-1 $R^{30}$;
  $C_2$-$C_4$ alkenyl substituted by 0-1 $R^{30}$;
  $C_2$-$C_4$ alkynyl substituted by 0-1 $R^{30}$;
  $C_6$-$C_{10}$ aryl substituted by 0-5 $R^{30}$;
  $C_3$-$C_7$ carbocyclyl substituted by 0-5 $R^{30}$; and
  5 to 14 membered heterocyclyl group substituted by 0-5 $R^{30}$, wherein said heterocyclyl group comprises one, two, or three heteroatoms selected from N, O, and S;
  5 to 14 membered heteroaryl group substituted by 0-5 $R^{30}$, wherein said heteroaryl group comprises one, two, or three heteroatoms selected from N, O, and S;
$R^{22}$ is H, —$NR^{23}R^{24}$, —$N_3$, halo, —$NO_2$, —CN, —$CF_3$, $C_1$-$C_4$ alkyl, $C_2$-$C_4$ alkenyl, $C_2$-$C_4$ alkynyl, $C_1$-$C_4$ haloalkyl, $C_3$-$C_7$ carbocyclyl, phenyl, —NHOH, $OR^{25}$, —$CH_2OR^{25}$, C(=O)$R^{25}$, C(=O)O$R^{25}$, OC(=O)$R^{25}$, C(=O)$NR^{23}R^{24}$, $NR^{23a}$C(=O)$R^{25}$, $NR^{23a}CO_2R^{25}$, OC(=O)$NR^{23}R^{24}$, $NR^{23a}$C(=S)$R^{25}$, $SR^{25}$, S(=O)$R^{25}$, S(=O)$_2R^{25}$; S(=O)$_2NR^{23}R^{24}$, or —$NR^{23a}$S(=O)$_2R^{25}$;
$R^{23}$ and $R^{24}$ at each occurrence are each independently selected from H or $C_1$-$C_6$ alkyl;
alternatively, $R^{23}$ and $R^{24}$, together with the nitrogen to which they are attached, form a 3-7 membered heterocyclic ring, wherein said 3-7 membered heterocyclic ring contains a nitrogen atom and optionally a second atom selected from N, O and S, wherein said 3-7 membered heterocyclic ring is substituted with 0-1 $C_1$-$C_4$ alkyl;
$R^{23a}$ at each occurrence is each independently selected from H or $C_1$-$C_4$ alkyl;
$R^{25}$ at each occurrence is each independently selected from H or $C_1$-$C_6$ alkyl; and
$R^{30}$ is H, F, Cl, Br, —$CF_3$, $C_1$-$C_6$ alkyl, and $C_1$-$C_6$ alkoxy.

In a preferred embodiment, ring A is

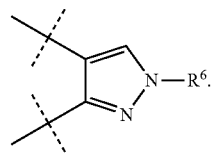

In a preferred embodiment, ring A is

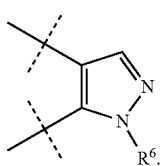

In a preferred embodiment, ring A is

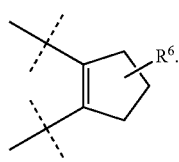

In a preferred embodiment, ring A is

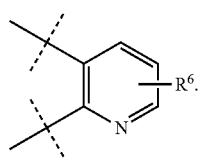

In a preferred embodiment, $R^1$, $R^2$, $R^3$, and $R^4$ at each occurrence are independently selected from H, F, Cl, Br, —OCH$_3$, —NO$_2$, —CN, and —CF$_3$.

In a preferred embodiment, $R^1$ is H and $R^2$, $R^3$, and $R^4$ at each occurrence are independently selected from H, F, Cl, Br, —OCH$_3$, —NO$_2$, —CN, and —CF$_3$.

In a preferred embodiment, $R^1$, $R^3$, and $R^4$ are each H and $R^2$ is selected from H, F, Cl, Br, —OCH$_3$, —NO$_2$, —CN, and —CF$_3$.

In a preferred embodiment, X is —NR$^9$R$^{10}$.

In a preferred embodiment, X is —NHR$^9$.

In a preferred embodiment, $R^6$ is C$_1$-C$_6$ alkyl substituted by 0-2 R$^{22}$.

In a preferred embodiment, $R^6$ is C$_3$-C$_7$ cycloalkyl substituted by 0-2 R$^{22}$.

In a preferred embodiment, $R^6$ is cyclopentyl.

In another first embodiment, the present invention provides novel compounds of Formula (III):

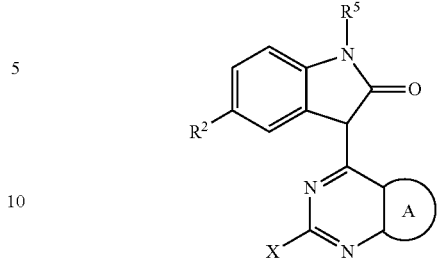

(III)

and stereoisomeric forms, mixtures of stereoisomeric forms, tautomeric forms, prodrugs, or pharmaceutically acceptable salt forms thereof, wherein:

ring A is

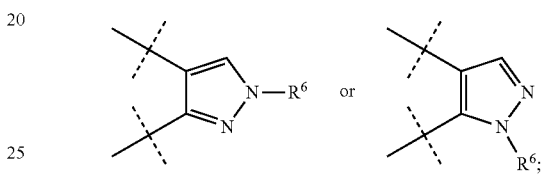

$R^2$ is selected from
  H, halo, —OR$^{11}$, —NO$_2$, —CN, —CF$_3$, —CHF$_2$, C$_2$-C$_4$ alkenyl, C$_2$-C$_4$ alkynyl, C$_1$-C$_4$ haloalkyl, and C$_1$-C$_4$ alkyl;

$R^5$ is H, methyl or a prodrug of an amino group;

$R^6$ is selected from H;
  C$_1$-C$_6$ alkyl substituted by 0-2 R$^{22}$;
  C$_2$-C$_6$ alkenyl substituted by 0-2 R$^{22}$;
  C$_2$-C$_6$ alkynyl substituted by 0-2 R$^{22}$; and
  C$_3$-C$_7$ cycloalkyl substituted by 0-2 R$^{22}$;

X is H, —NR$^9$R$^{10}$, halo, OR$^{12}$, C$_1$-C$_4$ alkyl, or C$_2$-C$_4$ alkenyl;

$R^9$ and $R^{10}$ at each occurrence are each independently selected from H, —NH$_2$;
  C$_1$-C$_6$ alkyl substituted by 0-1 R$^{19}$;
  C$_2$-C$_6$ alkenyl substituted by 0-1 R$^{19}$;
  C$_2$-C$_6$ alkynyl substituted by 0-1 R$^{19}$;
  C$_6$-C$_{10}$ aryl substituted by 0-5 R$^{19}$;
  C$_3$-C$_7$ carbocyclyl substituted by 0-5 R$^{19}$; and
  5 to 14 membered heterocyclyl group substituted by 0-5 R$^{19}$, wherein said heterocyclyl group comprises one, two, or three heteroatoms selected from N, O, and S;
  5 to 14 membered heteroaryl group substituted by 0-5 R$^{19}$, wherein said heteroaryl group comprises one, two, or three heteroatoms selected from N, O, and S;

alternatively, $R^9$ and $R^{10}$, together with the nitrogen to which they are attached, form a 3-7 membered heterocyclic ring, wherein said 3-7 membered heterocyclic ring contains a nitrogen atom and optionally a second atom selected from N, O, S, S(=O), and S(=O)$_2$, wherein said 3-7 membered heterocyclic ring is substituted with 0-1 R$^{17}$;

$R^{11}$ at each occurrence is independently selected from H, C$_1$-C$_4$ alkyl, and C$_1$-C$_4$ haloalkyl;

$R^{12}$ at each occurrence is independently selected from H, C$_1$-C$_4$ haloalkyl and C$_1$-C$_4$ alkyl substituted with 0-1 R$^{19}$;

$R^{17}$ is H or C$_1$-C$_4$ alkyl substituted by 0-1 R$^{19}$;

$R^{19}$ at each occurrence is independently selected from H, —NR$^{23}$R$^{24}$, halo, —NO$_2$, —CN, —CF$_3$, C$_1$-C$_4$ haloalkyl, —NHOH, OR$^{25}$, C(=O)R$^{25}$, C(=O)OR$^{25}$, OC(=O)R$^{25}$, C(=O)NR$^{23}$R$^{24}$, NHC(=O)R$^{25}$, NHCO$_2$R$^{25}$, OC(=O)

NR²³R²⁴, NHC(=S)R²⁵, SR²⁵, S(=O)R²⁵, S(=O)₂R²⁵; S(=O)₂NR²³R²⁴, —NHS(=O)₂R²⁵, $C_1$-$C_4$ alkyl substituted by 0-1 $R^{30}$;
$C_2$-$C_4$ alkenyl substituted by 0-1 $R^{30}$;
$C_2$-$C_4$ alkynyl substituted by 0-1 $R^{30}$;
$C_6$-$C_{10}$ aryl substituted by 0-5 $R^{30}$;
$C_3$-$C_7$ carbocyclyl substituted by 0-5 $R^{30}$; and
5 to 14 membered heterocyclyl group substituted by 0-5 $R^{30}$, wherein said heterocyclyl group comprises one, two, or three heteroatoms selected from N, O, and S;
5 to 14 membered heteroaryl group substituted by 0-5 $R^{30}$, wherein said heteroaryl group comprises one, two, or three heteroatoms selected from N, O, and S;

$R^{22}$ is H, —NR²³R²⁴, —N₃, halo, —NO₂, —CN, —CF₃, $C_1$-$C_4$ alkyl, $C_2$-$C_4$ alkenyl, $C_2$-$C_4$ alkynyl, $C_1$-$C_4$ haloalkyl, $C_3$-$C_7$ carbocyclyl, phenyl, —NHOH, OR²⁵, C(=O)R²⁵, C(=O)OR²⁵, OC(=O)R²⁵, C(=O)NR²³R²⁴, NHC(=O)R²⁵, NHCO₂R²⁵, OC(=O)NR²³R²⁴, NHC(=S)R²⁵, SR²⁵, S(=O)R²⁵, S(=O)₂R²⁵; S(=O)₂NR²³R²⁴, or —NHS(=O)₂R²⁵;

$R^{23}$ and $R^{24}$ at each occurrence are each independently selected from H or $C_1$-$C_4$ alkyl;

$R^{25}$ at each occurrence is each independently selected from H or $C_1$-$C_4$ alkyl; and $R^{30}$ is H, F, Cl, Br, —CF₃, $C_1$-$C_4$ alkyl, and $C_1$-$C_4$ alkoxy.

In a preferred embodiment, $R^2$ is selected from H, F, Cl, Br, —OCH₃, —NO₂, —CN, and —CF₃.

In a preferred embodiment, $R^6$ is cyclobutyl, cyclopentyl, or cyclohexyl.

In a preferred embodiment, $R^6$ is cyclopentyl.

In a preferred embodiment, X is —NR⁹R¹⁰.

In a preferred embodiment, X is —NHR⁹.

In a preferred embodiment, $R^6$ is cyclopentyl and X is —NR⁹R¹⁰.

In a preferred embodiment, $R^2$ is selected from F, Cl, Br, —OCH₃, —CN, and —CF₃; and X is —NR⁹R¹⁰.

In another first embodiment, the present invention provides novel compounds of Formula (II):

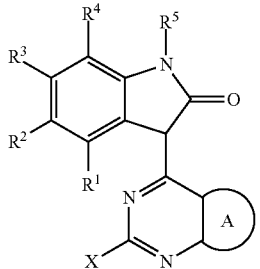

(II)

and stereoisomeric forms, mixtures of stereoisomeric forms, tautomeric forms or pharmaceutically acceptable salt forms thereof, wherein:

ring A is

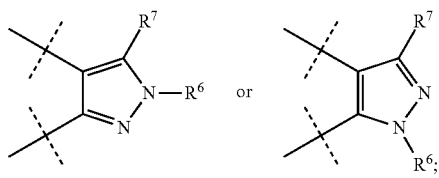

$R^1$, $R^2$, $R^3$, and $R^4$ at each occurrence are independently selected from H, F, Cl, Br, —OCH₃, —NO₂, —CN, and —CF₃;

$R^5$ is H;

$R^6$ is selected from H, methyl, ethyl, n-propyl, i-propyl, n-butyl, i-butyl, n-pentyl, i-pentyl, allyl, cyclopentyl, cyclohexyl, —CH₂CH₂OCH₃, —CH₂CH₂OCH₂CH₃, —CH₂CH₂CH₂N₃, and —CH₂CH₂CH₂NHCH₃;

$R^7$ is H or —NO₂;

X is selected from H, Cl, methyl, ethyl, propyl, butyl,
—OH; —OCH₂CH₂N(CH₃)₂; —OCH₂CH₂(pyrid-3-yl);
—NHCH₃; —NCH₂CH₃; —NHCH(CH₃)₂;
—NHCH₂CH₂CH₂CH₃; —NHCH₂CH(CH₃)₂;
—NHCH₂CH₂CF₃; —NHCH=CH₂;
—NHCH₂CH=CH₂;
—NHCH₂CH₂N(CH₃)₂; —N(CH₃)CH₂CH₂N(CH₃)₂;
—NHCH₂CH₂CH₂N(CH₃)₂;
—NHCH₂CH₂CH₂NH(CH₃);
—NHCH₂CH₂NH₂; —NHCH₂CH₂CH₂NH₂; —N(H)CH₂CH(NH₂)CH₃;
—N(CH₃)CH₂CH₂N(CH₂CH₃)₂; —NHNH₂;
—NHCH₂CH₂NHC(=O)CH₃;
—N(CH₂CH₂OCH₃)₂; —N(H)CH₂CH₂OCH₃; —N(H)CH₂CH₂CH₂OCH₃;
—N(H)CH₂CH₂OCH₂CH₃; —N(H)CH₂CH₂OCH₂CH₂CH₃;
—N(CH₂CH₂OH)₂; —N(H)CH₂CH(OH)CH₃; —N(H)CH₂CH(OH)CH₂CH₃;
—N(H)CH₂CH(OH)CH₂OH;
—NH(pyrid-3-yl); —NH(4-F-pyrid-3-yl); —NH(4-MeO-pyrid-3-yl); piperazin-1-yl;

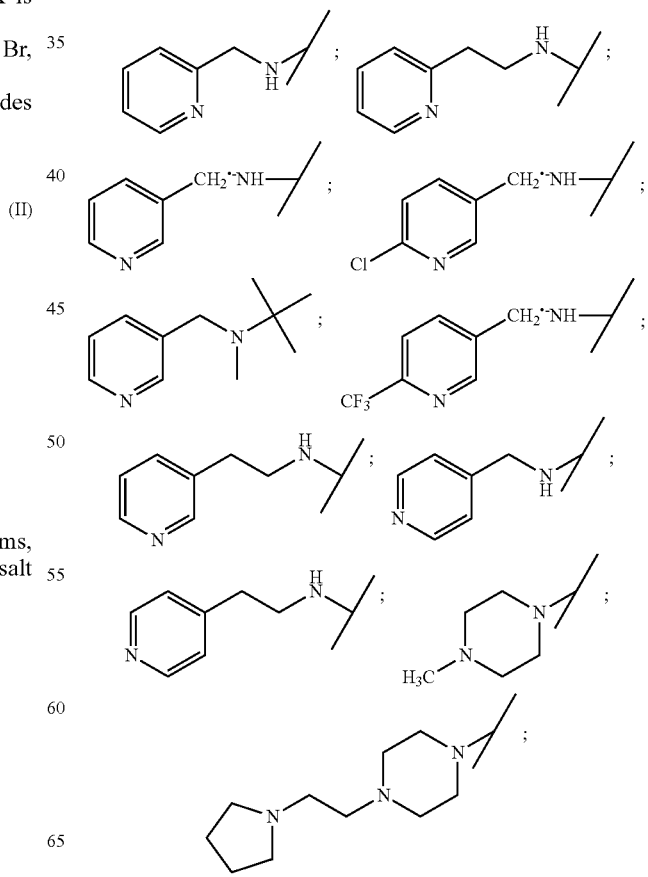

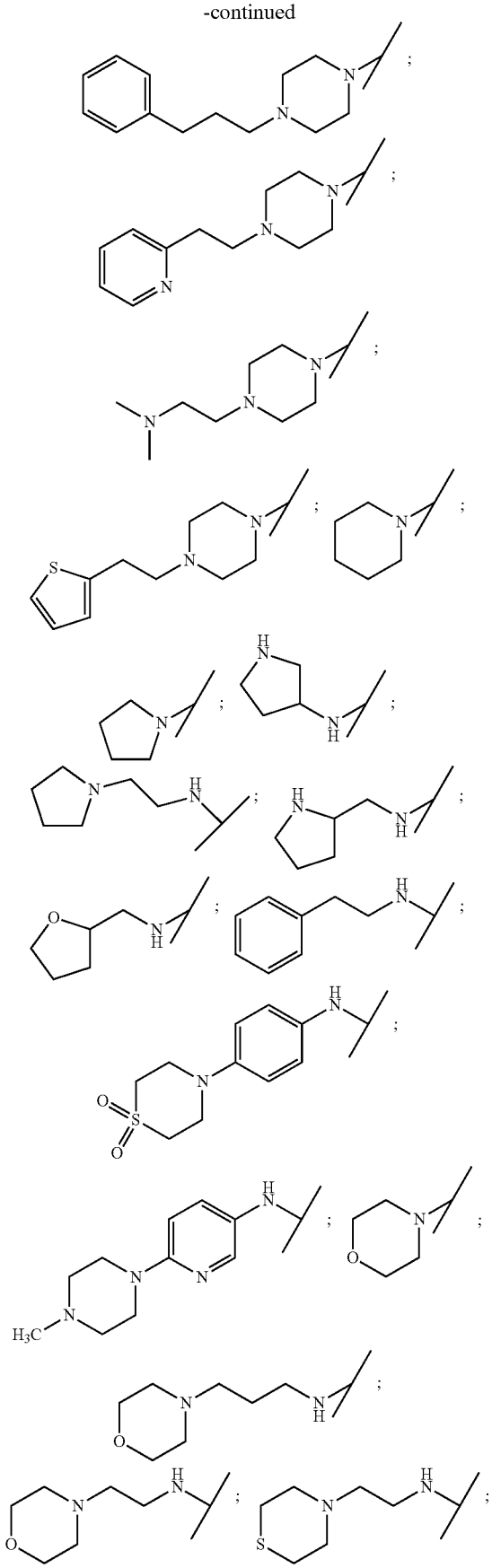

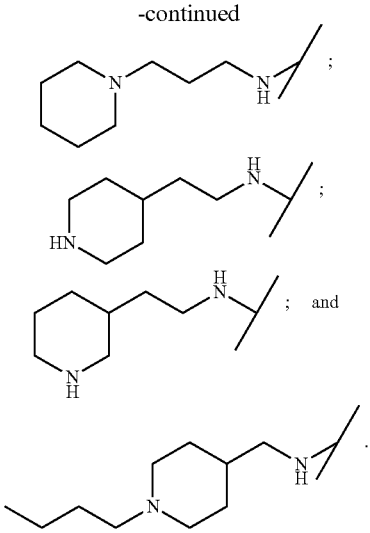

In another first embodiment, the present invention provides novel compounds of Formula (I) selected from the following Examples:

Example 30; Example 31; Example 32; Example 33; Example 34; Example 35; Example 36; Example 37; Example 38; Example 39; Example 40; Example 41; Example 42; Example 43; Example 45; Example 46; Example 47; Example 48; Example 49; Example 50; Example 51; Example 52; Example 53; Example 54; Example 55; Example 56; Example 57; Example 58; Example 59; Example 60; Example 61; Example 62; Example 63; Example 64; Example 65; Example 66; Example 67; Example 68; Example 69; Example 70; Example 71; Example 72; Example 73; Example 74; Example 75; Example 76; Example 82; Example 83; Example 84; Example 85; Example 86; Example 89; Example 90; Example 93; Example 94; Example 95; Example 96; Example 97; Example 98; Example 99; Example 100; Example 108; Example 109; Example 111; Example 113; Example 114; Example 115; Example 116; Example 117; Example 118; Example 119; Example 120; Example 121; Example 122; Example 123; Example 124; Example 125; Example 126; Example 127; Example 128; Example 129; Example 130; Example 131; Example 132; Example 133; Example 134; Example 135; Example 136; Example 137; Example 138; Example 139; Example 140; Example 141; Example 142; Example 143; Example 144; Example 148; Example 149; Example 150; Example 151; Example 152; Example 153; Example 154; Example 155; Example 156; Example 157; Example 158; Example 159; Example 160; Example 161; Example 162; Example 163; Example 164; Example 165; Example 166; Example 167; Example 168; Example 169; Example 170; Example 171; Example 172; Example 173; Example 174; Example 175; Example 176; Example 177; Example 178; Example 179; Example 180; Example 181; Example 182; Example 183; Example 184; Example 185; Example 186; Example 187; Example 188; Example 189; Example 190; Example 191; Example 192; Example 193; Example 194; Example 195; Example 196; Example 197; Example 198; Example 199; Example 200; Example 201; Example 202; Example 203; Example 204; Example 205; Example 211; Example 212; Example 213; Example 214; Example 215; Example 216; Example 217; Example 218; Example 219; Example 225; Example 226; Example 227; Example 228; Example 229; Example 230; Example 231; Example 232; Example 233; Example 234; Example 235; Example 236; Example 237; Example 238; Example 239; Example 240; Example 241; Example 242; Example 243; Example 244; Example 245; Example 246; Example 247; Example 248; Example 249; Example 250; Example 251; Example 252; Example 253; Example 254; Example 261; Example 262; Example 263; Example 264; Example 265; Example 266; Example 267; Example 268; Example 269; Example 270; Example 271; Example 272; Example 273; Example 275; Example 276; Example 277; Example 278; Example 279; Example 280; Example 287; Example 288; Example 289; Example 290; Example 291; Example 292; Example 293; Example 294; Example 295; Example 300; Example 301; Example 302; Example 303; Example 304; Example 304; Example 305; Example 306; Example 307; Example 309; Example 310; Example 314; Example 315; Example 316; Example 317; Example 318; Example 319; Example 320; Example 321; Example 322; Example 323; Example 324; Example 325; Example 326; Example 327; Example 328; Example 329; Example 330; Example 331; Example 332; Example 333; Example 334; Example 335; Example 336; Example 337; Example 338; Example 339; Example 340; Example 341; Example 342; Example 343; Example 344; Example 345; Example 346; Example 347; Example 348; Example 349; Example 350; Example 351; Example 352; Example 353; Example 354; Example 358; Example 359; Example 360; Example 361; Example 362; Example 363; Example 364; Example 365; Example 366; Example 367; Example 368; Example 369; Example 370; Example 371; Example 372; Example 373; Example 374; Example 375; Example 376; Example 377; Example 378; Example 379; Example 380; Example 381; and Example 382; and pharmaceutically acceptable salt forms thereof.

In a second embodiment, the present invention provides a method for treatment of diseases comprising administering to a subject in need thereof a therapeutically effective amount of a compound of Formula (I), or a pharmaceutically acceptable salt thereof, wherein the disease is selected from a chronic neurodegenerative disease, a neurotraumatic disease, depression and diabetes.

In a preferred embodiment, the present invention provides a method of treating or preventing chronic neurodegenerative diseases selected from Alzheimer's Disease, Parkinson's Disease, progressive supranuclear palsy, subacute panencephalitic parkinsonism, postencephalitic parkinsonism, dementia puglistica, guan-parkinsonial dementia complex, Pick's disease, corticobasal degeneration, frontotemporal dementia with parkinsonism, Huntington's disease, AIDS associated dementia, amyotrophic lateral sclerosis, and multiple sclerosis.

In a more preferred second embodiment the present invention provides a method wherein the compound is administered for the treatment of Alzheimer's Disease (AD).

In a third embodiment, the present invention provides a pharmaceutical composition comprising a compound of Formula (I), or a pharmaceutically acceptable salt or ester form thereof, and one or more pharmaceutically acceptable excipients.

In a preferred third embodiment, the present invention provides a pharmaceutical composition comprising a therapeutically effective amount of compound of Formula (I), or a pharmaceutically acceptable salt or ester form thereof, and one or more pharmaceutically acceptable excipients.

In a fourth embodiment, the present invention provides for the use of compounds of formula (I) or pharmaceutically acceptable salts thereof for the manufacture of a medicament for the treatment of a disease or disorder, as disclosed herein.

These and other objects, features and advantages of the substituted pyrazolopyrimidines will be disclosed in the following detailed description of the patent disclosure.

Definitions

The following terms and expressions contained herein are defined as follows:

As used herein, the term "about" refers to a range of values from ±10% of a specified value. For example, the phrase "about 50 mg" includes ±10% of 50, or from 45 to 55 mg.

As used herein, a range of values in the form "x-y" or "x to y", or "x through y", include integers x, y, and the integers there between. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, or 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched, alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons, such as methyl, ethyl, propyl, isopropyl, butyl, isobutyl, sec-butyl, and tert-butyl. A designation such as "$C_1$-$C_4$ alkyl" refers to an alkyl radical containing from 1 to 4 carbon atoms.

As used herein, the term "alkenyl" refers to a straight-chain, or branched, hydrocarbon group of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include, but are not limited to, ethenyl, propenyl, isopropenyl, butenyl, pentenyl, 2,4-pentadienyl, etc. Preferred alkenyl groups include ethenyl and propenyl.

As used herein, the term "alkynyl" refers to a straight chain, or branched hydrocarbon chains of 2 to 6 carbon atoms having at least one carbon-carbon triple bond. A designation "$C_2$-$C_6$ alkynyl" refers to an alkynyl radical containing from 2 to 6 carbon atoms. Examples include, but are not limited to, ethynyl, propynyl, isopropynyl, 3,5-hexadiynyl, etc.

As used herein, the term "alkylene" refers to a substituted or unsubstituted, branched or straight chained hydrocarbon of 1 to 6 carbon atoms, which is formed by the removal of two hydrogen atoms. A designation such as "$C_1$-$C_4$ alkylene" refers to an alkylene radical containing from 1 to 4 carbon atoms. Examples include, but are not limited to, methylene (—$CH_2$—), ethylene (—$CH_2CH_2$—), ethylidene (—CH($CH_3$)—), propylene (—$CH_2CH_2CH_2$—), iso-propylene (—CH(CH$_3$)CH$_2$—), propylidene (—CH(CH$_2$CH$_3$)—), butylene (—CH$_2$CH$_2$CH$_2$CH$_2$—), etc.

As used herein, the term "cycloalkylene" refers to a saturated or partially saturated mono- or bicyclic alkyl ring system containing 3 to 10 carbon atoms, which is formed by the removal of two hydrogen atoms. A designation such as "C$_3$-C$_6$ cycloalkylene" refers to a cycloalkyl radical containing from 3 to 6 ring carbon atoms. Preferred cycloalkylene groups include those containing 3, 4, 5, or 6 ring carbon atoms. Examples of cycloalkylene groups include such groups as cyclopropylene (—C$_3$H$_4$—), cyclobutylene (—C$_4$H$_6$—), cyclopentylene (—C$_5$H$_8$—), cyclopentenylene (—C$_5$H$_6$—), cyclohexylene (—C$_6$H$_{10}$—), and cyclohexenylene (—C$_6$H$_8$—).

As used herein, the term "phenylene" refers to a phenyl group with an additional hydrogen atom removed, i.e. a moiety with the structure of (—C$_6$H$_4$—).

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "C$_3$-C$_7$ cycloalkyl" refers to a cycloalkyl radical containing from 3 to 7 ring carbon atoms. Preferred cycloalkyl groups include those containing 3, 4, 5, or 6 ring carbon atoms. Examples of cycloalkyl groups include such groups as cyclopropyl, cyclobutyl, cyclopentyl, cyclohexyl, cycloheptyl, cyclooctyl, pinenyl, and adamantanyl.

As used herein, the term "cycloalkenyl" refers to partially unsaturated mono- or bicyclic alkenyl ring system containing 5 to 10 carbon atoms. A designation such as "C$_5$-C$_{10}$ cycloalkenyl" refers to a cycloalkenyl radical containing from 5 to 10 ring carbon atoms and one or more double bonds. Preferred cycloalkenyl groups include those containing 5 or 7 ring carbon atoms. Examples of cycloalkenyl groups include such groups as cyclopentenyl, cyclohexenyl, and cycloheptenyl.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the term "arylene" refers to an aryl group with an additional hydrogen atom removed, i.e. an aryl group bonded through two carbon atoms, for example phenylene.

As used herein, the term "heteroarylene" refers to a heteroaryl group with an additional hydrogen atom removed, i.e. a heteroaryl group bonded through two carbon atoms, for example furan-2,5-diyl; or a heteroaryl group bonded through a carbon atom and a nitrogen atom, for example pyrrol-1,2-diyl.

As used herein, the term "heterocycloalkylene" refers to a heterocycloalkyl group with an additional hydrogen atom removed, i.e. a heterocycloalkyl group bonded through two carbon atoms or a heterocycloalkyl group bonded through a carbon atom and a nitrogen atom.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups. Examples of heterocyclic groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl, as well as, pyrrolidinyl, pyrrolinyl, imidazolidinyl, imidazolinyl, pyrazolidinyl, pyrazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heterocycloalkyl" refers to a 3 to 7 membered cycloalkyl group in which one or more ring carbon atoms are replaced by at least one hetero atom such as —O—, —N—, or —S—. Examples of heterocycloalkyl groups include pyrrolidinyl, pyrrolinyl, imidazolidinyl, imidazolinyl, pyrazolidinyl, pyrazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heteroaryl" refers to an aromatic group containing 5 to 14 ring carbon atoms in which one or more ring carbon atoms are replaced by at least one hetero atom such as —O—, —N—, —S—, or —Se—. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, thiadiazolyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, "halo" or "halogen" includes fluoro, chloro, bromo, and iodo.

As used herein, the term "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl." Examples perhaloalkyl groups include $CF_3$ and $C_2F_5$.

As used herein, the term "subject" or "mammal" refers to a warm blooded animal such as a mammal, preferably a human, or a human child, which is afflicted with, or has the potential to be afflicted with, one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker New York, 1992, incorporated by reference herein in its entirety. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As used herein, "prodrug of an amino group" is intended to include a chemical moiety bonded to an amino group on a compound of the present invention, wherein when the compound of the present invention is administered to a mammalian subject, the chemical moiety bonded to the amino group cleaves to form a free amino, respectively. Examples include, but are not limited to, acetate, formate and benzoate derivatives of amine functional groups, as well as alkyl-C(=O)—, alkenyl-C(=O)—, alkynyl-C(=O)—, carbocyclyl-C(=O)—, carbocyclylalkyl-C(=O)—, alkyl-S(=O)$_2$—, carbocyclyl-S(=O)$_2$—, carbocyclylalkyl-S(=O)$_2$—, alkyl-NHC(=O)—, carbocyclyl-NHC(=O)—, carbocyclylalkyl-NHC(=O)—, alkyl-OC(=O)—, carbocyclyl-OC(=O)—, carbocyclylalkyl-OC(=O)—, alkyl-NH—C(=O)—NHS(=O)$_2$—, carbocyclyl-NH—C(=O)—NHS(=O)$_2$—, alkyl-S(=O)$_2$—NH—C(=O)—, and carbocyclyl-S(=O)$_2$—NH—C(=O)— groups.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of Formula (I) may contain protecting groups. For example, the amino acid side chain substituents of the compounds of Formula (I) can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P.G.M., "Protective Groups in Organic Synthesis" 2d. Ed., Wiley & Sons, 1991.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

As will be readily understood, functional groups present on the compounds of Formula (I) may contain protecting groups. For example, the amino acid side chain substituents of the compounds of Formula (I) can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P.G.M., "Protective Groups in Organic Synthesis" 2d. Ed., Wiley & Sons, 1991.

General routes to prepare the Examples of the present invention are shown in the Schemes and examples that follow. The reagents and starting materials are commercially available and/or, using well-known techniques, can be readily synthesized by one of ordinary skill in the art. All substituents in the synthetic Schemes, unless otherwise indicated, are as previously defined.

Compounds of invention can be synthesized following various synthetic schemes disclosed herein.

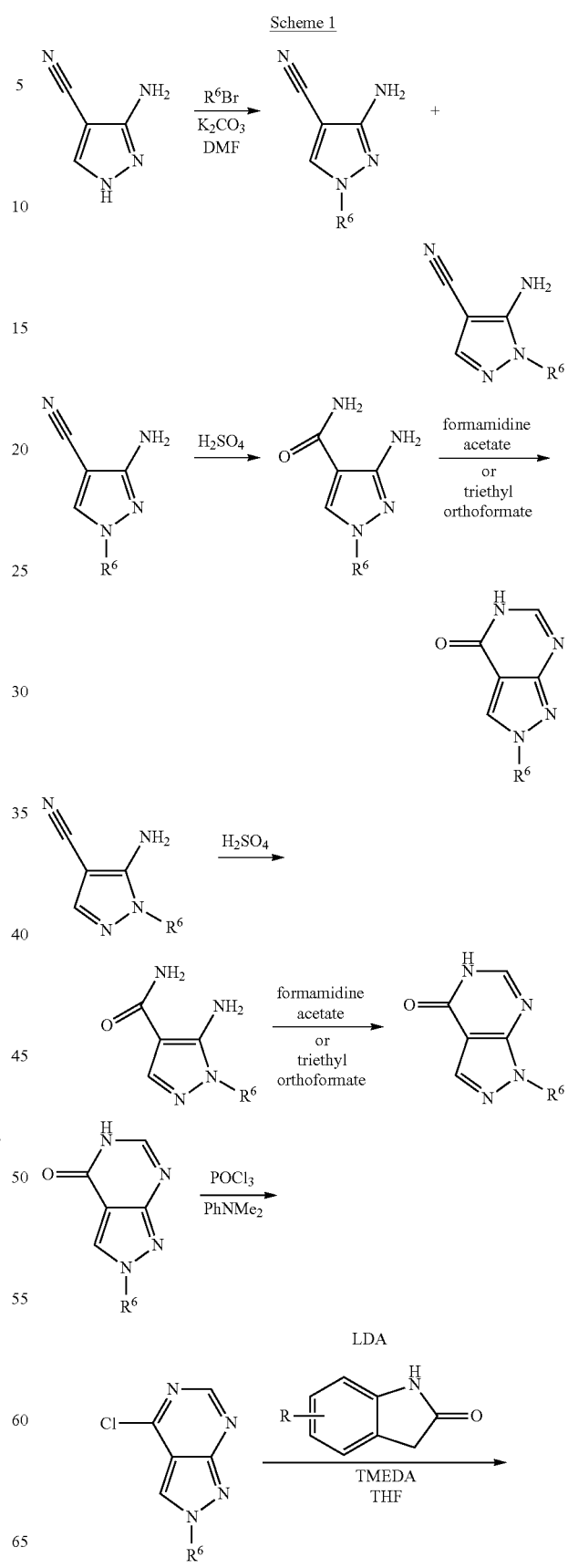

Scheme 1

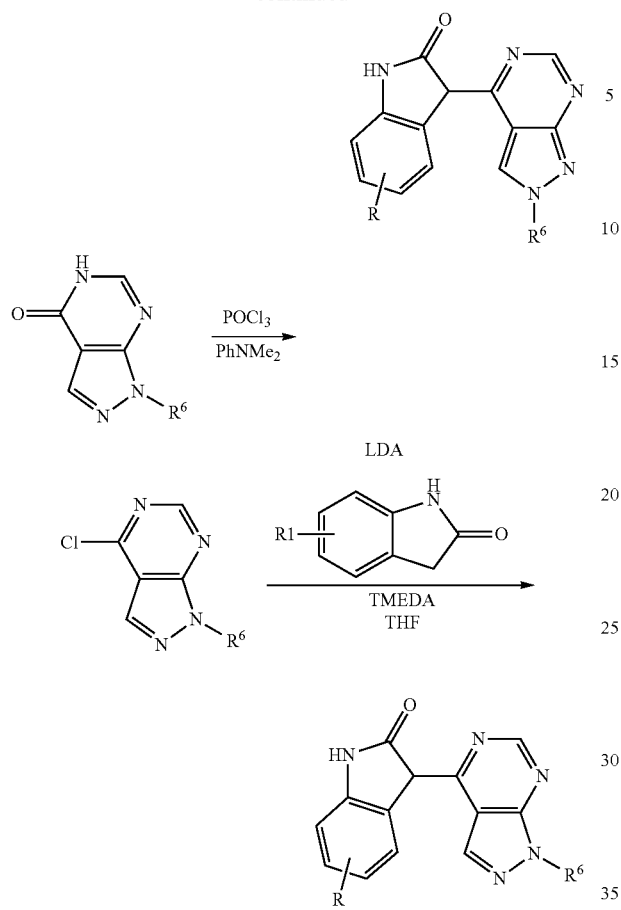
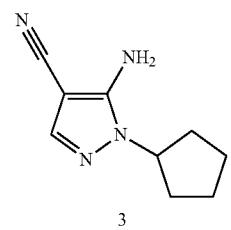

PATENT EXPERIMENTALS

The following Examples are exemplary only, and are not intended to limit the invention.

Compound 2 and 3

3-Amino-1-cyclopentyl-1H-pyrazole-4-carbonitrile

5-Amino-1-cyclopentyl-1H-pyrazole-4-carbonitrile

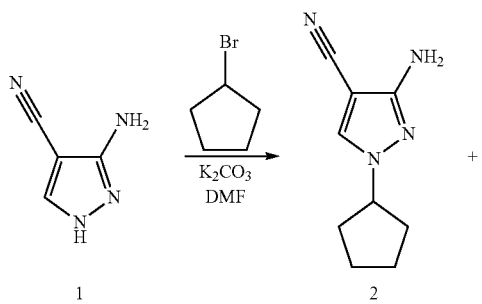

3-Amino-4-pyrazolecarbonitrile 1 (Acros, 4.32 g, 40.0 mmol), cyclopentylbromide (Acros, 7.15 g, 48 mmol) and anhydrous potassium carbonate (Fisher, 6.60 g, 48 mmol) were suspended in 30 mL anhydrous DMF and heated at 80° C. under argon overnight. An additional 3.5 g (23.5 mmol) of cyclopentylbromide and 3.3 g (24 mmol) of potassium carbonate were added and the reaction was subjected to an additional six hours at 80° C. The reaction was permitted to cool and the DMF was removed on a rotary evaporator. Water was added (100 mL) and the organics were extracted with dichloromethane (3×100 mL). The combined dichloromethane fractions were washed with water (50 mL) and brine (50 mL) and were dried (magnesium sulfate). Concentration of the organics afforded a solid which was subjected to flash chromatography on silica gel (2:1 hexane:ethyl acetate). Two white solids were obtained: 3 (1.67 g, 24%) elutes first and 2 (4.56 g, 65%) elutes second. Compound 2: mp 129-131° C.; MS (ES$^+$ calculated: 176.22; found: 177.05 M+H). HPLC (100% purity, retention time 9.235 minutes—Method A); $^1$H NMR (400 MHz, DMSO-d$_6$) δ 8.11 (s, 1H), 5.51 (br s, 2H), 4.45 (m, 1H), 1.97 (m, 2H), 1.84 (m, 2H), 1.72 (m, 2H), 1.59 (m, 2H). Compound 3: mp 113° C.; MS (ES$^+$ calculated: 176.22; found: 177.04 M+H). HPLC (88% purity, retention time 9.752 minutes—Method A); $^1$H NMR (400 MHz, DMSO-d$_6$) δ 7.52 (s, 1H), 5.75 (br s, 2H), 4.55 (m, 1H), 1.92 (m, 2H), 1.78 (m, 4H), 1.57 (m, 2H).

Pure compound 2 may be obtained without chromatography in 44% yield by trituration of the crude solid with a minimum amount of dichloromethane. Compound 2 is relatively insoluble in dichloromethane whereas 3 dissolves easily.

Compound 3

5-Amino-1-cyclopentyl-1H-pyrazole-4-carbonitrile

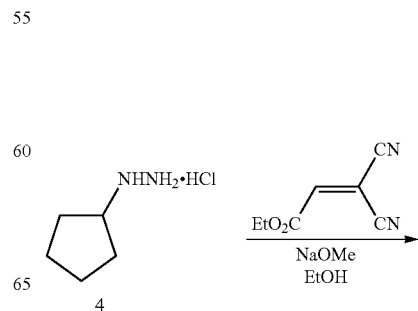

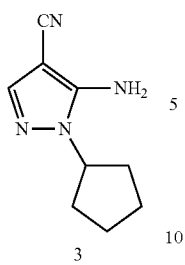

Alternate Synthesis of 3: Cyclopentylhydrazine hydrochloride[1] (1.08 g, 10 mmol) was dissolved in 100 mL anhydrous ethanol. Sodium methoxide (540 mg, 10 mmol) was added in one portion and the reaction mixture was stirred for ten minutes. Ethoxymethylenemalononitrile (Acros, 1.22 g, 10 mmol) was then added in small portions over several minutes. The reaction mixture was heated at 70° C. under argon overnight. The reaction mixture was concentrated and subjected to flash chromatography on silica gel (stepwise elution: dichloromethane followed by 1:1 hexane:ethyl acetate) to afford 600 mg (34%) of compound 3—identical in all respects with the material obtained above.

Compound 5 and 6

1-Allyl-3-amino-1H-pyrazole-4-carbonitrile

1-Allyl-5-amino-1H-pyrazole-4-carbonitrile

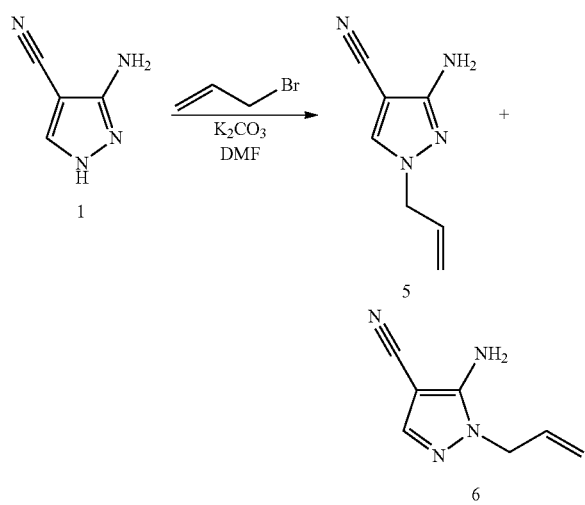

3-Amino-4-pyrazolecarbonitrile 1 (Acros, 1.08 g, 10.0 mmol), allylbromide (Acros, 1.45 g, 12 mmol) and anhydrous potassium carbonate (Fisher, 1.65 g, 12 mmol) were suspended in 10 mL anhydrous DMF and heated at 80° C. under argon overnight. The solution was concentrated. Water was added (100 mL) and the organics were extracted with dichloromethane (3×100 mL). The combined dichloromethane fractions were washed with water (50 mL) and brine (50 mL) and were dried (magnesium sulfate). Concentration of the organics afforded a solid which was subjected to flash chromatography on silica gel (gradient elution 2:1 to 3:2 hexane:ethyl acetate). 589 mg (40%) of a white solid was obtained which was seen by NMR to contain an inseparable mixture of 5 and 6 in a 2.1:1 ratio. This mixture was used without further purification.

Compound 7 and 8

3-Amino-1-cyclohexyl-1H-pyrazole-4-carbonitrile

5-Amino-1-cyclohexyl-1H-pyrazole-4-carbonitrile

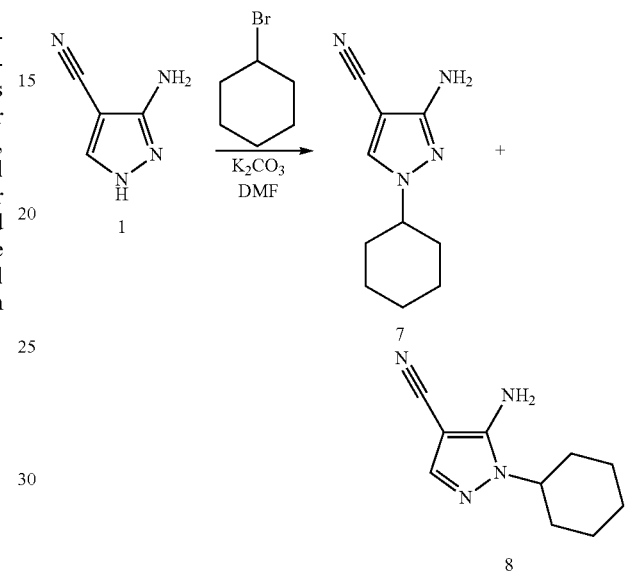

3-Amino-4-pyrazolecarbonitrile 1 (Acros, 6.48 g, 60.0 mmol), cyclohexylbromide (Acros, 11.74 g, 72 mmol), and anhydrous potassium carbonate (Fisher, 9.9 g, 72 mmol were combined in 40 mL of DMF and heated at 80° C. under argon overnight. The reaction was permitted to cool to room temperature. Water was added (100 mL) and the organics were extracted with dichloromethane (3×100 mL). The combined dichloromethane fractions were washed with water (50 mL) and brine (50 mL) and were dried (magnesium sulfate). Concentration of the organics afforded a solid which was subjected to flash chromatography on silica gel (gradient elution 3:1 to 2:1 hexane:ethyl acetate). Separation of the isomers was not fully achieved but a few fractions containing pure product were combined to afford 7—a white solid (1.18 g, 10%). Compound 7: mp 169-171° C.; HPLC (100% purity, retention time 8.416 minutes—Method B); $^1$H NMR (400 MHz, DMSO-d$_6$) δ 8.08 (s, 1H), 5.48 (br s, 2H), 3.87 (m, 1H), 1.92 (m, 2H), 1.75 (m, 2H), 1.61 (m, 2H), 1.31 (m, 2H), 1.16 (m, 2H).

Compound 8

5-Amino-1-cyclohexyl-1H-pyrazole-4-carbonitrile

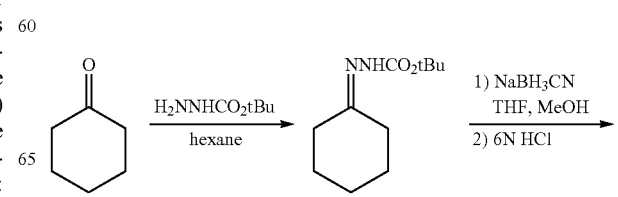

29

-continued

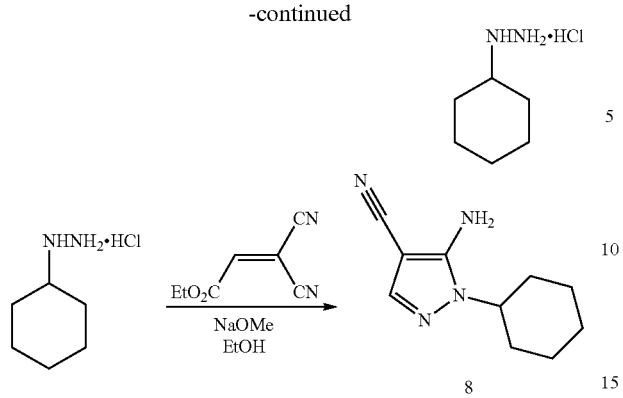

Alternate Synthesis of Compound 8: Cyclohexanone (Acros, 19.6 g, 200 mmol) and tert-butylcarbazate (Acros, 26.4 g, 200 mmol) were combined in 350 mL dry hexane and stirred under argon for ½ hour. The mixture was then subjected to reflux temperature for 1.5 hours and permitted to cool to room temperature. A white solid formed on cooling which was removed by filtration and dried in vacuo—40.31 g (95%): mp 147-149° C.; MS (ES+ calculated: 212.29; found: 235.05 M+Na). $^1$H NMR (400 MHz, DMSO-d$_6$) δ 9.47 (br s, 1H), 2.27 (m, 2H), 2.16 (m, 2H), 1.52 (m, 2H), 1.59 (m, 4H), 1.42 (s, 9H).

t-Butylcarboxycyclohexanone hydrazone generated above (40.02 g, 189 mmol) was dissolved in a mixture of 175 mL tetrahydrofuran and 225 mL anhydrous methanol. Sodium cyanoborohydride (Acros, 14.3 g, 227 mmol) was added in portions over ten minutes and the mixture was stirred under argon overnight at room temperature. 135 mL of 6N hydrochloric acid were then added dropwise and the mixture was refluxed for one hour. The reaction was permitted to cool to room temperature and a white solid was removed by filtration. The mother liquor was concentrated and residual water was removed by azeotroping with ethanol on a rotary evaporator (3×100 mL). The mixture was concentrated to dryness and was taken up into hot isopropanol (~300 mL). The solid that was present was removed by filtration and the mother liquor was concentrated to ½ volume at which point an equal volume of ethyl ether was added. This caused cyclohexylhydrazine hydrochloride to precipitate as a white solid. Yield (20.0 g, 93%).

To cyclohexylhydrazine hydrochloride (7.52 g, 50 mmol) generated above in 500 mL absolute ethanol was added sodium methoxide (Aldrich, 2.7 g, 50 mmol). The mixture was stirred briefly and ethoxymethylmalononitrile (Acros, 6.11 g, 50 mmol) was added in small portions over twenty minutes. The reaction mixture was then heated at 70° C. under argon overnight. On cooling, the reaction was concentrated and subjected to flash chromatography on silica gel (1:1 hexane:ethyl acetate) affording 6.3 g (66%) of a light brown solid. Compound 8: mp 99-103° C.; MS (ES+ calculated: 190.25; found: 191.15 M+H). HPLC (97% purity, retention time 11.135 minutes—Method A); $^1$H NMR (400 MHz, DMSO-d$_6$) δ 7.50 (s, 1H), 6.49 (br s, 2H), 4.02 (m, 1H), 1.80-1.10 (m, 10H).

30

Compound 10 and 11

3-Amino-1-cyclohexyl-1H-pyrazole-4-carboxylic acid ethyl ester

5-Amino-1-cyclohexyl-1H-pyrazole-4-carboxylic acid ethyl ester

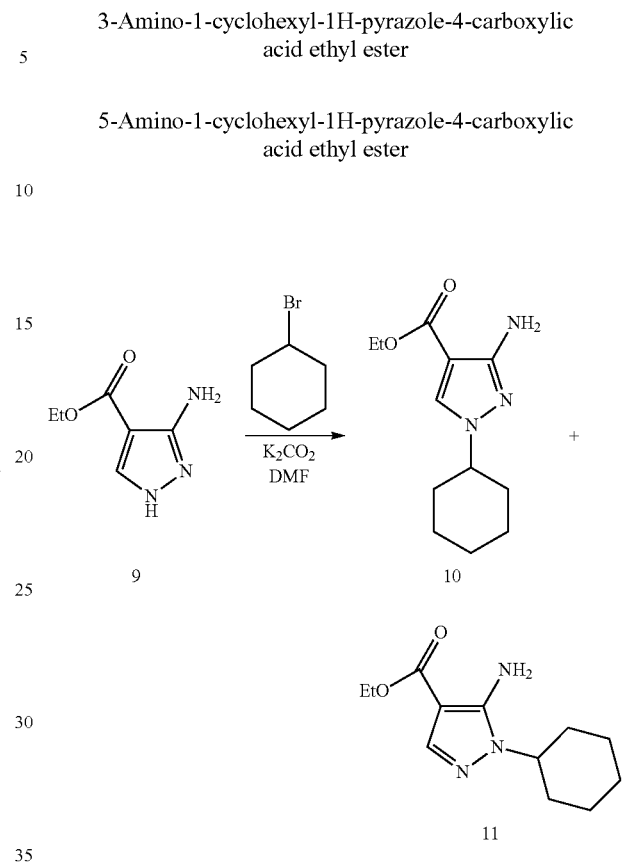

Ethyl-3-Aminopyrazole-4-carboxylate 9 (Acros, 15.5 g, 100.0 mmol), cyclohexylbromide (Acros, 21.9 g, 130 mmol), anhydrous potassium carbonate (Fisher, 27.6 g, 200 mmol), Adogen 464 (Acros, 2.5 g) and aqueous sodium hydroxide (0.1 mL of a 12.5M solution) were combined in 250 mL of toluene and refluxed under argon overnight. Additional cyclohexylbromide (21.9 g, 130 mmol) and potassium carbonate (27.6 g, 200 mmol) were then added and the reaction mixture was resubjected to the reaction conditions for an additional 24 hours. The reaction was permitted to cool to room temperature and the organics were washed with 100 mL water. The organic layer was separated and dried (magnesium sulfate). Concentration of the organics afforded a solid which was subjected to flash chromatography on silica gel (gradient elution 9:1 to 6:1 to 3:1 hexane:ethyl acetate) to afford two principle products. Compound 11 (923 mg, 4%) elutes first and Compound 10 (1.755 g, 7%) elutes second. A considerable amount of material was present in mixed fractions. Compound 10: MS (ES+ calculated: 237.30; found: 238.10 M+H). HPLC (98% purity, retention time 13.623 minutes—Method A); $^1$H NMR (400 MHz, DMSO-d$_6$) δ 7.44 (s, 1H), 6.19 (br s, 2H), 4.43 (q, J=7 Hz, 2H), 4.05 (m, 1H), 1.83-1.22 (m, 10H), 1.23 (t, J=7 Hz, 3H). Compound 11: MS (ES+ calculated: 237.30; found: 238.14 M+H). HPLC (100% purity, retention time 13.408 minutes—Method A); $^1$H NMR (400 MHz, DMSO-d$_6$) δ 7.87 (s, 1H), 5.29 (br s, 2H), 4.15 (q, J=7 Hz, 2H), 3.89 (m, 1H), 1.97-1.25 (m, 10H), 1.24 (t, J=7 Hz, 3H).

Compound 12

3-Amino-1-cyclopentyl-1H-pyrazole-4-carboxylic acid amide

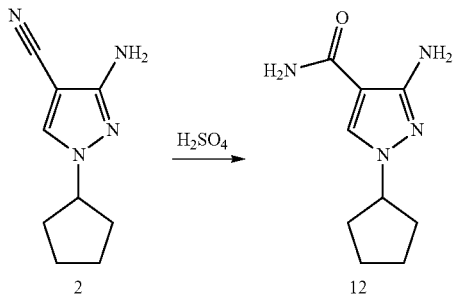

To concentrated sulfuric acid (Fisher, 8 mL) at 0° C. was added 2 (4.24 g, 24.0 mmol) in small portions. The reaction was permitted to warm to room temperature and was stirred for two hours. At the end of this period all solid had dissolved. This viscous mixture was then added slowly (violent) to 100 mL concentrated ammonium hydroxide solution (Fisher). The mixture was stirred for ten minutes and the white solid that formed was collected by filtration, was washed with water, and was dried in vacuo. Yield: 3.838 g (82%). Compound 12: mp 179-181° C.; MS (ES+ calculated: 194.24; found: 195.12 M+H). HPLC (100% purity, retention time 5.225 minutes—Method B); $^1$H NMR (400 MHz, DMSO-d$_6$) δ 7.94 (s, 1H), 7.14 (br s, 1H), 6.67 (br s, 1H), 5.32 (br s, 2H), 4.39 (m, 1H), 1.97 (m, 2H), 1.83 (m, 2H), 1.72 (m, 2H), 1.61 (m, 2H).

Compound 13

1-Allyl-3-amino-1H-pyrazole-4-carboxylic acid amide

1-Allyl-5-amino-1H-pyrazole-4-carboxylic acid amide

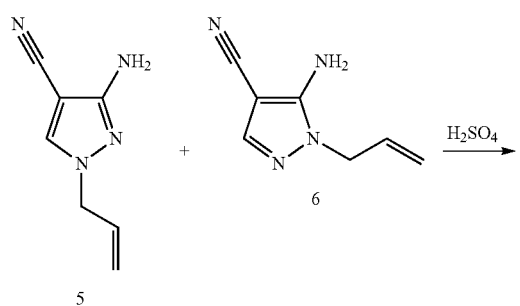

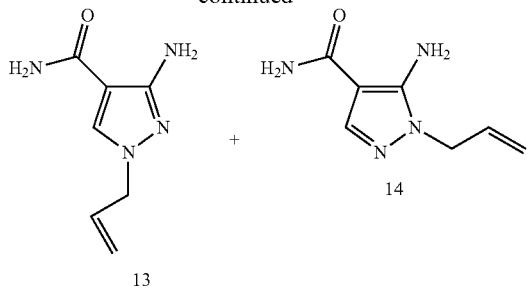

The mixture of solids derived from the preparation of 5 and 6 (589 mg, 4.0 mmol) was treated with concentrated sulfuric acid (1 mL) as for the preparation of 12 above. Following neutralization with concentrated ammonium hydroxide (10 mL) and filtration a mass of white solid was obtained which shrank considerably when washed with water. The resulting product was dried in vacuo affording 282 mg (42%) of 13 as a white solid. Compound 14 was determined to be present in the water wash but was not isolated from this reaction. Compound 13: mp 100-101° C.; MS (ES+ calculated: 166.18; found: 167.12 M+H). HPLC (94% purity, retention time 5.141 minutes—Method A); $^1$H NMR (400 MHz, DMSO-d$_6$) δ 7.87 (s, 1H), 7.19 (br s, 1H), 6.69 (br s, 1H), 5.95 (m, 1H), 5.34 (br s, 2H), 5.22 (d, J=1 Hz, 1H), 5.22 (m, 1H), 5.17 (m, 1H), 4.48 (d, J=6 Hz, 2H).

Compound 15

5-Amino-1-cyclohexyl-1H-pyrazole-4-carboxylic acid amide

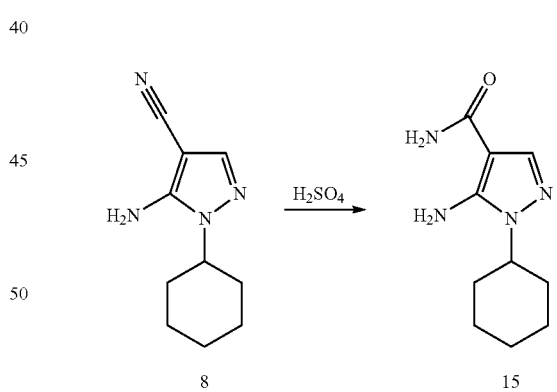

Compound 8 (6.3 g, 33.2 mmol) was treated with concentrated sulfuric acid (12 mL) as for the preparation of 12 above. The product was isolated via neutralization with concentrated ammonium hydroxide (225 mL), washing with water, and drying in vacuo as described for 12. 4.04 g (58%) of a white solid, Compound 15 were obtained. Compound 15: mp 274-278° C.; MS (ES+ calculated: 208.27; found: 209.14 M+H). HPLC (97% purity, retention time 6.498 minutes—Method A); $^1$H NMR (400 MHz, DMSO-d$_6$) δ 7.61 (s, 1H), 7.08 (br s, 1H), 6.58 (br s, 1H), 6.14 (br s, 2H), 3.97 (m, 1H), 1.86-1.58 (m, 7H), 1.44-1.28 (m, 2H), 1.28-1.06 (m, 1H).

Compound 16

5-Amino-1-cyclopentyl-1H-pyrazole-4-carboxylic acid amide

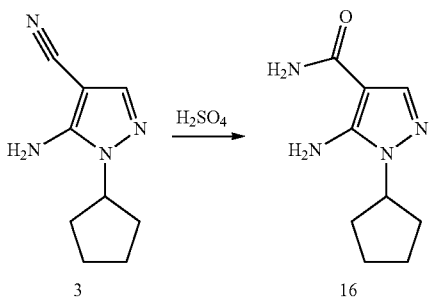

Compound 3 (3.34 g, 19.0 mmol) was treated with concentrated sulfuric acid (6 mL) as for the preparation of 12 above. The product was isolated via neutralization with concentrated ammonium hydroxide (80 mL), washing with water, and drying in vacuo as described for 12. 3.64 g (99%) of a fluffy white powder, Compound 16, was obtained. Compound 16: MS (ES$^+$ calculated: 194.24; found: 195.10 M+H). HPLC (97%) purity, retention time 1.739 minutes—Method C); $^1$H NMR (400 MHz, DMSO-d$_6$) δ 7.62 (s, 1H), 7.10 (br s, 1H), 6.60 (br s, 1H), 6.14 (br s, 2H), 4.52 (m, 1H), 1.97-1.67 (m, 6H), 1.63-1.50 (m, 2H).

Compound 17

2-Cyclopentyl-2,5-dihydro-pyrazolo[3,4-d]pyrimidin-4-one

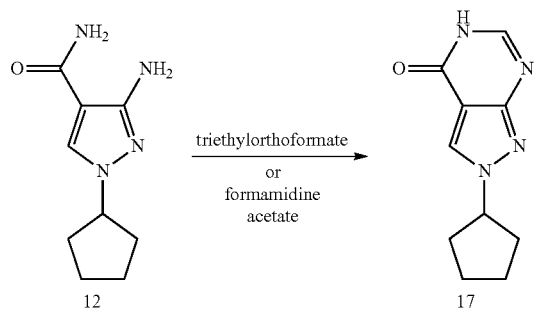 [SMILES: NC(=O)c1cn(C2CCCC2)nc1N ; O=c1[nH]cnc2nn(C3CCCC3)cc12]

Compound 12 (3.87 g, 20 mmol) was suspended in 60 mL triethylorthoformate (Acros) and refluxed under argon overnight (~150° C.). The reaction was concentrated and the solid obtained was triturated in ether, collected by filtration, and dried in vacuo to afford 3.782 g (93%) of a white solid. Compound 17: mp 271-273° C.; MS (ES$^+$ calculated: 204.23; found: 205.06 M+H). HPLC (100%) purity, retention time 6.104 minutes—Method B); $^1$H NMR (400 MHz, DMSO-d$_6$) δ 11.65 (br s, 1H), 8.55 (s, 1H), 7.91 (s, 1H), 4.86 (m, 1H), 2.12 (m, 2H), 2.00 (m, 2H), 1.83 (m, 2H), 1.66 (m, 2H). Compound 17 may also be prepared from 12 by refluxing with 2 equivalents of formamidine acetate in methoxyethanol. Concentration of the solution at the end of the reaction and neutralizing with ammonium hydroxide solution generates 17 identical in all respects with that derived from the triethylorthoformate procedure.

Compound 18

2-Cyclohexyl-2,5-dihydro-pyrazolo[3,4-d]pyrimidin-4-one

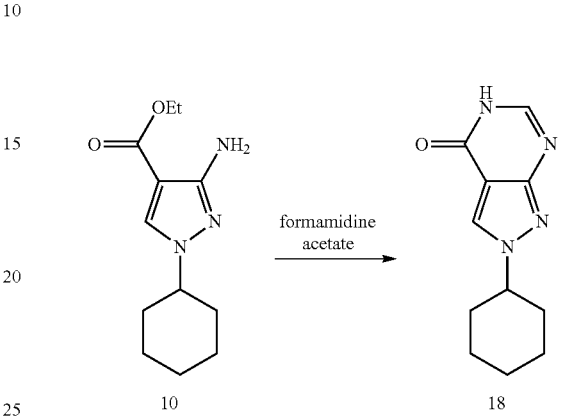

Compound 10 (1.8 g, 7.6 mmol) was combined with formamidine acetate (Acros, 1.58 g, 15.2 mmol) in 50 mL methoxyethanol (Acros) and refluxed under argon overnight. Starting material was still evident. Additional formamidine acetate (700 mg, 6.7 mmol) was added and the mixture was refluxed an additional 24 hours. The reaction was concentrated and the solid was treated with 100 mL 0.1N ammonium hydroxide solution. The product was then isolated by filtration, was washed with water, and was dried in vacuo to afford 1.03 g (62%) of a tan solid. Compound 18: mp 287-289° C.; MS (ES$^-$ calculated: 218.26; found: 217.54 M–H). HPLC (97%) purity, retention time 7.959 minutes—Method A); $^1$H NMR (400 MHz, DMSO-d$_6$) δ 11.64 (br s, 1H), 8.53 (s, 1H), 7.90 (s, 1H), 4.30 (m, 1H), 2.03 (m, 2H), 1.86-1.58 (m, 5H), 1.39 (m, 2H), 1.22 (m, 1H).

Compound 19

2-Allyl-2,5-dihydro-pyrazolo[3,4-d]pyrimidin-4-one

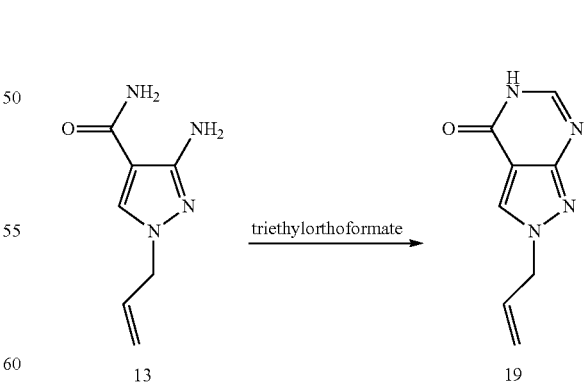

Compound 13 (282 mg, 1.70 mmol) was refluxed under argon in 5 mL triethylorthoformate overnight. The reaction was concentrated and the crude product was triturated with cold ethanol. Filtration afforded a white solid which was dried in vacuo to afford 111 mg (37%). Compound 19: mp 222-224° C.; MS (ES+ calculated: 176.18; found: 177.03 M+H). HPLC (100%) purity, retention time 7.395 minutes—Method A); ¹H NMR (400 MHz, DMSO-d$_6$) δ 11.70 (br s, 1H), 8.50 (s, 1H), 7.91 (s, 1H), 6.08 (m, 1H), 5.26 (d, J=10 Hz, 1H), 5.20 (d, J=15 Hz, 1H), 4.91 (d, J=6 Hz, 2H).

Compound 20

1-Cyclopentyl-1,5-dihydro-pyrazolo[3,4-d]pyrimidin-4-one

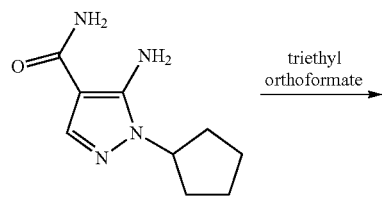

In a similar fashion as for the preparation of 19, compound 16 (3.639 g, 18.8 mmol) was refluxed in 75 mL triethylorthoformate affording 3.111 g (81%) of 20 as white crystals. Compound 20: mp 235-237° C.; MS (ES+ calculated: 204.23; found: 205.19 M+H). HPLC (100%) purity, retention time 2.674 minutes—Method C); ¹H NMR (400 MHz, DMSO-d$_6$) δ 12.12 (br s, 1H), 8.05 (s, 1H), 5.13 (m, 1H), 2.07 (m, 2H), 1.96 (m, 2H), 1.86 (m, 2H), 1.67 (m, 2H).

Compound 21

1-Cyclohexyl-1,5-dihydro-pyrazolo[3,4-d]pyrimidin-4-one

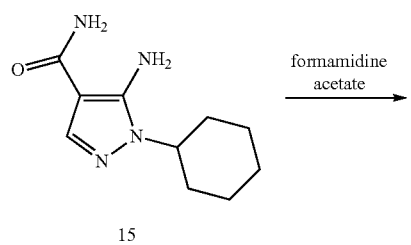

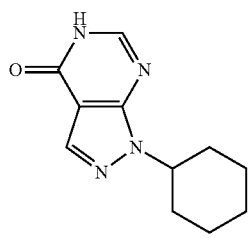

In a similar fashion as for the preparation of 18, compound 15 (4.04 g, 19.4 mmol) was reacted with formamidine acetate (4.03 g, 38.8 mmol) in 100 mL methoxyethanol to afford 3.717 g (88%) of 21 as a tan solid. Compound 21: mp 255-257° C.; MS (ES− calculated: 218.26; found: 217.15 M−H). HPLC (98%) purity, retention time 7.564 minutes—Method B); ¹H NMR (400 MHz, DMSO-d$_6$) δ 12.13 (br s, 1H), 8.14 (s, 1H), 4.56 (m, 1H), 1.98-1.58 (m, 6H), 1.69 (m, 1H), 1.42 (m, 2H), 1.22 (m, 1H).

Compound 22

4-Chloro-2-cyclopentyl-2H-pyrazolo[3,4-d]pyrimidine

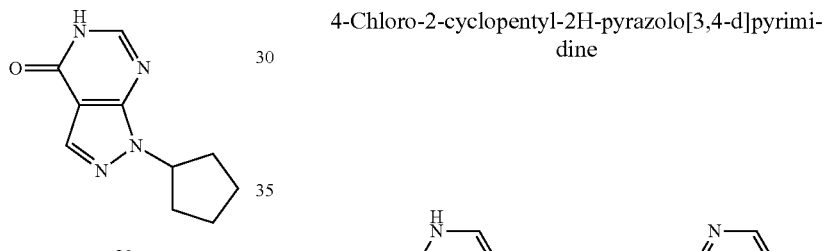

N,N-Dimethylaniline (Acros, 10 mL) was added to Compound 17 (3.10 g, 13.9 mmol) dissolved in phosphorus oxychloride (Acros, 90 mL) and the mixture was refluxed under argon at 110° C. for 90 minutes. Excess phosphorus oxychloride was removed in vacuo and the dark syrup was poured into ice water. The organics were extracted with three 50 mL portions of ether. The ether extracts were combined, were washed with water and brine, and were dried (magnesium sulfate). Concentration of the ether afforded a dark oil which was purified by flash chromatography on silica gel (gradient elution: 1-3% methanol: dichloromethane) to afford 2.74 g (88%) of a green oil. Compound 22: MS (ES+ calculated: 222.68; found: 223.12 M+H). HPLC (85%) purity, retention time 9.882 minutes—Method B); ¹H NMR (400 MHz, CDCl$_3$) δ 8.83 (s, 1H), 8.17 (s, 1H), 4.99 (m, 1H), 2.28 (m, 2H), 2.19 (m, 2H), 2.00 (m, 2H), 1.78 (m, 2H).

Compound 23

4-Chloro-2-cyclohexyl-2H-pyrazolo[3,4-d]pyrimidine

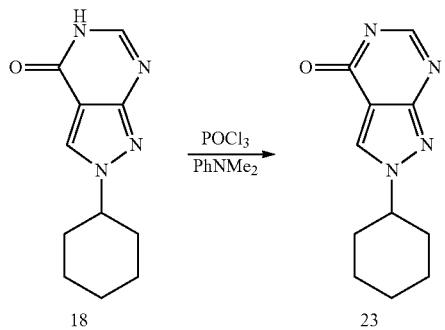

In a similar fashion as for the preparation of Compound 22, Compound 23 (0.50 g, 2.29 mmol) was treated with 25 mL phosphorus oxychloride and 3 mL N,N-dimethylaniline. Following flash chromatography on silica gel (gradient elution: 1-3% methanol: dichloromethane) there was obtained 360 mg (66%) of a yellow-green oil. Compound 23: MS (ES$^+$ calculated: 236.71; found: 237.24 M+H). HPLC (94%) purity, retention time 10.416 minutes—Method B); $^1$H NMR (400 MHz, DMSO-d$_6$) δ 8.97 (s, 1H), 8.79 (s, 1H), 4.59 (m, 1H), 2.12 (m, 2H), 1.93-1.86 (m, 4H), 1.70 (m, 1H), 1.46 (m, 2H), 1.27 (m, 1H).

Compound 24

4-Chloro-2-cyclohexyl-2H-pyrazolo[3,4-d]pyrimidine

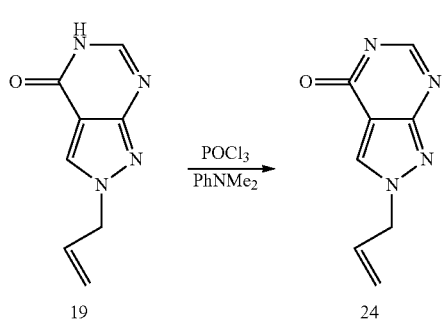

In a similar fashion as for the preparation of Compound 22, Compound 19 (110 mg, 0.63 mmol) was treated with 5 mL phosphorus oxychloride and 0.5 mL N,N-dimethylaniline. Following flash chromatography on silica gel (gradient elution: 1-3-5% methanol: dichloromethane) 77 mg (63%) of a dark yellow oil was obtained. Compound 24: MS (ES$^+$ calculated: 194.62; found: 195.07 M+H). $^1$H NMR (400 MHz, DMSO-d$_6$) δ 8.50 (s, 1H), 7.92 (s, 1H), 6.04 (m, 1H), 5.33-5.11 (m, 2H), 4.92 (m, 2H).

Compound 25

4-Chloro-1-cyclopentyl-1H-pyrazolo[3,4-d]pyrimidine

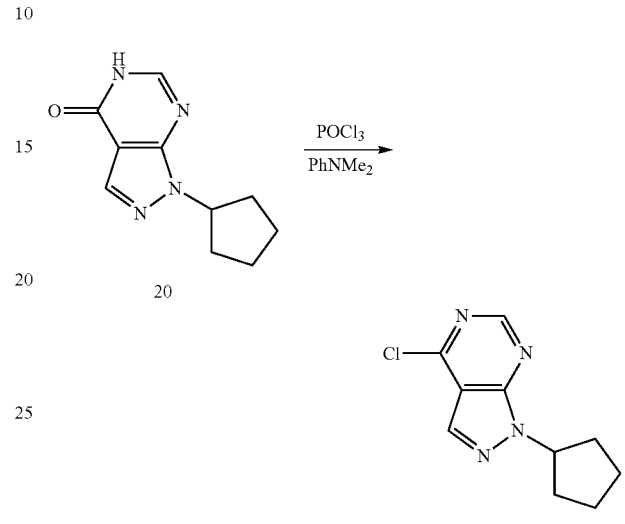

In a similar fashion as for the preparation of compound 22, Compound 20 (1.5 g, 7.35 mmol) was treated with 75 mL phosphorus oxychloride and 6 mL N,N-dimethylaniline. The reaction was subjected to an ether work-up as for 22 above (without columning) to afford 1.734 g (quantitative) of a yellow solid which was used without further purification. Compound 25: MS (ES$^+$ calculated: 222.68; found: 223.19 M+H).

Compound 26

4-Chloro-1-cyclohexyl-1H-pyrazolo[3,4-d]pyrimidine

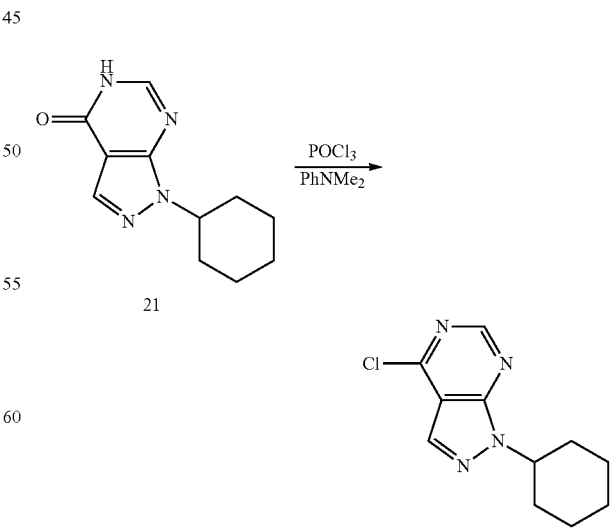

In a similar fashion as for the preparation of Compound 22, Compound 21 (1.5 g, 6.88 mmol) was treated with 70 mL phosphorus oxychloride and 6 mL N,N-dimethylaniline. The reaction was subjected to an ether work-up as for 22 above (without columning) to afford 800 mg (of a dark yellow oil which was used without further purification. Compound 26: MS (ES+ calculated: 236.71; found: 237.18 M+H).

Example 29

3-[9-((1R,2S,3R,4R)-2,3-Dihydroxy-4-methoxymethyl-cyclopentyl)-9H-purin-6-yl]-2-oxo-2,3-dihydro-1H-indole-5-carbonitrile

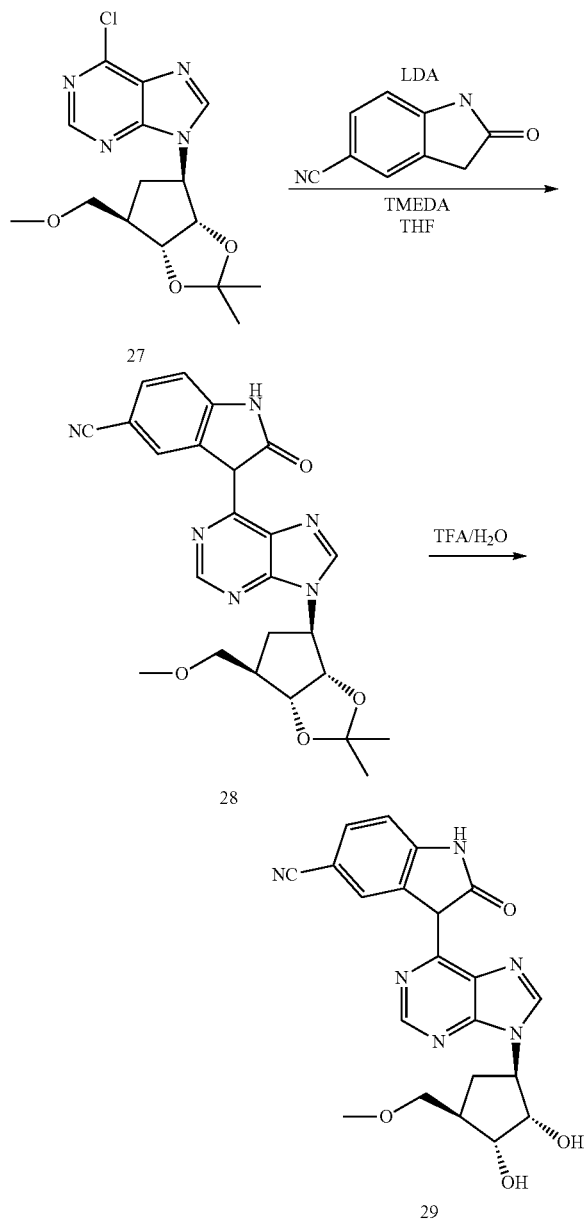

To 5-cyanooxindole (Combiblocks, 50.6 mg, 0.32 mmol) and N,N,N',N'-tetramethylethylenediamine (Acros, 0.10 mL, 0.64 mmol) in 10 mL anhydrous THF under argon at −78° C. was added lithium diisopropylamine (Acros, 0.32 mL of a 2.0M solution in THF/heptane, 0.64 mmol). The solution was stirred for fifteen minutes at which point a solution of Compound 27 (104 mg, 0.307 mmol) in 10 mL THF was added dropwise at such a rate as to maintain the temperature below −50° C. The reaction was stirred for ten minutes, external cooling was removed, and the reaction was permitted to warm to room temperature. An oil bath was applied and the mixture was refluxed overnight. The reaction was concentrated, water (50 mL) was added and the organics were extracted into dichloromethane (3×50 mL). The dichloromethane extracts were combined, were washed with water (50 mL) and brine (50 mL) and were dried (magnesium sulfate). Removal of the dichloromethane followed by flash chromatography on silica gel (gradient elution: 1-3% methanol: dichloromethane) afforded ~60 mg of an acetonide [MS (ES+ calculated: 460.50; found: 461.24 M+H)] which was treated immediately with a mixture of trifluoroacetic acid (24 mL) and water (3 mL) for 30 minutes at room temperature. The reaction mixture was concentrated and partitioned between saturated sodium bicarbonate solution (50 mL) and dichloromethane (50 mL). A solid formed at the interface which was filtered off. [The dichloromethane layer was determined to contain only polar impurities.] The material isolated at the interface was washed with water and was dried in vacuo to afford 15 mg (12%) of the diol as a yellow solid. Example 29: mp 230-236° C. (dec); MS (ES+ calculated: 420.43; found: 421.21 M+H). HPLC (95%) purity, retention time 8.089 minutes—Method B); $^1$H NMR (400 MHz, DMSO-$d_6$) δ 11.11 (br s, 1H), 9.60 (s, 1H), 8.68 (s, 1H), 8.61 (s, 1H), 7.38 (d, J=7 Hz, 1H), 7.04 (d, J=7 Hz, 1H), 5.06 (m, 1H), 4.82 (m, 2H), 4.33 (m, 1H), 3.83 (m, 1H), 3.46 (m, 1H), 3.28 (s, 3H), 2.31 (m, 1H), 2.17 (m, 1H), 1.67 (m, 1H).

Example 30

3-(2-Cyclopentyl-2H-pyrazolo[3,4-d]pyrimidin-4-yl)-2-oxo-2,3-dihydro-1H-indole-5-carbonitrile

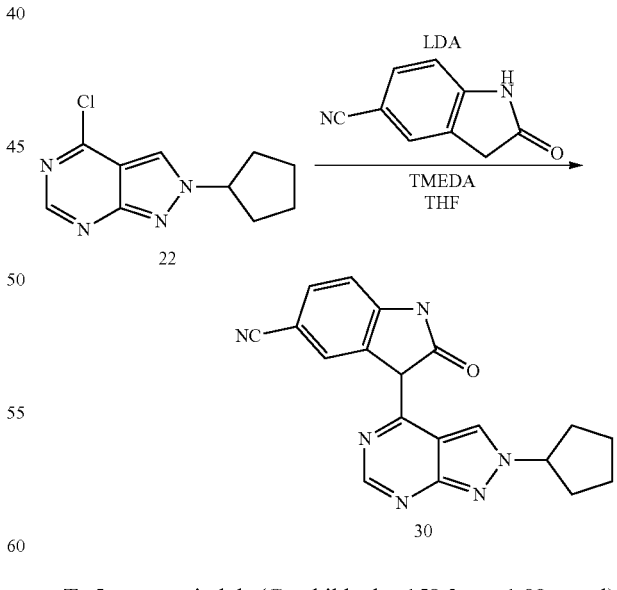

To 5-cyanooxindole (Combiblocks, 158.2 mg, 1.00 mmol) in 10 mL anhydrous tetrahydrofuran under argon was added N,N,N',N'-tetramethylethylenediamine (Acros, 0.30 mL, 2.00 mmol). The solution was cooled to −78° C. and lithium diisopropylamide (Acros, 1.0 mL of a 2.0M solution in THF/hexane, 2.00 mmol) was added dropwise. The reaction was stirred for fifteen minutes at which point a solution of Compound 22 (236 mg, 1.06 mmol) in 10 mL anhydrous tetrahydrofuran was added dropwise. The reaction was stirred an additional fifteen minutes and was warmed to room temperature for ½ hour. The mixture was then refluxed overnight. The reaction was quenched by addition of a small amount of a saturated ammonium chloride solution and concentrated. Dichloromethane (50 mL) and water (50 mL) were added and undissolved solid was filtered off. The solid was washed with dichloromethane and was taken up into a small amount of N,N-dimethylformamide and concentrated onto a small amount of silica gel. The silica containing product was applied to the top of a silica gel column and flash chromatography was effected (gradient elution: 1-3-5-10% methanol:dichloromethane to 1% ammonium hydroxide:10% methanol:89% dichloromethane) to afford 124 mg (36%) of a yellow-orange solid. Example 30: mp>300° C. (dec); MS (ES⁺ calculated: 344.28; found: 345.17 M+H). HPLC (100%) purity, retention time 12.154 minutes—Method B); ¹H NMR (400 MHz, DMSO-d₆) δ 13.17 (br s), 11.25 (s), 10.81 (br s), 10.61 (br s), 9.57 (s), 9.10 (s), 8.76 (s), 8.40 (s), 8.23 (br s), 8.14 (br s), 7.99 (s), 7.50 (d, J=9 Hz), 7.42 (m), 7.07 (d, J=8 Hz), 6.92 (m), 5.22 (m), 4.97 (m), 3.25 (m), 2.25-1.53 (m, 8H).

Example 31

5-Bromo-3-(2-Cyclopentyl-2H-pyrazolo[3,4-d]pyrimidin-4-yl)-2-oxo-1,3-dihydro-indol-2-one

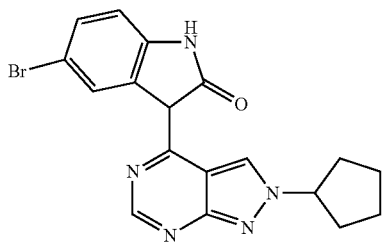

31

In a similar fashion as for the preparation of 30 above, 5-bromooxindole (Combiblocks, 99.6 mg, 0.47 mmol) was reacted with Compound 22 (110 mg, 0.5 mmol). Upon completion, the reaction was concentrated and the crude product obtained was purified by flash chromatography on silica gel (gradient elution: 1-3-5-10% methanol: dichloromethane) to afford 143 mg (76%) of a yellow solid. Example 31: mp 319-322° C. (dec); MS (ES⁺ calculated: 398.27; found: 398.44, 399.81 M+H). HPLC (100%) purity, retention time 13.050 minutes—Method B); ¹H NMR (400 MHz, DMSO-d₆) δ 10.88 (s), 10.27 (br s), 9.57 (s), 8.86 (s), 8.34 (d, J=3 Hz), 8.25 (br s), 7.74 (s), 7.21 (dd, J=2.9 Hz), 7.12 (d, J=7 Hz), 6.89 (d, J=8 Hz), 6.74 (d, J=8 Hz), 5.14 (m), 4.94 (m), 3.17 (d, J=5 Hz), 2.28-1.56 (m, 8H).

Example 32

6-Chloro-3-(2-Cyclopentyl-2H-pyrazolo [3,4-d]pyrimidin-4-yl)-2-oxo-1,3-dihydro-indol-2-one

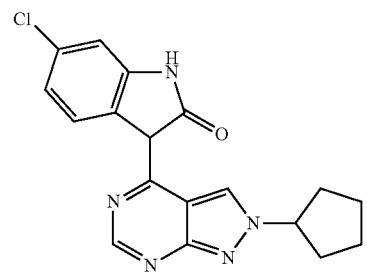

32

In a similar fashion as for the preparation of 31 above, 6-chlorooxindole (Combiblocks, 78.7 mg, 0.47 mmol) was reacted with Compound 22 (110 mg, 0.5 mmol). The crude product was purified by flash chromatography on silica gel (gradient elution: 1-3-5% methanol: dichloromethane) to afford 67 mg (40%) of a rust colored solid. Example 32: mp 294-296° C.; MS (ES⁺ calculated: 353.81; found: 354.27 M+H). HPLC (86%) purity, retention time 12.997 minutes—Method B); ¹H NMR (400 MHz, DMSO-d₆) δ 10.89 (s), 10.29 (br s), 9.55 (s), 8.97 (s), 8.33 (d, J=3 Hz), 8.17 (br s), 7.74 (d, J=8 Hz), 7.69 (m), 7.02 (dd, J=2.8 Hz), 6.94 (d, J=2 Hz), 6.81 (s), 5.13 (m), 4.93 (m), 4.19 (m), 3.33 (m), 2.22-1.53 (m, 8H).

Example 33

3-(2-Cyclopentyl-2H-pyrazolo[3,4-d]pyrimidin-4-yl)-5-nitro-1,3-dihydro-indol-2-one

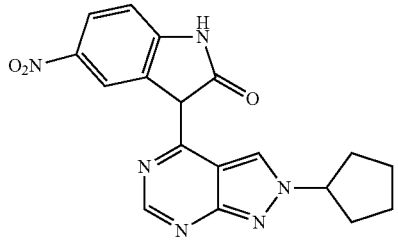

33

In a similar fashion as for the preparation of 31 above, 5-nitrooxindole (Combiblocks, 50 mg, 0.28 mmol) was reacted with Compound 22 (63 mg, 0.284 mmol). The crude product was purified by flash chromatography on silica gel (gradient elution: 1-3-5% methanol: dichloromethane) to afford 30 mg (29%) of a rust colored solid. Example 33: MS (ES⁻ calculated: 364.37; found: 364.03 M+). HPLC (76%) purity, retention time 11.582 minutes—Method B); ¹H NMR (400 MHz, DMSO-d₆) δ 13.73 (br s), 12.75 (br s), 11.40 (s), 10.84 (s), 10.73 (s), 9.63 (s), 9.58 (s), 9.27 (s), 9.19 (br s), 8.98

(s), 8.50 (m), 8.41 (s), 7.92 (m), 7.69 (m), 7.10 (m), 6.92 (m), 4.96 (m), 4.24 (m), 4.06 (m), 3.17 (m), 2.22-1.70 (m, 8 H).

Example 34

3-(2-Cyclopentyl-2H-pyrazolo [3,4-d]pyrimidin-4-yl)-5-trifluoromethyl-1,3-dihydro-indol-2-one

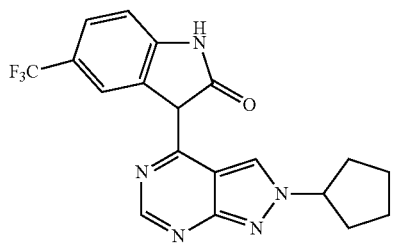

34

In a similar fashion as for the preparation of 31 above, 5-trifluoromethyloxindole (Combiblocks, 55.3 mg, 0.275 mmol) was reacted with Compound 22 (63 mg, 0.284 mmol). The crude product was purified by flash chromatography on silica gel (gradient elution: 1-3-5% methanol: dichloromethane) to afford 90 mg (84%) of a golden solid. Example 34: mp 292-293° C.; MS (ES+ calculated: 387.37; found: 388.18 M+H). HPLC (96%) purity, retention time 13.212 minutes—Method B); $^1$H NMR (400 MHz, DMSO-$d_6$) δ 13.92 (s), 12.50 (br s), 11.12 (s), 10.53 (s), 9.63 (s), 9.59 (s), 8.79 (s), 8.74 (s), 8.57 (br s), 8.40 (s), 8.37 (s), 8.31 (s), 7.87 (s), 7.39 (d, J=8 Hz), 7.31 (d, J=7 Hz), 7.10 (d, J=8 Hz), 6.94 (d, J=7 Hz), 5.05 (m), 4.95 (m), 3.18 (s), 2.27-1.55 (m, 8H).

Example 35

3-(2-Cyclopentyl-2H-pyrazolo[3,4-d]pyrimidin-4-yl)-5,7-difluoro-1,3-dihydro-indol-2-one

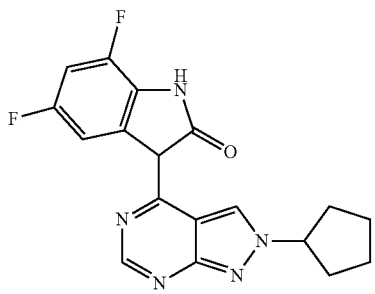

35

In a similar fashion as for the preparation of 31 above, 5,7-difluoromethyloxindole (Combiblocks, 47 mg, 0.28 mmol) was reacted with Compound 22 (65 mg, 0.293 mmol). The crude product was purified by flash chromatography on silica gel (gradient elution: 1-3-5% methanol: dichloromethane) to afford 19 mg (19%) of a yellow solid. Example 35: mp 296-297° C.; MS (ES+ calculated: 355.35; found: 386.16 M+H). HPLC (98%) purity, retention time 12.219 minutes—Method B); $^1$H NMR (400 MHz, DMSO-$d_6$) δ 11.19 (br s), 11.23 (s), 10.57 (s), 9.60 (s), 9.02 (s), 8.40 (s), 8.27 (s), 7.94 (m), 7.72 (m), 7.39 (d, J=9 Hz), 6.96 (m), 6.84 (m), 5.21 (m), 4.96 (m), 2.33-1.56 (m, 8H).

Example 36

5-Chloro-3-(2-Cyclopentyl-2H-pyrazolo [3,4-d]pyrimidin-4-yl)-2-oxo-1,3-dihydro-indol-2-one

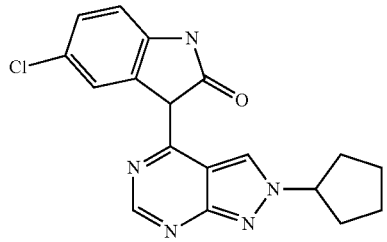

36

In a similar fashion as for the preparation of 31 above, 5-chlorooxindole (Combiblocks, 47 mg, 0.28 mmol) was reacted with Compound 22 (65 mg, 0.293 mmol). The crude product was purified by flash chromatography on silica gel (gradient elution: 1-3-5% methanol: dichloromethane) to afford 73 mg (74%) of a yellow solid. Example 36: mp 290-292° C.; MS (ES+ calculated: 353.81; found: 354.26 M+H). HPLC (80%) purity, retention time 12.595 minutes—Method B); $^1$H NMR (400 MHz, DMSO-$d_6$) δ 10.87 (s), 10.24 (br s), 9.57 (s), 8.91 (s), 8.35 (d, J=5 Hz), 8.23 (br s), 7.63 (s), 7.09 (dd, J=2.8 Hz), 6.98 (d, J=8 Hz), 6.93 (d, J=8 Hz), 6.77 (d, J=8 Hz), 5.17 (m), 4.94 (m), 4.07 (m), 3.17 (d, J=5 Hz), 2.28-1.61 (m, 8H).

Example 37

3-(2-Cyclopentyl-2H-pyrazolo[3,4-d]pyrimidin-4-yl)-1,3-dihydro-indo-2-one

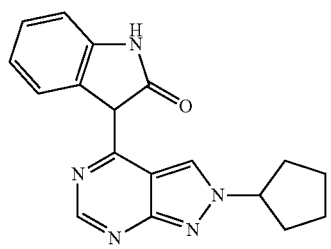

37

In a similar fashion as for the preparation of 31 above, 5-hydroxyindole (Combiblocks, 45 mg, 0.338 mmol) was reacted with Compound 22 (75 mg, 0.338 mmol). The crude product was purified by flash chromatography on silica gel (gradient elution: 1-3-5% methanol: dichloromethane) to afford 70 mg (65%) of a yellow-orange solid. Example 37: mp 289-292° C.; MS (ES+ calculated: 319.37; found: 320.18 M+H). HPLC (87%) purity, retention time 11.043 minutes—Method B); $^1$H NMR (400 MHz, DMSO-$d_6$) δ 10.76 (s), 10.22 (br s), 9.55 (br s), 8.98 (s), 8.30 (s), 8.17-7.86 (m), 7.78 (s), 7.06 (s), 6.94 (s), 5.14 (m), 4.97 (m), 2.59 (d, J=5 Hz), 2.27-1.55 (m, 8H).

Example 38

3-(2-Cyclopentyl-2H-pyrazolo [3,4-d]pyrimidin-4-yl)-2-oxo-2,3-dihydro-1H-indole-6-carbonitrile

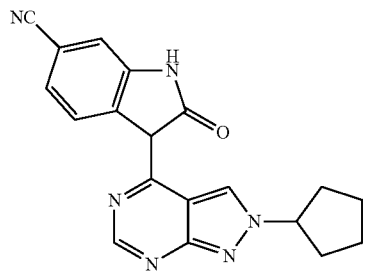

In a similar fashion as for the preparation of 31 above, 6-cyanooxindole (Combiblocks, 80 mg, 0.506 mmol) was reacted with Compound 22 (111 mg, 0.5 mmol). The crude product was purified by flash chromatography on silica gel (gradient elution: 1-3-5-10% methanol: dichloromethane) to afford 49 mg (28%) of a yellow solid. Example 38: mp 340-344° C.; MS (ES$^+$ calculated: 344.38; found: 345.17 M+H). HPLC (98%) purity, retention time 11.243 minutes—Method B); $^1$H NMR (400 MHz, DMSO-d$_6$) δ 11.66 (s), 11.06 (br s), 9.58 (s), 9.05 (s), 8.40 (d, J=2 Hz), 8.26 (br s), 8.03 (d, J=8 Hz), 7.42 (d, J=8 HzO, 7.31 (d, J=8 Hz), 7.15 (t, J=8 Hz), 7.03 (t, J=8 Hz), 5.16 (m), 4.97 (m), 4.08 (m), 2.27-1.55 (m, 8H).

Example 39

3-(2-Cyclopentyl-2H-pyrazolo[3,4-d]pyrimidin-4-yl)-2-oxo-2,3-dihydro-1H-indole-7-carbonitrile

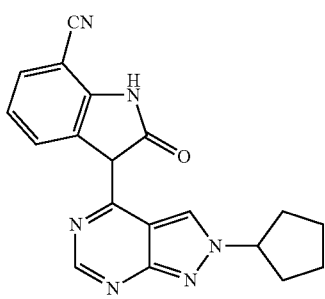

In a similar fashion as for the preparation of 31 above, 7-cyanooxindole (Combiblocks, 80 mg, 0.506 mmol) was reacted with Compound 22 (111 mg, 0.5 mmol). The crude product was purified by flash chromatography on silica gel (gradient elution: 1-3-5% methanol: dichloromethane) to afford 31 mg (18%) of a yellow solid. Example 39: mp>380° C.; MS (ES$^+$ calculated: 344.38; found: 345.16 M+H). HPLC (100%) purity, retention time 11.424 minutes—Method B); $^1$H NMR (400 MHz, DMSO-d$_6$) δ 14.29 (s), 11.09 (s), 10.48 (br s), 9.61 (s), 9.07 (s), 8.43 (s), 8.40 (m), 7.90 (d, J=8 Hz), 7.40 (dd, J=2.8 Hz), 7.35 (m), 7.25 (d, J=2 Hz), 7.08 (br s), 5.17 (m), 4.98 (m), 4.08 (m), 2.27-1.60 (m, 8H).

Example 40

3-(2-Cyclopentyl-2H-pyrazolo[3,4-d]pyrimidin-4-yl)-5-fluoro-1,3-dihydro-indol-2-one

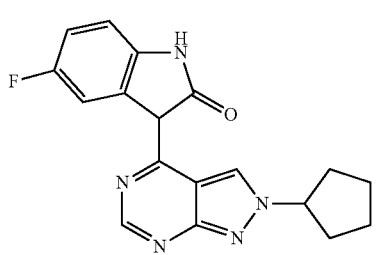

In a similar fashion as for the preparation of 31 above, 5-fluorooxindole (Combiblocks, 76 mg, 0.50 mmol) was reacted with Compound 22 (111 mg, 0.5 mmol). The crude product was purified by flash chromatography on silica gel (gradient elution: 1-3-5% methanol: dichloromethane) to afford 82 mg (49%) of a yellow solid. Example 40: mp 256-260° C.; MS (ES$^+$ calculated: 337.36; found: 338.18 M+H). HPLC (99%) purity, retention time 11.783 minutes—Method B); $^1$H NMR (400 MHz, DMSO-d$_6$) δ 10.77 (s), 10.10 (s), 9.59 (s), 9.00 (s), 8.34 (s), 8.21 (s), 8.02 (m), 7.51 (d, J=10 Hz), 6.90 (m), 6.75 (m), 5.20 (m), 4.93 (m), 2.22-1.56 (m, 8H).

Example 41

3-(2-Cyclopentyl-2H-pyrazolo[3,4-d]pyrimidin-4-yl)-6-fluoro-1,3-dihydro-indol-2-one

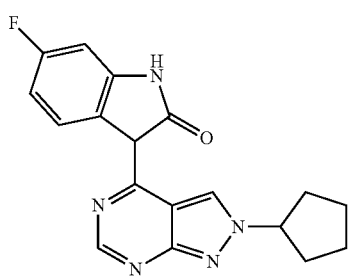

In a similar fashion as for the preparation of 31 above, 6-fluorooxindole (Combiblocks, 76 mg, 0.50 mmol) was reacted with Compound 22 (111 mg, 0.5 mmol). The crude product was purified by flash chromatography on silica gel (gradient elution: 1-3-5% methanol: dichloromethane) to afford 29 mg (17%) of a yellow solid. Example 41: mp 258-263° C.; MS (ES$^+$ calculated: 337.36; found: 338.15 M+H). HPLC (96%) purity, retention time 11.830 minutes—Method B); $^1$H NMR (400 MHz, DMSO-d$_6$) δ 13.90 (br s), 10.89 (br s), 10.25 (s), 9.53 (s), 8.96 (s), 8.30 (s), 8.14 (m), 7.74 (m), 6.94-9.55 (m), 5.13 (m), 4.91 (m), 3.44 (m), 2.22-1.56 (m, 8H).

Example 42

3-(2-Cyclopentyl-2H-pyrazolo[3,4-d]pyrimidin-4-yl)-4,5-difluoro-1,3-dihydro-indol-2-one

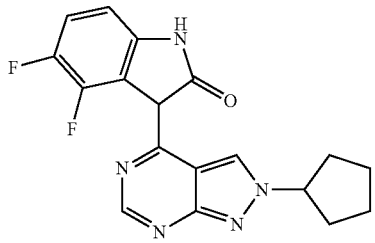

42

In a similar fashion as for the preparation of 31 above, 4,5-difluorooxindole (Combiblocks, 85 mg, 0.50 mmol) was reacted with Compound 22 (111 mg, 0.5 mmol). The crude product was purified by flash chromatography on silica gel (gradient elution: 1-3-5% methanol: dichloromethane) to afford 94 mg (53%) of a yellow solid. Example 42: mp 280-284° C.; MS (ES+ calculated: 355.35; found: 356.18 M+H). HPLC (99%) purity, retention time 11.490 minutes—Method B); $^1$H NMR (400 MHz, DMSO-d$_6$) δ 13.50 (br s), 10.72 (br s), 8.77 (br s), 8.29 (s), 7.05 (m), 6.68 (m), 5.00 (m), 2.22-1.50 (m, 8H).

Example 43

3-(2-Cyclopentyl-2H-pyrazolo[3,4-d]pyrimidin-4-yl)-5,7-dinitro-1,3-dihydro-indol-2-one

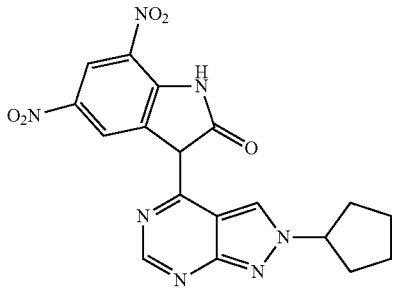

43

In a similar fashion as for the preparation of 31 above, 5,7-dinitrooxindole (Combiblocks, 112 mg, 0.506 mmol) was reacted with Compound 22 (111 mg, 0.5 mmol). The crude product was purified by flash chromatography on silica gel (gradient elution: 1-3-5% methanol: dichloromethane) to afford 41 mg (20%) of a yellow solid. Example 43: mp>300° C.; MS (ES+ calculated: 409.36; found: 410.19 M+H). HPLC (81%) purity, retention time 12.226 minutes—Method B); $^1$H NMR (400 MHz, DMSO-d$_6$) δ 11.31 (br s), 9.58 (br s), 9.46 (br s), 8.52 (br s), 8.43 (br s), 7.69 (m), 7.20 (m), 5.02 (m), 4.14 (m), 3.84 (m), 2.33-1.53 (m, 8H).

Example 44

1-(2-Cyclopentyl-2H-pyrazolo[3,4-d]pyrimidin-4-yl)-1,3-dihydro-benzoimidazol-2-one

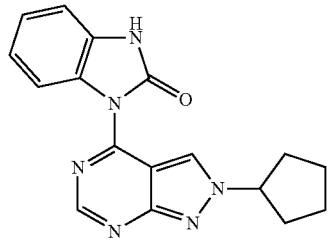

44

In a similar fashion as for the preparation of 31 above, 2-hydroxybenzimidazole (Acros, 68 mg, 0.506 mmol) was reacted with Compound 22 (111 mg, 0.5 mmol). The crude product was purified by flash chromatography on silica gel (gradient elution: 1-3% methanol: dichloromethane) to afford 47 mg (29%) of a yellow solid. Example 44: mp 236-240° C.; MS (ES+ calculated: 320.36; found: 321.17 M+H). HPLC (95%) purity, retention time 10.362 minutes—Method B); $^1$H NMR (400 MHz, DMSO-d$_6$) δ 11.55 (br s), 8.90 (s), 8.86 (s), 8.16 (d, J=8 Hz), 7.19 (m), 7.14 (m), 5.18 (m), 2.33-1.58 (m, 8H).

Example 45

3-(2-Cyclohexyl-2H-pyrazolo[3,4-d]pyrimidin-4-yl)-2-oxo-2,3-dihydro-1H-indole-5-carbonitrile

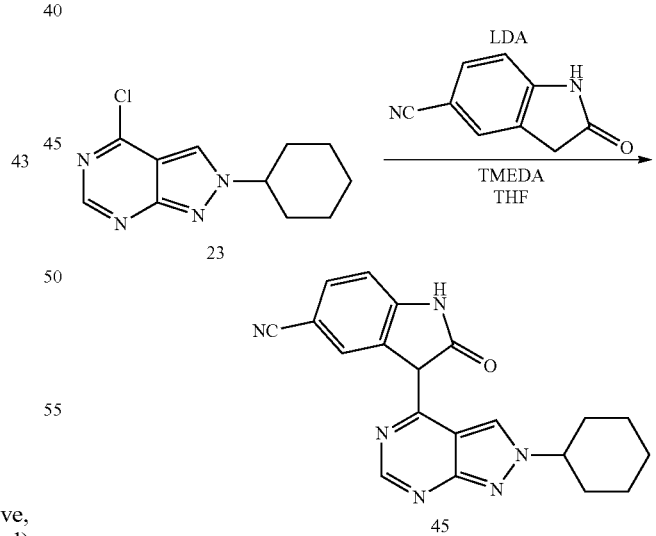

To 5-cyanooxindole (Combiblocks, 34 mg, 0.21 mmol) in 10 mL anhydrous tetrahydrofuran under argon was added N,N,N',N'-tetramethylethylenediamine (Acros, 0.06 mL, 0.40 mmol). The solution was cooled to −78° C. and lithium diisopropylamide (Acros, 0.21 mL of a 2.0M solution in THF/hexane, 0.42 mmol) was added dropwise. The reaction was stirred for fifteen minutes at which point a solution of Compound 23 (50 mg, 0.21 mmol) in 10 mL anhydrous tetrahydrofuran was added dropwise. The reaction was stirred an additional fifteen minutes and was warmed to room temperature for 0.5 hour. The mixture was then refluxed overnight. The reaction was concentrated and subjected to flash chromatography on silica gel (gradient elution: 1-3-5% methanol: dichloromethane) to afford 60 mg (80%) of a yellow solid. Example 45: mp>325° C.; HPLC (97%) purity, retention time 11.957 minutes—Method B); $^1$H NMR (400 MHz, DMSO-$d_6$) δ 11.27 (s), 9.57 (s), 9.09 (s), 8.39 (s), 8.00 (s), 7.49 (d, J=8 Hz), 7.08 (d, J=8 Hz), 3.40 (m), 2.20-1.20 (m, 10H).

Example 46

5-Bromo-3-(2-cyclohexyl-2H-pyrazolo[3,4-d]pyrimidin-4-yl)-1,3-dihydro-indol-2-one

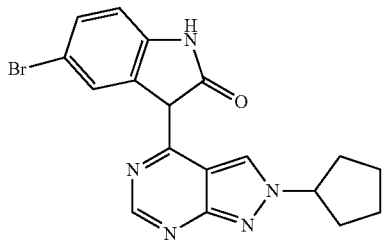

46

In a similar fashion as for the preparation of 45 above, 5-bromooxindole (Combiblocks, 45 mg, 0.21 mmol) was reacted with Compound 23 (50 mg, 0.21 mmol). The reaction was concentrated and the crude product was purified by flash chromatography on silica gel (gradient elution: 1-3-5% methanol: dichloromethane) to afford 50 mg (58%) of a brown solid. Example 46: mp 285-290° C.; MS (ES$^+$ calculated: 412.29; found: 412.48, 414.04 M+H). HPLC (85%) purity, retention time 12.686 minutes—Method B); $^1$H NMR (400 MHz, DMSO-$d_6$) δ 11.67 (br s), 10.90 (s), 10.27 (m), 9.57 (s), 8.87 (s), 8.60 (s), 8.54 (s), 8.35 (s), 8.19 (m), 7.92 (s), 7.74 (s), 7.21 (m), 7.12 (m), 6.89 (m), 6.74 (m), 4.59 (m), 4.37 (m), 2.25-1.10 (m, 10H).

Example 47

3-(2-cyclohexyl-2H-pyrazolo[3,4-d]pyrimidin-4-yl)-5-fluoro-1,3-dihydro-indol-2-one

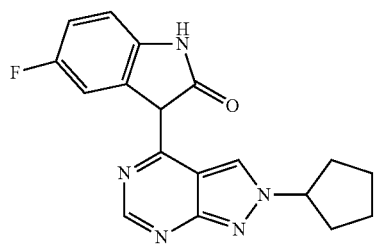

47

In a similar fashion as for the preparation of 45 above, 5-fluorooxindole (Combiblocks, 32 mg, 0.21 mmol) was reacted with Compound 23 (50 mg, 0.21 mmol). The reaction was concentrated and the crude product was purified by flash chromatography on silica gel (gradient elution: 1-3-5% methanol: dichloromethane) to afford 39 mg (53%) of a yellow solid. Example 47: mp 294-298° C.; HPLC (88%) purity, retention time 12.604 minutes—Method B); $^1$H NMR (400 MHz, trifluoroacetic acid-d) δ 8.72 (s), 8.54 (s), 7.13 (d, J=8 Hz), 6.88 (m), 6.78 (m), 3.72 (s), 2.15-0.85 (m, 10H).

Example 48

5-Chloro-3-(2-cyclohexyl-2H-pyrazolo[3,4-d]pyrimidin-4-yl)-1,3-dihydro-indol-2-one

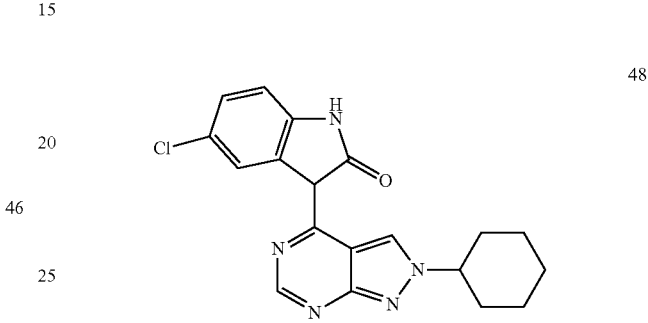

48

In a similar fashion as for the preparation of 45 above, 5-chlorooxindole (Combiblocks, 35 mg, 0.21 mmol) was reacted with Compound 23 (50 mg, 0.21 mmol). The reaction was concentrated and the crude product was purified by flash chromatography on silica gel (gradient elution: 1-3-5% methanol: dichloromethane) to afford 22 mg (28%) of an orange-yellow solid. Example 48: mp 294-298° C.; MS (ES$^+$ calculated: 367.84; found: 368.36 M+H). HPLC (78%) purity, retention time 13.406 minutes—Method B); $^1$H NMR (400 MHz, trifluoroacetic acid-d) δ 8.97 (s), 8.78 (s), 7.64 (s), 7.18 (d, J=8 Hz), 7.10 (d, J=8 Hz), 4.43 (m), 2.30-1.11 (m, 10H).

Example 49

3-(2-Cyclohexyl-2H-pyrazolo[3,4-d]pyrimidin-4-yl)-5-nitro-1,3-dihydroindol-2-one

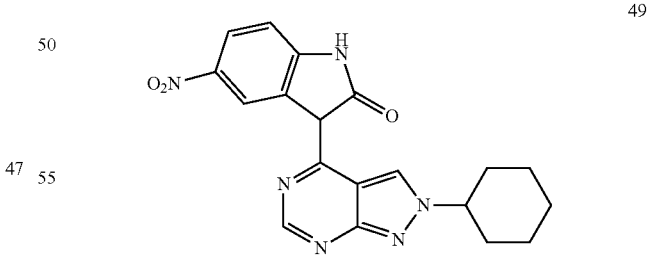

49

In a similar fashion as for the preparation of 45 above, 5-nitrooxindole (Combiblocks, 30 mg, 0.17 mmol) was reacted with Compound 23 (40 mg, 0.17 mmol). The reaction was concentrated and the crude product was purified by flash chromatography on silica gel (gradient elution: 1-3-5% methanol: dichloromethane) to afford 18 mg (28%) of a yellow-brown solid. Example 49: mp 301-304° C.; MS (ES$^+$ calculated: 378.39; found: 379.25 M+H). HPLC (100%)

purity, retention time 12.798 minutes—Method B); $^1$H NMR (400 MHz, trifluoroacetic acid-d) δ 9.21 (s, 1H), 9.00 (s, 1H), 8.73 (s, 1H), 8.42 (s, 1H), 7.52 (s, 1H), 5.28 (s, 1H), 4.62 (m, 1H), 2.56-1.11 (m, 10H).

Example 50

3-(2-cyclohexyl-2H-pyrazolo[3,4-d]pyrimidin-4-yl)-6-fluoro-1,3-dihydro-indol-2-one

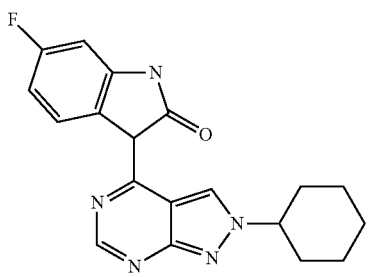

In a similar fashion as for the preparation of 45 above, 6-fluorooxindole (Combiblocks, 32 mg, 0.21 mmol) was reacted with Compound 23 (50 mg, 0.21 mmol). The reaction was concentrated and the crude product was purified by flash chromatography on silica gel (gradient elution: 1-3-5% methanol: dichloromethane) to afford 22 mg (30%) of an orange solid. Example 50: mp 297-300° C.; MS (ES$^+$ calculated: 351.39; found: 352.18 M+H). HPLC (89%) purity, retention time 12.457 minutes—Method B); $^1$H NMR (400 MHz, trifluoroacetic acid-d) δ 9.00 (s, 1H), 8.79 (s, 1H), 7.70 (s, 1H), 6.97 (m, 2H), 4.48 (m, 1H), 2.47-1.24 (m, 10H).

Example 51

6-Chloro-3-(2-cyclohexyl-2H-pyrazolo[3,4-d]pyrimidin-4-yl)-1,3-dihydro-indol-2-one

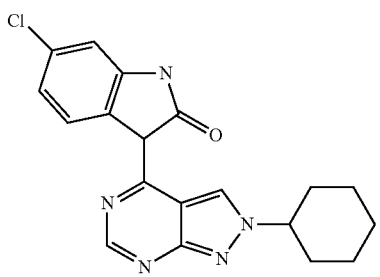

In a similar fashion as for the preparation of 45 above, 6-chlorooxindole (Combiblocks, 35 mg, 0.21 mmol) was reacted with Compound 23 (50 mg, 0.21 mmol). The reaction was concentrated and the crude product was purified by flash chromatography on silica gel (gradient elution: 1-3-5% methanol: dichloromethane) to afford 19 mg (25%) of an orange solid. Example 51: mp 299-303° C.; MS (ES$^+$ calculated: 367.84; found: 368.38 M+H). HPLC (97%) purity, retention time 13.852 minutes—Method B); $^1$H NMR (400 MHz, trifluoroacetic acid-d) δ 9.00 (s, 1H), 8.77 (s, 1H), 7.63 (m, 1H), 7.28 (m, 2H), 4.50 (m, 1H), 2.50-1.30 (m, 10H).

Example 52

3-(2-Cyclohexyl-2H-pyrazolo[3,4-d]pyrimidin-4-yl)-5-methoxy-1,3-dihydro-indol-2-one

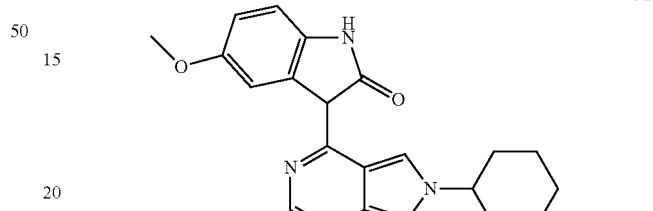

In a similar fashion as for the preparation of 45 above, 5-methoxyoxindole (36 mg, 0.22 mmol) was reacted with Compound 23 (50 mg, 0.21 mmol). The reaction was concentrated and the crude product was purified by flash chromatography on silica gel (gradient elution: 1-2-3% methanol: dichloromethane) to afford 17 mg (22%) of a yellow solid. Example 52: MS (ES$^+$ calculated: 363.42; found: 364.18 M+H). HPLC (62%) purity, retention time 12.048 minutes—Method B); $^1$H NMR (400 MHz, DMSO-d$_6$) δ 10.54 (s, 1H), 8.88 (s, 1H), 8.29 (s, 1H), 7.26 (s, 2H), 6.83 (d, J=8 Hz, 1H), 6.69 (d, J=8 Hz, 1H), 4.56 (m, 1H), 2.20-1.15 (m, 10H).

Example 53

3-(2-Cyclohexyl-2H-pyrazolo [3,4-d]pyrimidin-4-yl)-5-trifluoromethyl-1,3-dihydro-indol-2-one

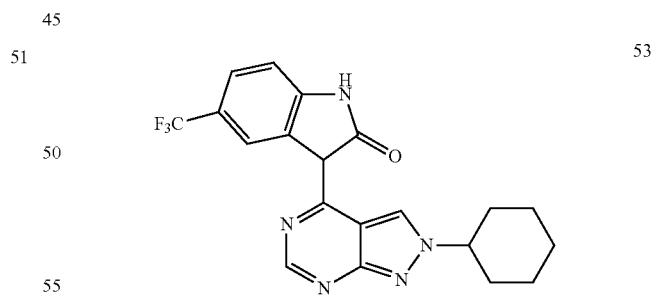

In a similar fashion as for the preparation of 45 above, 5-trifluoromethyloxindole (Combiblocks, 44 mg, 0.22 mmol) was reacted with Compound 23 (50 mg, 0.21 mmol). The reaction was concentrated and the crude product was purified by flash chromatography on silica gel (gradient elution: 1-5% methanol: dichloromethane) to afford 58 mg (69%) of a yellow solid. Example 53: mp>300° C.; MS (ES$^+$ calculated: 401.39; found: 402.20 M+H). HPLC (92%) purity, retention time 14.161 minutes—Method B); $^1$H NMR (400 MHz, trifluoroacetic acid-d) δ 9.10 (s, 1H), 8.84 (s, 1H), 8.03 (s, 1H), 7.68 (s, 1H), 7.40 (s, 1H), 4.50 (m, 1H), 2.60-1.23 (m, 10H).

Example 54

5-Bromo-3-(1-cyclopentyl-1H-pyrazolo[3,4-d]pyrimidin-4-yl)-1,3-dihydro-indol-2-one

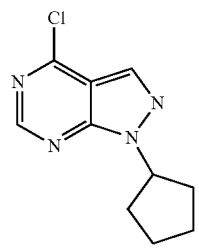 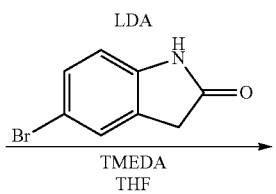

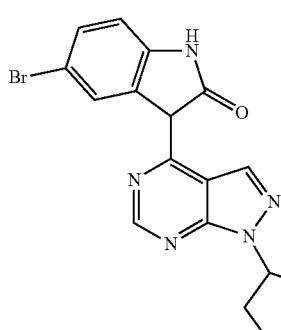

54

To 5-bromooxindole (Combi-Blocks, 136 mg, 0.64 mmol) and N,N,N',N'-tetramethylethylenediamine (Acros, 0.193 mL, 1.28 mmol) in 10 mL anhydrous THF under argon at −78° C. was added lithium diisopropylamine (Acros, 0.64 mL of a 2.0M solution in THF/heptane, 1.28 mmol). The solution was stirred for fifteen minutes at which point a solution of Compound 25 (150 mg, 0.676 mmol) in 10 mL THF was added dropwise at such a rate as to maintain the temperature below −50° C. The reaction was stirred for ten minutes, external cooling was removed, and the reaction was permitted to warm to room temperature. An oil bath was applied and the mixture was refluxed for 6 hours. The reaction was concentrated. The residue was dissolved in dichloromethane and applied to flash chromatography on silica gel (gradient elution: 1-3% methanol: dichloromethane). Fractions determined to contain 54 by LC/MS were concentrated and dried in vacuo to afford 80 mg (30%) of an orange solid. Example 54: mp 287-290° C., 270° C. (soft); MS (ES+ calculated: 398.27; found: 398.39, 399.85 M+H). HPLC (88%) purity, retention time 13.496 minutes—Method B); $^1$H NMR (400 MHz, DMSO-d$_6$) δ 14.54 (br s, 1H), 10.87 (br s, 1H), 8.52 (s, 1H), 8.46 (s, 1H), 7.80 (s, 1H), 7.20 (d, J=8 Hz, 1H), 6.91 (d, J=8 Hz, 1H), 5.25 (m, 1H), 2.12 (m, 2H), 2.02 (m, 2H), 1.92 (m, 2H), 1.72 (m, 2H).

Example 55

3-(1-Cyclopentyl-1H-pyrazolo[3,4-d]pyrimidin-4-yl)-2-oxo-2,3-dihydro-1H-indole-5-carbonitrile

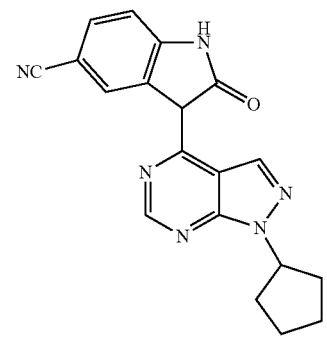

55

Using the procedure outlined for 54, 5-cyanooxindole (Combi-Blocks, 116 mg, 0.736 mmol) and Compound 25 (172 mg, 0.775 mmol) were refluxed overnight affording 30 mg (11%) of yellow crystals. Example 55: mp>300° C.; MS (ES+ calculated: 344.38; found: 345.21 M+H). HPLC (95%) purity, retention time 4.946 minutes—Method C); $^1$H NMR (400 MHz, DMSO-d$_6$) δ 14.53 (br s, 1H), 11.20 (s, 1H), 8.68 (s, 1H), 8.53 (s, 1H), 8.01 (s, 1H), 7.47 (d, J=8 Hz, 1H), 7.07 (d, J=8 Hz, 1H), 5.26 (m, 1H), 2.11 (m, 2H), 2.00 (m, 2H), 1.89 (m, 2H), 1.68 (m, 2H).

Example 56

3-(1-Cyclopentyl-1H-pyrazolo[3,4-d]pyrimidine-4-yl)-5-trifluoromethyl-1,3-dihydro-indol-2-one

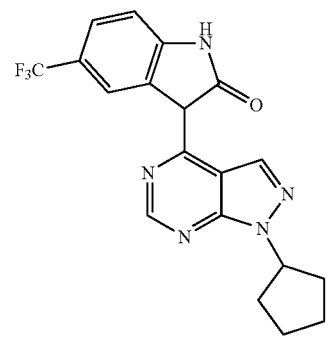

56

Using the procedure outlined for 54, 5-trifluoromethyloxindole (Combi-Blocks, 68 mg, 0.338 mmol) and Compound 25 (75 mg, 0.338 mmol) were refluxed overnight affording 25 mg (19%) of yellow solid. Example 56: mp>300° C.; MS (ES+ calculated: 387.37; found: 388.19 M+H). HPLC (96%) purity, retention time 6.279 minutes—Method C); $^1$H NMR (400 MHz, DMSO-d$_6$) δ 14.50 (br s, 1H), 11.12 (s, 1H), 8.53

(s, 1H), 8.44 (s, 1H), 7.93 (s, 1H), 7.40 (d, J=8 Hz, 1H), 7.10 (d, J=8 Hz, 1H), 5.25 (m, 1H), 2.22 (m, 2H), 2.11 (m, 2H), 2.01 (m, 2H), 1.81 (m, 2H).

Example 57

3-(1-Cyclopentyl-1H-pyrazolo[3,4-d]pyrimidin-4-yl)-5-nitro-1,3-dihydro-indol-2-one

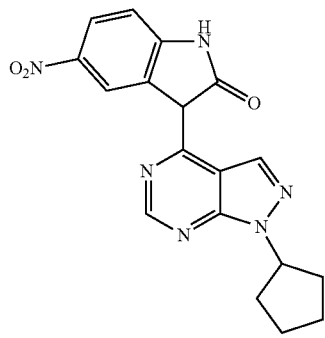

57

Using the procedure outlined for 54, 5-nitrooxindole (Combi-Blocks, 60.2 mg, 0.338 mmol) and Compound 25 (75 mg, 0.338 mmol) were refluxed overnight affording 25 mg (20%) of orange solid. Example 57: mp>300° C. (dec); MS (ES$^+$ calculated: 364.37; found: 365.19 M+H). HPLC (85%) purity, retention time 5.504 minutes—Method C); $^1$H NMR (400 MHz, DMSO-d$_6$) δ 14.30 (br s, 1H), 11.40 (s, 1H), 8.55 (m, 2H), 7.99 (d, J=8 Hz, 1H), 7.08 (d, J=8 Hz, 1H), 5.29 (m, 1H), 2.13 (m, 2H), 2.02 (m, 2H), 1.92 (m, 2H), 1.74 (m, 2H).

Example 58

5-Chloro-3-(1-cyclopentyl-1H-pyrazolo[3,4-d]pyrimidin-4-yl)-1,3-dihydro-indol-2-one

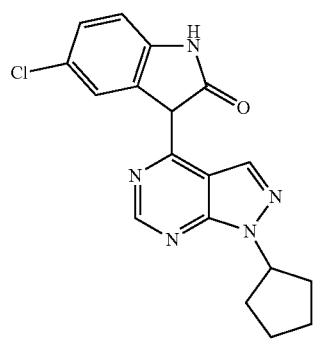

58

Using the procedure outlined for 54, 5-chlorooxindole (Aldrich, 56.6 mg, 0.338 mmol) and Compound 25 (75 mg, 0.338 mmol) were refluxed overnight affording 17 mg (14%) of yellow solid. Example 58: mp 304-306° C.; MS (ES$^+$ calculated: 353.81; found: 354.29 M+H). HPLC (94%) purity, retention time 6.119 minutes—Method C); $^1$H NMR (400 MHz, DMSO-d$_6$) δ 14.59 (br s, 1H), 10.87 (s, 1H), 8.49 (s, 1H), 7.66 (s, 1H), 7.08 (dd, J=2.8 Hz, 1H), 6.94 (d, J=8 Hz, 1H), 5.26 (m, 1H), 2.13 (m, 2H), 2.02 (m, 2H), 1.91 (m, 2H), 1.72 (m, 2H).

Example 59

6-Chloro-3-(1-cyclopentyl-1H-pyrazolo[3,4-d]pyrimidin-4-yl)-1,3-dihydro-indol-2-one

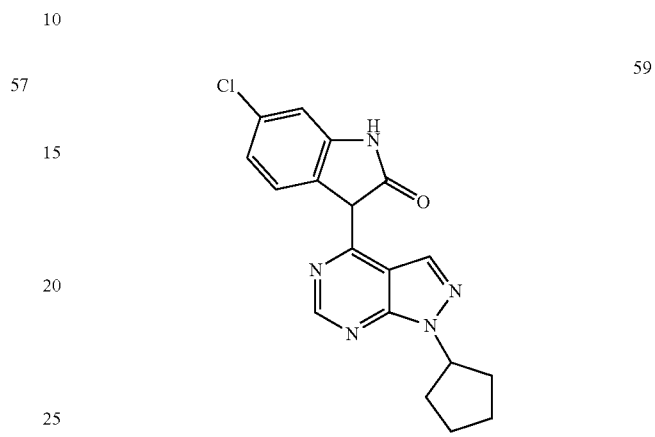

59

Using the procedure outlined for 54, 6-chlorooxindole (Combi-Blocks, 56.6 mg, 0.338 mmol) and Compound 25 (75 mg, 0.338 mmol) were refluxed overnight affording 26 mg (22%) of yellow solid. Example 59: mp 288-291° C.; MS (ES$^+$ calculated: 353.81; found: 354.29 M+H). HPLC (99%) purity, retention time 6.017 minutes—Method C); $^1$H NMR (400 MHz, DMSO-d$_6$) δ 14.61 (br, s, 1H), 10.88 (s, 1H), 8.62 (s, 1H), 8.48 (s, 1H), 7.80 (d, J=8 Hz, 1H), 7.03 (d, J=8 Hz, 1H), 6.93 (s, 1H), 5.24 (m, 1H), 2.12 (m, 2H), 2.00 (m, 2H), 1.91 (m, 2H), 1.72 (m, 2H).

Example 60

3-(1-cyclopentyl-1H-pyrazolo[3,4-d]pyrimidin-4-yl)-5,7-dinitro-1,3-dihydro-indol-2-one

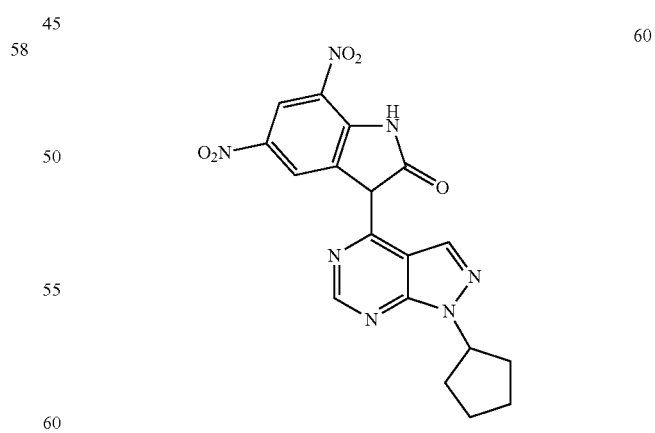

60

Using the procedure outlined for 54, 5,7-dinitrooxindole (Combi-Blocks, 100 mg, 0.45 mmol) and Compound 25 (100 mg, 0.45 mmol) were refluxed overnight affording 7 mg (4%) of yellow solid. Example 60: mp 242-246° C.; MS (ES$^+$ calculated: 409.36; found: 410.24 M+H). HPLC (95%) purity, retention time 6.416 minutes—Method C); $^1$H NMR (400 MHz, DMSO-d$_6$) δ 13.15 (br s, 1H), 9.02 (s, 1H), 8.81 (s, 1H), 8.65 (s, 1H), 8.40 (s, 1H), 6.95 (s, 1H), 5.36 (m, 1H), 2.18 (m, 2H), 2.05 (m, 2H), 1.92 (m, 2H), 1.75 (m, 2H).

Example 61

3-(1-cyclopentyl-1H-pyrazolo[3,4-d]pyrimidin-4-yl)-5,7-difluoro-1,3-dihydro-indol-2-one

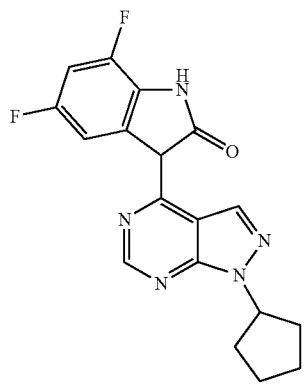

Using the procedure outlined for 54, 5,7-difluorooxindole (Oakwood, 76 mg, 0.45 mmol) and Compound 25 (100 mg, 0.45 mmol) were refluxed overnight affording 20 mg (13%) of bright yellow solid. Example 61: mp>300° C.; MS (ES$^+$ calculated: 355.35; found: 356.17 M+H). HPLC (95%) purity, retention time 5.780 minutes—Method C); $^1$H NMR (400 MHz, DMSO-d$_6$) δ 14.74 (br s, 1H), 11.23 (s, 1H), 8.61 (s, 1H), 8.55 (s, 1H), 7.38 (d, J=8 Hz), 6.93 (t, J=8 Hz, 1H) 5.27 (m, 1H), 2.15 (m, 2H), 2.01 (m, 2H), 1.93 (m, 2H), 1.73 (m, 2H).

Example 62

3-(1Cyclopentyl-1H-pyrazolo[3,4-d]pyrimidin-4-yl)-1,3-dihydro-indol-2-one

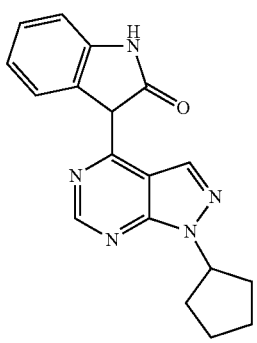

Using the procedure outlined for 54, oxindole (Combi-Blocks, 59.9 mg, 0.45 mmol) and Compound 25 (100 mg, 0.45 mmol) were refluxed overnight affording 32 mg (22%) of yellow solid. Example 62: mp 228-231° C.; MS (ES$^+$ calculated: 319.37; found: 320.16 M+H). HPLC (92%) purity, retention time 5.288 minutes—Method C); $^1$H NMR (400 MHz, DMSO-d$_6$) δ 14.72 (br s, 1H), 1074 (s, 1H), 8.60 (s, 1H), 8.45 (s, 1H), 7.80 (d, J=8 Hz, 1H), 7.02 (m, 2H), 6.93 (d, J=8 Hz, 1H), 5.25 (m, 1H), 2.12 (m, 2H), 2.02 (m, 2H), 1.91 (m, 2H), 1.73 (m, 2H).

Example 63

3-(1-Cyclopentyl-1H-pyrazolo[3,4-d]pyrimidin-4-yl)-2-oxo-2,3-dihydro-1H-indole-6-carbonitrile

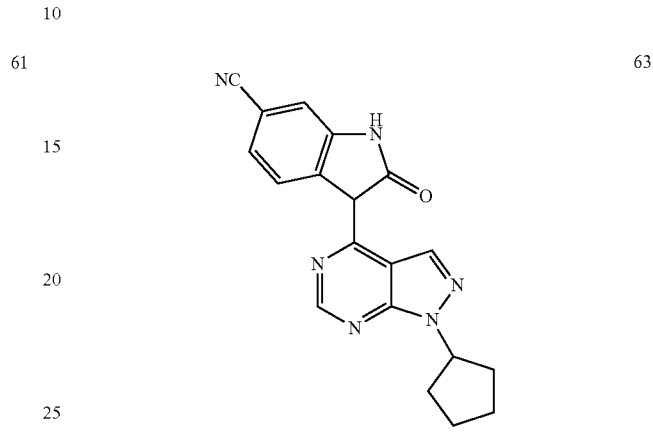

Using the procedure outlined for 54, 6-cyanooxindole (Combi-Blocks, 80 mg, 0.505 mmol) and Compound 25 (111 mg, 0.5 mmol) were refluxed overnight affording 75 mg (44%) of orange solid. Example 63: mp 335-338° C.; MS (ES$^+$ calculated: 344.38; found: 345.19 M+H). HPLC (94%) purity, retention time 12.942 minutes—Method B); $^1$H NMR (400 MHz, DMSO-d$_6$) δ 11.08 (s, 1H), 8.69 (s, 1H), 8.58 (s, 1H), 7.93 (d, J=8 Hz, 1H), 7.40 (d, J=8 Hz, 1H), 7.24 (s, 1H), 5.28 (m, 1H), 2.13 (m, 2H), 2.03 (m, 2H), 1.91 (m, 2H), 1.72 (m, 2H).

Example 64

3-(1-Cyclopentyl-1H-pyrazolo[3,4-d]pyrimidin-4-yl)-2-oxo-2,3-dihydro-1H-indole-7-carbonitrile

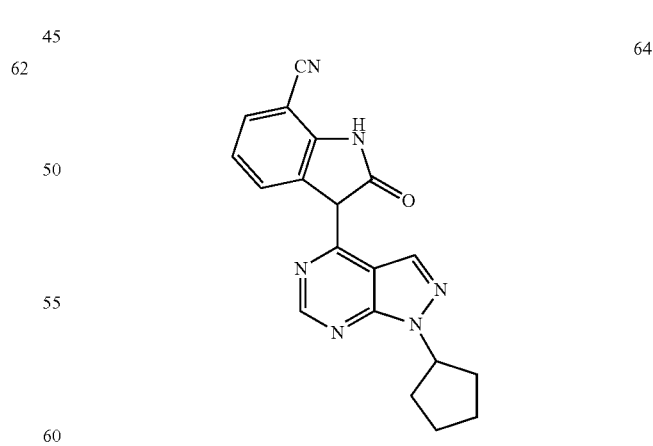

Using the procedure outlined for 54, 7-cyanooxindole (Combi-Blocks, 80 mg, 0.505 mmol) and Compound 25 (111 mg, 0.5 mmol) were refluxed overnight affording 47 mg (27%) of orange solid. Example 64: mp 327-332° C.; MS (ES$^+$ calculated: 344.38; found: 345.18 M+H). HPLC (95%) purity, retention time 13.114 minutes—Method B); $^1$H NMR (400 MHz, DMSO-d$_6$) δ 14.58 (br s, 1H), 11.65 (s, 1H), 8.68 (s, 1H), 8.55 (s, 1H), 8.08 (d, J=8 Hz, 1H), 7.39 (d, J=8 Hz, 1H), 7.15 (t, J=8 Hz, 1H), 5.28 (m, 1H), 2.13 (m, 2H), 2.02 (m, 2H), 1.91 (m, 2H), 1.72 (m, 2H).

Example 65

3-(1-Cyclopentyl-1H-pyrazolo[3,4-d]pyrimidin-4-yl)-5-fluoro-1,3-dihydro-indol-2-one

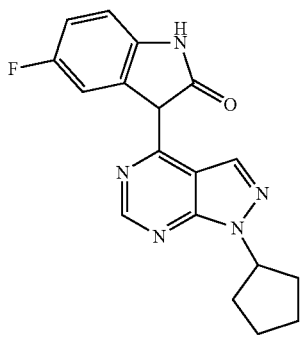

65

Using the procedure outlined for 54, 5-fluorooxindole (Combi-Blocks, 76 mg, 0.503 mmol) and Compound 25 (111 mg, 0.5 mmol) were refluxed overnight affording 25 mg (15%) of orange-yellow solid. Example 65: mp 254-257° C.; MS (ES$^+$ calculated: 337.36; found: 338.21 M+H). HPLC (80%) purity, retention time 13.366 minutes—Method B); $^1$H NMR (400 MHz, DMSO-d$_6$) δ 10.77 (s, 1H), 8.57 (s, 1H), 8.49 (s, 1H), 8.05 (s, 1H), 7.48 (d, J=10 Hz, 1H), 6.88 (d, J=10 Hz, 1H), 5.26 (m, 1H), 2.12 (m, 2H), 2.02 (m, 2H), 1.91 (m, 2H), 1.72 (m, 2H).

Example 66

3-(1-Cyclopentyl-1H-pyrazolo[3,4-d]pyrimidin-4-yl)-6-fluoro-1,3-dihydro-indol-2-one

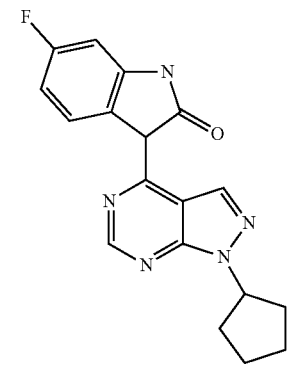

66

Using the procedure outlined for 54, 6-fluorooxindole (Combi-Blocks, 76 mg, 0.503 mmol) and Compound 25 (111 mg, 0.5 mmol) were refluxed overnight affording 42 mg (25%) of orange-yellow solid. Example 66: mp 230-233° C.; MS (ES$^+$ calculated: 337.36; found: 338.24 M+H). HPLC (77%) purity, retention time 13.591 minutes—Method B); $^1$H NMR (400 MHz, DMSO-d$_6$) δ 10.87 (s, 1H), 8.59 (s, 1H), 8.44 (s, 1H), 7.77 (dd, J=5,8 Hz, 1H), 6.81 (t, J=9 Hz, 1H), 6.74 (d, J=9 Hz, 1H), 5.24 (m, 1H), 2.11 (m, 2H), 2.01 (m, 2H), 1.90 (m, 2H), 1.70 (m, 2H).

Example 67

3-(1-Cyclopentyl-1H-pyrazolo[3,4-d]pyrimidin-4-yl)-4,5-difluoro-1,3-dihydro-indol-2-one

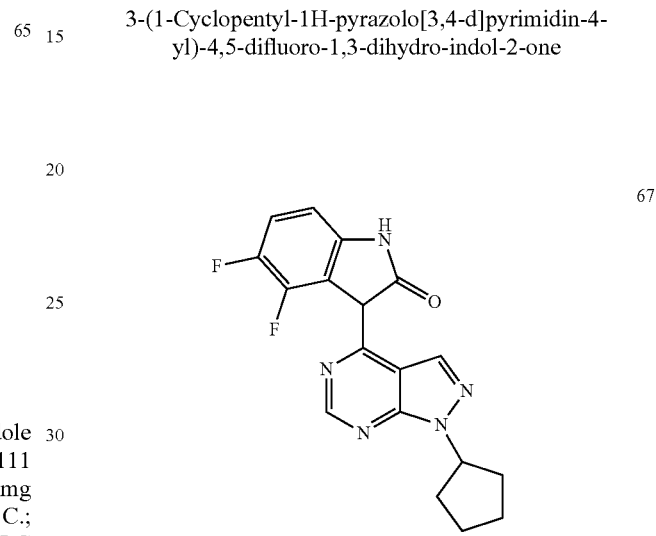

67

Using the procedure outlined for 54, 4,5-difluorooxindole (Combi-Blocks, 85 mg, 0.503 mmol) and Compound 25 (111 mg, 0.5 mmol) were refluxed overnight affording 27 mg (15%) of yellow solid. Example 67: mp>300° C.; MS (ES$^+$ calculated: 355.35; found: 356.20 M+H). HPLC (90%) purity, retention time 13.323 minutes—Method B); $^1$H $^1$H NMR (400 MHz, DMSO-d$_6$) δ 10.87 (br s, 1H), 8.49 (s, 1H), 8.16 (d, J=8 Hz, 1H), 7.03 (m, 1H), 6.7 (m, 1H), 5.22 (m, 1H), 2.09 (m, 2H), 2.00 (m, 2H), 1.89 (m, 2H), 1.70 (m, 2H).

Example 68

3-(1-Cyclohexyl-1H-pyrazolo [3,4-de]pyrimidin-4-yl)-2-oxo-2,3-dihydro-1H-indole-5-carbonitrile

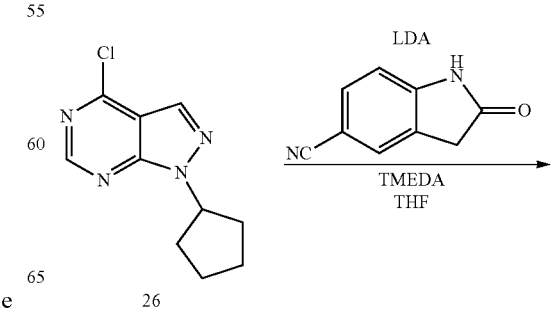

26

-continued

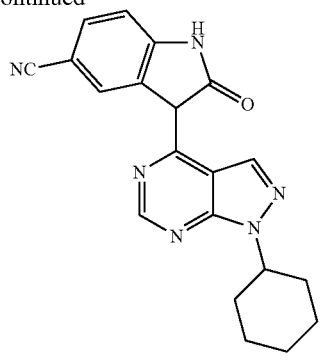

68

To 5-cyanooxindole (Combi-Blocks, 67 mg, 0.424 mmol) and N,N,N',N'-tetramethylethylenediamine (Acros, 0.128 mL, 0.848 mmol) in 5 mL anhydrous THF under argon at −78° C. was added lithium diisopropylamine (Acros, 0.424 mL of a 2.0M solution in THF/heptane, 0.848 mmol). The solution was stirred for fifteen minutes at which point a solution of Compound 26 (100 mg, 0.424 mmol) was added as a solid. The reaction was stirred for ten minutes, external cooling was removed, and the reaction was permitted to warm to room temperature. An oil bath was applied and the mixture was refluxed overnight. The reaction was concentrated. The residue was dissolved in dichloromethane and applied to flash chromatography on silica gel (gradient elution: 1-3% methanol: dichloromethane). Fractions determined to contain 68 by LC/MS were concentrated and the resulting solid was triturated in methanol and filtered. The solid was dried in vacuo to afford 60 mg (39%) of a yellow solid. Example 68: mp>300° C.; MS (ES⁺ calculated: 358.41; found: 359.19 M+H). HPLC (96%) purity, retention time 5.275 minutes—Method C); ¹H NMR (400 MHz, DMSO-d₆) δ 14.53 (br s, 1H), 11.23 (br s, 1H), 8.69 (s, 1H), 8.54 (s, 1H), 8.02 (s, 1H), 7.48 (d, J=9 Hz, 1H), 7.07 (d, J=8 Hz, 1H), 4.71 (m, 1H), 1.94 (m, 6H), 1.72 (m, 1H), 1.48 (m, 2H), 1.28 (m, 1H).

Example 69

3-(1-Cyclohexyl-1H-pyrazolo[3,4-d]pyrimidin-4-yl)-2-oxo-2,3-dihydro-1H-indole-6-carbonitrile

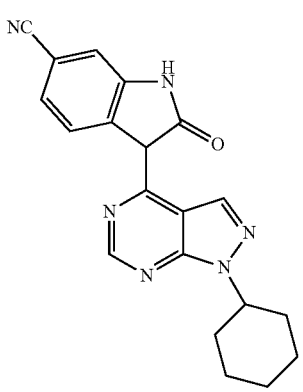

69

Using the procedure outlined for 68, 6-cyanooxindole (Combi-Blocks, 67 mg, 0.424 mmol) and Compound 26 (100 mg, 0.424 mmol) were refluxed overnight affording 30 mg (20%) of dark yellow solid. Example 69: mp>300° C.; MS (ES⁺ calculated: 358.41; found: 359.22 M+H). HPLC (98%) purity, retention time 5.526 minutes—Method C); ¹H NMR (400 MHz, DMSO-d₆) δ 14.77 (br s, 1H), 11.08 (s, 1H), 8.69 (s, 1H), 8.59 (s, 1H), 7.94 (d, J=8 Hz, 1H), 7.41 (d, J=7 Hz, 1H), 7.24 (s, 1H), 4.73 (m, 1H), 1.91 (m, 6H), 1.71 (m, 1H), 1.48 (m, 2H), 1.29 (m, 1H).

Example 70

3-(1-Cyclohexyl-1H-pyrazolo[3,4-d]pyrimidin-4-yl)-2-oxo-2,3-dihydro-1H-indole-7-carbonitrile

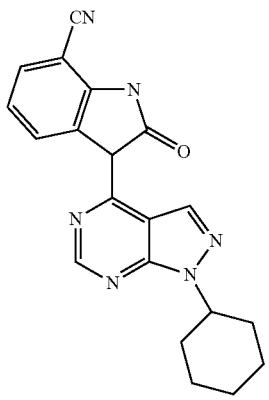

70

Using the procedure outlined for 68, 7-cyanooxindole (Combi-Blocks, 67 mg, 0.424 mmol) and Compound 26 (100 mg, 0.424 mmol) were refluxed overnight affording 27 mg (18%) of yellow solid. Example 70: mp>300° C.; MS (ES⁺ calculated: 358.41; found: 359.28 M+H). HPLC (96%) purity, retention time 5.814 minutes—Method C); ¹H NMR (400 MHz, DMSO-d₆) δ 14.58 (br s, 1H), 11.65 (s, 1H), 8.67 (s, 1H), 8.55 (s, 1H), 8.08 (d, J=8 Hz, 1 Hz), 7.39 (d, J=8 Hz, 1H), 7.15 (t, J=8 Hz), 4.71 (m, 1H), 1.91 (m, 6H), 1.71 (m, 1H), 1.47 (m, 2H), 1.29 (m, 1H).

Example 71

3-(1-Cyclohexyl-1H-pyrazolo[3,4-d]pyrimidin-4-yl)-5-trifluoromethyl-1,3-dihydro-indol-2-one

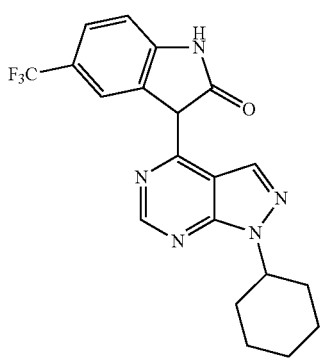

71

Using the procedure outlined for 68, 5-trifluoromethyloxindole (Combi-Blocks, 85 mg, 0.424 mmol) and Compound 26 (100 mg, 0.424 mmol) were refluxed overnight affording 45 mg (26%) of bright yellow solid. Example 71: mp>300° C.; MS (ES+ calculated: 401.39; found: 402.25 M+H). HPLC (93%) purity, retention time 6.578 minutes—Method C); $^1$H NMR (400 MHz, DMSO-$d_6$) δ 14.46 (br s, 1H), 11.13 (s, 1H), 8.53 (s, 1H), 8.44 (s, 1H), 7.93 (s, 1H), 7.40 (d, J=8 Hz, 1H), 7.11 (d, J=8 Hz, 1H), 4.72 (m, 1H), 1.92 (m, 6H), 1.71 (m, 1H), 1.48 (m, 2H), 1.31 (m, 1H).

Example 72

3-(1-Cyclohexyl-1H-pyrazolo[3,4-d]pyrimidin-4-yl)-5-fluoro-1,3-dihydro-indol-2-one

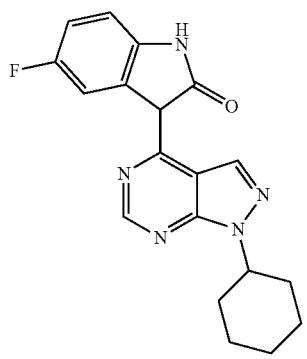

72

Using the procedure outlined for 68, 5-fluorooxindole (Combi-Blocks, 64 mg, 0.424 mmol) and Compound 26 (100 mg, 0.424 mmol) were refluxed overnight affording 50 mg (34%) of yellow solid. Example 72: mp 282-286° C.; MS (ES+ calculated: 351.39; found: 352.21 M+H). HPLC (98%) purity, retention time 5.780 minutes—Method C); $^1$H NMR (400 MHz, DMSO-$d_6$) δ 14.75 (br s, 1H), 1077 (s, 1H), 8.57 (s, 1H), 8.49 (s, 1H), 7.49 (d, J=10 Hz, 1H), 6.89 (m, 2H), 4.70 (m, 1H), 1.90 (m, 6H), 1.71 (m, 1H), 1.47 (m, 2H), 1.29 (m, 1H).

Example 73

3-(1-Cyclohexyl-1H-pyrazolo[3,4-d]pyrimidin-4-yl)-6-fluoro-1,3-dihydro-indol-2-one

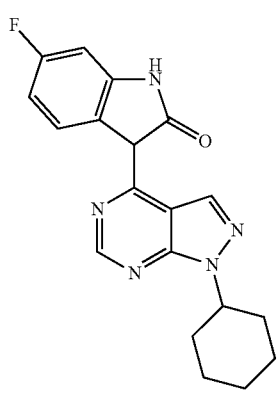

73

Using the procedure outlined for 68, 6-fluorooxindole (Combi-Blocks, 64 mg, 0.424 mmol) and Compound 26 (100 mg, 0.424 mmol) were refluxed overnight affording 15 mg (10%) of bright yellow solid. Example 73: mp 277-280° C.; MS (ES+ calculated: 351.39; found: 352.18 M+H). HPLC (94%) purity, retention time 5.820 minutes—Method C); $^1$H NMR (400 MHz, DMSO-$d_6$) δ 14.54 (br s, 1H), 10.87 (s, 1H), 8.59 (s, 1H), 8.44 (s, 1H), 7.78 (dd, J=5,8 Hz, 1H), 6.81 (m, 1H), 6.74 (m, 1H), 4.68 (m, 1H), 1.91 (m, 6H), 1.71 (m, 1H), 1.49 (m, 2H), 1.28 (m, 1H).

Example 74

5-Chloro-3-(1-Cyclohexyl-1H-pyrazolo[3,4-d]pyrimidin-4-yl)-1,3-dihydro-indol-2-one

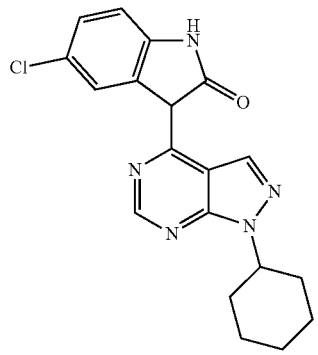

74

Using the procedure outlined for 68, 5-chlorooxindole (Aldrich, 70.4 mg, 0.424 mmol) and Compound 26 (100 mg, 0.424 mmol) were refluxed overnight affording 21 mg (13%) of yellow solid. Example 74: mp 300-305° C.; MS (ES+ calculated: 367.84; found: 368.33 M+H). HPLC (97%) purity, retention time 15.299 minutes—Method B); $^1$H NMR (400 MHz, DMSO-$d_6$) δ 10.86 (br s, 1H), 8.49 (s, 1H), 8.48 (s, 1H), 7.66 (s, 1H), 7.07 (d, J=8 Hz, 1H), 6.93 (d, J=8 Hz, 1H), 4.70 (m, 1H), 1.93-1.28 (m, 10H).

Example 75

5-Bromo-3-(1-Cyclohexyl-1H-pyrazolo[3,4-d]pyrimidin-4-yl)-1,3-dihydro-indol-2-one

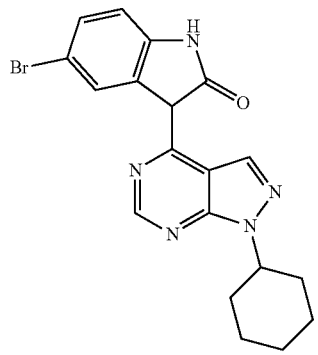

75

Using the procedure outlined for 68, 5-bromooxindole (Combi-Blocks, 89 mg, 0.424 mmol) and Compound 26 (100 mg, 0.424 mmol) were refluxed overnight affording 50 mg (29%) of yellow solid. Example 75: mp 305-308° C.; MS (ES+ calculated: 412.29; found: 412.51, 413.84 M+H). HPLC (96%) purity, retention time 15.590 minutes—Method B); $^1$H NMR (400 MHz, DMSO-$d_6$) δ 10.87 (br s, 1H), 8.50 (s, 1H), 8.45 (s, 1H), 7.78 (s, 1H), 7.20 (d, J=8 Hz, 1H), 6.90 (d, J=8 Hz, 1H), 4.70 (m, 1H), 2.08-1.25 (m, 10H).

Example 76

3-(2-Allyl-2H-pyrazolo[3,4-d]pyrimidin-4-yl)-2-oxo-2,3-dihydro-1H-indole-5-carbonitrile In a similar fashion as for the preparation of 45 above, 5-cyanooxindole (Combiblocks, 60 mg, 0.38 mmol) was reacted with Compound 24 (77 mg, 0.40 mmol). The reaction was concentrated and the crude product was triturated successively with methanol and water. A yellow-orange solid was obtained which was dried in vacuo. Yield: 67 mg (56%). Example 76: mp>300° C.; MS (ES+ calculated: 316.32; found: 317.09 M+H). HPLC (95%) purity, retention time 9.183 minutes—Method B); $^1$H NMR (400 MHz, DMSO-$d_6$) δ 13.14 (br s), 11.27 (s), 10.81 (br s), 10.63 (br s), 9,54 (s), 9.14 (s), 8.77 (br s), 8.40 (s), 8.19 (m), 7.97 (s, 1H), 7.51 (d, J=9 Hz), 7.42 (m), 7.07 (d, J=8 Hz), 6.94 (m), 6.10 (m 1H), 5.29 (m, 2H), 5.33-4.94 (m, 2H).

Compound 77

2-Cyclopentyl-2,7-dihydro-pyrazolo[3,4-d]pyrimidine-4,6-dione

Compound 12 (1 g, 5.15 mmol) was mixed with urea (Fisher, 3 g, 50 mmol) and fused at 200° C. for ninety minutes. The solution was allowed to cool briefly and 10 mL water was added. The solution was boiled for one hour. The white solid present was removed by filtration and was determined to contain additional urea. The solid was recombined with 20 mL water and resubjected to boiling for an additional hour. On cooling and filtration, a white solid was obtained which was dried in vacuo. Yield: 837 mg, (74%). Compound 77: mp>300° C.; MS (ES+ calculated: 220.23; found: 221.17 M+H). HPLC (92%) purity, retention time 5.112 minutes—Method B); $^1$H NMR (400 MHz, DMSO-$d_6$) δ 11.30 (br s, 1H), 10.63 (br s, 1H), 8.37 (s, 1H), 4.69 (m, 1H), 2.06 (m, 2H), 1.92 (m, 2H), 1.77 (m, 2H), 1.63 (m, 2H).

Scheme 2

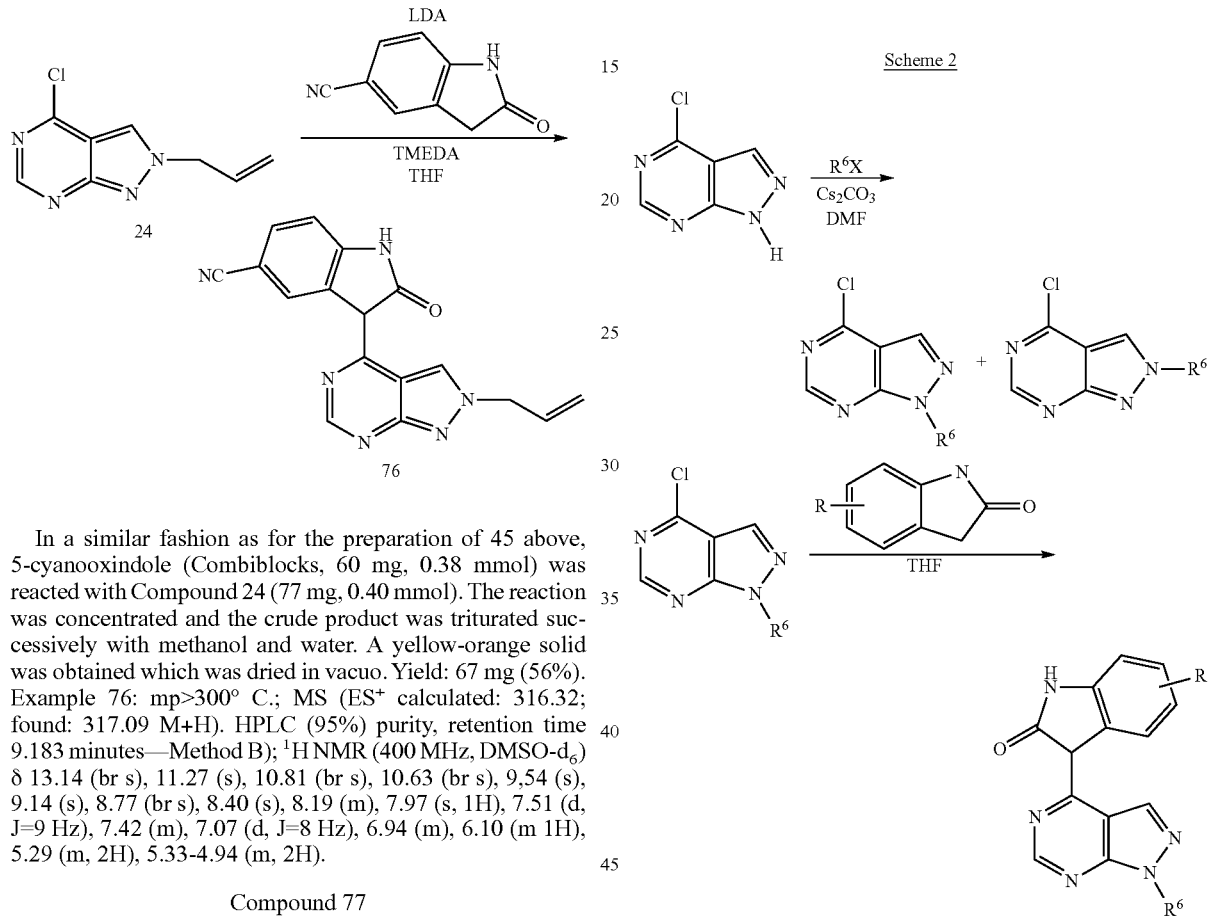

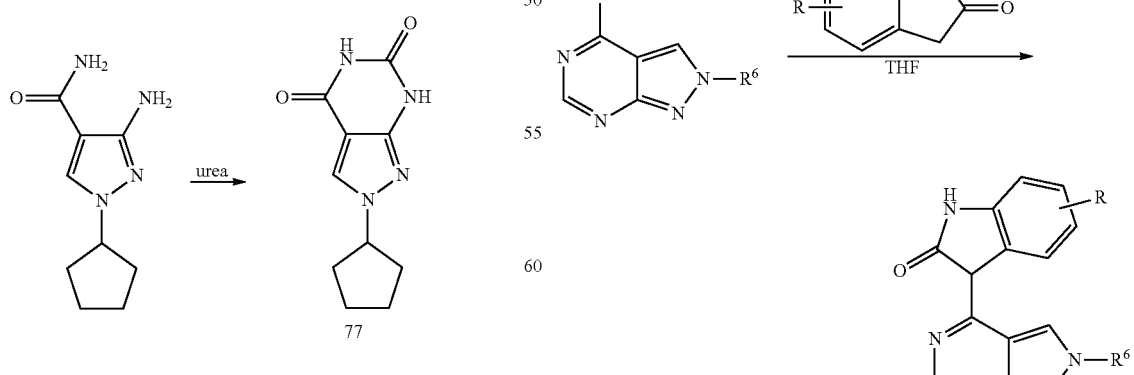

Compound 79

4-Chloro-1H-pyrazolo[3,4-d]pyrimidine

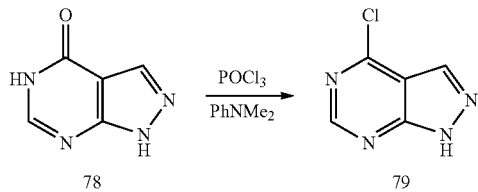

To a mixture of commercially available 4-hydroxypyrazolo[3,4-d]pyrimidine (78) (Acros, 14.5 g, 106.5 mmol) stirred in POCl$_3$ (375 mL) was added N,N-dimethylaniline (21 mL). The mixture was refluxed for 1.5 h. After cooling, excess POCl$_3$ was removed by rotarty evaporation and pumped on high vacuum before pouring over 500 mL ice while stirring. The mixture was stirred for 10 min before extracting with ethyl ether (6×250 mL). The combined organic layer was washed with ice water (3×100 mL) and dried over MgSO$_4$ and filtered. The ethyl ether was stripped and the resulting pale yellow solid (10 g, 61%) was pumped on high vacuum overnight. Compound 79: mp>300° C., dec. 125° C.; MS (ES$^+$ calculated: 154.56; found: 156.21 M+H). HPLC (98% purity, retention time 6.033 minutes—method D) $^1$H NMR (400 MHz, DMSO-d$_6$) δ 14.55 (bs, 1H), 8.84 (s, 1H), 8.46 (s, 1H).

Compound 80

4-Chloro-2-methyl-2H-pyrazolo[3,4-d]pyrimidine

Compound 81

4-Chloro-1-methyl-2H-pyrazolo[3,4-d]pyrimidine

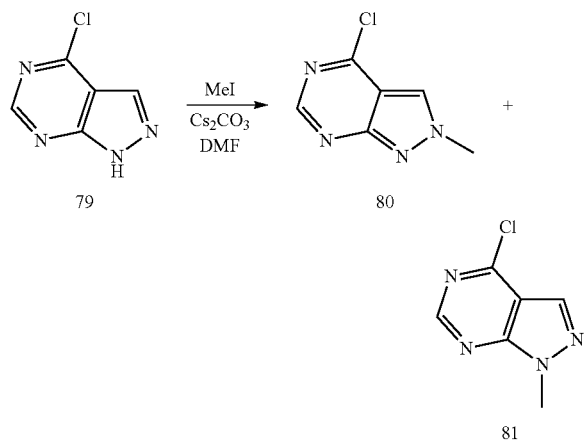

Cesium carbonate (Acros, 2.12 g, 6.51 mmol) was added to compound 79 (1.00 g, 5.9 mmol) in N,N-dimethylformamide (Acros, 30 mL) at 0° C. followed immediately by methyl iodide (Acros, 1.01 g, 7.1 mmol). The mixture was stirred for three hours. Cesium carbonate was removed by filtration and the filter cake was washed with a small amount of DMF. The filtrate and washings were concentrated and the reaction mixture was subjected to flash chromatography on silica gel (gradient elution 9:1 to 4:1 to 0:1 dichloromethane:ethyl acetate) to afford two white solids: Compound 80 (220 mg, 22%) elutes second and Compound 81 (663 mg, 67%) elutes first. Compound 80: mp 196-200° C.; MS (ES$^+$ calculated: 168.59; found: 169.57 M+H). HPLC (100% purity, retention time 4.627 minutes—Method B); $^1$H NMR (300 MHz, DMSO-d$^6$): 8.91 (s, 1H), 8.90 (s, 1H), 4.25 (s, 3H). Compound 81: mp 97-99° C.; MS (ES$^+$ calculated: 168.59; found: 169.37 M+H). HPLC (100% purity, retention time 6.582 minutes—Method B); $^1$H NMR (400 MHz, DMSO-d$_6$) δ 8.98 (s, 1H), 8.48 (s, 1H), 4.09 (s, 3H).

Example 82

5-Bromo-3-(2-methyl-2H-pyrazolo[3,4-d]pyrimidin-4-yl)-1,3-dihydro-indol-2-one

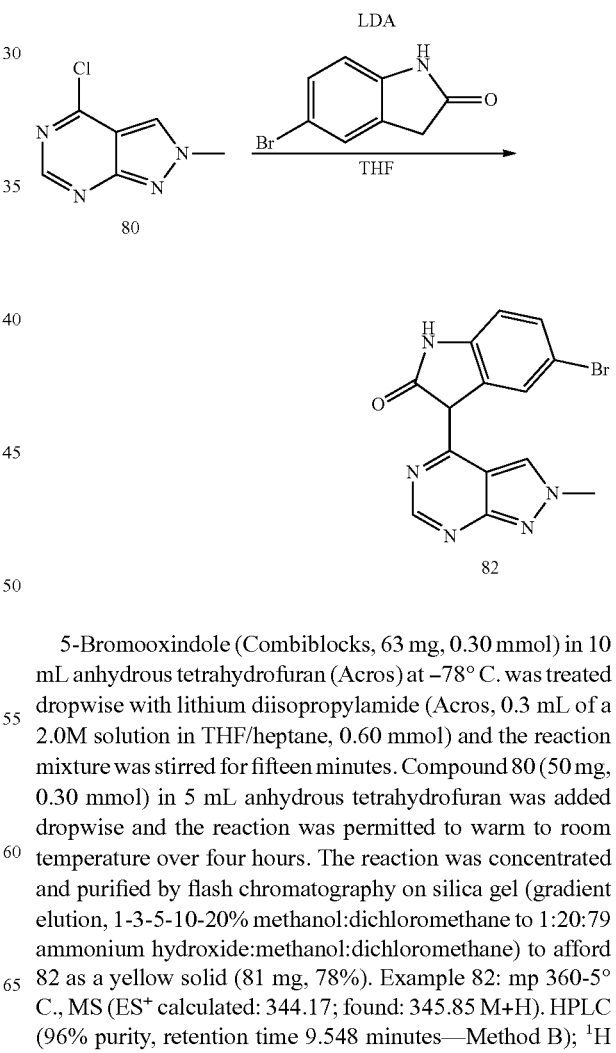

5-Bromooxindole (Combiblocks, 63 mg, 0.30 mmol) in 10 mL anhydrous tetrahydrofuran (Acros) at −78° C. was treated dropwise with lithium diisopropylamide (Acros, 0.3 mL of a 2.0M solution in THF/heptane, 0.60 mmol) and the reaction mixture was stirred for fifteen minutes. Compound 80 (50 mg, 0.30 mmol) in 5 mL anhydrous tetrahydrofuran was added dropwise and the reaction was permitted to warm to room temperature over four hours. The reaction was concentrated and purified by flash chromatography on silica gel (gradient elution, 1-3-5-10-20% methanol:dichloromethane to 1:20:79 ammonium hydroxide:methanol:dichloromethane) to afford 82 as a yellow solid (81 mg, 78%). Example 82: mp 360-5° C., MS (ES$^+$ calculated: 344.17; found: 345.85 M+H). HPLC (96% purity, retention time 9.548 minutes—Method B); $^1$H NMR (400 MHz, DMSO-d$_6$) δ 10.90 (s), 9.48 (s), 8.89 (s), 8.34 (s), 7.74 (s), 7.22 (d, J=8 Hz), 6.89 (d, J=8 Hz), 4.17 (s, 3H).

Example 83

5-Chloro-3-(2-methyl-2H-pyrazolo[3,4-d]pyrimidin-4-yl)-1,3-dihydro-indol-2-one

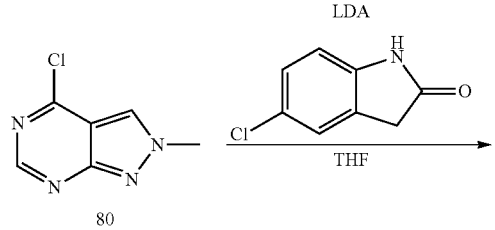

Preparation of Example 83: In an identical fashion as for the synthesis of Example 82, Example 83 was prepared as a yellow solid from compound 80 in quantitative yield. Example 83: mp 341-4° C., MS (ES$^+$ calculated: 299.72; found: 300.16 M+H). HPLC (100% purity, retention time 9.323 minutes—Method B); $^1$H NMR (400 MHz, DMSO-d$_6$) δ 10.89 (s), 9.48 (s), 8.93 (s), 8.34 (s), 7.64 (s), 7.09 (d, J=8 Hz), 6.93 (d, J=8 Hz), 4.17 (s, 3H).

Example 84

3-(2-Methyl-2H-pyrazolo [3,4-d]pyrimidin-4-yl)-2-oxo-2,3-dihydro-1H-indole-5-carbonitrile

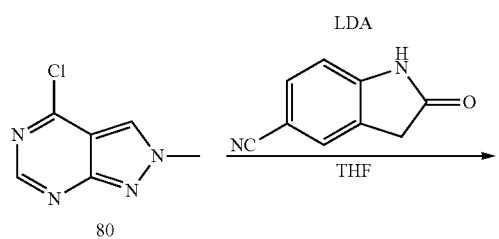

-continued

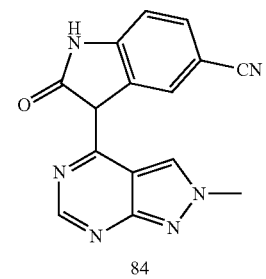

In an identical fashion as for the synthesis of Example 82, Example 84 was prepared as a yellow solid from compound 80 in 50% yield. Example 84: mp>350° C., MS (ES$^+$ calculated: 290.29; found: 291.07 M+H). HPLC (100% purity, retention time 7.467 minutes—Method B); $^1$H NMR (400 MHz, DMSO-d$_6$) δ 11.27 (s), 9.49 (s), 9.11 (s), 8.39 (s), 7.99 (s), 7.50 (d, J=8 Hz), 7.08 (d, J=8 Hz), 4.19 (s, 3H).

Example 85

5-Bromo-3-(1-methyl-1H-pyrazolo[3,4-d]pyrimidin-4-yl)-1,3-dihydro-indol-2-one

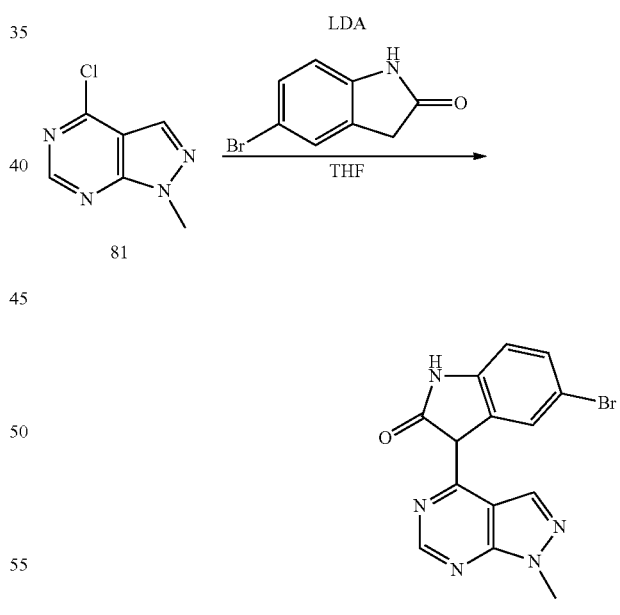

In an identical fashion as for the synthesis of 82, Example 85 was prepared as a yellow solid from compound 81 in 20% yield. Example 85: mp>350° C., MS (ES$^+$ calculated: 344.17; found: 345.86 M+H). HPLC (95% purity, retention time 11.124 minutes—Method B); $^1$H NMR (400 MHz, DMSOd$_6$) δ 10.91 (s), 8.51 (s), 8.43 (s), 7.77 (s), 7.20 (d, J=8 Hz), 6.90 (d, J=8 Hz), 3.99 (s, 3H), 3.93 (s). -

Example 86

5-Chloro-3-(1-methyl-1H-pyrazolo[3,4-d]pyrimidin-4-yl)-1,3-dihydro-indol-2-one

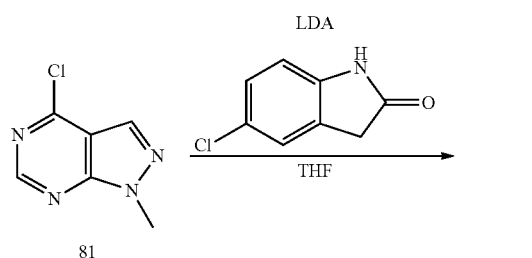

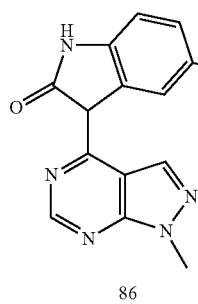

In an identical fashion as for the synthesis of 82, Example 86 was prepared as a yellow solid from compound 81 in 49% yield. Example 86: mp>320° C., MS (ES+ calculated: 299.72; found: 300.09 M+H). HPLC (99% purity, retention time 10.772 minutes—Method B); $^1$H NMR (400 MHz, DMSO-d$_6$) δ 10.90 (s), 8.52 (s), 8.47 (s), 7.65 (s), 7.08 (d, J=8 Hz), 6.94 (d, J=8 Hz), 3.99 (s, 3H), 3.93 (s).

Compound 87 and 88

2-(propyl-3-azido)-4-Chloro-2H-pyrazolo[3,4-d]pyrimidine 1-(propyl-3-azido)-4-Chloro-1H-pyrazolo[3,4-d]pyrimidine

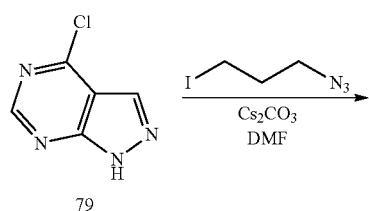

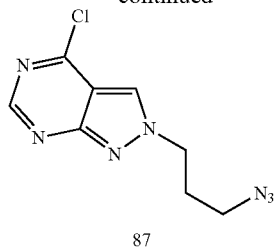

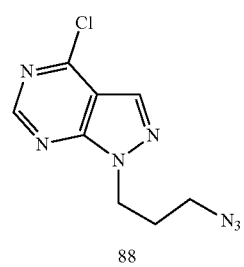

In an identical fashion as for the alkylation of 79 with iodomethane, Compound 87 and Compound 88 were prepared as yellow solids in 10% and 40% yields, respectively. Compound 87: MS (ES+ calculated: 237.65; found: 238.29 M+H). HPLC (100% purity, retention time 7.76 minutes—Method B); $^1$H NMR (300 MHz, DMSO-d$^6$): 8.84 (s, 1H), 8.31 (s, 1H), 4.64 (t, J=7 Hz, 2H), 3.42 (t, J=7 Hz, 2H), 2.35 (t, J=7 Hz, 2H). Compound 88: MS (ES+ calculated: 237.65; found: 238.02 M+H). HPLC (99% purity, retention time 10.002 minutes—Method B); $^1$H NMR (400 MHz, DMSO-d$_6$) δ 8.88 (s, 1H), 8.51 (s, 1H), 4.55 (t, J=7 Hz, 2H), 3.38 (t, J=7 Hz, 2H), 2.13 (t, J=7 Hz, 2H).

Example 89

3-[2-(3-azido-propyl)-2H-pyrazolo[3,4-d]pyrimidin-4-yl]-5-bromo-1,3-dihydro-indol-2-one

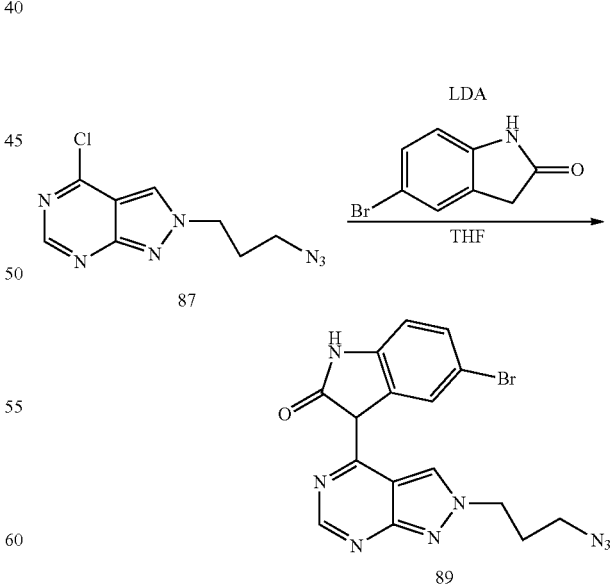

In an identical fashion as for the preparation of Example 82, Compound 87 was alkylated to produce Example 89 in 91% yield. Compound 89: mp 252-6° C., MS (ES+ calculated: 413.24; found: 414.87 M+H). HPLC (97% purity, retention time 11.337 minutes—Method B); $^1$H NMR (400 MHz, DMSO-d$_6$) δ 0.90 (s), 9.53 (s), 8.93 (s), 8.34 (s), 7.75 (s), 7.22 (d, J=8 Hz, 1H), 6.89 (d, J=8 Hz, 1H), 4.53-4.38 (m, 2H), 3.44-3.38 (m, 2H), 2.17-2.11 (m, 2H).

Example 90

3-[2-(3-methylamino-propyl)-2H-pyrazolo[3,4-d]pyrimidin-4-yl]-5-bromo-1,3-dihydro-indol-2-one

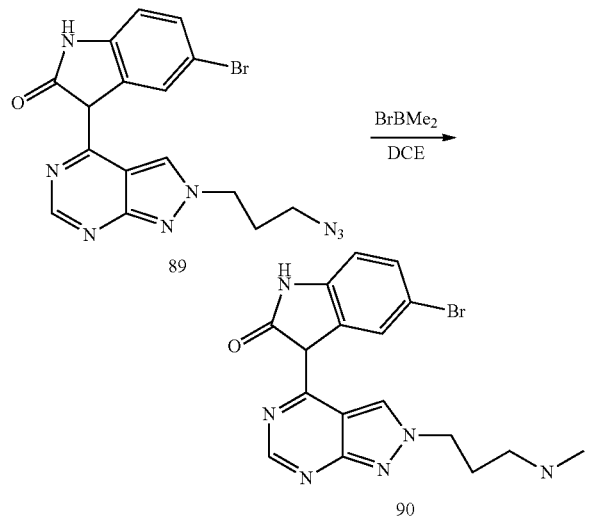

Example 89 (20 mg, 48.4 μmol) was suspended in 5 mL anhydrous 1,2-dichloroethane (Acros) and treated with bromodimethylborane (Acros, 5 μL, 50 μmol). The mixture was stirred overnight. Additional bromodimethylborane (in 50 μmol aliquots) was added on three occasions over three days with a drop of N-methylpyrrolidinone (Acros, anhydrous) being added on each occasion to promote solubility. The reaction was concentrated and ethanol was added (5 mL). The reaction was stirred ten minutes and reconcentrated. The solid was taken up into a small amount of methanol (approximately 1-2 mL) and dichloromethane was added to turbidity. The solution was allowed to sit for several hours and a yellow solid was isolated by filtration. The solid was washed with a small amount of anhydrous dichloromethane and was dried in vacuo. Yield: 12 mg (51%) of the hydrobromide salt. Example 90: mp 240-3° C., MS (ES$^+$ calculated: 401.27; found: 402.90 M+H). HPLC (87% purity, retention time 8.813 minutes—Method A); $^1$H NMR (400 MHz, DMSO-d$_6$) δ 10.92 (s), 9.537 (s), 8.92 (s), 8.36 (s), 7.75 (s), 7.23 (m), 7.14 (m), 6.90 (m), 6.77 (m), 4.55-4.42 (m), 2.92 (m), 2.51 (m), 2.32-2.18 (m).

Compound 91 and 92

4-Chloro-1-propyl-1H-pyrazolo [3,4-d]pyrimidine

4-Chloro-2-propyl-1H-pyrazolo [3,4-d]pyrimidine

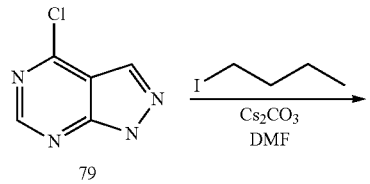

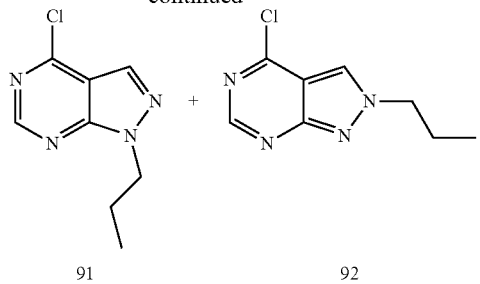

Cs$_2$CO$_3$ was added to a solution of 79 (2.0 g, 13 mmol) in 60 mL anhydrous DMF at 0° C. 1-Iodopropane (Acros, 1.52 mL, 15.6 mmol) was added to the suspension and allowed to stir for 3.5 h at 0° C. The reaction mixture was filtered and the solid was washed with dichloromethane. The filtrate was concentrated to dryness and the residue was dissolved in 9:1 hex/EtOAc and applied to flash chromatography on silica gel (gradient elution: 9:1, 4:1, 0:1 hexane:ethylacetate). Fractions determined to contain 91 and 92 by LC/MS were concentrated to afford 830 mg (33%) of clear colorless oil 91 and 296 mg (12%) yellow solid 92. Compound 91: MS (ES$^+$ calculated: 196.64; found: 197.09 M+H). HPLC (100% purity, retention time 10.314 minutes—method D) $^1$H NMR (300 MHz, DMSO-d$^6$): 8.87 (s, 1H), 8.48 (s, 1H), 4.45 (t, J=7 Hz, 2H), 1.91 (m, 2H), 0.85 (t, J=7, 3H). Compound 92: mp 93-95° C.; MS (ES$^+$ calculated: 196.64; found: 197.09 M+H). HPLC (90% purity, retention time 7.931 minutes—method D) $^1$H NMR (400 MHz, DMSO-d$_6$) δ 8.67 (s, 1H), 8.53 (s, 1H), 4.37 (t, J=7, 2H), 1.92 (m, 2H), 0.83 (t, J=7, 3H).

Example 93

3-(1-propyl-1H-pyrazolo[3,4-d]pyrimidin-4-yl)-2-oxo-2,3-dihydro-1H-indole-5-carbonitrile

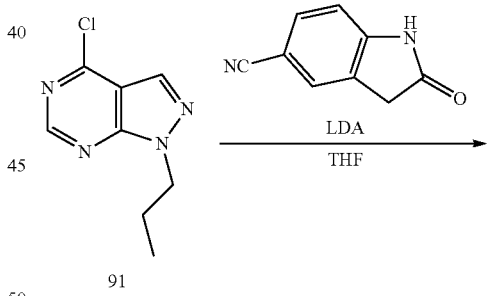

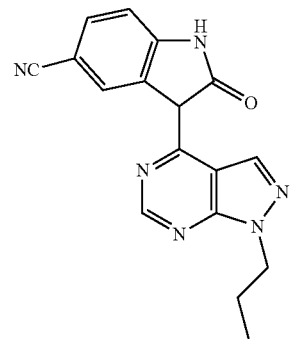

5-cyanooxindole (Combiblocks, 161 mg, 1.02 mmol) in 5 mL anhydrous tetrahydrofuran was stirred under argon. The solution was cooled to −78° C. and lithium diisopropylamide (Acros, 1.02 mL of a 2.0M solution in THF/hexane, 2.04 mmol) was added dropwise. The reaction was stirred for fifteen minutes at which point Compound 91 (200 mg, 1.02 mmol) was added. The reaction was stirred an additional fifteen minutes and was warmed to room temperature over 0.5 hour. The mixture was then stirred overnight at room temperature. The reaction was concentrated and subjected to flash chromatography on silica gel (gradient elution: 1-3-5% methanol: dichloromethane) to afford 30 mg (9%) of a yellow solid after trituration in MeOH. Example 93: mp>300° C.; MS (ES+ calculated: 318.34; found: 319.18 M+H). HPLC (99%) purity, retention time 4.068 minutes—Method C); $^1$H NMR (400 MHz, DMSO-d$_6$) δ 11.25 (s, 1H), 8.71 (s, 1H), 8.55 (s, 1H), 8.02 (s, 1H), 7.48 (d, J=8, 1H), 7.07 (d, J=8, 1H), 4.35 (t, 2H), 1.88 (m, 2H), 0.87 (t, J=7, 3H).

Example 94

5-Bromo-3-(1-propyl-2H-pyrazolo[3,4-d]pyrimidin-4-yl)-1,3-dihydro-indol-2-one

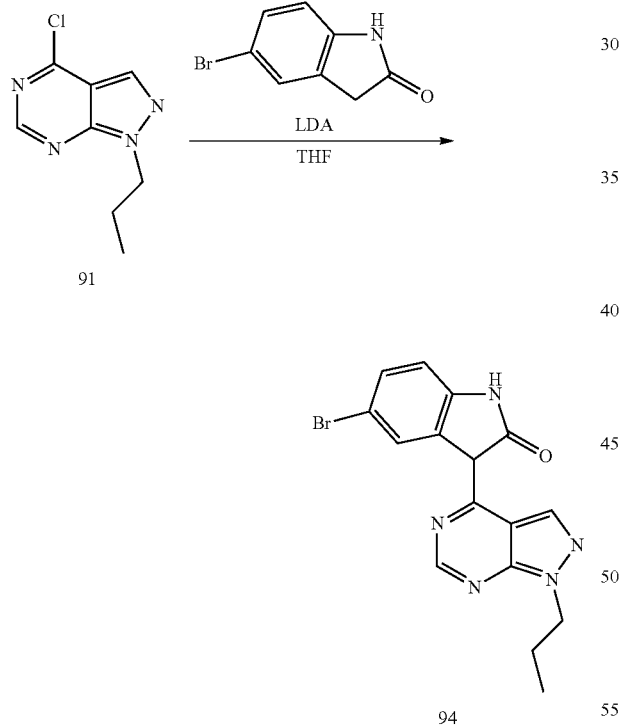

Using the procedure outlined for Example 93, 5-bromooxindole (Combiblocks, 108 mg, 0.51 mmol) and Compound 91 (100 mg, 0.51 mmol) were stirred overnight to afford 86 mg (45%) of a yellow solid. Example 94: mp 295-300° C.; MS (ES+ calculated: 372.23; found: 372.47 M+H). HPLC (99%) purity, retention time 5.243 minutes—Method C); $^1$H NMR (400 MHz, DMSO-d$_6$) δ 14.58 (s), 10.90 (s, 1H), 8.51 (s, 1H), 8.45 (s, 1H), 7.78 (s, 1H), 7.20 (d, 1H), 6.90 (d, J=8, 1H), 4.33 (t, 2H), 1.88 (m, 2H), 0.87 (t, J=7, 3H).

Example 95

5-Chloro-3-(1-propyl-2H-pyrazolo[3,4-d]pyrimidin-4-yl)-1,3-dihydro-indol-2-one

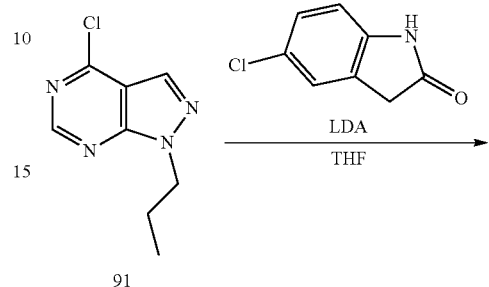

Using the procedure outlined for Example 93, 5-chlorooxindole (Combiblocks, 85.5 mg, 0.51 mmol) and Compound 91 (100 mg, 0.51 mmol) were stirred overnight to afford 62 mg (37%) of a yellow solid. Example 95: mp 293-297° C.; MS (ES+ calculated: 327.78; found: 328.28 M+H). HPLC (99%) purity, retention time 5.056 minutes—Method C); $^1$H NMR (400 MHz, DMSO-d$_6$) δ 14.61 (s), 10.89 (s, 1H), 8.49 (d, J=7, 2H), 7.65 (s, 1H), 7.08 (d, J=8, 1H), 6.93 (d, J=8), 4.33 (t, J=7, 2H), 1.88 (m, 2H), 0.87 (t, J=7, 3H).

Example 96

3-(2-propyl-1H-pyrazolo[3,4-d]pyrimidin-4-yl)-2-oxo-2,3-dihydro-1H-indole-5-carbonitrile

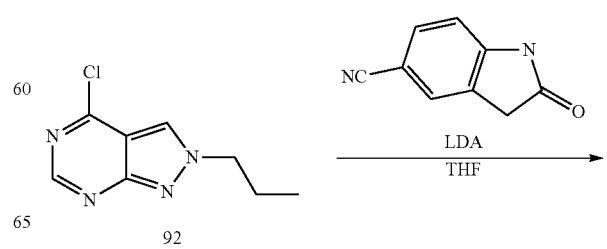

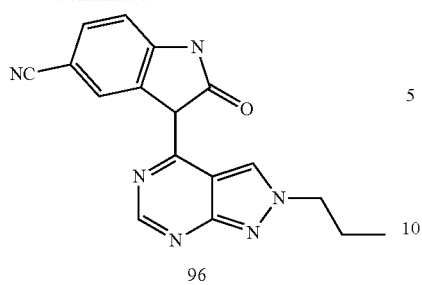

96

5-cyanooxindole (Combiblocks, 40.4 mg, 0.255 mmol) in 1.5 mL anhydrous tetrahydrofuran was stirred under argon. The solution was cooled to −78° C. and lithium diisopropylamide (Acros, 0.255 mL of a 2.0M solution in THF/hexane, 0.51 mmol) was added dropwise. The reaction was stirred for fifteen minutes at which point Compound 92 (50 mg, 0.255 mmol) was added. The reaction was stirred an additional fifteen minutes and was warmed to room temperature over 0.5 hour. The mixture was then stirred overnight at room temperature. The reaction was concentrated and subjected to flash chromatography on silica gel (gradient elution: 1-3-5% methanol: dichloromethane) to afford 18 mg (22%) of a yellow solid after trituration in MeOH. Example 96: mp>300° C.; MS (ES+ calculated: 318.34; found: 319.14 M+H). HPLC (98%) purity, retention time 3.532 minutes—Method C); $^1$H NMR (400 MHz, DMSO-d$_6$) δ 11.25 (s), 9.52 (s), 9.13 (s), 8.40 (s), 7.98 (s), 7.49 (d), 7.09 (d), 4.40 (m), 4.36 (bs), 4.10 (bs), 1.90 (m), 0.88 (m).

Example 97

5-Bromo-3-(2-propyl-2H-pyrazolo[3,4-d]pyrimidin-4-yl)-1,3-dihydro-indol-2-one

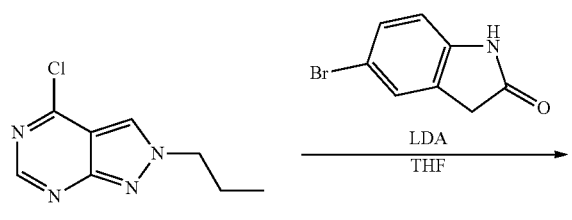

Using the procedure outlined for 96, 5-bromooxindole (Combiblocks, 54 mg, 0.255 mmol) and Compound 92 (50 mg, 0.255 mmol) were stirred overnight to afford 35 mg (37%) of an orange solid. Example 97: mp>300° C.; MS (ES+ calculated: 372.23; found: 373.79 M+H). HPLC (98%) purity, retention time 4.271 minutes—Method C); $^1$H NMR (400 MHz, DMSO-d$_6$) δ 14.09 (s), 10.89 (s), 9.50 (s). 8.90 (s), 8.34 (s), 7.73 (s), 7.23 (d), 6.90 (d), 4.41 (t, J=7), 1.93 (m), 0.86 (m).

Example 98

5-Chloro-3-(2-propyl-2H-pyrazolo[3,4-d]pyrimidin-4-yl)-1,3-dihydro-indol-2-one

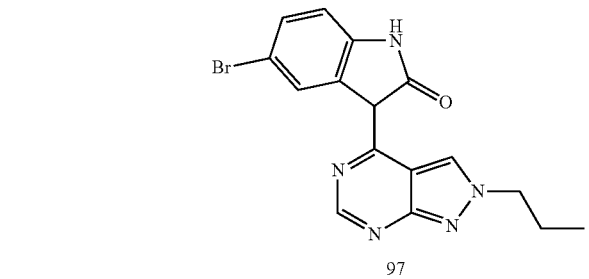

Using the procedure outlined for 96, 5-chlorooxindole (Combiblocks, 42.7 mg, 0.255 mmol) and Compound 92 (50 mg, 0.255 mmol) were stirred overnight to afford 55 mg (66%) of a yellow solid. Example 98: mp 302-306° C.; MS (ES+ calculated: 327.78; found: 328.27 M+H). HPLC (98%) purity, retention time 4.145 minutes—Method C); $^1$H NMR (400 MHz, DMSO-d$_6$) δ 10.88 (s), 9.52 (s), 8.95 (s), 8.35 (s), 7.62 (s), 7.10 (d), 6.95 (d), 4.42 (t, J=7), 1.93 (m), 0.90 (m).

Example 99

3-(1-propyl-2H-pyrazolo[3,4-d]pyrimidin-4-yl)-5-trifluoromethyl-1,3-dihydro-indol-2-one

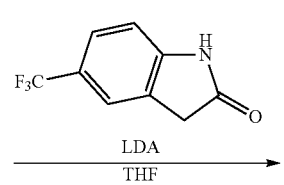

92

Using the procedure outlined for 96, 5-trifluoromethyloxindole (Combiblocks, 36 mg, 0.179 mmol) and Compound 92 (35 mg, 0.179 mmol) were stirred overnight to afford 35 mg (54%) of a white solid. Example 99: mp 293-295° C.; MS (ES+ calculated: 361.33; found: 362.17 M+H). HPLC (98%) purity, retention time 4.145 minutes—Method C); $^1$H NMR (400 MHz, DMSO-$d_6$) δ 11.12 (s), 9.53 (s), 8.85 (s), 8.35 (d), 8.06 (t), 7.87 (s), 7.40 (d), 7.10 (d), 4.23 (m), 1.87 (m), 0.87 (m).

Example 100

3-(1-propyl-2H-pyrazolo[3,4-d]pyrimidin-4-yl)-5-fluoro-1,3-dihydro-indol-2-one

Using the procedure outlined for 96, 5-fluorooxindole (Combiblocks, 27 mg, 0.179 mmol) and compound 92 (35 mg, 0.179 mmol) were stirred overnight to afford 30 mg (54%) of a yellow solid. Example 100: mp 288-292° C.; MS (ES+ calculated: 311.32; found: 312.13 M+H). HPLC (93%) purity, retention time 3.762 minutes—Method C); $^1$H NMR (400 MHz, DMSO-$d_6$) δ 14.32 (s), 10.79 (s), 9.03 (s), 8.34 (s), 7.50 (d, J=10), 6.91 (s), 4.42 (s), 1.92 (s), 0.89 (m).

Compounds 101 and 102

3-Amino-1-propyl-1H-pyrazole-4-carbonitrile

5-Amino-1-propyl-1H-pyrazole-4-carbonitrile

3-Amino-4-pyrazolecarbonitrile 1 (Acros, 3.24 g, 30.0 mmol), propylbromide (Acros, 4.43 g, 36 mmol) and anhydrous potassium carbonate (Fisher, 5.0 g, 36 mmol) were suspended in 20 mL anhydrous DMF and heated at 80° C. in a sealed tube under argon overnight. The reaction was permitted to cool and the DMF was removed on a rotary evaporator. Water was added (100 mL) and the organics were extracted with dichloromethane (3×100 mL). The combined dichloromethane fractions were washed with water (50 mL) and brine (50 mL) and were dried (magnesium sulfate). Concentration of the organics afforded an oil which was subjected to flash chromatography on silica gel (1-3% methanol/dichloromethane). Two white crystals were obtained: compound 101 (1.88 g, 42%) elutes first and compound 102 (711 mg, 16%) elutes second. Compound 101: mp 85-90° C.; MS (ES+ calculated: 150.18; found: 151.15 M+H). HPLC (99%) purity, retention time 5.8 minutes—Method A); $^1$H NMR (400 MHz, DMSO-$d_6$) δ 8.07 (s, 1H), 5.52 (s, 2H), 3.82 (t, J=7, 2H), 1.70 (m, 2H), 0.79 (t, J=7, 3H). Compound 102: mp 162-164° C.; MS (ES+ calculated: 150.18; found: 151.18 M+H). HPLC (95%) purity, retention time 6.4 minutes—Method A); $^1$H$^1$H NMR (400 MHz, DMSO-$d_6$) δ 7.51 (s, 1H), 6.53 (s, 2H), 3.82 (t, J=7, 2H), 2.95 (m, 2H), 0.81 (t, J=7, 3H).

Compound 103

3-Amino-1-propyl-1H-pyrazole-4-carboxylic acid amide

To concentrated sulfuric acid (Fisher, 1.5 mL) at 0° C. was added 101 (931 mg, 6.21 mmol). The reaction was permitted to warm to room temperature and was stirred for three hours. At the end of this period all solid had dissolved. This viscous mixture was then added slowly (violent) to 15 mL concentrated ammonium hydroxide solution (Fisher). The mixture was stirred for ten minutes and the white solid that formed was collected by filtration, was washed with water, and was dried in vacuo. The filtrate was also concentrated, triturated in water and filtered. Both white crystal solids were compound 103. Yield: 850 mg (82%). Compound 103: mp 160-163° C.; MS (ES+ calculated: 168.20; found: 169.31 M+H). HPLC (99% purity, retention time 5.358 minutes—Method D); $^1$H NMR (400 MHz, DMSO-$d_6$) δ 7.86 (s, 1H), 7.18 (bs, 1H), 6.70 (bs, 1H), 5.33 (s, 2H), 3.78 (t, J=7, 2H), 1.70 (m, 2H), 0.81 (t, J=7, 3H).

Compound 104

2-Propyl-2H-pyrazolo[3,4-d]pyrimidine-4,6-diol

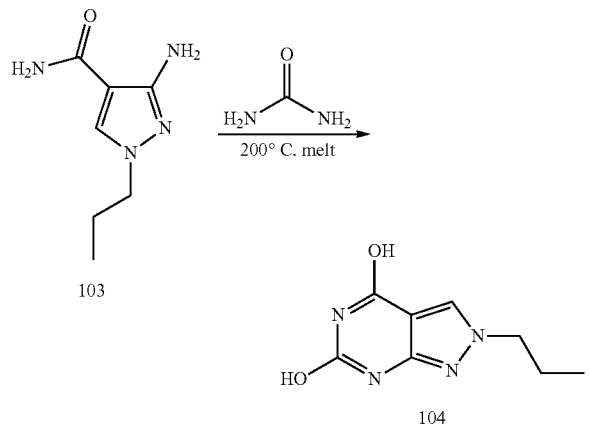

Compound 103 (510 mg, 3.03 mmol) and urea (Fisher, 1.5 g, 25 mmol) were melted at 200° C. with stirring. After 1.5 h the reaction was allowed to cool to 100° C. when 10 mL water was added and the reaction mixture was boiled overnight. The mixture was cooled and filtered followed by water wash. The white solid was dried in vacuo to afford 412 mg (70%) of compound 104. Compound 104: mp>300° C.; MS (ES+ calculated: 194.19; found: 195.19 M+H). HPLC (99% purity, retention time 5.828 minutes—Method D); $^1$H NMR (400 MHz, DMSO-$d_6$) δ 11.34 (s, 1H), 10.66 (s, 1H), 8.33 (s, 1H), 4.05 (t, J=7, 2H), 1.78 (m, 2H), 0.82 (t, J=7, 3H).

Compound 105

4,6-Dichloro-2-propyl-1H-pyrazolo[3,4-d]pyrimidine

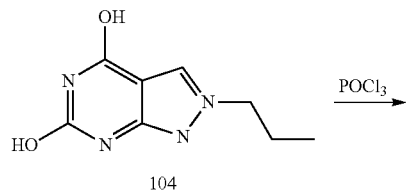

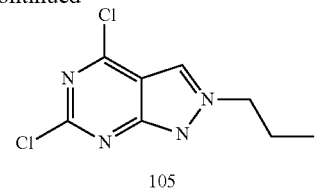

A mixture of commercially available 4,6-dihydroxypyrazolo[3,4-d]pyrimidine 104 (Acros, 400 mg, 2.06 mmol) stirred in POCl$_3$ (10 mL) was refluxed overnight. After cooling, excess POCl$_3$ was removed by rotarty evaporation and pumped on high vacuum before adding ice chips while stirring. The mixture was stirred for 10 min before the white precipitate was filtered and dried in vacuo. Yield 407 mg (85%). Compound 105: mp 80-84° C.; MS (ES+ calculated: 232.10; found: 233.00 M+H). HPLC (99%) purity, retention time 10.091 minutes—method D) $^1$H NMR (400 MHz, DMSO-$d_6$) δ 9.07 (s, 1H), 4.46 (t, J=7, 2H), 1.95 (m, 2H), 0.85 (t, J=7, 3H).

Compound 107

4,6-Dichloro-5-[1,3]dioxolan-2-yl-pyrimidine

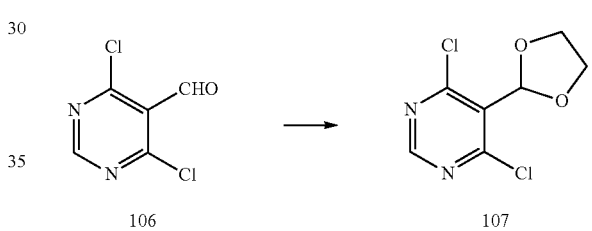

A mixture of 300 ml benzene and 8.2 ml ethylene glycol was heated to reflux and 100 ml solution was distilled off. To the hot solution was added 4,6-dichloro-5-pyrimidinecarbaldehyde (Bionet, 8.6 g, 48.6 mmol) and p-toluenesulfonic acid monohydrate (Aldrich, 150 mg, 0.8 mmol). The mixture was returned to reflux and water was removed via Dean-Stark trap over 3 h. After cooling, the solvents were removed under vacuum to yield a dry, yellow solid. The solids were slurried in H$_2$O (30 ml)/saturated NaHCO$_3$ solution (30 ml). White solid 107 was filtered off and dried under vacuum (8.8 g, 82%). Compound 107: mp 108-110° C.; MS (ES+ calculated: 221.04; found: 221/223 M+H). $^1$H NMR (400 MHz, DMSO-$d_6$) δ 8.95 (s, 1H), 6.26 (s, 1H), 4.23 (m, 2H), 4.05 (m, 2H).

Example 108

3-(1-methyl-1H-pyrazolo[3,4-d]pyrimidin-4-yl)-2-oxo-2,3-dihydro-1H-indole-5-carbonitrile

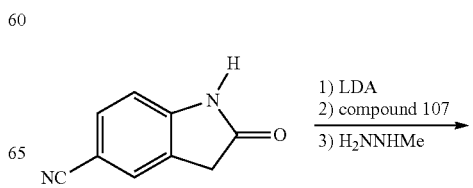

-continued

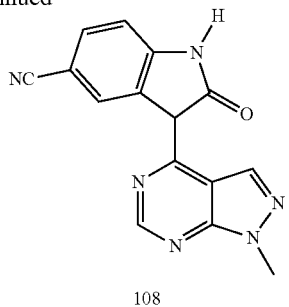

108

A solution of 5-cyanooxindole (Combiblocks, 31.6 mg, 0.2 mmol) in 2 mL anhydrous tetrahydrofuran under argon was cooled to −78° C. and lithium diisopropylamide (Acros, 0.2 mL of a 2.0M solution in THF/hexane, 0.4 mmol) was added dropwise. The reaction was stirred for fifteen minutes at which point a solution of compound 107 (46.8 mg, 0.21 mmol) in 2 mL anhydrous tetrahydrofuran was added dropwise. The reaction was stirred an additional fifteen minutes and was warmed to room temperature for 1 hour. The orange solution was quenched with methylhydrazine (1000 and stirred at ambient temperature 16 h. The solvents were removed under vacuum and methanol (1 ml) was added to the solids. After 10 min. of stirring, the tan solids were filtered off (5.0 mg, 8.6%). Example 108: mp>300° C. (dec); MS (ES+ calculated: 290.29; found: 291 M+H). $^1$H NMR (400 MHz, DMSO-$d_6$) δ 14.59 (br s, 1H), 11.27 (s, 1H), 8.70 (s, 1H), 8.56 (s, 1H), 8.01 (s, 1H), 7.48 (d, J=8.6 Hz, 1H), 7.08 (d, J=8.6 Hz, 1H), 4.01 (s, 3H).

Example 109

2-Oxo-3-(1H-pyrazolo[3,4-d]pyrimidin-4-yl)-2,3-dihydro-1H-indole-5-carbonitrile

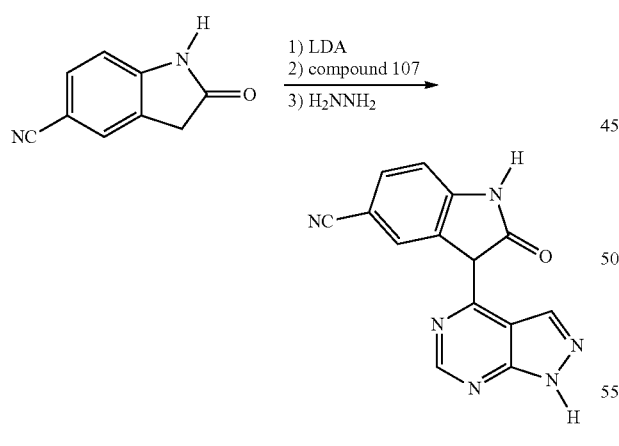

109

A solution of 5-cyanooxindole (Combiblocks, 79.0 mg, 0.5 mmol) in 5 mL anhydrous tetrahydrofuran under argon was cooled to −78° C. and lithium diisopropylamide (Acros, 0.5 mL of a 2.0M solution in THF/hexane, 1.0 mmol) was added dropwise. The reaction was stirred for fifteen minutes at which point a solution of compound 107 (113 mg, 0.53 mmol) in 5 mL anhydrous tetrahydrofuran was added dropwise. The reaction was stirred an additional fifteen minutes and was warmed to room temperature for 1 hour. The orange solution was quenched with hydrazine monohydrate (120 μl) and stirred at ambient temperature 24 h, then at reflux for 16 h. The solvents were removed under vacuum and methanol (1 ml) was added to the solids. After 10 min. of stirring, the tan solids were filtered off. Methanol addition and filtration was repeated 3 times to give a dark brown solid (21 mg, 15%). Example 109: mp>300° C. (dec); MS (ES+ calculated: 276.26; found: 277 M+H). $^1$H NMR (400 MHz, DMSO-$d_6$) δ 14.29 (br s), 11.57 (s), 11.25 (s), 10.01 (br s), 9.45 (s), 9.27 (s), 8.70 (m), 8.50 (s), 8.37 (s), 8.02 (s), 7.82 (s), 7.47 (d, J=9 Hz), 7.06 (d, J=8 Hz), 6.79 (m).

Compound 110

4-Chloro-2-pentyl-2H-pyrazolo[3,4-d]pyrimidine

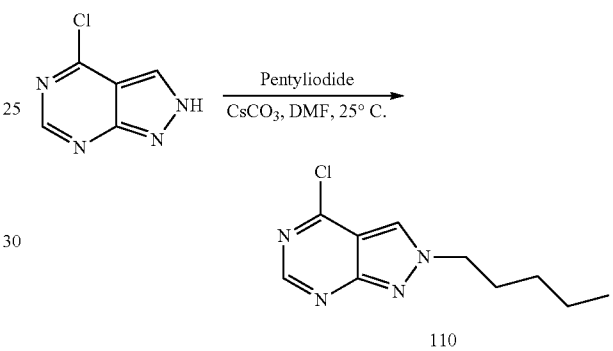

110

To a suspension of 79 (3.00 g, 19.41 mmol) and CsCO$_3$ (6.95 g, 21.34 mmol) in 50 mL of anhydrous DMF was charged pentyliodide (3.04 mL, 23.29 mmol) drop wise with a syringe. Allow reaction to stir at room temperature for 36 h. After filtering the solids, the remaining DMF was concentrated in vacuo. The residue was resuspended in water and dichloromethane, the layers separated and the aqueous layer extracted with 2×20 mL portions of dichlormethane. The combined organic was dried over MgSO$_4$, filtered and concentrated in vacuo. The resulting reddish solid was purified via column chromatography on 150 g SiO$_2$, eluted sequentially with the following concentrations of ethyl acetate in dichloromethane:10%, 20%, 50%, 100%. The most polar eluted compound was collected, stripped to a brown oily solid, (189 mg, 4.3%) and used in the next reaction. MS (m/e) 225 (M+1).

Example 111

3-(2-pentyl-1H-pyrazolo[3,4-d]pyrimidin-4-yl)-2-oxo-2,3-dihydro-1H-indole-6-carbonitrile

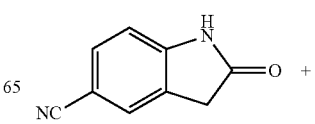

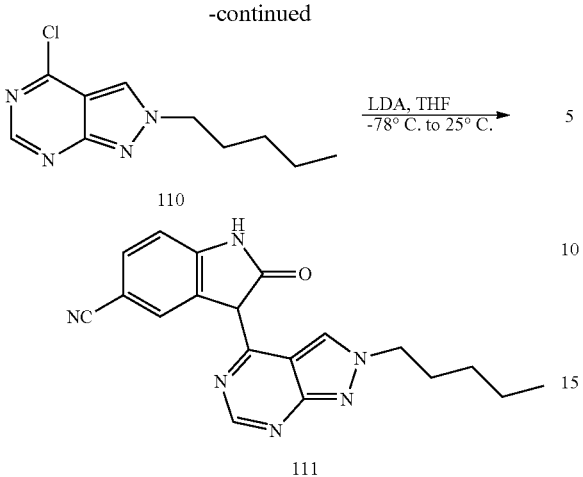

To the 5-cyanooxindole 110 (71 mg, 0.45 mmol) in 2 mL of anhydrous THF stirring at −78° C., was added LDA (Acros 2.0 m in THF/n-pentane, 5604, 1.125 mmol) drop wise with a syringe. The anionic solution was stirred at −78° C. for 45 minutes. To the solution was added the isolated 4-chloropyrazolo-2-n-pentyl[3,4-d]pyrimidine in 1 mL anhydrous THF. The solution was stirred at −78° C. for 1 hour and then allowed to warm and stir at room temperature for 2 hours. The reaction was quenched with 2 mL of saturated NH$_4$Cl, transferred to a separatory funnel and partitioned between dichloromethane and water. After extracting the water layer with 2×20 mL portions of dichloromethane, the combined organic was dried over MgSO$_4$, filtered and concentrated in vacuo. The resulting residue was purified via flash chromatography on 60 g SiO$_2$, and eluted with 5% methanol in dichloromethane yielding a yellow solid (44 mg, 28%). Example 111: mp=290° C. dec., $^1$H NMR (400 MHz, DMSO-d$_6$) δ 11.25 (s, 1H), 9.50 (s, 1H), 9.10 (s, 1H), 8.35 (d, J=4 Hz), 7.95 (s, 1H), 7.5 (d, J=8 Hz, 1H), 7.05 (d, J=8 Hz, 1H), 4.45 (t, J=7 Hz, 1H), 4.20 (t, J=7 Hz, 1H), 1.90 (m, 2H), 1.3 (m, 4H), 0.85 (t, J=7 Hz, 3H); MS m/e 347 (M+1), HPLC (99% purity, retention time 9.82 minutes, method B).

Compound 112

4,6-Dichloro-2-cyclopentyl-2H-pyrazolo[3,4-d]pyrimidine

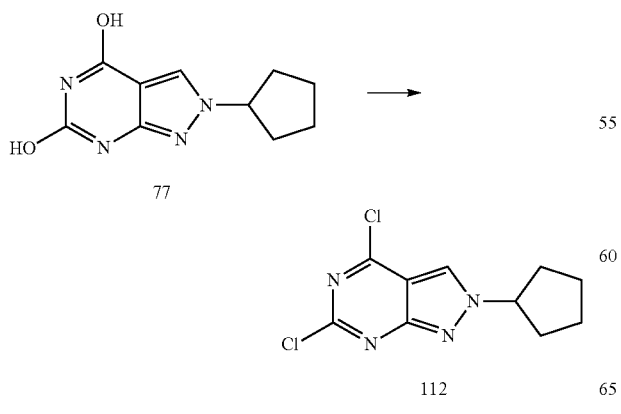

To a 50 mL flask was added compound 77 (500 mg, 2.27 mmol) and POCl$_3$ (8 mL) and the mixture was heated to reflux for 1.5 h. After cooled to room temperature, the reaction was concentrated in vacuo. The residue was quenched with ice-water (30 mL) and basified with NaOH (10 N) solution to pH 9. The precipitation was filtered and washed with water, dried to give 504 mg (86%) of the desired compound 112. Compound 112: $^1$H NMR (400 MHz, DMSO-d$_6$) δ 9.10 (s, 1H), 5.11 (m, 1H), 2.22-1.71 (m, 8H); MS (m/e) 257 (M+1).

Example 113

3-(6-Chloro-2-cyclopentyl-2H-pyrazolo[3,4-d]pyrimidin-4-yl)-2-oxo-2,3-dihydro-1H-indole-5-carbonitrile

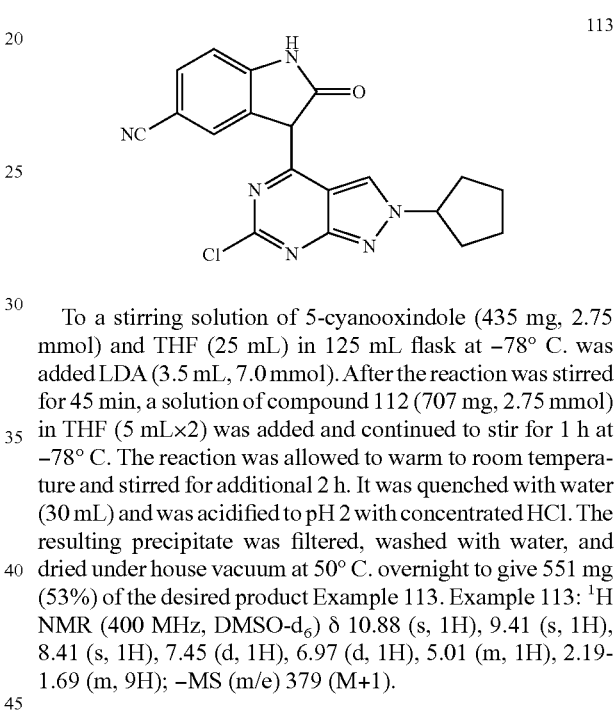

To a stirring solution of 5-cyanooxindole (435 mg, 2.75 mmol) and THF (25 mL) in 125 mL flask at −78° C. was added LDA (3.5 mL, 7.0 mmol). After the reaction was stirred for 45 min, a solution of compound 112 (707 mg, 2.75 mmol) in THF (5 mL×2) was added and continued to stir for 1 h at −78° C. The reaction was allowed to warm to room temperature and stirred for additional 2 h. It was quenched with water (30 mL) and was acidified to pH 2 with concentrated HCl. The resulting precipitate was filtered, washed with water, and dried under house vacuum at 50° C. overnight to give 551 mg (53%) of the desired product Example 113. Example 113: $^1$H NMR (400 MHz, DMSO-d$_6$) δ 10.88 (s, 1H), 9.41 (s, 1H), 8.41 (s, 1H), 7.45 (d, 1H), 6.97 (d, 1H), 5.01 (m, 1H), 2.19-1.69 (m, 9H); −MS (m/e) 379 (M+1).

Example 113A

5-Chloro-3-(6-chloro-2-cyclopentyl-2H-pyrazolo[3,4-d]pyrimidin-4-yl)-1,3-dihydro-indol-2-one

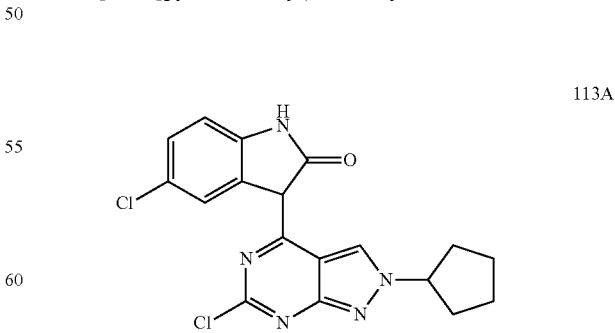

Experimental data: $^1$H NMR (400 MHz, DMSO-d$_6$) δ 10.50 (s, 1H), 9.34 (s, 1H), 8.10 (s, 1H), 7.05 (m, 1H), 6.83 (m, 1H), 4.99 (s, 1H), 2.18-1.69 (m, 9H); −MS (m/e) 388 (M+1).

Scheme 3 discloses a general procedure for the preparation of compounds of Formula XI. To a reaction vessel can be added a compound of Formula X, about 10 equivalents of a compound of formula NHR$^9$R$^{10}$, and 2-methoxyethanol. The reaction mixture can be heated to reflux for about 6 to 7 hours. The reaction when complete can be cooled to room temperature, can be concentrated and the residue can be purified by column chromatography to give the desired product.

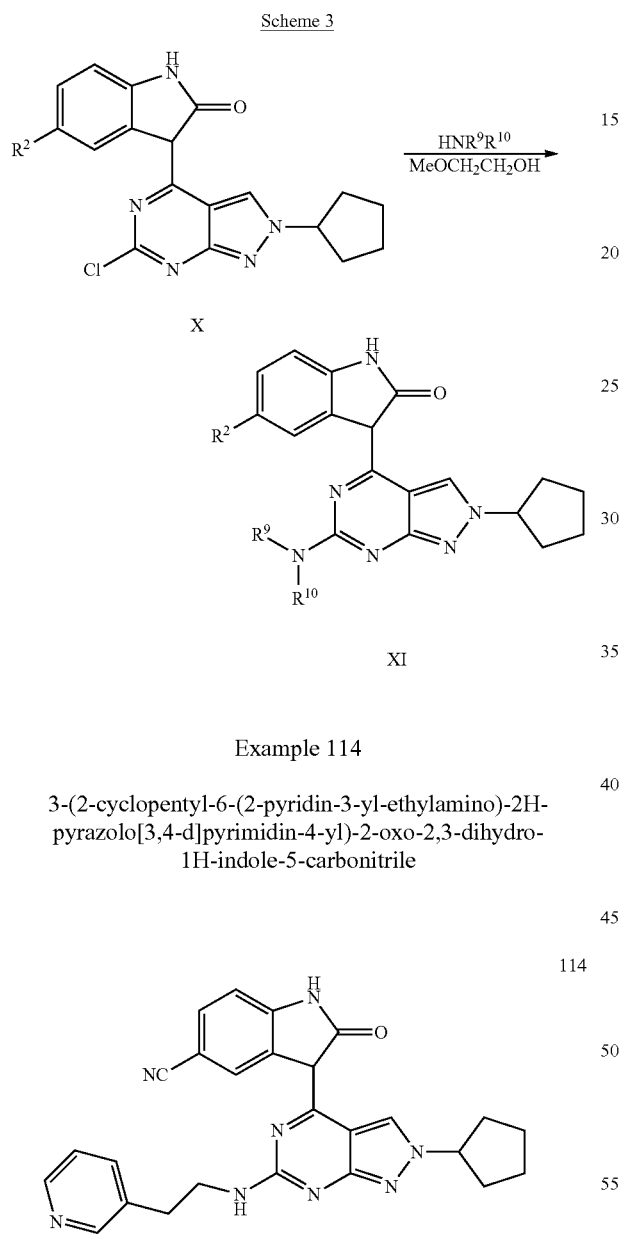

Example 114

3-(2-cyclopentyl-6-(2-pyridin-3-yl-ethylamino)-2H-pyrazolo[3,4-d]pyrimidin-4-yl)-2-oxo-2,3-dihydro-1H-indole-5-carbonitrile To a Carousel tube was added Example 113 (200 mg, 0.528 mmol), 3-(2-aminoethyl)pyridine (645 mg, 5.28 mmol), and 2-methoxyethanol (8 mL). The reaction mixture was heated to reflux for 6.5 h. After cooled to room temperature, the reaction was concentrated and the residue was purified by Biotage (CH$_2$Cl$_2$/MeOH 10:1) to give 204 mg (83%) the desired product. Example 114: $^1$H NMR (400 MHz, DMSO-d$_6$) δ 11.63 (s, 1H), 10.39 (s, 1H), 9.50 (s, 1H), 8.72 (s, 1H), 8.51 (s, 1H), 8.43 (m, 1H), 7.74 (m, 1H), 7.34-7.28 (m, 2H), 6.86 (m, 1H), 4.83 (m, 1H), 3.77 (s, 2H), 3.00 (m, 2H), 2.17-1.67 (m, 9H); MS (m/e) 465 (M+1).

The following Examples 115-144 in Table 1 were prepared according to procedures disclosed herein, using the appropriate starting materials, including the general procedure for the preparation of compounds of Formula XI, disclosed herein, displacement of halogens by amines, alcohols or water, and/or using methods generally known to one skilled in the art.

TABLE 1

| Example | R$^2$ | —X |
|---|---|---|
| 115 | —CN | CH$_3$NH— |
| 116 | —CN | CH$_3$CH$_2$CH$_2$CH$_2$NH— |
| 117 | —CN | 4-methylpiperazin-1-yl |
| 118 | —CN | morpholin-4-yl |
| 119 | —CN | N,N-dimethylaminoethylamino |
| 120 | —CN | —OH |
| 121 | —CN | N,N-diethylaminoethyl(methyl)amino |
| 122 | —CN | 2-methoxyethyl(methyl)amino |
| 123 | —CN | (pyridin-2-ylmethyl)amino |
| 124 | —CN | NH$_2$NH— |
| 125 | —CN | (2-(pyridin-2-yl)ethyl)amino |
| 126 | —CN | (2-(pyridin-4-yl)ethyl)amino |

TABLE 1-continued

| Example | R² | —X |
|---|---|---|
| 127 | —CN | (pyrrolidine-ethyl-piperazine-N-methyl) |
| 128 | —CN | (phenyl-propyl-piperazine-N-methyl) |
| 129 | —CN | (pyridin-2-yl-ethyl-piperazine-N-methyl) |
| 130 | —CN | (thiophen-2-yl-ethyl-piperazine-N-methyl) |
| 131 | —CN | (piperidin-N-methyl) |
| 132 | —CN | (pyrrolidin-N-methyl) |
| 133 | —CN | (pyridin-3-yl-methyl-NH-methyl) |
| 134 | —CN | (phenethyl-NH-methyl) |
| 135 | —CN | (4-(1,1-dioxo-thiomorpholin-4-yl)phenyl-NH-methyl) |

TABLE 1-continued

| Example | R² | —X |
|---|---|---|
| 136 | —CN | (pyrrolidin-1-yl-ethyl-NH-methyl) |
| 137 | —CN | (6-(4-methylpiperazin-1-yl)pyridin-3-yl-NH-methyl) |
| 138 | —CN | (N,N-dimethylaminopropyl-NH-methyl) |
| 139 | —CN | (morpholin-4-yl-propyl-NH-methyl) |
| 140 | —Cl | (N,N-dimethylaminoethyl-N-methyl) |
| 141 | —Cl | (N,N-dimethylamino-ethoxy-methyl) |
| 142 | —Cl | CH₃NH— |
| 143 | —Cl | (morpholin-N-methyl) |
| 144 | —Cl | (N,N-dimethylaminoethyl-(4-methylpiperazin-1-yl)-methyl) |

Example 115

3-(2-cyclopentyl-6-methylamino-2H-pyrazolo[3,4-d]pyrimidin-4-yl)-2-oxo-2,3-dihydro-1H-indole-5-carbonitrile Experimental data: $^1$H NMR (400 MHz, DMSO-d$_6$) δ 11.70 (s, 1H), 10.37 (s, 1H), 9.49 (s, 1H), 8.75 (s, 1H), 7.28 (m, 1H), 6.85 (m, 1H), 4.83 (m, 1H), 3.01 (s, 3H), 2.13-1.68 (m, 9H); MS (m/e) 374 (M+1).

Example 116

3-(6-butylamino-2-cyclopentyl-2H-pyrazolo [3,4-d]
pyrimidin-4-yl)-2-oxo-2,3-dihydro-1H-indole-5-
carbonitrile Experimental data: $^1$H NMR (400 MHz, DMSO-d$_6$) δ
10.37 (s, 1H), 9.48 (s, 1H), 8.69 (s, 1H), 7.27 (m, 1H), 6.85
(m, 1H), 4.82 (m, 1H), 3.46 (s, 2H), 2.13-1.44 (m, 13H), 0.94
(m, 4H); MS (m/e) 416 (M+1).

Example 117

3-(2-cyclopentyl-6-(4-methyl-piperazin-1-yl)-2H-
pyrazolo[3,4-d]pyrimidin-4-yl)-2-oxo-2,3-dihydro-
1H-indole-5-carbonitrile Experimental data: $^1$H NMR (400 MHz, DMSO-d$_6$) δ
10.35 (s, 1H), 9.47 (s, 1H), 8.49 (s, 1H), 7.25 (m, 1H), 6.85
(m, 1H), 4.85 (m, 1H), 3.84 (m, 3H), 2.60 (s, 4H), 2.34-1.68
(m, 13H); MS (m/e) 443 (M+1).

Example 118

3-(2-cyclopentyl-6-morpholin-4-yl-2H-pyrazolo[3,4-
d]pyrimidin-4-yl)-2-oxo-2,3-dihydro-1H-indole-5-
carbonitrile Experimental data: $^1$H NMR (400 MHz, DMSO-d$_6$) δ
10.44 (s, 1H), 9.49 (s, 1H), 8.47 (s, 1H), 7.30 (m, 1H), 6.87
(m, 1H), 4.87 (m, 1H), 3.78 (m, 8H), 2.15-1.69 (m, 9H); MS
(m/e) 430 (M+1).

Example 119

3-(2-cyclopentyl-6-(2-dimethylamino-ethylamino)-
2H-pyrazolo [3,4-d]pyrimidin-4-yl)-2-oxo-2,3-dihy-
dro-1H-indole-5-carbonitrile Experimental data: $^1$H NMR (400 MHz, DMSO-d$_6$) δ
10.32 (s, 1H), 9.48 (s, 1H), 8.68 (s, 1H), 7.25 (m, 1H), 6.84
(m, 1H), 4.80 (m, 1H), 3.57 (s, 2H), 2.65 (s, 2H), 2.31 (s, 6H),
2.15-1.68 (m, 10H); MS (m/e) 431 (M+1).

Example 120

3-(2-cyclopentyl-6-hydroxy-2H-pyrazolo [3,4-d]
pyrimidin-4-yl)-2-oxo-2,3-dihydro-1H-indole-5-
carbonitrile Experimental data: $^1$H NMR (400 MHz, DMSO-d$_6$) δ
12.92 (s, 1H), 11.83 (s, 1H), 11.33 (s, 1H), 8.93 (s, 1H), 7.95
(s, 1H), 7.53 (m, 1H), 7.07 (m, 1H), 5.05 (m, 1H), 2.14-1.69
(m, 8H)

Example 121

3-{2-cyclopentyl-6-[(2-diethylamino-ethyl)-methyl-
amino]-2H-pyrazolo [3,4-d]pyrimidin-4-yl}-2-oxo-2,
3-dihydro-1H-indole-5-carbonitrile Experimental data: $^1$H NMR (400 MHz, DMSO-d$_6$) δ
10.22 (s, 1H), 9.47 (s, 1H), 8.61 (s, 1H), 7.19 (m, 1H), 6.82
(m, 1H), 4.80 (m, 1H), 3.78 (s, 2H), 3.33 (s, 3H), 2.99 (s, 2H),
2.85 (s, 4H), 2.12-1.68 (m, 9H), 1.12 (s, 6H); MS (m/e) 473
(M+1).

Example 122

3-[2-cyclopentyl-6-(2-dimethylamino-ethoxy)-2H-
pyrazolo[3,4-d]pyrimidin-4-yl]-2-oxo-2,3-dihydro-
1H-indole-5-carbonitrile Experimental data: $^1$H NMR (400 MHz, DMSO-d$_6$) δ
11.81 (s, 1H), 10.41 (s, 1H), 9.45 (m, 1H), 8.53 (s, 1H), 7.29
(m, 1H), 6.86 (m, 1H), 4.86 (m, 1H), 3.82 (s, 4H), 2.15-1.67
(m, 14H).

Example 123

3-{2-cyclopentyl-6-[(pyridin-2-yl-methyl)amino]-
2H-pyrazolo[3,4-d]pyrimidin-4-yl}-2-oxo-2,3-dihy-
dro-1H-indole-5-carbonitrile Experimental data: $^1$H NMR (400 MHz, DMSO-d$_6$) δ
10.37 (s, 1H), 9.48 (s, 1H), 8.57 (s, 1H), 7.76 (m, 2H), 7.41
(m, 1H), 7.26 (m, 2H), 6.83 (m, 1H), 4.83 (m, 3H), 2.13-1.68
(m, 10H); MS (m/e) 451 (M+1).

Example 124

3-(2-cyclopentyl-6-hydrazino-2H-pyrazolo [3,4-d]
pyrimidin-4-yl)-2-oxo-2,3-dihydro-1H-indole-5-
carbonitrile Experimental data: $^1$H NMR (400 MHz, DMSO-d$_6$) δ
10.30 (s, 1H), 9.50 (s, 1H), 9.36 (s, 1H), 8.82 (s, 1H), 7.24 (m,
1H), 6.82 (m, 1H), 4.82 (m, 1H), 2.16-1.68 (m, 11H); MS
(m/e) 375 (M+1).

Example 125

3-[2-cyclopentyl-6-(2-pyridin-2-yl-ethylamino)-2H-
pyrazolo [3,4-d]pyrimidin-4-yl]-2-oxo-2,3-dihydro-
1H-indole-5-carbonitrile Experimental data: $^1$H NMR (400 MHz, DMSO-d$_6$) δ
10.40 (s, 1H), 9.49 (s, 1H), 8.73 (s, 1H), 8.54 (m, 1H), 7.73
(m, 1H), 7.37-7.23 (m, 4H), 6.86 (m, 1H), 4.83 (m, 1H), 3.89
(s, 2H), 3.16 (m, 2H), 2.15-1.67 (m, 9H); MS (m/e) 465
(M+1).

Example 126

3-(2-cyclopentyl-6-(2-pyridin-4-yl-ethylamino)-2H-
pyrazolo [3,4-d]pyrimidin-4-yl)-2-oxo-2,3-dihydro-
1H-indole-5-carbonitrile Experimental data: $^1$H NMR (400 MHz, DMSO-d$_6$) δ
10.41 (s, 1H), 9.50 (s, 1H), 8.48 (m, 3H), 7.33 (m, 4H), 6.86
(m, 1H), 4.83 (m, 1H), 3.78 (s, 2H), 3.01 (s, 2H), 2.15-1.68
(m, 9H); MS (m/e) 465 (M+1).

Example 127

3-{2-cyclopentyl-6-[4-(2-pyrrolidin-1-yl-ethyl)-pip-
erazin-1-yl]-2H-pyrazolo[3,4-d]pyrimidin-4-yl}-2-
oxo-2,3-dihydro-1H-indole-5-carbonitrile Experimental data: $^1$H NMR (400 MHz, DMSO-d$_6$) δ
10.06 (s, 1H), 9.41 (s, 1H), 8.53 (s, 1H), 7.11 (m, 1H), 6.79
(m, 1H), 4.77 (m, 1H), 3.84 (s, 5H), 3.03 (m, 6H), 2.58 (s, 6H),
2.11-1.68 (m, 12H); MS (m/e) 526 (M+1).

Example 128

3-{2-cyclopentyl-6-[4-(3-phenyl-propyl)-piperazin-1-yl]-2H-pyrazolo[3,4-d]pyrimidin-4-yl}-2-oxo-2,3-dihydro-1H-indole-5-carbonitrile Experimental data: $^1$H NMR (400 MHz, DMSO-d$_6$) δ 10.40 (s, 1H), 9.47 (s, 1H), 8.50 (s, 1H), 7.28-7.17 (m, 6H), 6.86 (m, 1H), 4.84 (m, 1H), 3.84 (s, 4H), 2.65 (m, 6H), 2.42 (s, 2H), 2.15-1.67 (m, 11H); MS (m/e) 547 (M+1).

Example 129

3-{2-cyclopentyl-6-[4-(2-pyridin-2-yl-ethyl)-piperazin-1-yl]-2H-pyrazolo [3,4-d]pyrimidin-4-yl}-2-oxo-2,3-dihydro-1H-indole-5-carbonitrile Experimental data: $^1$H NMR (400 MHz, DMSO-d$_6$) δ 10.41 (s, 1H), 9.48 (s, 1H), 8.48 (m, 2H), 7.71 (m, 1H), 7.69 (m, 2H), 7.20 (m, 1H), 6.86 (m, 1H), 4.86 (m, 1H), 3.83 (s, 4H), 2.96 (s, 2H), 2.70 (m, 6H), 2.17-1.69 (m, 9H); MS (m/e) 534 (M+1).

Example 130

3-{2-cyclopentyl-6-[4-(2-thiophen-2-yl-ethyl)-piperazin-1-yl]-2H-pyrazolo[3,4-d]pyrimidin-4-yl}-2-oxo-2,3-dihydro-1H-indole-5-carbonitrile Experimental data: $^1$H NMR (400 MHz, DMSO-d$_6$) δ 11.90 (s, 1H), 10.43 (s, 1H), 9.48 (s, 1H), 8.51 (s, 1H), 7.31 (m, 2H), 6.96-6.86 (m, 2H), 4.86 (m, 1H), 3.85 (s, 4H), 3.03 (s, 2H), 2.65 (s, 6H), 2.17-1.69 (m, 9H); MS (m/e) 539 (M+1).

Example 131

3-(2-cyclopentyl-6-piperidin-1-yl-2H-pyrazolo[3,4-d]pyrimidin-4-yl)-2-oxo-2,3-dihydro-1H-indole-5-carbonitrile Experimental data: $^1$H NMR (400 MHz, DMSO-d$_6$) δ 11.82 (s, 1H), 10.42 (s, 1H), 9.47 (s, 1H), 8.54 (s, 1H), 7.48 (m, 1H), 6.86 (m, 1H), 4.87 (m, 1H), 3.83 (s, 4H), 2.15-1.67 (m, 14H); MS (m/e) 428 (M+1).

Example 132

3-(2-cyclopentyl-6-pyrrolidin-1-yl-2H-pyrazolo [3,4-d]pyrimidin-4-yl)-2-oxo-2,3-dihydro-1H-indole-5-carbonitrile Experimental data: $^1$H NMR (400 MHz, DMSO-d$_6$) δ 11.66 (s, 1H), 10.39 (s, 1H), 9.51 (s, 1H), 8.59 (s, 1H), 7.29 (m, 1H), 6.86 (m, 1H), 4.85 (m, 1H), 3.66 (s, 4H), 2.19-1.68 (m, 12H); MS (m/e) 414 (M+1).

Example 133

3-{2-cyclopentyl-6-[(pyridin-3-ylmethyl)amino]-2H-pyrazolo[3,4-d]pyrimidin-4-yl}-2-oxo-2,3-dihydro-1H-indole-5-carbonitrile Experimental data: $^1$H NMR (400 MHz, DMSO-d$_6$) δ 10.18 (s, 1H), 9.45 (s, 1H), 8.60 (m, 2H), 7.81 (m, 2H), 7.48 (s, 1H), 7.16 (m, 1H), 6.79 (m, 1H), 4.78 (m, 1H), 4.71 (s, 2H), 3.93 (s, 1H), 2.13-1.66 (m, 9H); MS (m/e) 451 (M+1).

Example 134

3-(2-cyclopentyl-6-2-phenethylamino-2H-pyrazolo [3,4-d]pyrimidin-4-yl)-2-oxo-2,3-dihydro-1H-indole-5-carbonitrile Experimental data: $^1$H NMR (400 MHz, DMSO-d$_6$) δ 11.59 (s, 1H), 10.39 (s, 1H), 9.50 (s, 1H), 8.74 (s, 1H), 7.32-7.29 (m, 6H), 6.86 (m, 1H), 4.83 (m, 1H), 3.74 (s, 2H), 2.98 (m, 2H), 2.17-1.67 (m, 9H); MS (m/e) 464 (M+1).

Example 135

3-{2-Cyclopentyl-6-[4-(1,1-dioxo-1$\lambda^6$-thiomorpholin-4-yl)-phenylamino]-2H-pyrazolo[3,4-d]pyrimidin-4-yl}-2-oxo-2,3-dihydro-1H-indole-5-carbonitrile Experimental data: $^1$H NMR (400 MHz, DMSO-d$_6$) δ 10.40 (s, 1H), 9.52 (s, 1H), 8.51 (s, 1H), 7.47 (m, 2H), 7.37 (m, 1H), 7.09 (m, 3H), 6.82 (m, 1H), 4.85 (m, 1H), 3.80 (s, 4H), 3.15 (s, 4H), 2.16-1.67 (m, 9H); MS (m/e) 569 (M+1).

Example 136

3-[2-cyclopentyl-6-(2-pyrrolidin-1-yl-ethylamino)-2H-pyrazolo[3,4-d]pyrimidin-4-yl]-2-oxo-2,3-dihydro-1H-indole-5-carbonitrile Experimental data: $^1$H $^1$H NMR (400 MHz, DMSO-d$_6$) δ 10.19 (s, 1H), 9.45 (s, 1H), 8.72 (s, 1H), 7.18 (m, 1H), 6.81 (m, 1H), 4.78 (m, 1H), 2.71 (m, 3H), 2.46 (m, 6H), 2.20-1.60 (m, 13H); MS (m/e) 457 (M+1).

Example 137

3-{2-cyclopentyl-6-[6-(4-methyl-piperazin-1-yl)-pyridin-3-yl-amino]-2H-pyrazolo [3,4-d]pyrimidin-4-yl}-2-oxo-2,3-dihydro-1H-indole-5-carbonitrile Experimental data: $^1$H NMR (400 MHz, DMSO-d$_6$) δ 10.31 (s, 1H), 9.65 (s, 1H), 8.32 (m, 1H), 7.61 (m, 1H), 7.25 (m, 1H), 6.95 (m, 1H), 6.86 (m, 1H), 6.73 (m, 1H), 4.94 (m, 1H), 4.64 (m, 3H), 4.06 (m, 2H), 3.90 (m, 2H), 3.55 (s, 3H), 3.20 (m, 2H), 2.18-1.67 (m, 9H); MS (m/e) 535 (M+1).

Example 138

3-[2-cyclopentyl-6-(3-dimethylamino-propylamino)-2H-pyrazolo[3,4-d]pyrimidin-4-yl]-2-oxo-2,3-dihydro-1H-indole-5-carbonitrile Experimental data: $^1$H NMR (400 MHz, DMSO-d$_6$) δ 10.01 (s, 1H), 9.43 (s, 1H), 8.65 (s, 1H), 7.09 (m, 1H), 6.79 (m, 1H), 4.75 (m, 1H), 3.69 (m, 2H), 3.17 (s, 2H), 2.84 (m, 2H), 2.51 (s, 6H), 2.15-1.62 (m, 10H); MS (m/e) 445 (M+1).

Example 139

3-[2-cyclopentyl-6-(3-morpholin-4-yl-propylamino)-2H-pyrazolo[3,4-d]pyrimidin-4-yl]-2-oxo-2,3-dihydro-1H-indole-5-carbonitrile Experimental data: $^1$H NMR (400 MHz, DMSO-d$_6$) δ 10.36 (s, 1H), 9.48 (s, 1H), 8.70 (s, 1H), 7.27 (m, 1H), 6.85

(m, 1H), 4.82 (m, 1H), 3.63 (s, 4H), 3.32 (s, 4H), 2.46-2.31 (m, 6H), 2.18-1.67 (m, 10H); MS (m/e) 487 (M+1).

Example 140

5-Chloro-3-{2-cyclopentyl-6-[(2-dimethylamino-ethyl)-methyl-amino]-2H-pyrazolo[3,4-d]pyrimidin-4-yl}-1,3-dihydro-indol-2-one Experimental data: $^1$H NMR (400 MHz, DMSO-d$_6$) δ 9.90 (s, 1H), 9.51 (s, 1H), 8.28 (s, 1H), 6.83 (m, 1H), 6.69 (m, 1H), 4.81 (m, 1H), 3.81 (s, 2H), 3.26 (s, 3H), 2.69 (s, 2H), 2.31-1.69 (m, 15H); MS (m/e) 454 (M+1).

Example 141

5-Chloro-3-[2-cyclopentyl-6-(2-diethylamino-ethoxy)-2H-pyrazolo [3,4-d]pyrimidin-4-yl]-1,3-dihydro-indol-2-one Experimental data: $^1$H NMR (400 MHz, DMSO-d$_6$) δ 11.66 (s, 1H), 9.98 (s, 1H), 9.48 (s, 1H), 8.27 (s, 1H), 6.87 (m, 1H), 6.70 (m, 1H), 4.83 (m, 1H), 3.81 (s, 4H), 2.21-1.65 (m, 14H).

Example 142

5-Chloro-3-[2-cyclopentyl-6-(methylamino)-2H-pyrazolo[3,4-d]pyrimidin-4-yl]-1,3-dihydro-indol-2-one Experimental data: $^1$H NMR (400 MHz, DMSO-d$_6$) δ 11.54 (s, 1H), 9.97 (s, 1H), 9.48 (s, 1H), 8.44 (s, 1H), 6.86 (m, 1H), 6.70 (m, 1H), 4.80 (m, 1H), 3.00 (s, 3H), 2.13-1.68 (m, 9H); MS (m/e) 383 (M+1).

Example 143

5-Chloro-3-(2-cyclopentyl-6-morpholin-4-yl-2H-pyrazolo [3,4-d]pyrimidin-4-yl)-1,3-dihydro-indol-2-one Experimental data: $^1$H NMR (400 MHz, DMSO-d$_6$) δ 10.00 (s, 1H), 9.49 (s, 1H), 8.22 (s, 1H), 6.87 (m, 1H), 6.71 (m, 1H), 4.84 (m, 1H), 3.77 (m, 8H), 2.14-1.69 (m, 9H); MS (m/e) 439 (M+1).

Example 144

5-Chloro-3-{2-cyclopentyl-6-[4-(2-dimethylamino-ethyl)-piperazin-1-yl]-2H-pyrazolo[3,4-d]pyrimidin-4-yl}-1,3-dihydro-indol-2-one Experimental data: $^1$H NMR (400 MHz, DMSO-d$_6$) δ 9.72 (s, 1H), 9.44 (s, 1H), 8.25 (s, 1H), 6.74 (m, 1H), 6.67 (m, 1H), 4.77 (m, 1H), 3.80 (s, 4H), 2.56 (s, 6H), 2.36 (s, 8H), 2.18-1.68 (m, 9H); MS (m/e) 509 (M+1).

Compound 145

1-Methyl-1,5-dihydro-pyrazolo[3,4-d]pyrimidin-4-one

A stirred solution of 107 (1 g, 0.0056 mols) in methanol (5 mL) was stirred overnight at room temperature. The reaction mixture was concentrated in vacuo, triturated with ether and collected by filtration to yield a yellow solid (0.8 g, 95% yield). HPLC (82% purity, retention time 2.52 min.-method F), $^1$H NMR (400 MHz, DMSO-d$_6$) δ 12.15 (s, 1H), 8.07 (d, 1H), 8.04 (s, 1H), 3.80 (s, 3H).

Compound 146

1-Methyl-3-nitro-1,5-dihydro-pyrazolo[3,4-d]pyrimidin-4-one

The nitration to form compound 146 was accomplished following a literature procedure.[3] To a stirred solution of 145 (0.75 g, 0.005 mols) in HNO$_3$ (1.42 d, 6 mL) and concentrated H$_2$SO$_4$ (12 mL) was heated to 100° C. for 2 h. The mixture was cooled to room temperature and poured over ice. The resulting precipitate was collected by filtration and dried in vacuo to give a yellow solid (0.5 g, 52% yield). m.p. 291-296° C., HPLC (86% purity, retention time 0.872 min.-method F), $^1$H NMR (400 MHz, DMSO-d$_6$) δ 12.69 (s, 1H), 8.25 (d, 1H), 3.1 (s, 3H).

Compound 147

4-Chloro-1-methyl-3-nitro-1H-pyrazolo[3,4-d]pyrimidine

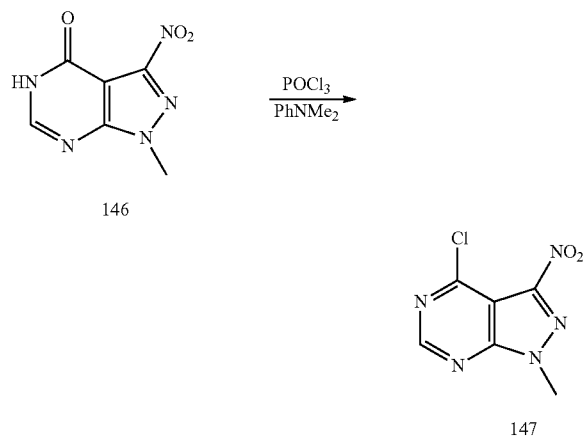

146

147

Following the procedure for the preparation of compound 25, compound 146 (0.25 g, 1.28 mmol) was treated with phosphorous oxychloride (10 mL) and N,N-dimethylaniline (1 mL). Concentration of the ether afforded 0.270 g (98%) of a red solid which was used without further purification. MS (ES$^+$ calculated—213.58; found—214.20 M+H)HPLC (85%) purity, retention time 4.700 minutes-(Method D); $^1$H NMR (400 MHz, DMSO-d$_6$) δ 9.09 (s, 1H), 4.21 (s, 3H).

Example 148

3-(1-Methyl-3-nitro-1H-pyrazolo[3,4-d]pyrimidin-4-yl)-2-oxo-2,3-dihydro-1H-indole-5-carbonitrile

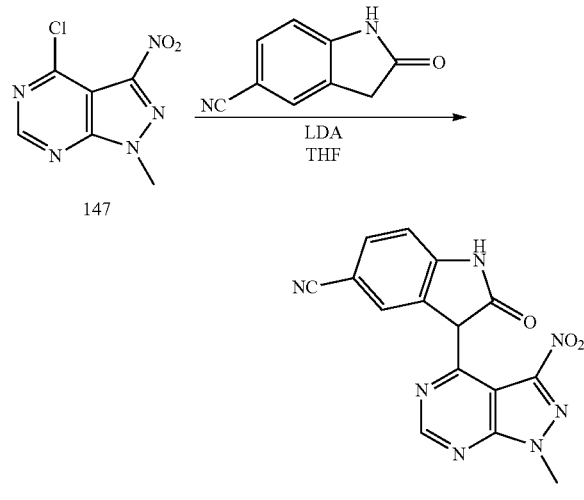

147

148

Utilizing the same procedure for the preparation of Example 29, Example 148 was prepared with some modifications. To 5-cyanooxindole (0.192 g, 1.21 mmol) in anhydrous THF (10 mL) under nitrogen at −78° C. was added lithium diisopropylamine (Acros, 1.22 mL of a 2.0M solution in THF/heptane, 2.43 mmol). The solution was stirred for fifteen minutes at which point a solution of compound 147 (0.27 g, 1.29 mmol) in THF (10 mL) was added dropwise. After addition was complete the external cooling bath was removed and the reaction was allowed to warm to room temperature. After 2 hours the reaction was complete. The reaction was quenched by the addition of a small amount of a saturated ammonium chloride solution and concentrated. Dichloromethane (5 mL) and water (5 mL) were added and undissolved solid was filtered. The solid was washed with minimal dichloromethane, as slight product solubility was observed. A red solid (0.285 g, 70%) was obtained and was used without further purification: mp>300 C (dec); MS (ES$^+$ calculated—335.28; found—336.16 M+H). HPLC (84%) purity; retention time 4.491 minutes-Method D); $^1$H NMR (400 MHz, DMSO-d$_6$) δ 8.39 (s, 1H), 7.32 (s, 1H) 6.99 (d, J=6.24 Hz), 4.03 (s, 1H), 4.00 (s, 3H). HPLC Method E:10-100% Acetonitrile over 7 minutes. HPLC purity determined at 290 nm.

The following Examples 149-168 in Table 2 were prepared according to procedures disclosed herein including the general procedure for the preparation of compounds of Formula XI, disclosed herein, and using methods generally known to one skilled in the art.

TABLE 2

| Example | R$^2$ | X |
|---|---|---|
| 149 | —CN | /—NHCH$_2$CH═CH$_2$ |
| 150 | —CN | /—NHCH(CH$_3$)$_2$ |
| 151 | —CN | /—NH(CH$_2$)$_2$NHCOCH$_3$ |
| 152 | H | /—Cl |
| 153 | —CF$_3$ | /—Cl |
| 154 | H | /—NHCH$_3$ |
| 155 | H | /—NH(CH$_2$)$_2$-3-pyridyl |
| 156 | H | /—NHCH$_2$-3-pyridyl |
| 157 | H | /—NH(CH$_2$)$_3$—N-morpholine |
| 158 | H | /—NH(CH$_2$)$_2$NHCOCH$_3$ |
| 159 | —CF$_3$ | /—NHCH$_3$ |
| 160 | —CF$_3$ | /—NH(CH$_2$)$_2$-3-pyridyl |
| 161 | —CF$_3$ | /—NHCH$_2$-3-pyridyl |
| 162 | —CF$_3$ | /—NH(CH$_2$)$_3$—N-morpholine |
| 163 | —CF$_3$ | /—NH(CH$_2$)$_2$NHCOCH$_3$ |
| 164 | —CN | /—O(CH$_2$)$_2$-3-pyridyl |
| 165 | —CN | /—NHCH$_2$CH(CH$_3$)$_2$ |
| 166 | —CN | /—NHCH$_2$CH$_3$ |
| 167 | —CN | /—N(CH$_2$CH$_2$OCH$_3$)$_2$ |
| 168 | —CN | /—N(CH$_2$CH$_2$OH)$_2$ |

Example 149

3-(6-Allylamino-2-cyclopentyl-2H-pyrazolo[3,4-d]pyrimidin-4-yl)-2-oxo-2,3-dihydro-1H-indole-5-carbonitrile A mixture of compound 113 (50 mg, 0.13 mmol), in allylamine (0.99 mL, 1.3 mmol) and 2-methoxyethanol (5 mL)

were heated to 130° C. for 3 h. The reaction was concentrated, treated with methanol, and filtered. The solid was washed with methanol and ethyl ether to give 32 mg (61%) of the desired product. Example 149: $^1$H NMR (400 MHz, DMSO-$d_6$) δ 11.6 (bs, 1H), 10.4 (s, 1H), 9.5 (s, 1H), 8.7 (s, 1H), 7.3 (d, 1H), 6.8 (d, 1H), 6.0 (m, 1H), 5.0-5.3 (m, 2H), 4.8 (m, 2H), 4.2 (s, 2H), 1.6-2.2 (m, 8H); MS (m/e) 400 (M+1); HPLC (99%) purity, retention time 4.212 minutes—Method C; mp>300° C.

Example 150

3-(2-cyclopentyl-6-isopropylamino-2H-pyrazolo [3,4-d]pyrimidin-4-yl)-2-oxo-2,3-dihydro-1H-indole-5-carbonitrile Example 150 was made in a similar manner to Example 149 using the appropriate starting materials. Experimental data: $^1$HNMR (400 MHz, DMSO-$d_6$) δ 11.3 (bs, 1H), 10.4 (s, 1H), 9.5 (s, 1H), 8.7 (s, 1H), 7.3 (d, 1H), 6.9 (d, 1H), 4.8 (m, 1H), 4.3 (m, 1H), 3.2 (m, 1H), 1.6-2.2 (m, 8H), 1.3 (d, 6H); MS (m/e) 402 (M+1); HPLC (98%) purity, retention time 4.227 minutes—Method C; mp>300° C.

Example 151

3-(6-(2-acetylamino-ethylamino)-2-cyclopentyl-2H-pyrazolo [3,4-d]pyrimidin-4-yl)-2-oxo-2,3-dihydro-1H-indole-5-carbonitrile Example 151 was made in a similar manner to Example 149 using the appropriate starting materials. Experimental data: $^1$HNMR (400 MHz, DMSO-$d_6$) δ 11.7 (bs, 1H), 10.4 (s, 1H), 9.5 (s, 1H), 8.7 (bs, 1H), 8.0 (m, 1H), 7.3 (d, 1H), 6.8 (d, 1H), 4.8 (m, 1H), 3.6 (m, 2H), 3.4 (m, 3H), 1.6-2.2 (m, 11H); MS (m/e) 445 (M+1); HPLC (99%) purity, retention time 3.538 minutes—Method C; mp>300° C.

Example 152

3-(6-Chloro-2-cyclopentyl-2H-pyrazolo[3,4-d]pyrimidin-4-yl)-1,3-dihydro-indol-2-one To a solution of Oxindole (260 mg, 1.95 mmol) and THF (5 mL) in a 125 mL flask at −78° C. was added 2M LDA in THF/Heptane (1.95 mL, 3.9 mmol). After the reaction was stirred for 30 min, a solution of compound 112 (500 mg, 1.95 mmol) in THF (5 mL) was added and the reaction was continued for 15 min at −78° C. Next, the reaction was let come to room temperature and stirred for an additional 2 h. It was quenched with water (2 mL) and concentrated. The solid was redissolved in methanol and concentrated onto silica gel. The silica gel was placed onto a column saturated with methylene chloride. The compound was eluted with a gradient of methylene chloride to 2% methanol/methylene chloride. The most pure fractions were concentrated, treated with ethyl ether, and filtered to give 530 mg (77%) of the desired product. Example 152: $^1$H NMR (400 MHz, DMSO-$d_6$) δ 11.0-11.2 (bs, 1H), 9.0-9.2 (bs, 1H), 7.7-7.9 (bs, 1H), 6.8-7.2 (m, 4H), 4.8-5.2 (bs, 1H), 1.6-2.3 (m, 8H); MS (m/e) 354 (M+1); HPLC (96%) purity, retention time 5.206 minutes—Method C; mp 270-273° C.

Example 153

3-(6-Chloro-2-cyclopentyl-2H-pyrazolo [3,4-d]pyrimidin-4-yl)-5-trifluoromethyl-1,3-dihydro-indol-2-one To a solution of 5-Trifluoromethyloxindole (390 mg, 1.95 mmol) and THF (5 mL) in a 125 mL flask at −78° C. was added 2M LDA in THF/Heptane (1.95 mL, 3.9 mmol). After the reaction was stirred for 30 min, a solution of compound 112 (500 mg, 1.95 mmol) in THF (5 mL) was added and the reaction was continued for 15 min at −78° C. Next, the reaction was let come to room temperature and stirred for an additional 2 h. It was quenched with water (2 mL) and concentrated. The solid was redissolved in methanol and concentrated onto silica gel. The silica gel was placed onto a column saturated with methylene chloride. The compound was eluted with a gradient of methylene chloride to 2% methanol/methylene chloride. The most pure fractions were concentrated, treated with ethyl ether, and filtered to give 517 mg (63%) of the desired product. Example 153: $^1$HNMR (400 MHz, DMSO-$d_6$) δ 10.7 (bs, 1H), 9.5 (bs, 1H), 8.5 (bs, 1H), 7.3 (d, 1H), 7.0 (d, 1H), 4.9-5.0 (m, 1H), 1.6-2.2 (m, 8H); MS (m/e) 422 (M+1); HPLC (98%) purity, retention time 5.979 minutes—Method C; mp>300° C.

Example 154

3-(2-cyclopentyl-6-methylamino-2H-pyrazolo [3,4-d]pyrimidin-4-yl)-1,3-dihydro-indol-2-one A mixture of Compound 152 (40 mg, 0.11 mmol), 2M Methylamine in THF (0.55 mL, 1.1 mmol) and 2-methoxyethanol (2 mL) were heated to 130° C. overnight. The reaction was concentrated, treated with methanol, and filtered. The solid was washed with methanol and ethyl ether to give 23 mg (61%) of the desired product. Example 154: $^1$H NMR (400 MHz, DMSO-$d_6$) δ 13.8 (s, 1H), 10.7 (s, 1H), 8.8 (s, 1H), 7.7 (d, 1H), 7.5 (s, 1H), 6.9-7.1 (m, 2H), 5.0 (m, 1H), 3.0 (m, 1H), 2.8 (s, 3H), 1.6-2.2 (m, 8H); MS (m/e) 349 (M+1); HPLC (99%) purity, retention time 3.632 minutes—Method C; mp>300° C.

Example 155

3-[2-cyclopentyl-6-(2-pyridin-3-yl-ethylamino)-2H-pyrazolo [3,4-d]pyrimidin-4-yl]-1,3-dihydro-indol-2-one Example 155 was prepared in a similar manner to Example 154 as disclosed herein using the appropriate starting materials. Experimental data: $^1$H NMR (400 MHz, DMSO-$d_6$) δ 13.8 (s, 1H), 10.7 (s, 1H), 8.8 (s, 1H), 8.4-8.6 (m, 2H), 7.6-7.8 (m, 2H), 7.2-7.5 (m, 1H), 6.9-7.1 (m, 2H), 6.8 (d, 1H), 5.0 (m, 1H), 3.8 (m, 1H), 3.6 (m, 2H), 2.8-3.0 (m, 2H), 1.6-2.2 (m, 8H); MS (m/e) 440 (M+1); HPLC (90%) purity, retention time 3.376 minutes—Method C; mp 258-260° C.

Example 156

3-{2-cyclopentyl-6-[(pyridin-3-ylmethyl)-amino]-2H-pyrazolo [3,4-d]pyrimidin-4-yl}-1,3-dihydro-indol-2-one Example 156 was prepared in a similar manner to Example 154 as disclosed herein using the appropriate starting materials. Experimental data: $^1$HNMR (400 MHz, DMSO-$d_6$) δ 13.8 (s, 1H), 10.7 (s, 1H), 8.8 (s, 1H), 8.6 (s, 1H), 8.4 (m, 1H), 8.3 (m, 1H), 7.7-7.8 (m, 2H), 7.0 (m, 1H), 6.9 (m, 1H), 5.0 (m, 1H), 4.8 (m, 1H), 4.6 (d, 2H), 1.6-2.2 (m, 8H); MS (m/e) 426 (M+1); HPLC (97%) purity, retention time 3.476 minutes—Method C; mp 216-218° C.

Example 157

3-[2-cyclopentyl-6-(3-morpholin-4-yl-propylamino)-2H-pyrazolo[3,4-d]pyrimidin-4-yl]-1,3-dihydro-indol-2-one Example 157 was prepared in a similar manner to Example 154 as disclosed herein using the appropriate starting materials. Experimental data: $^1$HNMR (400 MHz, DMSO-$d_6$) δ 13.8 (s, 1H), 10.7 (s, 1H), 8.8 (s, 1H), 7.7 (m, 2H), 7.0 (m, 2H), 5.0 (m, 1H), 3.6 (m, 4H), 3.5 (m, 1H), 2.4 (m, 6H), 1.6-2.2 (m, 12H); MS (m/e) 462 (M+1); HPLC (99%) purity, retention time 3.457 minutes—Method C; mp 242-245° C.

Example 158

3-(2-cyclopentyl-6-(2-acetylamino-ethylamino)-2H-pyrazolo[3,4-d]pyrimidin-4-yl)-1,3-dihydro-indol-2-one Example 158 was prepared in a similar manner to Example 154 as disclosed herein using the appropriate starting materials. Experimental data: $^1$HNMR (400 MHz, DMSO-$d_6$) δ 13.8 (s, 1H), 10.7 (s, 1H), 8.8 (s, 1H), 7.7-8.0 (m, 3H), 6.8-7.0 (m, 2H), 5.0 (m, 1H), 3.3 (m, 1H), 3.0 (s, 3H), 1.6-2.2 (m, 12H); MS (m/e) 420 (M+1); HPLC (95%) purity, retention time 3.558 minutes—Method C; mp 238-240° C.

Example 159

3-(-2-cyclopentyl-6-methylamino-2H-pyrazolo[3,4-d]pyrimidin-4-yl)-5-trifluoromethyl-1,3-dihydro-indol-2-one A mixture of Compound 153 (40 mg, 0.095 mmol), 2M Methylamine in THF (0.55 mL, 0.95 mmol) and 2-methoxyethanol (2 mL) were heated to 130° C. overnight. The reaction was concentrated, treated with methanol, and filtered. The solid was washed with methanol and ethyl ether to give 25 mg (63%) of the desired product. Example 159: $^1$HNMR (400 MHz, DMSO-$d_6$) δ 11.6 (s, 1H), 10.3 (s, 1H), 9.5 (s, 1H), 8.8 (s, 1H), 7.2 (d, 1H), 6.9 (m, 2H), 4.8 (m, 1H), 3.0 (d, 3H), 1.6-2.2 (m, 8H); MS (m/e) 417 (M+1); HPLC (99%) purity, retention time 4.444 minutes—Method C; mp>300° C.

Example 160

3-[2-cyclopentyl-6-(2-pyridin-3-yl-ethylamino)-2H-pyrazolo[3,4-d]pyrimidin-4-yl]-5-trifluoromethyl-1,3-dihydro-indol-2-one Example 160 was prepared in a similar manner to Example 153 as disclosed herein using the appropriate starting materials. Experimental data: $^1$HNMR (400 MHz, DMSO-$d_6$) δ 11.4 (s, 1H), 10.3 (s, 1H), 9.5 (s, 1H), 8.7 (s, 1H), 8.4-8.6 (m, 3H), 7.7 (m, 1H), 7.4 (m, 1H), 7.3 (m, 1H), 7.0 (m, 1H), 4.8 (m, 1H), 3.8 (m, 2H), 2.9 (m, 2H) 1.6-2.2 (m, 8H); MS (m/e) 508 (M+1); HPLC (97%) purity, retention time 3.989 minutes—Method C; mp 278-280° C.

Example 161

3-{2-cyclopentyl-6-[(pyridin-3-ylmethyl)-amino]-2H-pyrazolo[3,4-d]pyrimidin-4-yl}-5-trifluoromethyl-1,3-dihydro-indol-2-one Example 161 was prepared in a similar manner to Example 153 as disclosed herein using the appropriate starting materials. Experimental data: $^1$HNMR (400 MHz, DMSO-$d_6$) δ 11.7 (s, 1H), 10.3 (s, 1H), 9.5 (s, 1H), 8.7 (m, 2H), 8.5 (m, 1H), 7.8 (m, 1H), 7.5 (m, 1H), 7.3 (m, 1H), 7.2 (m, 1H), 6.8 (d, 1H), 4.8 (m, 3H), 1.6-2.2 (m, 8H); MS (m/e) 494 (M+1); HPLC (96%) purity, retention time 4.041 minutes—Method C; mp>300° C.

Example 162

3-[2-cyclopentyl-6-(3-morpholin-4-yl-propylamino)-2H-pyrazolo[3,4-d]pyrimidin-4-yl]-5-trifluoromethyl-1,3-dihydro-indol-2-one Example 162 was prepared in a similar manner to Example 153 as disclosed herein using the appropriate starting materials. Experimental data: $^1$HNMR (400 MHz, DMSO-$d_6$) δ 11.4 (s, 1H), 10.3 (s, 1H), 9.5 (s, 1H), 8.8 (s, 1H), 7.2 (d, 1H), 7.0 (m, 1H), 6.8 (d, 1H), 4.9 (m, 1H), 3.6 (m, 4H), 2.4 (m, 6H), 1.6-2.2 (m, 12H); MS (m/e) 530 (M+1); HPLC (99%) purity, retention time 4.041 minutes—Method C; mp 288-291° C.

Example 163

3-(2-cyclopentyl-6-(2-acetylamino-ethylamino)-2H-pyrazolo[3,4-d]pyrimidin-4-yl)-5-trifluoromethyl-1,3-dihydro-indol-2-one Example 163 was prepared in a similar manner to Example 153 as disclosed herein using the appropriate starting materials. Experimental data: $^1$HNMR (400 MHz, DMSO-$d_6$) δ 11.5 (s, 1H), 10.3 (s, 1H), 9.5 (s, 1H), 8.8 (s, 1H), 8.0 (m, 1H), 7.2 (d, 1H), 6.9 (m, 2H), 4.8 (m, 1H), 3.6 (m, 2H), 3.4 (m, 2H), 1.6-2.2 (m, 11H); MS (m/e) 488 (M+1); HPLC (99%) purity, retention time 4.314 minutes—Method C; mp>300° C.

Example 164

3-[2-cyclopentyl-6-(2-pyridin-3-yl-ethoxy)-2H-pyrazolo[3,4-d]pyrimidin-4-yl]-2-oxo-2,3-dihydro-1H-indole-5-carbonitrile Example 164 was prepared in a similar manner to Example 153 as disclosed herein using the appropriate starting materials. Experimental data: m.p. 302-304° C.; MS (ES$^+$ calculated: 465.52; found: 466.03 M+H). HPLC (98.5% purity, retention time 9.067 minutes—Method B); $^1$HNMR (400 MHz, DMSO-$d_6$) δ 10.33 (s, 1H), 9.97 (s, 1H), 9.90 (d, 1H), 9.68 (s, 1H), 8.72 (d, 1H), 8.53 (s, 1H), 8.27 (t, 1H), 7.25 (d, 1H), 6.88 (d, 1H), 4.98 (m, 1H), 4.86 (br s, 1H), 3.84 (t, 2H), 3.34 (m, 1H), 3.15 (t, 2H), 2.20 (m, 2H), 2.06 (m, 2H), 1.89 (m, 2H), 1.72 (m, 2H).

Example 165

3-(2-cyclopentyl-6-isobutylamino-2H-pyrazolo [3,4-d]pyrimidin-4-yl)-2-oxo-2,3-dihydro-1H-indole-5-carbonitrile Example 165 was prepared in a similar manner to Example 153 as disclosed herein using the appropriate starting materials. Experimental data: m.p. 297-298.5° C.; MS (ES$^+$ calculated: 415.50; found: 416.27 M+H). HPLC (99% purity, retention time 11.175 minutes—Method B); $^1$HNMR (400 MHz, DMSO-d$_6$) δ 11.43 (br s, 1H), 10.39 (s, 1H), 9.50 (s, 1H), 8.70 (s, 1H), 7.29 (d, 1H), 6.86 (d, 1H), 4.82 (m, 1H), 3.32 (m, 3H), 2.13 (m, 2H), 1.97 (m, 3H), 1.82 (m, 2H), 1.68 (m, 2H), 1.00 (d, 6H).

Example 166

3-(2-cyclopentyl-6-ethylamino-2H-pyrazolo[3,4-d]pyrimidin-4-yl)-2-oxo-2,3-dihydro-1H-indole-5-carbonitrile Example 166 was prepared in a similar manner to Example 153 as disclosed herein using the appropriate starting materials. Experimental data: m.p. 373° C. (dec.); MS (ES$^+$ calculated: 387.45; found: 388.22 M+H). HPLC (99% purity, retention time 9.721 minutes—Method B); $^1$HNMR (400 MHz, DMSO-d$_6$) δ 11.59 (s, 1H), 10.37 (s, 1H), 9.48 (s, 1H), 8.74 (s, 1H), 7.27 (d, 1H), 6.85 (d, 1H), 4.83 (m, 1H), 3.51 (m, 2H), 3.31 (s, 1H), 2.14 (m, 2H), 1.97 (m, 2H), 1.82 (m, 2H), 1.68 (m, 2H), 1.28 (t, 3H).

Example 167

3-{6-[bis-(2-methoxyethyl)amino]-2-cyclopentyl-2H-pyrazolo[3,4-d]pyrimidin-4-yl}-2-oxo-2,3-dihydro-1H-indole-5-carbonitrile Example 167 was prepared in a similar manner to Example 153 as disclosed herein using the appropriate starting materials. Experimental data: m.p. 248.5-249° C.; MS (ES$^+$ calculated: 475.55; found: 476.29 M+H). HPLC (99% purity, retention time 11.720 minutes—Method B); $^1$HNMR (400 MHz, DMSO-d$_6$) δ 11.64 (s, 1H), 10.42 (s, 1H), 9.52 (s, 1H), 8.42 (s, 1H), 7.29 (d, 1H), 6.87 (d, 1H), 4.87 (m, 1H), 3.93 (s, 4H), 3.65 (m, 4H), 3.61 (m, 1H), 3.32 (s, 6H), 2.16 (m, 2H), 1.98 (m, 2H), 1.84 (m, 2H), 1.70 (m, 2H).

Example 168

3-{6-[bis(2-hydroxyethyl)amino]-2-cyclopentyl-2H-pyrazolo[3,4-d]pyrimidin-4-yl}-2-oxo-2,3-dihydro-1H-indole-5-carbonitrile Example 168 was prepared in a similar manner to Example 153 as disclosed herein using the appropriate starting materials. Experimental data: m.p. 243-243.5° C.; MS (ES$^+$ calculated: 447.50; found: 448.23 M+H). HPLC (95% purity, retention time 9.084 minutes—Method B); $^1$HNMR (400 MHz, DMSO-d$_6$) δ 11.56 (br s, 1H), 10.40 (s, 1H), 9.51 (s, 1H), 8.43 (s, 1H), 7.28 (d, 1H), 6.86 (d, 1H), 5.07 (br s, 2H), 4.84 (m, 1H), 3.87 (s, 4H), 3.78 (m, 4H), 3.70 (m, 1H), 1.97 (m, 2H), 1.83 (m, 2H), 1.69 (m, 2H).

The following Examples 169-182 in Table 3 were prepared according to procedures disclosed herein using appropriate starting materials and including methods generally known to one skilled in the art.

TABLE 3

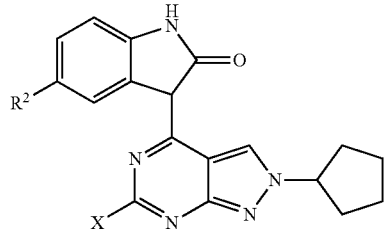

| Example | R$^2$ | X |
|---|---|---|
| 169 | CN | 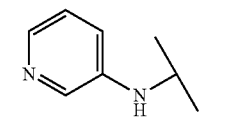 |
| 170 | CN | 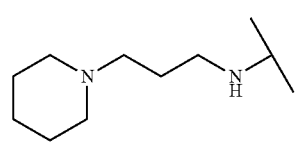 |
| 171 | CN | 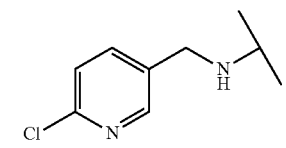 |
| 172 | CN | 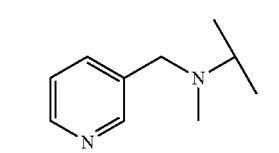 |
| 173 | CN | 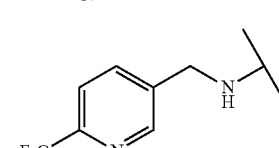 |
| 174 | CN | 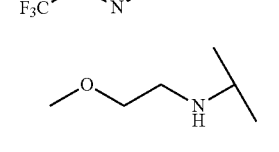 |
| 175 | CN | 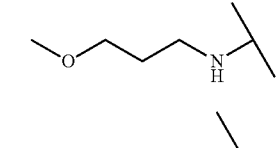 |
| 176 | CN | 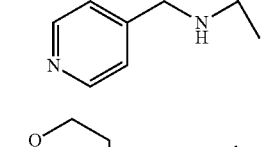 |
| 177 | CN | 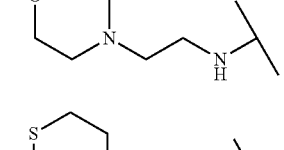 |
| 178 | CN | 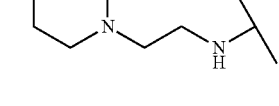 |

TABLE 3-continued

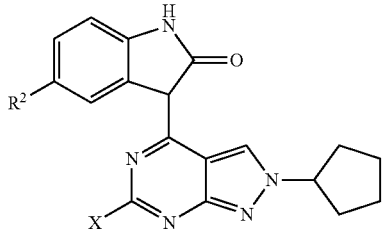

| Example | R² | X |
|---------|-----|---|
| 179 | Br | 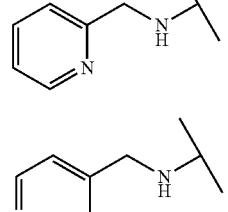 |
| 180 | Br | 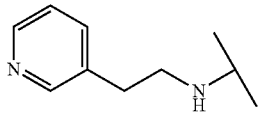 |
| 181 | Br |  |
| 182 | Br | Cl |

Example 169

3-[2-Cyclopentyl-6-(pyridin-3-ylamino)-2H-pyrazolo [3,4-d]pyrimidin-4-yl]-2-oxo-2,3-dihydro-1H-indole-5-carbonitrile Experimental data: $^1$H NMR (400 MHz, DMSO-$d_6$) δ 10.31 (s, 1H), 9.66 (s, 1H), 9.32 (m, 1H), 9.08 (m, 1H), 8.49 (m, 1H), 7.94-7.80 (m, 2H), 7.24-7.22 (m, 1H), 6.88-6.81 (m, 3H), 4.97 (m, 1H), 2.22-1.69 (m, 8H); MS (m/e) 437 (M+1).

Example 170

3[2-Cyclopentyl-6-(3-piperidin-1-yl-propylamino)-2H-pyrazolo[3,4-d]pyrimidin-4-yl]-2-oxo-2,3-dihydro-1H-indole-5-carbonitrile Experimental data: $^1$H NMR (400 MHz, DMSO-$d_6$) δ 10.27 (s, 1H), 9.46 (s, 1H), 8.73 (s, 1H), 8.03 (s, 1H), 7.22 (s, 1H), 6.82 (m, 1H), 4.81 (m, 1H), 3.46 (m, 2H), 3.08 (m, 2H), 2.63 (m, 2H), 2.43 (m, 2H), 2.15-1.38 (m, 17H); MS (m/e) 485 (M+1).

Example 171

3-{6-[(6-Chloro-pyridin-3-ylmethyl)-amino]-2-cyclopentyl-2H-pyrazolo[3,4-d]pyrimidin-4-yl}-2-oxo-2,3-dihydro-1H-indole-5-carbonitrile Experimental data: $^1$H NMR (400 MHz, DMSO-$d_6$) δ 11.92 (s, 1H), 10.32 (s, 1H), 9.47 (s, 1H), 8.44 (m, 2H), 7.88 (m, 1H), 7.47 (m, 1H), 7.21 (m, 1H), 6.82 (m, 1H), 4.82-4.74 (m, 3H), 2.14-1.66 (m, 9H); MS (m/e) 485 (M+1).

Example 172

3-[2-Cyclopentyl-6-(methyl-pyridin-3-ylmethyl-amino)-2H-pyrazolo [3,4-d]pyrimidin-4-yl]-2-oxo-2,3-dihydro-1H-indole-5-carbonitrile Experimental data: $^1$H NMR (400 MHz, DMSO-$d_6$) δ 11.95 (s, 1H), 10.42 (s, 1H), 9.54 (s, 1H), 8.56 (s, 1H), 8.47 (m, 1H), 8.31 (s, 1H), 7.75 (m, 1H), 7.36 (m, 1H), 7.22 (m, 1H), 6.82 (m, 1H), 5.09 (s, 2H), 4.88 (m, 1H), 3.28 (s, 3H), 2.17-1.68 (m, 8H); MS (m/e) 465 (M+1).

Example 173

3-{2-Cyclopentyl-6-[(6-trifluoromethyl-pyridin-3-ylmethyl)-amino]-2H-pyrazolo [3,4-d]pyrimidin-4-yl}-2-oxo-2,3-dihydro-1H-indole-5-carbonitrile Experimental data: $^1$H NMR (400 MHz, DMSO-$d_6$) δ 11.95 (s, 1H), 10.40 (s, 1H), 9.50 (s, 1H), 8.80 (s, 1H), 8.41 (s, 1H), 8.09 (m, 1H), 7.88 (m, 2H), 7.25 (m, 1H), 6.83 (m, 1H), 4.89 (s, 2H), 4.84 (m, 1H), 2.17-1.69 (m, 8H); MS (m/e) 519 (M+1).

Example 174

3-[2-Cyclopentyl-6-(2-methoxy-ethylamino)-2H-pyrazolo [3,4-d]pyrimidin-4-yl]-2-oxo-2,3-dihydro-1H-indole-5-carbonitrile Experimental data: $^1$H NMR (400 MHz, DMSO-$d_6$) δ 11.53 (s, 1H), 10.39 (s, 1H), 9.49 (s, 1H), 8.66 (s, 1H), 7.29 (m, 1H), 6.86 (m, 1H), 4.83 (m, 1H), 3.65-3.51 (m, 4H), 3.33 (s, 3H), 2.17-1.67 (m, 9H); MS (m/e) 418 (M+1).

Example 175

3-[2-Cyclopentyl-6-(3-methoxy-propylamino)-2H-pyrazolo [3,4-d]pyrimidin-4-yl]-2-oxo-2,3-dihydro-1H-indole-5-carbonitrile Experimental data: $^1$H NMR (400 MHz, DMSO-$d_6$) δ 10.14 (s, 1H), 9.44 (s, 1H), 8.71 (s, 1H), 7.16 (m, 1H), 6.80 (m, 1H), 4.77 (m, 1H), 3.48 (m, 4H), 3.32 (m, 2H), 3.23 (s, 3H), 2.14-1.60 (m, 10H); MS (m/e) 432 (M+1).

Example 176

3-{2-Cyclopentyl-6-[(pyridin-4-ylmethyl)-amino]-2H-pyrazolo[3,4-d]pyrimidin-4-yl}-2-oxo-2,3-dihydro-1H-indole-5-carbonitrile Experimental data: $^1$H NMR (400 MHz, DMSO-$d_6$) δ 10.27 (s, 1H), 9.47 (s, 1H), 8.55 (m, 2H), 8.48 (m, 2H), 7.40 (m, 2H), 7.19 (m, 1H), 6.79 (m, 1H), 4.80 (m, 1H), 4.74 (s, 2H), 3.94 (s, 1H), 2.14-1.66 (m, 8H); MS (m/e) 451 (M+1).

Example 177

3-[2-Cyclopentyl-6-(2-morpholin-4-yl-ethylamino)-2H-pyrazolo[3,4-d]pyrimidin-4-yl]-2-oxo-2,3-dihydro-1H-indole-5-carbonitrile Experimental data: $^1$H NMR (400 MHz, DMSO-$d_6$) δ 10.37 (s, 1H), 9.48 (s, 1H), 8.70 (s, 1H), 7.27 (m, 1H), 6.85 (m, 1H), 4.83 (m, 1H), 3.68 (m, 4H), 3.59 (m, 2H), 3.31 (m, 4H), 2.65 (m, 2H), 2.53 (m, 2H), 2.16-1.67 (m, 8H); MS (m/e) 473 (M+1).

Example 178

3-[2-Cyclopentyl-6-(2-thiomorpholin-4-yl-ethylamino)-2H-pyrazolo[3,4-d]pyrimidin-4-yl]-2-oxo-2,3-dihydro-1H-indole-5-carbonitrile Experimental data: $^1$H NMR (400 MHz, DMSO-$d_6$) δ 10.34 (s, 1H), 9.48 (s, 1H), 8.70 (m, 1H), 7.27 (m, 1H), 6.85 (m, 1H), 4.83 (m, 1H), 3.57 (m, 2H), 2.85-2.55 (m, 12H), 2.16-1.67 (m, 8H); MS (m/e) 489 (M+1).

Example 179

5-Bromo-3-{2-cyclopentyl-6-[(pyridin-2-ylmethyl)-amino]-2H-pyrazolo[3,4-d]pyrimidin-4-yl}-1,3-dihydro-1H-indol-2-one Experimental data: $^1$H NMR (400 MHz, DMSO-$d_6$) δ 10.82 (s, 1H), 9.97 (s, 1H), 9.49 (s, 1H), 8.57 (m, 1H), 8.44 (m, 1H), 7.79 (m, 1H), 7.50 (m, 1H), 7.43 (m, 1H), 7.30 (m, 1H), 6.97 (m, 1H), 6.65 (m, 1H), 4.85 (m, 2H), 4.80 (m, 1H), 2.15-1.67 (m, 8H); MS (m/e) 504 (M).

Example 180

5-Bromo-3-{2-cyclopentyl-6-[(pyridin-4-ylmethyl)-amino]-2H-pyrazolo[3,4-d]pyrimidin-4-yl}-1,3-dihydro-1H-indol-2-one Experimental data: $^1$H NMR (400 MHz, DMSO-$d_6$) δ 9.88 (s, 1H), 9.48 (s, 1H), 8.49 (m, 2H), 8.28 (s, 1H), 7.39 (m, 3H), 6.91 (m, 1H), 6.62 (m, 1H), 4.77 (m, 3H), 2.15-1.66 (m, 9H); MS (m/e) 504 (M).

Example 181

5-Bromo-3-[2-cyclopentyl-6-(2-pyridin-3-yl-ethylamino)-2H-pyrazolo[3,4-d]pyrimidin-4-yl]-1,3-dihydro-1H-indol-2-one Experimental data: $^1$H NMR (400 MHz, DMSO-$d_6$) δ 11.37 (s, 1H), 9.98 (s, 1H), 9.49 (s, 1H), 8.62-8.42 (m, 3H), 7.72 (m, 2H), 7.33 (m, 1H), 6.99 (m, 1H), 6.67 (m, 1H), 4.80 (m, 1H), 3.78 (m, 2H), 3.03 (m, 2H), 2.16-1.68 (m, 8H); MS (m/e) 518 (M).

Example 182

5-Bromo-3-(6-chloro-2-cyclopentyl-2H-pyrazolo[3,4-d]pyrimidin-4-yl)-1,3-dihydro-indol-2-one Experimental data: $^1$H NMR (400 MHz, DMSO-$d_6$) δ 10.48 (s, 1H), 9.34 (s, 1H), 8.26 (s, 1H), 7.17 (m, 1H), 6.78 (m, 1H), 4.98 (m, 1H), 2.20-1.20 (m, 9H); MS (m/e) 433 (M+1).

Example 183

3-(6-Chloro-2-propyl-2H-pyrazolo[3,4-d]pyrimidin-4-yl)-2-oxo-2,3-dihydro-1H-indole-5-carbonitrile

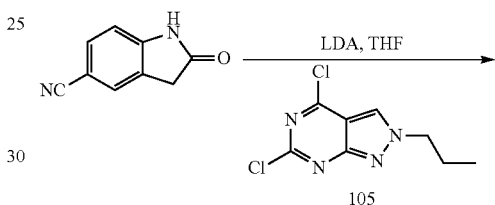

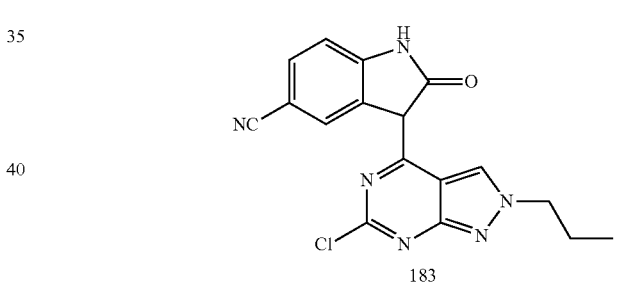

To a stirring solution of 5-cyanooxindole (103 mg, 0.649 mmol) and anhydrous THF (5 mL) in a 15 mL flask at −78° C. was added LDA (649 μL, 1.3 mmol). The reaction mixture was stirred for 15 min before adding the compound 105 (150 mg, 0.649 mmol) as a solid. Following an additional 15 min at −78° C., the reaction was allowed to warm to room temperature and stirred for additional 5 h. The reaction mixture was concentrated to dryness, taken up into MeOH and concentrated onto silica gel and pumped dry before subjecting it to flash chromatography on silica gel (gradient elution: 1-10% methanol: dichloromethane) to afford 115 mg (50%) of a yellow solid after trituration in MeOH. Example 183: mp>300° C.; MS (ES$^+$ calculated: 352.79; found: 353.29 M+H). HPLC (99%) purity, retention time 11.253 minutes—Method D); $^1$H NMR (400 MHz, DMSO-$d_6$) δ 10.9 (br s, 1H), 9.37 (s, 1H), 8.41 (bs, 1H), 7.46 (d, J=8 Hz, 1H), 6.97 (d, J=8 Hz, 1H), 4.30 (t, J=7 Hz, 2H), 1.88 (q, J=3 Hz, 2H), 0.87 (t, J=7 Hz, 3H).

Example 184

2-Oxo-3-{2-propyl-6-[(pyridin-3-ylmethyl)-amino]-2H-pyrazolo[3,4-d]pyrimidin-4-yl}-2,3-dihydro-1H-indole-5-carbonitrile

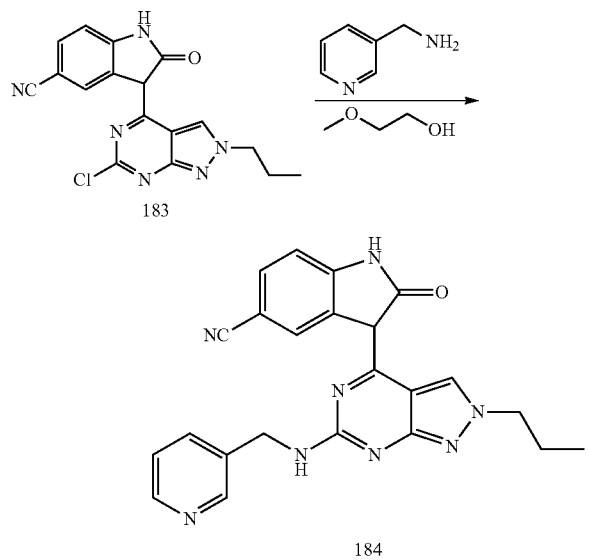

Example 183 (25 mg, 0.071 mmol) and 3-(aminomethyl)pyridine (71.8 µL, 0.71 mmol) were stirred in 1 mL methoxyethanol overnight at 130° C. in an aluminum block. The reaction mixture was concentrated to dryness and triturated in 3:1 ether/MeOH. The resulting solid was filtered and pumped dry to afford 23 mg (76%) of a dark yellow solid. Example 184: mp 291-295° C.; MS (ES+ calculated: 424.47; found: 425.21 M+H). HPLC (99%) purity, retention time 8.438 minutes—Method D); $^1$H NMR (400 MHz, DMSO-d$_6$) δ 11.8 (br s, 1H), 10.39 (s, 1H), 9.43 (s, 1H), 8.64 (s, 1H), 8.46 (d, 1H), 7.83 (d, 1H), 7.37 (dd, J=5 Hz, J=3 Hz, 1H), 7.25 (d, J=8 Hz, 1H), 4.79 (s 2H), 4.16 (t, J=7 Hz, 2H), 1.83 (m, 2H), 1.09 (t, J=7 Hz, 2H), 0.86 (t, J=7 Hz, 3H).

Example 185

2-Oxo-3-[2-propyl-6-(2-pyridin-3-yl-ethylamino)-2H-pyrazolo[3,4-d]pyrimidin-4-yl]-2,3-dihydro-1H-indole-5-carbonitrile

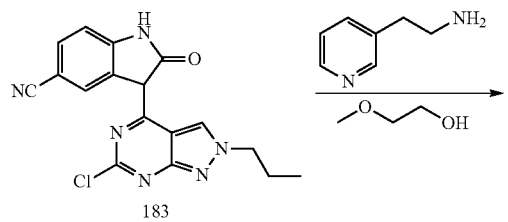

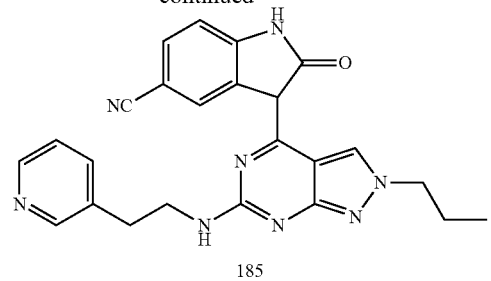

Using the procedure outlined for Example 184, Example 183 (25 mg, 0.071 mmol) and 3-(aminoethyl)pyridine (86.7 mg, 0.71 mmol) were stirred in 1 mL methoxyethanol overnight at 130° C. in an aluminum block. The reaction mixture was concentrated to dryness and triturated in a small amount of MeOH. The resulting solid was filtered and pumped dry to afford 15 mg (48%) of a yellow solid. Example 185: mp 302-305° C.; MS (ES+ calculated: 438.50; found: 439.20 M+H). HPLC (99%) purity, retention time 2.996 minutes—Method C); $^1$H NMR (400 MHz, DMSO-d$_6$) δ 11.2 (br s, 1H), 10.40 (s, 1H), 9.43 (s, 1H), 8.71 (s, 1H), 8.51 (s, 1H), 8.42 (d, J=5 Hz, 1H), 7.74 (d, J=8 Hz, 1H), 7.33 (m, 2H), 6.86 (d, J=8 Hz, 1H), 4.16 (t, J=7 Hz, 2H), 3.77 (br s, 2H), 3.01 (m2H), 1.84 (m, 2H), 0.86 (t, J=7 Hz, 3H).

Example 186

2-Oxo-3-{2-propyl-6-[(pyridine-4-ylmethyl)-amino]-2H-pyrazolo[3,4-d]pyrimidin-4-yl}-2,3-dihydro-1H-indole-5-carbonitrile

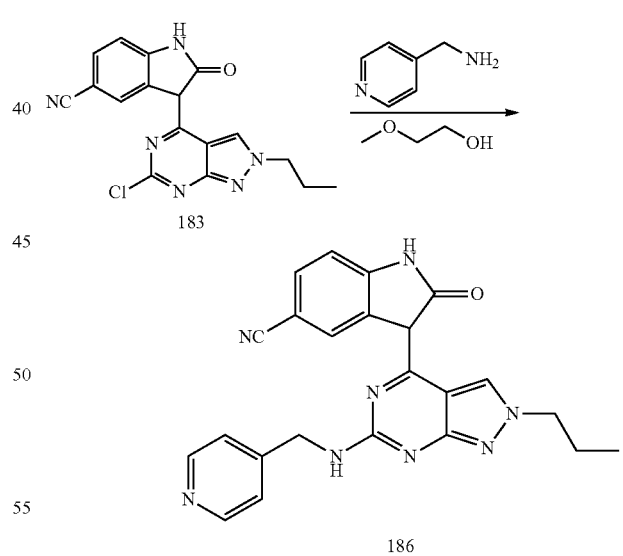

Using the procedure outlined for Example 184, Example 183 (25 mg, 0.071 mmol) and 4-(aminomethyl)pyridine (71.8 µL, 0.71 mmol) were stirred in 1 mL methoxyethanol overnight at 130° C. in an aluminum block. The reaction mixture was concentrated to dryness and triturated in a small amount of MeOH. The resulting solid was filtered and pumped dry to afford 24 mg (79%) of a yellow solid. Example 186: mp 299-302° C.; MS (ES+ calculated: 424.47; found: 425.20 M+H). HPLC (92%) purity, retention time 2.90 minutes—

Method C); $^1$H NMR (400 MHz, DMSO-d$_6$) δ 11.87 (br s, 1H), 10.38 (s, 1H), 9.44 (s, 1H), 8.49 (d, J=5 Hz, 2H), 8.33 (br s, 1H), 7.40 (d, J=5 Hz, 1H), 7.23 (d, J=8 Hz, 1H), 6.80 (d, J=8 Hz, 1H), 6.86 (d, J=8 Hz, 1H), 4.16 (t, J=7 Hz, 2H), 3.17 (s, J=5 Hz, 2H), 1.84 (m, 2H), 0.87 (t, J=7 Hz, 3H).

Example 187

2-Oxo-3-[2-propyl-6-(2-pyridin-2-yl-ethylamino)-2H-pyrazolo[3,4-d]pyrimidin-4-yl]-2,3-dihydro-1H-indole-5-carbonitrile

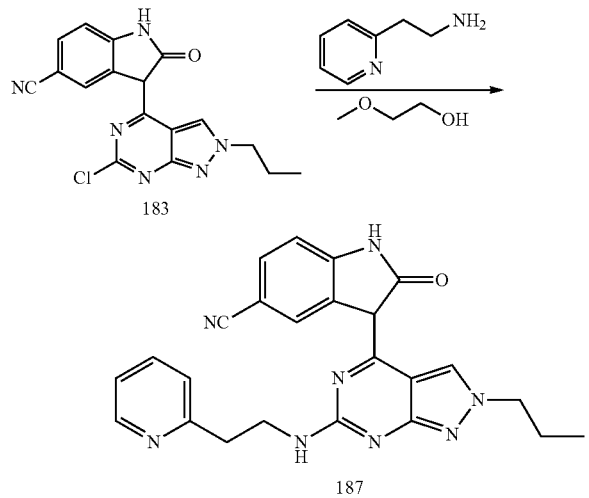

Using the procedure outlined for Example 184, Example 183 (25 mg, 0.071 mmol) and 2-(aminoethyl)pyridine (84.5 µL, 0.71 mmol) were stirred in 1 mL methoxyethanol overnight at 130° C. in an aluminum block. The reaction mixture was concentrated to dryness and triturated in a small amount of MeOH. The resulting solid was filtered and pumped dry to afford 23 mg (74%) of a yellow solid. Example 187: mp>300° C.; MS (ES$^+$ calculated: 438.50; found: 439.22 M+H). HPLC (96%) purity, retention time 3.040 minutes—Method C); $^1$H NMR (400 MHz, DMSO-d$_6$) δ 11.55 (br s, 1H), 10.40 (s, 1H), 9.43 (s, 1H), 8.73 (s, 1H), 8.55 (m, 1H), 7.73 (m, 1H) 7.35 (d, J=8, 1H), 7.25 (m, 3H), 6.86 (d, J=8 Hz, 1H), 4.16 (t, J=7 Hz, 2H), 3.90 (br s, 2H), 3.16 (m, 2H), 1.84 (m, 2H), 0.86 (t, J=7 Hz, 3H).

Example 188

5-Bromo-3-(6-chloro-2-propyl-2H-pyrazolo[3,4-d]pyrimidin-4-yl)-1,3-dihydro-indol-2-one

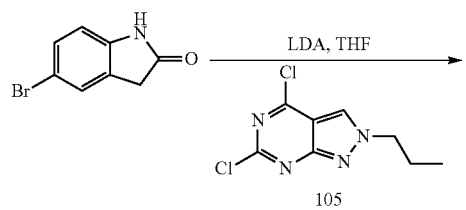

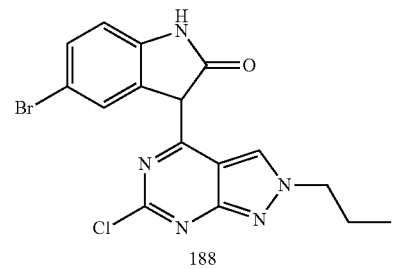

To a stirring solution of 5-bromooxindole (229 mg, 1.08 mmol) and anhydrous THF (10 mL) in a 25 mL flask at −78° C. was added LDA (1.08 mL, 2.16 mmol). The reaction mixture was stirred for 15 min before adding the substrate 105 (250 mg, 1.08 mmol) as a solid. Following an additional 15 min at −78° C., the reaction was allowed to warm to room temperature and stirred overnight (reaction may have been complete after 2 h). The reaction mixture was concentrated to dryness, taken up into MeOH and concentrated onto silica gel and pumped dry before subjecting it to flash chromatography on silica gel (gradient elution: 1-2-3% methanol: dichloromethane) to afford 210 mg (48%) of a yellow solid that precipitated in the reaction tubes and was triturated in MeOH. Example 188: mp >300° C.; MS (ES$^+$ calculated: 406.67; found: 407.87 M+H). HPLC (99%) purity, retention time 12.31 minutes—Method D); $^1$H NMR (400 MHz, DMSO-d$_6$) δ 10.5 (br s, 1H), 9.31 (s, 1H), 8.26 (br s, 1H), 7.17 (d, J=8 Hz, 1H), 6.79 (d, J=8 Hz, 1H), 4.28 (br s, 2H), 1.86 (q, J=3 Hz, 2H), 0.87 (t, J=8 Hz, 3H).

Example 189

5-Bromo-3-[2-propyl-6-(2-pyridin-3-yl-ethylamino)-2H-pyrazolo [3,4-d]pyrimidin-4-yl]-1,3-dihydro-indol-2-one

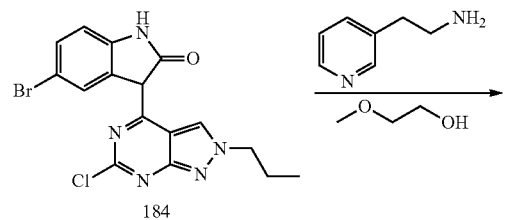

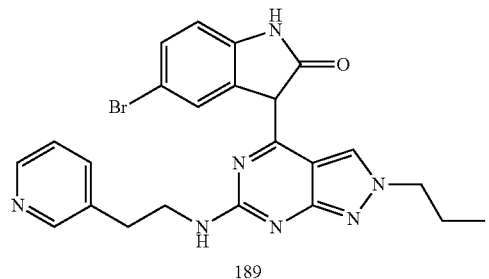

Using the procedure outlined for Example 184, Example 188 (25 mg, 0.0614 mmol) and 3-(aminoethyl)pyridine (75 mg, 0.614 mmol) were stirred in 1 mL methoxyethanol overnight at 130° C. in an aluminum block. The reaction mixture was concentrated to dryness and triturated in a small amount of MeOH. The resulting solid was filtered and pumped dry to afford 15 mg (50%) of a yellow solid. Example 189: mp 294-297° C.; MS (ES+ calculated: 492.38; found: 492.50 M+H). HPLC (80%) purity, retention time 3.437 minutes—Method C); $^1$H NMR (400 MHz, DMSO-$d_6$) δ 11.3 (br s, 1H), 10.01 (s, 1H), 9.42 (s, 1H), 8.52 (m, 2H), 8.43 (s, 1H), 7.73 (m, 1H), 7.65 (m, 1H), 7.32 (m, 2H), 6.98 (m, 1H), 6.67 (d, J=8 Hz) 4.14 (t, J=7 Hz, 2H), 3.78 (br s, 2H), 3.38 (m), 3.03 (m 2H), 1.84 (m, 2H), 0.86 (m, 3H).

Example 190

5-Bromo-3-{2-propyl-6-[(pyridine-4-ylmethyl)-amino]-2H-pyrazolo[3,4-d]pyrimidin-4-yl}-1,3-dihydro-indol-2-one

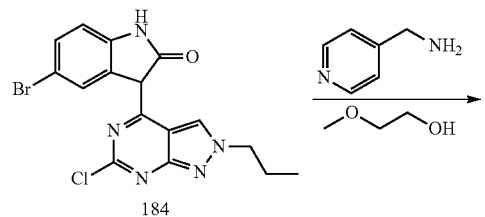

184

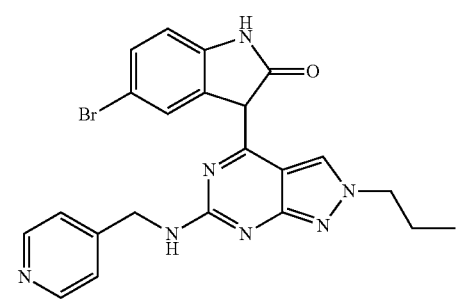

190

Using the procedure outlined for Example 184, Example 188 (25 mg, 0.0614 mmol) and 4-(aminomethyl)pyridine (62 μL, 0.614 mmol) were stirred in 1 mL methoxyethanol overnight at 130° C. in an aluminum block. The reaction mixture was concentrated to dryness and triturated in a small amount of MeOH. The resulting solid was filtered and pumped dry to afford 4 mg (14%) of a yellow solid. Example 190: mp>300° C.; MS (ES+ calculated: 478.36; found: 478.61 M+H). HPLC (74%) purity, retention time 3.461 minutes—Method C); $^1$H NMR (400 MHz, DMSO-$d_6$) δ 11.69 (br s, 1H), 9.4 (s, 1H), 8.50 (d, J=6 Hz), 8.24 (s, 1H), 7.42 (d, J=7 Hz, 1H), 6.93 (d, J=8 Hz, 1H), 4.79 (d, J=6 Hz, 1H), 4.14 (m, 2H), 1.84 (m, 2H), 0.87 (t, J=7 Hz, 3H).

Example 191

5-Bromo-3-[2-propyl-6-(2-pyridin-2-yl-ethylamino)-2H-pyrazolo [3,4-d]pyrimidin-4-yl]-1,3-dihydro-indol-2-one

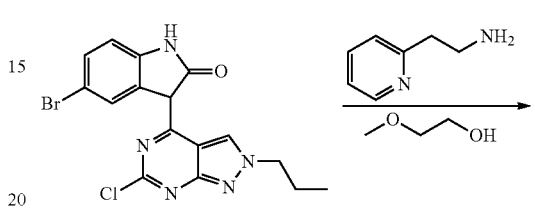

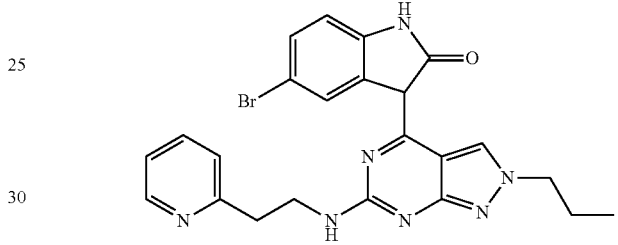

Using the procedure outlined for Example 184, Example 188 (25 mg, 0.0614 mmol) and 2-(aminoethyl)pyridine (73 μL, 0.614 mmol) were stirred in 1 mL methoxyethanol overnight at 130° C. in an aluminum block. The reaction mixture was concentrated to dryness and triturated in a small amount of MeOH. The resulting solid was filtered and pumped dry to afford 14 mg (46%) of a yellow solid. Example 191: mp 283-291° C.; MS (ES+ calculated: 492.38; found: 492.41 M+H). HPLC (86%) purity, retention time 3.60 minutes—Method C); $^1$H NMR (400 MHz, DMSO-$d_6$) δ 11.32 (br s, 1H), 10.02 (s, 1H), 9.42 (s, 1H), 8.55 (d, 2H), 7.75 (m, 1H) 7.37 (d, J=8, 1H), 7.26 (m, 3H), 7.00 (d, 1H), 6.67 (d, J=8 Hz, 1H), 4.13 (t, J=7 Hz, 2H), 3.91 (br s, 2H), 3.19 (m, 2H), 1.83 (m, 2H), 0.86 (m, 3H).

Example 192

5-Bromo-3-[2-propyl-6-(3,3,3-trifluoro-propylamino)-2H-pyrazolo[3,4-d]pyrimidin-4-yl]-1,3-dihydro-indol-2-one

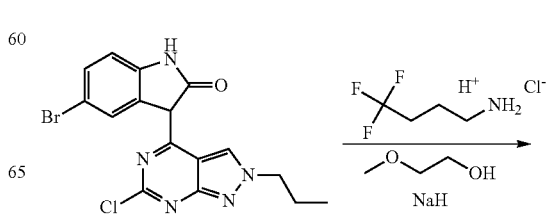

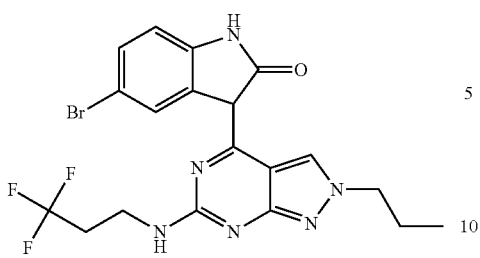

Example 188 (25 mg, 0.0614 mmol) and 3,3,3-trifluoro-n-propylamine hydrochloride. (89 mg, 0.614 mmol) were stirred in 1 mL methoxyethanol before adding NaH (19.6 mg, 0.491 mmol) and heated overnight at 130° C. in an aluminum block. The reaction mixture was concentrated to dryness and triturated in a small amount of MeOH. The resulting solid was filtered and pumped dry to afford 24 mg (81%) of a yellow solid. Example 192: mp>300° C.; MS (ES+ calculated: 483.29; found: 483.61 M+H). HPLC (99%) purity, retention time 4.915 minutes—Method C); $^1$H NMR (400 MHz, DMSO-$d_6$) δ 11.53 (br s, 1H), 10.86 (s, 1H), 10.02 (s, 1H), 9.43 (s, 1H), 8.45 (s, 1H), 7.01 (d, 2H) 6.67 (d, 1H), 4.14 (t, J=7 Hz, 2H), 3.76 (br s, 2H), 2.70 (m, 2H), 1.83 (m, 2H), 0.86 (m, 3H).

Example 193

3-(6-Allylamino-2-propyl-2H-pyrazolo[3,4-d]pyrimidin-4-yl)-5-bromo-1,3-dihydro-indol-2-one

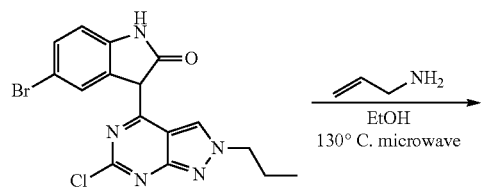

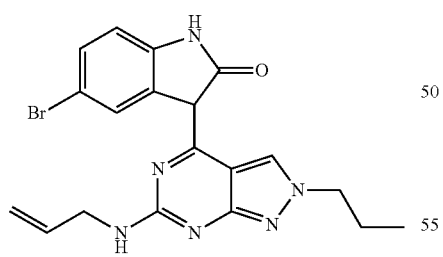

Example 188 (34 mg, 0.0835 mmol) and allylamine (62.7 μL, 0.835 mmol) were heated in 1 mL EtOH at 130° C. in microwave for 10 min. Upon cooling, the product precipitated in the reaction tube. The resulting solid was filtered and pumped dry to afford 30 mg (84%) of a bright yellow solid. Example 193: mp 322-326° C.; MS (ES+ calculated: 427.31; found: 428.3 M+H). HPLC (100%) purity, retention time 4.223 minutes—Method C); $^1$H NMR (400 MHz, DMSO-$d_6$) δ 11.37 (s, 1H), 9.98 (s, 1H), 9.41 (s, 1H), 8.52 (s, 1H), 7.11 (br s, 1H), 7.01 (d, 1H), 6.66 (d, J=8 Hz, 1H), 6.03 (m, 1H), 5.30 (d, 1H), 5.15 (d, 1H) 4.13 (s, 4H), 1.83 (m, 2H), 0.86 (m, 3H).

Example 194

5-Bromo-3-[6-((S)-2-hydroxy-propylamino)-2-propyl-2H-pyrazolo[3,4-d]pyrimidin-4-yl]-1,3-dihydro-indol-2-one

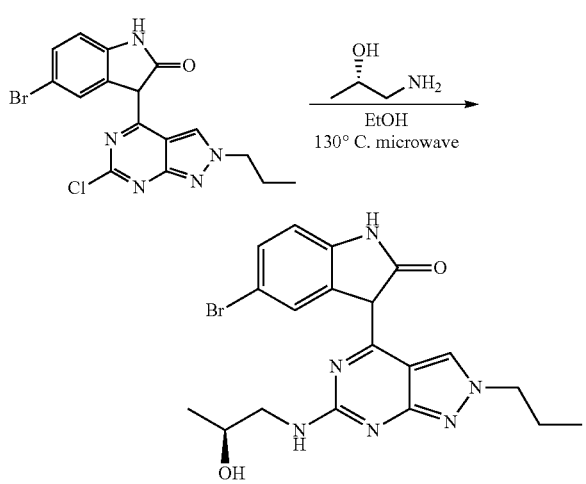

Using the procedure outlined for Example 184, Example 188 (30 mg, 0.0737 mmol) and (S)-(+)-1-amino-2-propanol (58 μL, 0.737 mmol) were heated in 1 mL EtOH at 130° C. in microwave for 10 min. Upon cooling, the product precipitated in the reaction tube. The resulting solid was filtered and pumped dry to afford 32 mg (97%) of a bright yellow solid. Example 194: mp 322-326° C.; MS (ES+ calculated: 445.32; found: 445.65 M+H). HPLC (97%) purity, retention time 3.735 minutes—Method C); $^1$H NMR (400 MHz, DMSO-$d_6$) δ 11.12 (br s, 1H), 9.99 (s, 1H), 9.41 (s, 1H), 8.52 (s, 1H), 7.00 (d, 1H), 6.68 (d, J=8 Hz, 1H), 4.97 (br s, 1H), 4.13 (t, J=7 Hz, 2H), 3.94 (br s, 1H), 3.65 (br s, 1H) 3.23 (m, 1H), 1.83 (m, 2H), 1.22 (d, J=6 Hz, 2H), 1.10 (d, J=6 Hz, 1H), 0.86 (m, 3H).

Example 195

5-Bromo-3-[6-((R)-2-hydroxy-propylamino)-2-propyl-2H-pyrazolo[3,4-d]pyrimidin-4-yl]-1,3-dihydro-indol-2-one

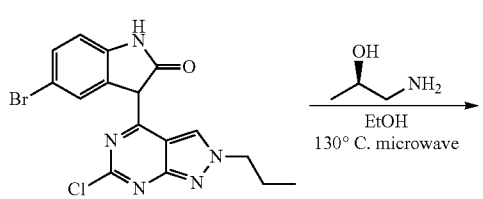

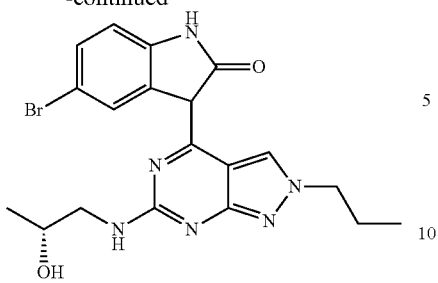

Using the procedure outlined for Example 184, Example 188 (30 mg, 0.0737 mmol) and (R)-(−)-1-amino-2-propanol (58 μL, 0.737 mmol) were heated in 1 mL EtOH at 130° C. in microwave for 10 min. Upon cooling, the product precipitated in the reaction tube. The resulting solid was filtered and pumped dry to afford 27 mg (82%) of a yellow solid. Example 195: mp 310° C. (dec); MS (ES+ calculated: 445.32; found: 445.66 M+H). HPLC (95%) purity, retention time 3.741 minutes—Method C); $^1$H NMR (400 MHz, DMSO-$d_6$) δ 11.12 (br s, 1H), 9.99 (s, 1H), 9.41 (s, 1H), 8.52 (s, 1H), 7.00 (d, 1H), 6.68 (d, J=8 Hz, 1H), 4.97 (br s, 1H), 4.13 (t, J=7 Hz, 2H), 3.94 (br s, 1H), 3.65 (br s, 1H) 3.23 (m, 1H), 1.83 (m, 2H), 1.22 (d, J=6 Hz, 2H), 1.10 (d, J=6 Hz, 1H), 0.86 (m, 3H).

Example 196

5-Bromo-3-{2-propyl-6-[(pyridin-3-ylmethyl)-amino]-2H-pyrazolo[3,4-d]pyrimidin-4-yl}-1,3-dihydro-indol-2-one

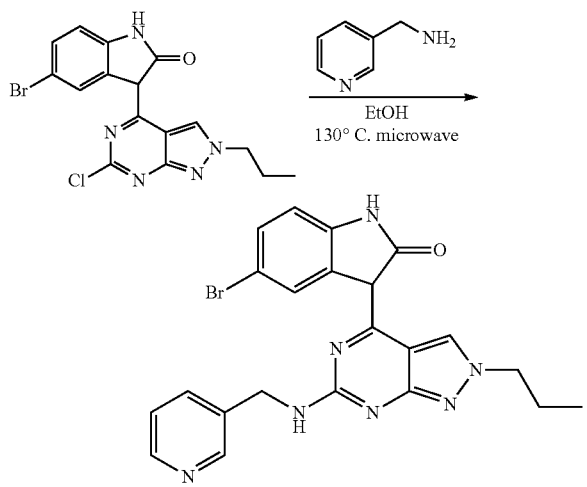

Using the procedure outlined for Example 184, Example 188 (30 mg, 0.0737 mmol) and 3-(aminoethyl)pyridine (74.6 μL, 0.737 mmol) were stirred in 1 mL EtOH at 130° C. in microwave for 10 min. Upon cooling, the product precipitated in the reaction tube. The resulting solid was filtered and pumped dry to afford 15 mg (43%) of a yellow solid. Example 196: mp 277-281° C.; MS (ES+ calculated: 478.36; found: 478.54 M+H). HPLC (92%) purity, retention time 3.490 minutes—Method C); $^1$H NMR (400 MHz, DMSO-$d_6$) δ 9.98 (s, 1H), 9.42 (s, 1H), 8.66 (s, 1H), 8.45 (s, 1H), 8.40 (m, 1H), 7.83 (d, 1H), 7.48 (br s, 1H), 7.35 (m, 1H), 6.66 (d, 1H) 4.78 (d, 2H), 4.14 (t, J=7 Hz, 2H), 1.84 (m, 2H), 0.86 (m, 3H).

Example 197

5-Bromo-3-[6-(2-dimethylamino-ethylamino)-2-propyl-2H-pyrazolo[3,4-d]pyrimidin-4-yl]-1,3-dihydro-indol-2-one

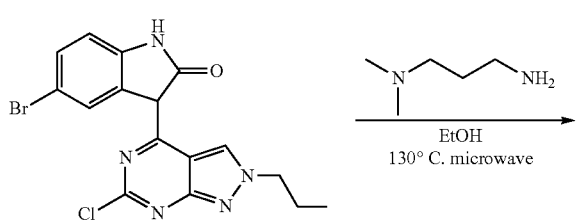

Using the procedure outlined for Example 184, Example 188 (30 mg, 0.0737 mmol) and N,N-dimethylaminoethylamine (65 μL, 0.737 mmol) were heated in 1 mL EtOH at 130° C. in microwave for 10 min. Upon cooling, the product precipitated in the reaction tube. The resulting solid was filtered and pumped dry to afford 16 mg (47%) of a yellow solid. Example 197: mp 270-274° C.; MS (ES+ calculated: 458.36; found: 458.69 M+H). HPLC (96%) purity, retention time 3.534 minutes—Method C); $^1$H NMR (400 MHz, DMSO-$d_6$) δ 9.97 (s, 1H), 9.41 (s, 1H), 8.51 (s, 1H), 6.99 (d, J=8 Hz, 1H), 6.85 (br s, 1H), 6.66 (d, J=8 Hz, 1H), 4.13 (t, J=7 Hz, 2H), 3.58 (br d, 1H), 2.61 (m, 2H) 2.28 (s, 6H), 1.83 (m, 2H), 0.86 (m, 3H).

Example 198

5-Bromo-3-[6-(3-dimethylamino-propylamino)-2-propyl-2H-pyrazolo [3,4-d]pyrimidin-4-yl]-1,3-dihydro-indol-2-one

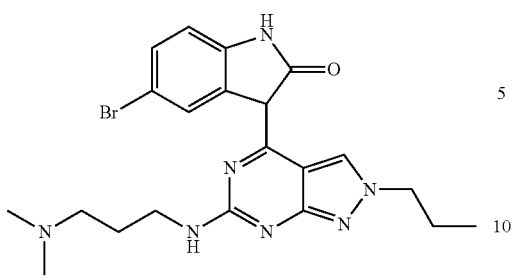

Using the procedure outlined for Example 184, Example 188 (30 mg, 0.0737 mmol) and N,N-dimethylaminopropylamine (93 μL, 0.737 mmol) were heated in 1 mL EtOH at 130° C. in microwave for 10 min. Upon cooling, the product precipitated in the reaction tube. The resulting solid was filtered and pumped dry to afford 25 mg (79%) of a yellow solid. Example 198: mp 286-290° C.; MS (ES+ calculated: 472.39; found: 472.62 M+H). HPLC (98%) purity, retention time 3.464 minutes—Method C); $^1$H NMR (400 MHz, DMSO-$d_6$) δ 9.92 (s, 1H), 9.41 (s, 1H), 8.54 (s, 1H), 7.10 (br s, 1H), 6.97 (d, J=8 Hz, 1H), 6.65 (d, J=8 Hz, 1H), 4.13 (t, J=7 Hz, 2H), 3.49 (br d, 1H), 2.24 (s, 6H), 1.83 (m, 4H), 0.86 (m, 3H).

Example 199

3-[6-(3-Amino-propylamino)-2-propyl-2H-pyrazolo [3,4-d]pyrimidin-4-yl]-5-bromo-1,3-dihydro-indol-2-one

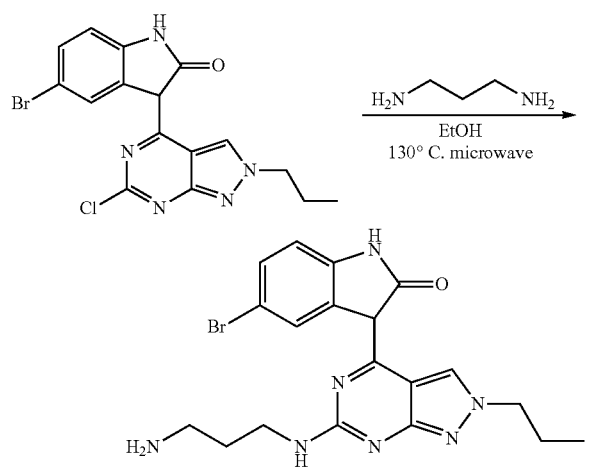

Using the procedure outlined for Example 184, Example 188 (40 mg, 0.0983 mmol) and 1,3-propanediamine (83 μL, 0.983 mmol) were heated in 1 mL EtOH at 130° C. in microwave for 10 min. Upon cooling, the product precipitated in the reaction tube. The resulting solid was filtered and pumped dry to afford 33 mg (76%) of a yellow solid. Example 199: mp>300° C.; MS (ES+ calculated: 444.34; found: 444.61 M+H). HPLC (94%) purity, retention time 3.297 minutes—Method C); $^1$H NMR (400 MHz, DMSO-$d_6$) δ 9.50 (s, 1H), 9.37 (s, 1H), 8.57 (s, 1H), 7.75 (br s), 6.77 (d, J=8 Hz, 1H), 6.57 (d, J=8 Hz, 1H), 6.35 (br s, 1H) 4.07 (t, J=7 Hz, 2H), 3.50 (s, 2H), 2.84 (m, 1H), 1.83 (m, 4H), 0.86 (m, 3H).

Example 200

3-[6-(2-Amino-ethylamino)-2-propyl-2H-pyrazolo [3,4-d]pyrimidin-4-yl]-5-bromo-1,3-dihydro-indol-2-one

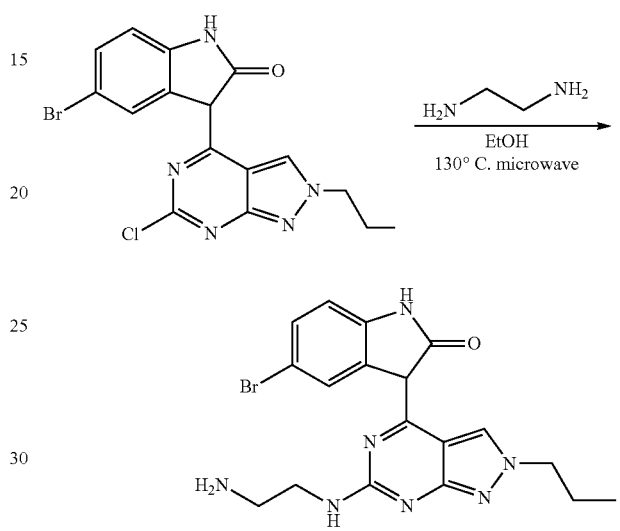

Using the procedure outlined for Example 184, Example 188 (40 mg, 0.0983 mmol) and 1,3-ethanediamine (65.7 μL, 0.983 mmol) were heated in 1 mL EtOH at 130° C. in microwave for 10 min. Upon cooling, the product precipitated in the reaction tube. The resulting solid was filtered and pumped dry to afford 28 mg (66%) of a yellow solid. Example 200: mp 272-276° C.; MS (ES+ calculated: 430.31; found: 430.70 M+H). HPLC (87%) purity, retention time 3.383 minutes—Method C); $^1$H NMR (400 MHz, DMSO-$d_6$) δ 9.56 (s, 1H), 9.38 (s, 1H), 8.55 (s, 1H), 7.45 (br s), 6.80 (d, J=8 Hz, 1H), 6.58 (d, J=8 Hz, 1H), 6.47 (br s, 1H) 4.09 (m, 2H), 3.50 (s, 2H), 3.03 (s, 2H), 1.83 (m, 4H), 0.86 (m, 3H).

Example 201

5-Bromo-3-[6-(3-methylamino-propylamino)-2-propyl-2H-pyrazolo [3,4-d]pyrimidin-4-yl]-1,3-dihydro-indol-2-one hydrochloride

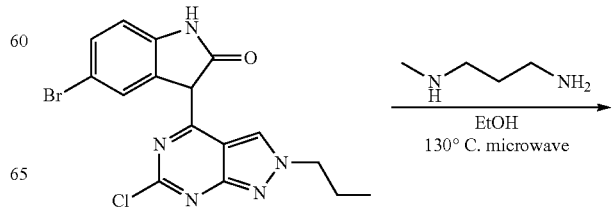

-continued

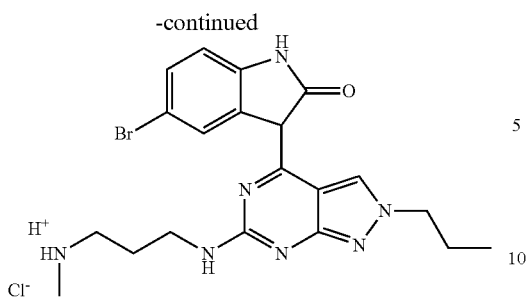

Using the procedure outlined for Example 184, Example 188 (50 mg, 0.123 mmol) and N-(3-aminopropyl)-N-methyl carbamic acid t-butyl ester (231 mg, 1.23 mmol) were heated in 1 mL EtOH at 130° C. in microwave for 10 min. Upon cooling, the product precipitated in the reaction tube. The resulting solid was filtered and pumped dry before stirring in 5 mL of 4N HCl/dioxane for 1 h at RT. The reaction mixture was pumped dry, triturated in ether and filtered to afford 39 mg (64%) of a yellow solid. Example 201: mp 271-273° C.; MS (ES⁺ calculated: 458.61; found: 459.4 M+H). HPLC (94%) purity, retention time 3.406 minutes—Method C); $^1$H NMR (400 MHz, DMSO-d$_6$) δ 8.73 (s, 1H), 7.07 (s, 1H), 6.76 (s, 1H), 4.07 (s, 1H), 3.50 (s, 2H), 3.02 (s, 1H), 2.55 (m, 3H), 2.02 (s, 2H), 1.84 (m, 2H), 0.86 (m, 3H).

Example 202

5-Bromo-3-[6-(2-morpholin-4-yl-ethylamino)-2-propyl-2H-pyrazolo [3,4-d]pyrimidin-4-yl]-1,3-dihydro-indol-2-one

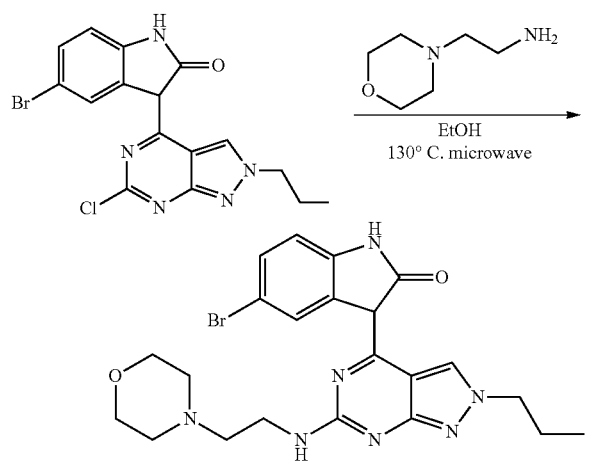

Using the procedure outlined for Example 184, Example 188 (30 mg, 0.0737 mmol) and N-(2-aminoethyl) morpholine (96.7 µL, 0.737 mmol) were heated in 1 mL EtOH at 130° C. in microwave for 10 min. Upon cooling, the product precipitated in the reaction tube. The resulting solid was filtered and pumped dry to afford 30 mg (81%) of a yellow solid. Example 202: mp 299-303° C.; MS (ES⁺ calculated: 500.40; found: 500.60 M+H). HPLC (95%) purity, retention time 3.739 minutes—Method C); $^1$H NMR (400 MHz, DMSO-d$_6$) δ 9.97 (s, 1H), 9.41 (s, 1H), 8.51 (br s, 1H), 7.00 (d, 1H), 6.87 (m, 1H), 6.66 (d, J=8 Hz, 1H), 4.13 (t, J=7 Hz, 2H), 3.64 (m, 8H), 2.65 (t, 2H), 1.83 (m, 4H), 0.86 (m, 3H).

Example 203

5-Bromo-3-[6-(3-morpholin-4-yl-propylamino)-2-propyl-2H-pyrazolo [3,4-d]pyrimidin-4-yl]-1,3-dihydro-indol-2-one

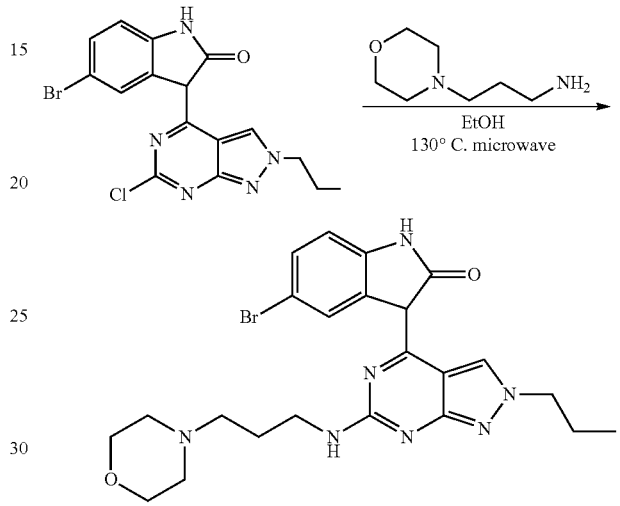

Using the procedure outlined for Example 184, Example 188 (30 mg, 0.0737 mmol) and N-(3-aminopropyl) morpholine (107 µL, 0.737 mmol) were heated in 1 mL EtOH at 130° C. in microwave for 10 min. Upon cooling, the product precipitated in the reaction tube. The resulting solid was filtered and pumped dry to afford 30 mg (95%) of a yellow solid. Example 203: mp 298-303° C.; MS (ES⁺ calculated: 514.43; found: 514.51 M+H). HPLC (98%) purity, retention time 3.569 minutes—Method C); $^1$H NMR (400 MHz, DMSO-d$_6$) δ 9.56 (s, 1H), 9.38 (s, 1H), 8.55 (s, 1H), 7.45 (br s), 6.80 (d, J=8 Hz, 1H), 6.58 (d, J=8 Hz, 1H), 6.47 (br s, 1H) 4.09 (m, 2H), 3.50 (s, 2H), 3.03 (s, 2H), 2.37 (m, 2H), 1.83 (m, 4H), 0.86 (m, 3H).

Example 204

3-(6-Chloro-2-propyl-2H-pyrazolo [3,4-d]pyrimidin-4-yl)-2-oxo-2,3-dihydro-1H-indole-5-sulfonic acid dimethylamide

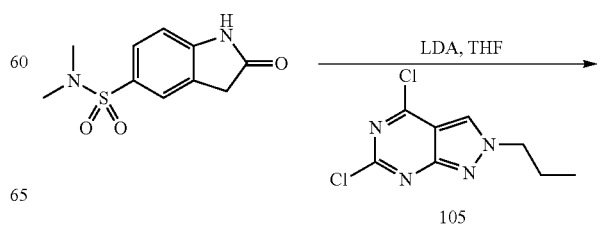

105

-continued

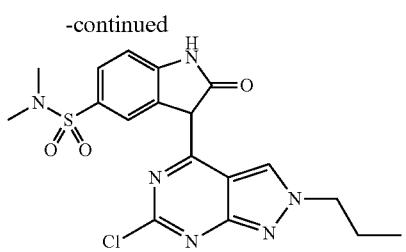

To a stirring solution of 5-dimethylsulfonamideoxindole (208 mg, 0.866 mmol) and anhydrous THF (7.5 mL) in a 15 mL flask at −78° C. was added LDA (0.866 mL, 1.732 mmol). The reaction mixture was stirred for 15 min before adding the substrate 105 (200 mg, 0.866 mmol) as a solid. Following an additional 15 min at −78° C., the reaction was allowed to warm to room temperature and stirred over weekend (reaction may have been complete after 2 h). The reaction mixture was concentrated to dryness, taken up into MeOH and concentrated onto silica gel and pumped dry before subjecting it to flash chromatography on silica gel (gradient elution: 1-5% methanol: dichloromethane) to afford 196 mg (52%) of a yellow solid that precipitated in the reaction tubes and was triturated in ether. Example 204: mp>300° C.; MS (ES+ calculated: 434.91; found: 435.42 M+H). HPLC (83%) purity, retention time 4.24 minutes—Method C); $^1$H NMR (400 MHz, DMSO-d6) δ 10.73 (br s, 1H), 9.35 (br s, 1H), 8.62 (br s, 1H), 7.40 (d, J=8 Hz, 1H), 6.98 (d, J=8 Hz, 1H), 4.26 (t, J=3 Hz, 2H), 2.62 (s, 6H) 1.86 (q, J=3 Hz, 2H), 0.87 (t, J=8 Hz, 3H).

Example 205

3-[6-(2-Dimethylamino-ethylamino)-2-propyl-2H-pyrazolo [3,4-d]pyrimidin-4-yl]-2-oxo-2,3-dihydro-1H-indole-5-sulfonic acid dimethylamide

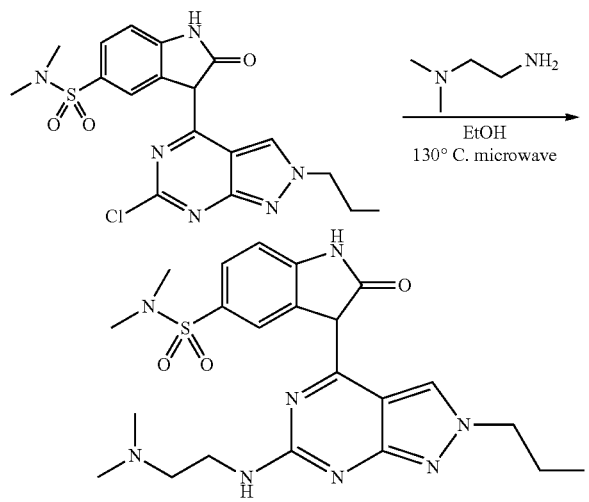

Using the procedure outlined for Example 184, Example 188 (50 mg, 0.115 mmol) and N,N-dimethylaminoethylamine (101 mg, 1.15 mmol) were heated in 1 mL EtOH at 130° C. in microwave for 10 min. Upon cooling, the product precipitated in the reaction tube. The resulting solid was filtered and pumped dry to afford 39 mg (70%) of a yellow solid. Example 205: mp 259-263° C.; MS (ES+ calculated: 486.60; found: 487.30 M+H). HPLC (96%) purity, retention time 2.972 minutes—Method C); $^1$H NMR (400 MHz, DMSO-d$_6$) δ 10.15 (br s, 1H), 9.39 (s, 1H), 8.83 (s, 1H), 7.20 (d, J=8 Hz, 1H), 6.86 (d, J=8 Hz, 1H), 4.12 (t, J=7 Hz, 2H), 3.58 (br s, 2H), 2.77 (t, 1H) 2.57 (s, 9H), 2.22 (s, 6H), 2.16 (s, 2H), 1.83 (m, 2H), 0.86 (m, 3H).

Scheme 4 discloses a general procedure for the preparation of compounds of the invention wherein R$^6$ is an alkoxyalkyl group and R$^2$ is chloro.

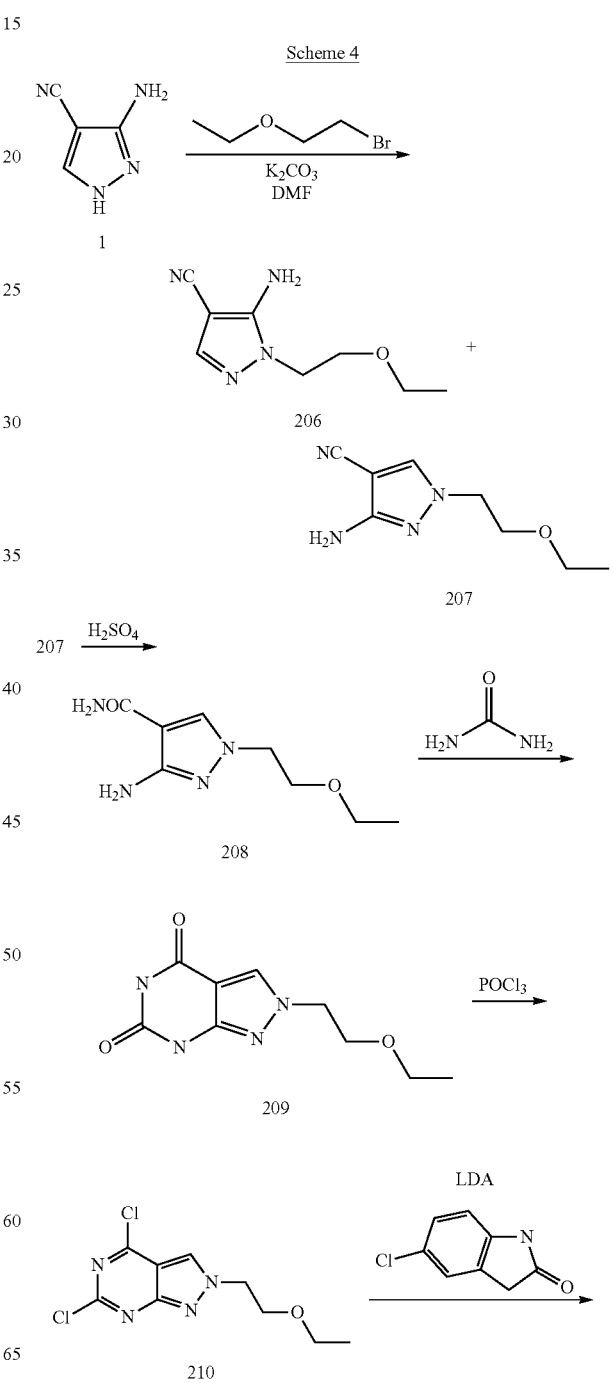

-continued

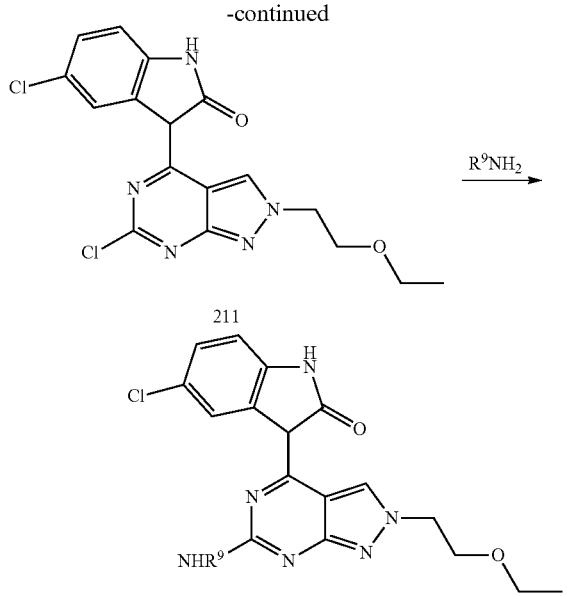

Compound 206 and 207

5-Amino-1-(2-ethoxyethyl)-1H-pyrazole-4-carbonitrile

3-Amino-1-(2-ethyoxyethyl)-1H-pyrazole-4-carbonitrile

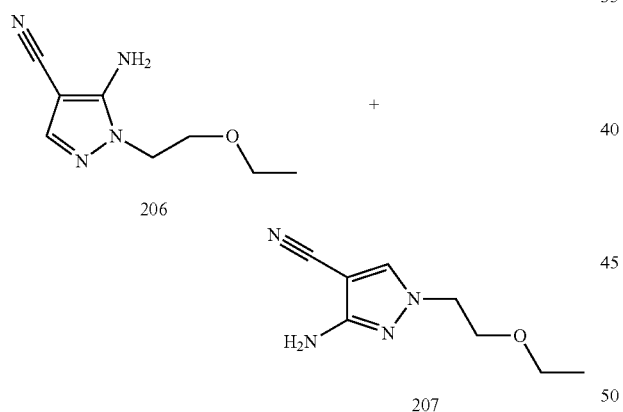

3-Amino-4-cyanopyrazole 1 (3.24 g, 30.0 mmol), 2-bromoethoxyethylether (6.12 g, 40.0 mmol), and potassium carbonate (5.53 g, 40.0 mmol) were combined in 20 mL anhydrous N,N-dimethylformamide and heated under argon at 80° C. overnight. Solids were removed by filtration and the mother liquor was concentrated to afford after chromatography on silica (gradient elution 2:1 to 0:1 petroleum ether:ethyl acetate) two products: KA—a higher RF white solid (2.08 g, 39%) and KB—a lower RF pale yellow solid (2.21 g, 41%). Compound 206: mp 130-132° C.; MS (ES$^+$ calculated: 180.21; found: 181.16 M+H). HPLC (92% purity, retention time 6.533 minutes—Method A); $^1$H NMR (400 MHz, DMSO-d$^6$): δ 7.53 (s, 1H), 6.48 (s, 2H), 4.03 (t, J=6 Hz, 2H), 3.62 (t, J=6 Hz, 2H), 3.42 (q, J=7 Hz, 2H), 1.06 (t, J=7 Hz, 3H). Compound 207: mp 65-67° C.; MS (ES$^+$ calculated: 180.21; found: 181.16 M+H). HPLC (100% purity, retention time 5.277 minutes—Method A); $^1$H NMR (400 MHz, DMSO-d$^6$): δ 8.04 (s, 1H), 5.51 (s, 2H), 4.00 (t, J=6 Hz, 2H), 3.64 (t, J=6 Hz, 2H), 3.41 (q, J=7 Hz, 2H), 1.06 (t, J=7 Hz, 3H).

Compound 208

3-Amino-1-(2-ethoxyethyl)-1H-pyrazole-4-carboxylic acid amide

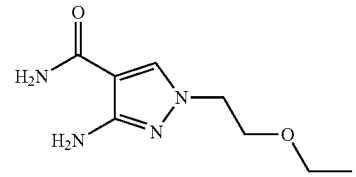

Compound 207 (2.39 g, 13.3 mmol) was added in one portion to 3 mL concentrated sulfuric acid. The mixture was stirred for two hours at which point the mixture had become homogeneous. The sulfuric acid solution was added dropwise (violent) to 30 mL cold concentrated ammonium hydroxide solution. The mixture was stirred under an air stream to dryness over 72 hours. Several milliliters of water were added and a light brown solid was collected by filtration. The solid was dried in vacuo to afford 1.977 g (75%). Compound 208: MS (ES$^+$ calculated: 198.23; found: 199.80 M+H). HPLC (73% purity, retention time 2.944 minutes—Method B); $^1$H NMR (400 MHz, DMSO-d$^6$): δ 7.87 (s, 1H), 7.20 (br s, 1H), 6.67 (br s, 1H), 5.33 (s, 2H), 3.96 (t, J=5 Hz, 2H), 3.64 (t, J=5 Hz, 2H), 3.39 (q, J=7 Hz, 2H), 1.07 (t, J=7 Hz, 3H).

Compound 209

2-(2-Ethoxyethyl)-2,7-dihydropyrazolo[3,4-d]pyrimidine-4,6-dione

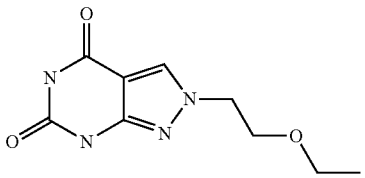

Compound 208 (1.85 g, 0.93 mmol) and urea (5.55 g, 92.5 mmol) were mixed and heated at 200° C. to form a melt for two hours. The solution was permitted to cool to room temperature and 10 mL water was added. The mixture was refluxed for one hour, was permitted to cool, and the product was collected by filtration to afford a tan solid (0.995 g, 47%). Compound 209: mp>300° C.; MS (ES$^+$ calculated: 224.22; found: 224.21 M+). HPLC (75% purity, retention time 3.785 minutes—Method A); $^1$H NMR (400 MHz, DMSO-d$^6$): δ

9.60 (br s, 2H), 8.27 (s, 1H), 4.23 (t, J=6 Hz, 2H), 3.72 (t, J=6 Hz, 2H), 3.43 (q, J=7 Hz, 2H), 1.05 (t, J=7 Hz, 3H).

Compound 210

4,6-Dichloro-2-(2-ethoxyethyl)-2H-pyrazolo[3,4-d]pyrimidine

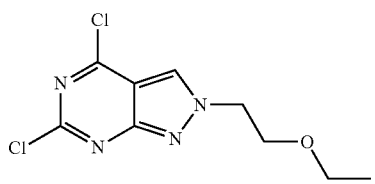

Compound 209 (1 g, 4.5 mmol) was suspended in 50 mL phosphorus oxychloride and was refluxed under argon overnight. The now homogeneous solution was concentrated in vacuo. Ice was added and the mixture was basified by the addition of 10N sodium hydroxide solution. The organics were extracted into ether. The ether was dried (magnesium sulfate) and was concentrated to afford 0.982 g (84%) of a white solid. Compound 210: MS (ES+ calculated: 261.11; found: 261.57 M+). HPLC (95% purity, retention time 11.686 minutes—Method A); $^1$H NMR (400 MHz, DMSO-d$^6$): δ 9.02 (s, 1H), 4.65 (t, J=5 Hz, 2H), 3.90 (t, J=5 Hz, 2H), 3.43 (q, J=7 Hz, 2H), 1.03 (t, J=7 Hz, 3H).

Example 211

5-Chloro-3-[6-chloro-2-(2-ethoxy-ethyl)-2H-pyrazolo[3,4-d]pyrimidin-4-yl]-1,3-dihydro-indol-2-one

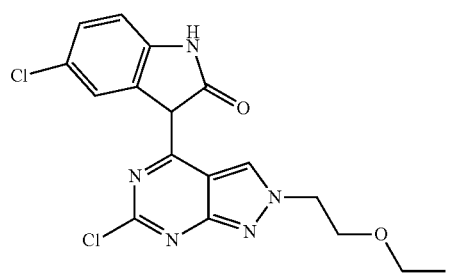

To 5-chlorooxindole (168 mg, 1.0 mmol) in 5 mL anhydrous tetrahydrofuran under argon at −78° C. was added lithium diisopropylamide (1.05 mL of a 2.0M solution in THF/hexane, 2.1 mmol) dropwise. The solution was stirred fifteen minutes at which point Compound 210 (261 mg, 1.0 mmol) was added in one portion. The solution was permitted to warm to room temperature and was stirred for two hours. The solution was then concentrated and subjected to chromatography on silica (gradient elution 1 to 3% methanol:dichloromethane). Fractions containing the desired product were further purified by trituration with methanol to afford following filtration 290 mg (74%) of a yellow solid. Example 211: mp>300° C.; MS (ES+ calculated: 392.25; found: 392.61 M+). HPLC (100% purity, retention time 11.993 minutes—Method B); $^1$H NMR (400 MHz, DMSO-d$^6$): δ 10.44 (br s, 1H), 9.30 (br s, 1H), 8.07 (br s, 1H), 7.04 (m, 1H), 6.80 (m, 1H), 4.46 (m, 2H), 3.80 (m, 2H), 3.47 (m, 2H), 1.08 (t, J=7 Hz, 3H).

Example 212

5-Chloro-3-[2-(2-ethoxy-ethyl)-6-(2-pyridin-3-yl-ethylamino)-2H-pyrazolo [3,4-d]pyrimidin-4-yl]-1,3-dihydro-indol-2-one

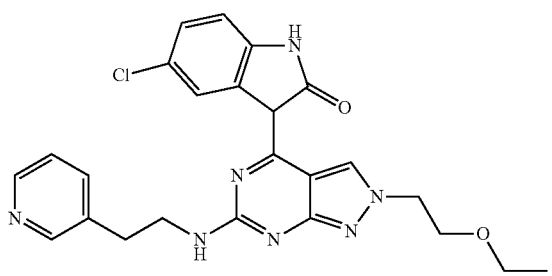

Example 211 (30 mg, 0.076 mmol) and 3-(2'-aminoethyl)pyridine (93 mg, 0.76 mmol) were combined in 2 mL ethanol and subjected to reaction in a microwave at 200° C. for ten minutes. On cooling, a brown yellow solid formed which was isolated by filtration. The solid was dried in vacuo affording 6 mg (17%). Example 212: mp 224-6° C.; MS (ES+ calculated: 477.96; found: 478.49 M+H). HPLC (86% purity, retention time 7.996 minutes—Method B); $^1$H NMR (400 MHz, DMSO-d$^6$): δ 10.82 (s, 1H), 10.00 (br s, 1H), 9.47 (s, 1H), 8.60-8.80 (m, 3H), 7.74 (m, 1H), 7.32 (m, 1H), 6.90-6.60 (m, 2H), 4.32 (m, 2H), 3.80 (m, 2H), 3.44 (m, 4H), 3.00 (m, 2H), 1.05 (m, 3H).

Example 213

5-Chloro-3-{2-(2-ethoxy-ethyl)-6[(pyridin-3-ylmethyl)-amino]-2H-pyrazolo[3,4-d]pyrimidin-4-yl}-1,3-dihydro-indol-2-one

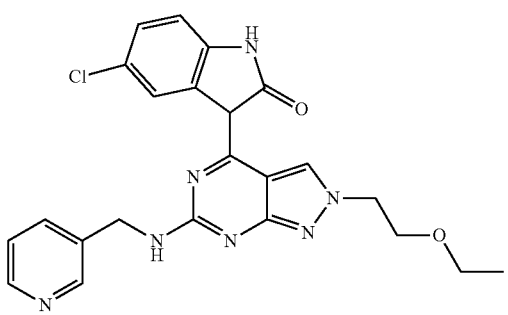 [SMILES: CCOCCn1cc2c(C3C(=O)Nc4ccc(Cl)cc43)nc(NCc3cccnc3)nc2n1]

Example 211 (30 mg, 0.076 mmol) and 3-aminomethylpyridine (82 mg, 0.76 mmol) were combined in 2 mL ethanol and subjected to reaction in a microwave at 130° C. for ten minutes. On cooling a yellow solid formed which was isolated by filtration. The solid was dried in vacuo affording 22 mg (62%). Example 213: mp 294-6° C.; MS (ES+ calculated: 463.93; found: 464.44 M+H). HPLC (92% purity, retention time 8.063 minutes—Method B); $^1$H NMR (400 MHz, DMSO-d$^6$): δ 10.87 (s, 1H), 9.97 (s, 1H), 9.44 (s, 1H), 8.65-8.48 (m, 2H), 7.80-7.35 (m, 3H), 6.83 (m, 1H), 6.64 (m, 1H), 4.85-4.30 (m, 4H), 3.74 (m, 2H), 3.44 (m, 3H), 1.07 (m, 3H).

Example 214

5-Chloro-3-{2-(2-ethoxy-ethyl)-6-[(pyridine-4-ylmethyl)-amino]-2H-pyrazolo[3,4-d]pyrimidin-4-yl}-1,3-dihydro-indol-2-one

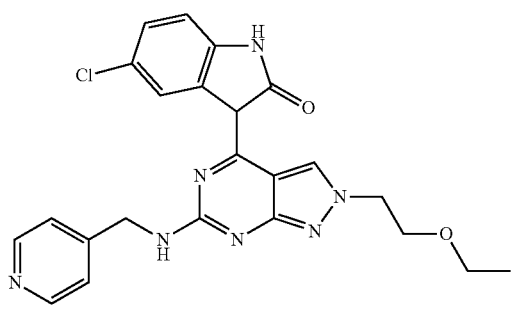 [SMILES: CCOCCn1cc2c(C3C(=O)Nc4ccc(Cl)cc43)nc(NCc3ccncc3)nc2n1]

Example 211 was reacted with 4-aminomethylpyridine to afford a yellow solid. Yield: 45%. Example 214: mp 298-9° C.; MS (ES$^+$ calculated: 463.93; found: 464.46 M+H). HPLC (81% purity, retention time 7.855 minutes—Method B); $^1$H NMR (400 MHz, DMSO-d$^6$): δ 10.90 (s, 1H), 10.00 (s, 1H), 9.45 (s, 1H), 8.50 (m, 2H), 8.10 (s, 1H), 7.38 (m, 2H), 6.81 (m, 1H), 6.65 (m, 1H), 4.80-4.24 (m, 4H), 3.76 (m, 2H), 3.48 (m, 2H), 1.08 (m, 3H).

Example 215

5-Chloro-3-[2-(2-ethoxy-ethyl)-6-(3-methylamino-propylamino)-2H-pyrazolo [3,4-d]pyrimidin-4-yl]-1,3-dihydro-indol-2-one

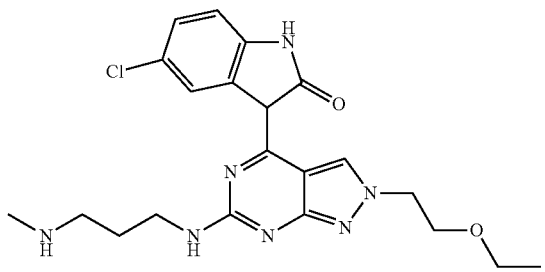

Example 211 was reacted with N-(3-aminopropyl)-N-methylcarbamic acid-t-butyl ester. The product obtained by filtration from the ethanolic solution was taken up into 4 mL 4N hydrochloric acid:dioxane and stirred at room temperature for one hour. The reaction was concentrated and the solid was triturated with ethyl ether to afford after filtering 28 mg (77%) of a yellow solid—isolated as the hydrochloride salt. Example 215: mp 275-7° C.; MS (ES$^+$ calculated: 443.94; found: 444.46 M+H). HPLC (100% purity, retention time 7.847 minutes—Method B); $^1$H NMR (400 MHz, DMSO-d$^6$): δ 10.15 (br s, 1H), 9.40 (br s, 1H), 9.83 (m, 2H), 8.34 (br s, 1H), 7.66 (br s, 1H), 7.00 (m, 1H), 6.84 (m, 1H), 4.45 (m, 4H), 3.80 (m, 2H), 3.60-3.45 (m, 5H), 3.04 (m, 2H), 2.56 (m, 2H), 2.02 (m, 2H), 1.08 (m, 3H).

Example 216

5-Chloro-3-[6-(2-dimethylamino-ethylamino)-2-(2-ethoxy-ethyl)-2H-pyrazolo[3,4-d]pyrimidin-4-yl]-1,3-dihydro-indol-2-one

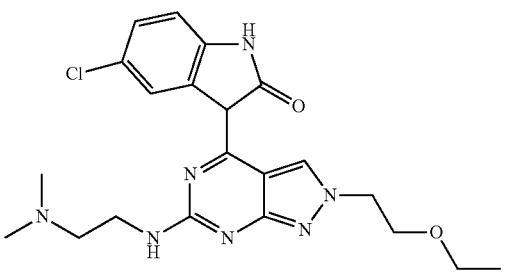 [SMILES: CCOCCn1cc2c(C3C(=O)Nc4ccc(Cl)cc43)nc(NCCN(C)C)nc2n1]

Example 211 was reacted with N,N-dimethylethylenediamine to afford a yellow solid. Yield:59%. Example 216: mp 293-5° C.; MS (ES$^+$ calculated: 443.94; found: 444.49 M+H). HPLC (96% purity, retention time 8.086 minutes—Method B); $^1$H NMR (400 MHz, DMSO-d$^6$): δ 9.97 (s, 1H), 9.43 (s, 1H), 8.34 (br s, 1H), 6.88 (m, 2H), 6.69 (d, J=8 Hz, 1H), 4.30 (m, 2H), 3.76 (m, 2H), 3.67 (m, 2H), 3.40 (m, 2H), 3.27 (m, 2H), 2.64 (m, 2H), 2.30 (s, 6H), 1.07 (m, 3H).

Example 217

5-Chloro-3-[2-(2-ethoxy-ethyl)-6-(2-morpholin-4-yl-ethylamino)-2H-pyrazolo [3,4-d]pyrimidin-4-yl]-1,3-dihydro-indol-2-one

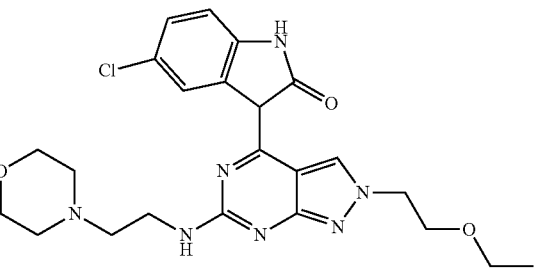

Example 211 was reacted with N-aminoethylmorpholine to afford a yellow solid. Yield: 62%. Example 217: mp 293-4° C.; MS (ES$^+$ calculated: 485.98; found: 486.45 M+H). HPLC (100% purity, retention time 8.513 minutes—Method B); $^1$H NMR (400 MHz, DMSO-d$^6$): δ 10.84 (s, 1H), 10.00 (s, 1H), 9.47 (s, 1H), 8.38 (br s, 1H), 6.88 (m, 2H), 6.69 (m, 1H), 4.32

(m, 2H), 3.78 (m, 2H), 3.63 (m, 8H), 3.43 (m, 2H), 2.63 (m, 2H), 2.37 (m, 2H), 1.07 (m, 3H).

Example 218

5-Chloro-3-[2-(2-ethoxy-ethyl)-6-((R)-2-hydroxy-propylamino)-2H-pyrazolo[3,4-d]pyrimidin-4-yl]-1,3-dihydro-indol-2-one

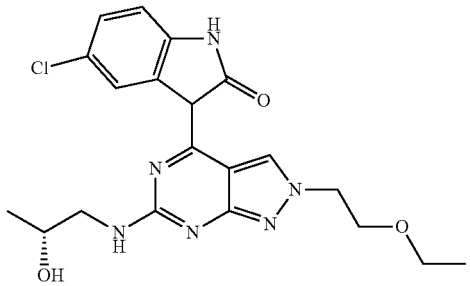 [SMILES: CCOCCn1cc2c(C3C(=O)Nc4ccc(Cl)cc43)nc(NC[C@@H](C)O)nc2n1]

Example 211 was reacted with (R)-2-hydroxy-1-aminopropane to afford a yellow solid. Yield:95%. Example 218: mp>300° C.; MS (ES+ calculated: 430.90; found: 431.46 M+H). HPLC (99% purity, retention time 11.949 minutes—Method A); $^1$H NMR (400 MHz, DMSO-d$^6$): δ 11.08 (br s, 1H), 9.95 (s, 1H), 9.42 (s, 1H), 8.32 (s, 1H), 6.85 (m, 1H), 6.68 (m, 1H), 4.96 (br s, 1H), 4.30 (m, 2H), 3.78 (m, 2H), 3.67 (br s, 1H), 3.49 (m, 2H), 1.20 (d, J=6 Hz, 3H), 1.07 (m, 3H).

Example 219

5-Chloro-3-[2-(2-ethoxy-ethyl)-6-((S)-2-hydroxy-propylamino)-2H-pyrazolo [3,4-d]pyrimidin-4-yl]-1,3-dihydro-indol-2-one

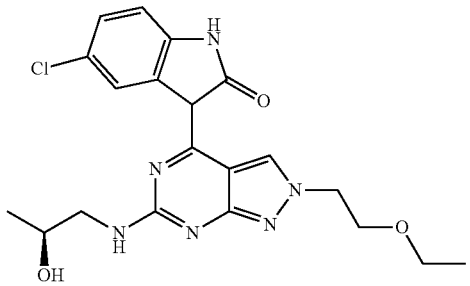 [SMILES: CCOCCn1cc2c(C3C(=O)Nc4ccc(Cl)cc43)nc(NC[C@H](C)O)nc2n1]

Example 211 was reacted with (S)-2-hydroxy-1-aminopropane to afford a yellow solid. Yield:89%. Example 219: mp>300° C.; MS (ES+ calculated: 430.90; found: 431.43 M+H). HPLC (99% purity, retention time 11.924 minutes—Method A); $^1$H NMR (400 MHz, DMSO-d$^6$): δ 11.10 (br s, 1H), 9.95 (s, 1H), 9.43 (s, 1H), 8.32 (s, 1H), 6.82 (m, 1H), 6.66 (m, 1H), 4.96 (br s, 1H), 4.30 (m, 2H), 3.78 (m, 2H), 3.67 (br s, 1H), 3.43 (m, 2H), 1.20 (d, J=6 Hz, 3H), 1.07 (m, 3H).

Scheme 5 discloses a general procedure for the preparation of compounds of the invention wherein R$^6$ is an alkoxyalkyl group and R$^2$ is bromo.

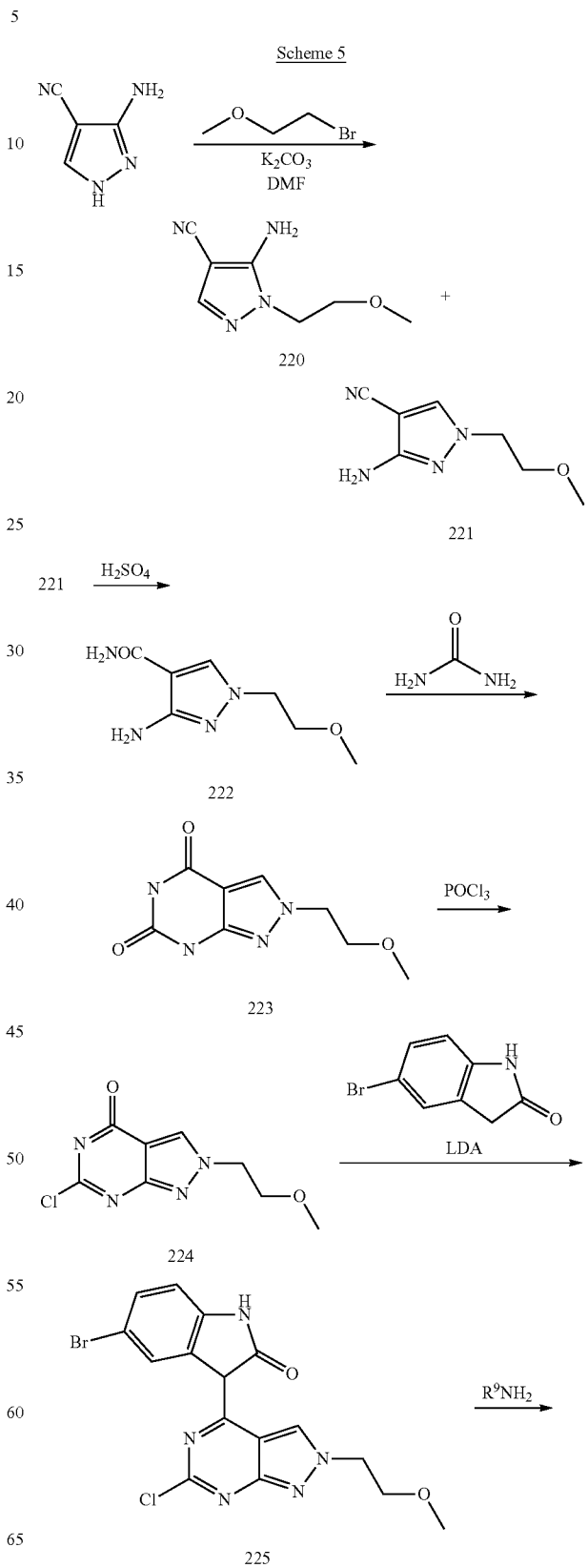

-continued

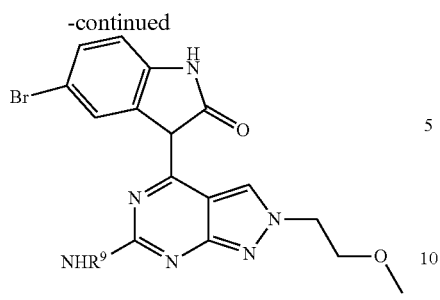

Compound 220 and 221

5-Amino-1-(2-methoxyethyl)-1H-pyrazole-4-carbonitrile

3-Amino-1-(2-methoxyethyl)-1H-pyrazole-4-carbonitrile

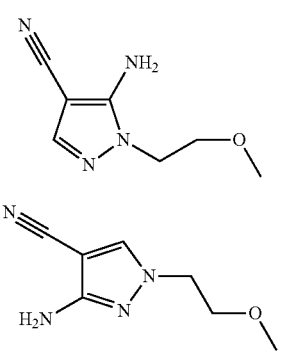

220

221

3-Amino-4-cyanopyrazole (1) was reacted with bromomethylmethyl ether to afford LA (43%) and LB (49%) as white solids. Compound 220: mp 120-122° C.; MS (ES+ calculated: 166.18; found: 167.26 M+H). HPLC (90% purity, retention time 4.716 minutes—Method A); $^1$H NMR (400 MHz, DMSO-d$^6$): δ 7.52 (s, 1H), 6.49 (br s, 2H), 4.04 (t, J=5 Hz, 2H), 3.59 (t, J=5 Hz, 2H), 3.29 (s, 3H). Compound 221: mp 105-107° C.; MS (ES+ calculated: 166.18; found: 168.09 M+H). HPLC (900% purity, retention time 3.641 minutes—Method B); $^1$H NMR (400 MHz, DMSO-d$^6$): δ 8.04 (s, 1H), 5.51 (s, 2H), 4.00 (t, J=5 Hz, 2H), 3.60 (t, J=5 Hz, 2H), 33.29 (s, 3H).

Compound 222

3-Amino-1-(2-methoxyethyl)-1H-pyrazole-4-carboxylic acid amide

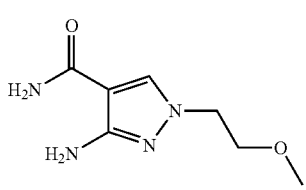

Compound 221 was reacted with sulfuric acid to afford LC as a white solid (100%). Compound 222: MS (ES+ calculated: 184.20; found: 185.64 M+H). HPLC (92% purity, retention time 2.138 minutes—Method A); $^1$H NMR (400 MHz, DMSO-d$^6$): δ 7.87 (s, 1H), 7.20 (br s, 1H), 6.69 (br s, 1H), 5.33 (s, 2H), 3.97 (t, J=5 Hz, 2H), 3.60 (t, J=5 Hz, 2H), 3.22 (s, 3H).

Compound 223

2-(2-Methoxyethyl)-2,7-dihydropyrazolo[3,4-d]pyrimidine-4,6-dione

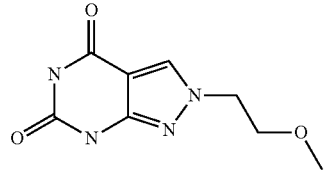

Compound 222 was reacted with urea to afford a white solid. Yield:81%. Compound 223: mp 295-302° C.; MS (ES+ calculated: 210.19; found: 211.20 M+). HPLC (90% purity, retention time 2.833 minutes—Method B); $^1$H NMR (400 MHz, DMSO-d$^6$): δ 11.06 (br s, 1H), 10.64 (br s, 1H), 8.28 (s, 1H), 4.25 (t, J=5 Hz, 2H), 3.69 (t, J=5 Hz, 2H), 3.23 (s, 3H).

Compound 224

4,6-Dichloro-2-(2-methoxyethyl)-2H-pyrazolo[3,4-d]pyrimidine

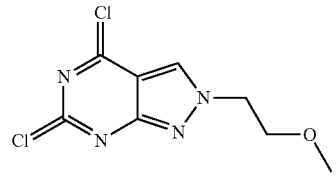

Compound 223 was reacted with phosphorus oxychloride to afford a white solid. Yield: 83%. Compound 224: MS (ES+ calculated: 247.09; found: 247.97 M+). HPLC (94% purity, retention time 7.685 minutes—Method B); $^1$H NMR (400 MHz, DMSO-d$^6$): δ 9.03 (s, 1H), 4.66 (t, J=5 Hz, 2H), 3.86 (t, J=5 Hz, 2H), 3.24 (s, 3H).

Example 225

5-Bromo-3-[6-chloro-2-(2-methoxy-ethyl)-2H-pyrazolo[3,4-d]pyrimidin-4-yl]-1,3-dihydro-indol-2-one

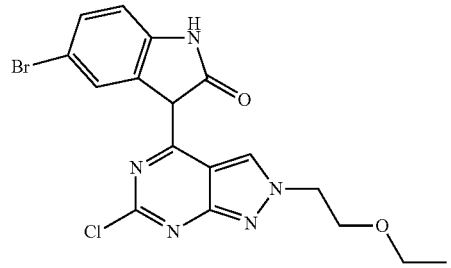 [SMILES: CCOCCn1cc2c(C3C(=O)Nc4ccc(Br)cc43)nc(Cl)nc2n1]

5-bromooxindole was condensed with Compound 224 to afford an orange solid. Yield: 93%. Example 225: mp>300° C.; MS (ES+ calculated: 422.67; found: 423.90 M+H). HPLC (96% purity, retention time 11.474 minutes—Method B); $^1$H NMR (400 MHz, DMSO-d⁶): δ 10.48 (br s, 1H), 9.26 (br s, 1H), 8.26 (br s, 1H), 7.16 (m, 1H), 6.72 (m, 1H), 4.46 (m, 2H), 3.77 (m, 2H), 3.27 (s, 3H).

Example 226

5-Bromo-3-[2-(2-methoxy-ethyl)-6-(3-methylamino-propylamino)-2H-pyrazolo[3,4-d]pyrimdin-4-yl]-1,3-dihydro-indol-2-one

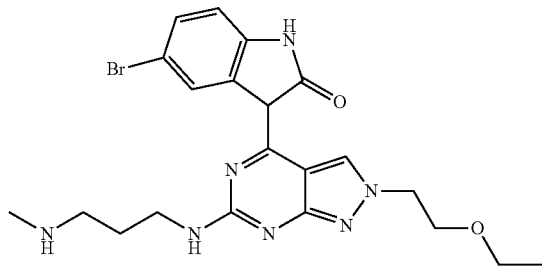 [SMILES: CCOCCn1cc2c(C3C(=O)Nc4ccc(Br)cc43)nc(NCCCNC)nc2n1]

Example 225 was reacted with N-(3-aminopropyl)-N-methylcarbamic acid-t-butyl ester. The product obtained by filtration from the ethanolic solution was taken up into 4 mL 4N hydrochloric acid:dioxane and stirred at room temperature for one hour. The reaction was concentrated and the solid was triturated with ethyl ether to afford after filtering 28 mg (77%) of a yellow solid—isolated as the hydrochloride salt. Example 226: mp 232-6° C.; MS (ES⁺ calculated: 474.36; found: 475.88 M+H). HPLC (85% purity, retention time 7.465 minutes—Method B); ¹H NMR (400 MHz, DMSO-d⁶): δ 10.05 (br s, 1H), 9.42 (br s, 1H), 9.00 (br s, 1H), 8.72 (br s, 2H), 8.06 (br s, 1H), 7.18 (br s, 1H), 6.72 (br s, 1H), 4.37 (m, 2H), 3.76 (m, 2H), 3.56 (m, 2H), 3.26 (br s, 3H), 2.97 (m, 2H), 2.52 (m, 3H), 2.06 (m, 2H).

Example 227

5-Bromo-3-[2-(2-methoxy-ethyl)-6-(2-piperidin-4-yl-ethylamino)-2H-pyrazolo[3,4-d]pyrimidin-4-yl]-1,3-dihydro-indol-2-one

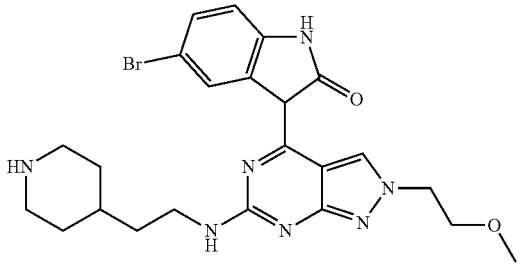 [SMILES: COCCn1cc2c(C3C(=O)Nc4ccc(Br)cc43)nc(NCCC3CCNCC3)nc2n1]

Example 225 was reacted with 4-aminoethyl-1-N—BOC piperidine to afford after removal of the BOC group a yellow solid—the hydrochloride salt. Yield:74%. Example 227: mp 248-51° C.; MS (ES⁺ calculated: 514.43; found: 515.92 M+H). HPLC (97% purity, retention time 7.507 minutes—Method B); ¹H NMR (400 MHz, DMSO-d⁶): δ 11.53 (br s, 1H), 10.08 (br s, 1H), 9.37 (br s, 1H), 8.70 (br s, 1H), 8.39 (br s, 1H), 7.20 (br s, 1H), 7.07 (br s, 1H), 6.70 (br s, 1H), 4.34 (m, 2H), 3.73 (s, 3H), 3.50 (m, 2H), 2.81 (m, 2H), 1.87 (m, 2H), 1.70 (m, 1H), 1.60 (m, 2H), 1.34 (m, 2H).

Example 228

5-Bromo-3-[2-(2-methoxy-ethyl)-6-(2-piperidin-3-yl-ethylamino)-2H-pyrazolo[3,4-d]pyrimidin-4-yl]-1,3-dihydro-indol-2-one

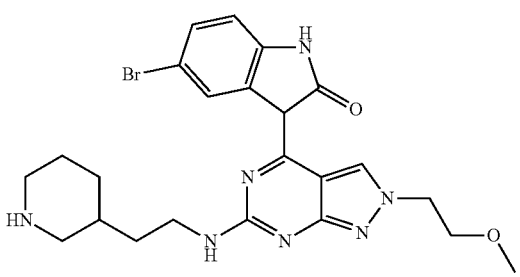 [SMILES: COCCn1cc2c(C3C(=O)Nc4ccc(Br)cc43)nc(NCCC3CCCNC3)nc2n1]

Example 225 was reacted with 3-aminoethyl-1-N—BOC piperidine to afford after removal of the BOC group a yellow solid—the hydrochloride salt. Yield:59%. Example 228: mp 270-3° C.; MS (ES⁺ calculated: 514.43; found: 515.92 M+H). HPLC (100% purity, retention time 7.674 minutes—Method B); ¹H NMR (400 MHz, DMSO-d⁶): δ 11.03 (br s, 1H), 10.08 (br s, 1H), 9.41 (br s, 1H), 8.71 (br s, 1H), 8.46 (br s, 1H), 7.20 (br s, 1H), 7.08 (br s, 1H), 6.73 (br s, 1H), 4.80-1.10 (m, 17H), 3.74 (s, 3H).

Example 229

5-Bromo-3-[6-(2-dimethylamino-ethylamino)-2-(2-methoxy-ethyl)-2H-pyrazolo[3,4-d]pyrimdin-4-yl]-1,3-dihydro-indol-2-one

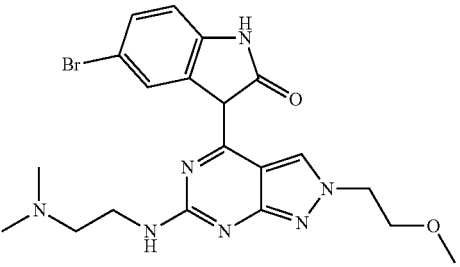

Example 225 was reacted with N,N-dimethylethylenediamine to afford a yellow solid. Yield:65%. Example 229: mp 291-2° C.; MS (ES⁺ calculated: 474.36; found: 475.84 M+H). HPLC (95% purity, retention time 7.827 minutes—Method B); ¹H NMR (400 MHz, DMSO-d⁶): δ 10.80 (br s, 1H), 9.95 (br s, 1H), 9.38 (s, 1H), 8.47 (br s, 1H), 6.98 (d, J=8 Hz, 1H), 6.64 (d, J=8 Hz, 1H), 4.30 (m, 2H), 3.72 (m, 2H), 3.56 (m, 2H), 3.26 (s, 3H), 2.60 (m, 2H), 2.24 (s, 6H).

Example 230

5-Bromo-3-[6((S)-2-hydroxy-propylamino)-2-(2-methoxy-ethyl)-2H-pyrazolo [3,4-d]pyrimidin-4-yl]-1,3-dihydro-indol-2-one

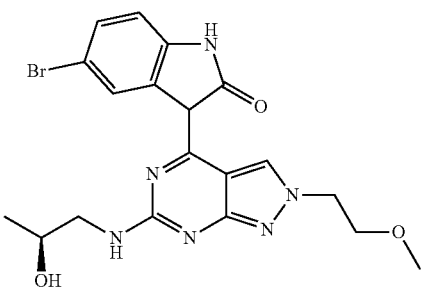 [SMILES: COCCn1cc2c(C3C(=O)Nc4ccc(Br)cc43)nc(NC[C@H](C)O)nc2n1]

Example 225 was reacted with (S)-2-hydroxy-1-aminopropane to afford a yellow solid. Yield:82%. Example 230: mp>300° C.; MS (ES⁺ calculated: 461.32; found: 462.79 M+H). HPLC (94% purity, retention time 8.225 minutes—Method B); ¹H NMR (400 MHz, DMSO-d⁶): δ 11.16 (br s, 1H), 10.00 (s, 1H), 9.39 (s, 1H), 8.50 (s, 1H), 6.98 (d, J=8 Hz, 1H), 6.63 (d, J=8 Hz, 1H), 4.97 (br s, 1H), 4.41 (m, 1H), 4.30 (m, 2H), 3.90 (br s, 1H), 3.76 (m, 1H), 3.68 (m, 2H), 3.23 (s, 3H), 1.20 (d, J=8 Hz, 3H).

Example 231

5-Bromo-3-[6-((R)-2-hydroxy-propylamino)-2-(2-methoxy-ethyl)-2H-pyrazolo[3,4-d]pyrimidin-4-yl]-1,3-dihydro-indol-2-one

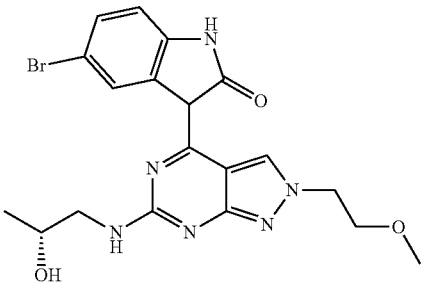 [SMILES: COCCn1cc2c(C3C(=O)Nc4ccc(Br)cc43)nc(NC[C@@H](C)O)nc2n1]

Example 225 was reacted with (R)-2-hydroxy-1-aminopropane to afford a yellow solid. Yield:64%. Example 231: mp>300° C.; MS (ES⁺ calculated: 461.32; found: 462.79 M+H). HPLC (98% purity, retention time 8.242 minutes—Method B); ¹H NMR (400 MHz, DMSO-d⁶): δ 11.10 (br s, 1H), 9.96 (s, 1H), 9.40 (s, 1H), 8.48 (s, 1H), 6.98 (d, J=8 Hz, 1H), 6.63 (d, J=8 Hz, 1H), 4.97 (br s, 1H), 4.46 (m, 1H), 4.31 (m, 2H), 3.92 (br s, 1H), 3.77 (m, 1H), 3.72 (m, 2H), 3.24 (s, 3H), 1.19 (d, J=8 Hz, 3H).

Example 232

5-Bromo-3-{2-(2-methoxy-ethyl)-6-[(pyridin-3-ylmethyl)-amino]-2H-pyrazolo[3,4-d]pyrimidin-4-yl}-1,3-dihydro-indol-2-one

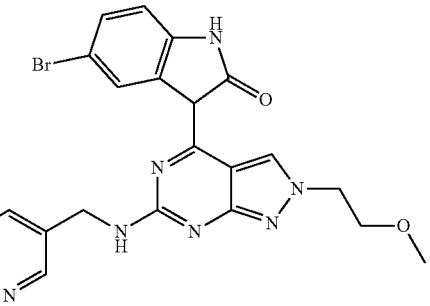

Example 225 was reacted with 3-aminomethylpyridine to afford a yellow solid. Yield: 65%. Example 232: mp 300-301° C.; MS (ES⁺ calculated: 494.35; found: 495.82 M+H). HPLC (89% purity, retention time 7.618 minutes—Method B); ¹H NMR (400 MHz, DMSO-d⁶): δ 10.87 (s, 1H), 10.01 (s, 1H), 9.44 (s, 1H), 8.70-8.40 (m, 4H), 7.37 (m, 1H), 6.96 (m, 1H), 6.60 (m, 1H), 4.80 (m, 2H), 4.34 (m, 2H), 3.77 (m, 2H), 3.24 (s, 3H).

Example 233

5-Bromo-3-[6-(3-dimethylamino-propylamino)-2-(2-methoxy-ethyl)-2H-pyrazolo [3,4-d]pyrimidin-4-yl]-1,3-dihydro-indol-2-one

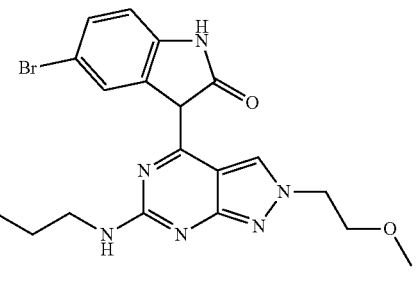

Compound 225 was reacted with N,N-dimethylpropylenediamine to afford a yellow solid. Yield:58%. Example 233: mp 297-8° C.; MS (ES⁺ calculated: 488.39; found: 489.89 M+H). HPLC (94% purity, retention time 7.519 minutes—Method B); ¹H NMR (400 MHz, DMSO-d⁶): δ 10.80 (s, 1H), 9.90 (s, 1H), 9.40 (s, 1H), 8.52 (s, 1H), 67.0 (d, J=8 Hz, 2H), 6.68 (d, J=8 Hz, 1H), 4.30 (m, 2H), 3.74 (m, 2H), 3.50 (m, 2H), 3.35 (m, 2H), 3.21 (s, 3H), 2.27 (s, 6H), 1.82 (m, 2H).

Example 234

5-Bromo-3-[2-(2-methoxy-ethyl)-6-(2-morpholin-4-yl-ethylamino)-2H-pyrazolo[3,4-d]pyrimidin-4-yl]-1,3-dihydro-indol-2-one

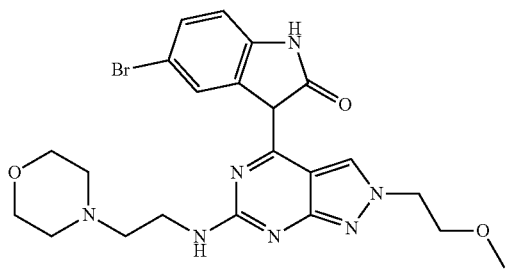 [SMILES: COCCn1cc2c(C3C(=O)Nc4ccc(Br)cc43)nc(NCCN3CCOCC3)nc2n1]

Example 225 was reacted with N-aminoethylmorpholine to afford a yellow solid. Yield: 55%. Example 234: mp>300° C.; MS (ES+ calculated: 516.40; found: 517.82 M+H). HPLC (97% purity, retention time 8.150 minutes—Method B); $^1$HNMR (400 MHz, DMSO-d$^6$): δ 10.82 (s, 1H), 10.00 (s, 1H), 9.42 (s, 1H), 8.48 (br s, 1H), 7.02 (m, 2H), 6.62 (m, 1H), 4.32 (m, 2H), 3.72 (m, 2H), 3.63 (m, 8H), 3.31 (m, 5H), 2.70 (m, 2H).

Example 235

5-Bromo-3-[2-(2-methoxy-ethyl)-6-(2-methoxy-ethylamino)-2H-pyrazolo [3,4-d]pyrimidin-4-yl]-1,3-dihydro-indol-2-one

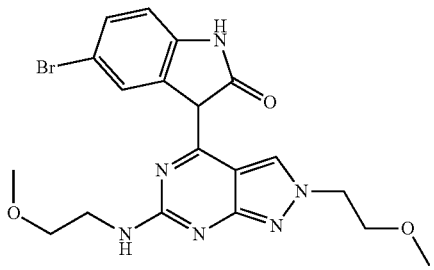 [SMILES: COCCNc1nc(C2C(=O)Nc3ccc(Br)cc32)c2cn(CCOC)nc2n1]

Example 225 was reacted with 2-methoxyethylamine to afford a yellow solid. Yield: 100%. Example 235: mp>300° C.; MS (ES+ calculated: 461.32; found: 462.77 M+H). HPLC (97% purity, retention time 8.518 minutes—Method B); $^1$H NMR (400 MHz, DMSO-d$^6$): δ 11.20 (br s, 1H), 10.00 (s, 1H), 9.40 (s, 1H), 8.46 (s, 1H), 6.96 (d, J=8 Hz, 2H), 6.64 (d, J=8 Hz, 1H), 4.30 (m, 2H), 3.70 (m, 2H), 3.68 (m, 2H), 3.50 (m, 2H), 3.29 (s, 3H), 3.22 (s, 3H).

Example 236

5-Bromo-3-[6-chloro-2-(2-ethoxy-ethyl)-2H-pyrazolo [3,4-d]pyrimidin-4-yl)-1,3-dihydro-indol-2-one

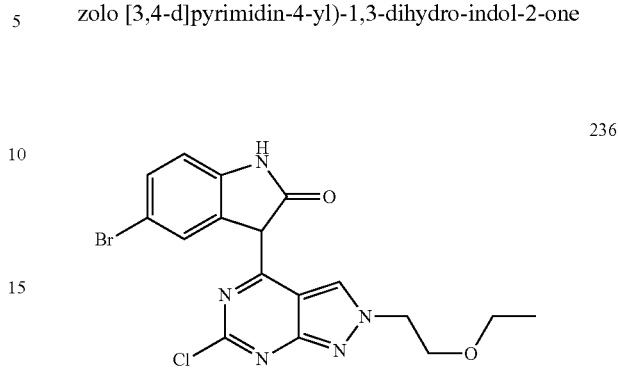

To a stirring solution of 5-bromooxindole (163 mg, 0.769 mmol) and anhydrous THF (7 mL) in a 15 mL flask at −78° C. was added LDA (0.769 mL, 1.538 mmol). The reaction mixture was stirred for 15 min before adding the Compound 210 (200 mg, 0.769 mmol) as a solid. Following an additional 15 min at −78° C., the reaction was allowed to warm to room temperature and stirred overnight. The reaction mixture was concentrated to dryness, taken up into MeOH and concentrated onto silica gel and pumped dry before subjecting it to flash chromatography on silica gel (gradient elution: 1-10% methanol: dichloromethane) to afford 228 mg (68%) of a yellow solid after concentrated and was triturated in ether. Example 236: mp 260-263° C.; MS (ES+ calculated: 436.70; found: 437.92 M+H). HPLC (91%) purity, retention time 4.946 minutes—Method C); $^1$H NMR (400 MHz, DMSO-d6) δ 10.50 (br s, 1H), 9.3 (br s, 1H), 8.3 (br s, 1H), 7.17 (d, J=8 Hz, 1H), 6.79 (d, J=8 Hz, 1H), 4.47 (s, 2H), 3.80 (m, 2H), 3.45 (m), 2.62 (s, 6H) 1.08 (m, 3).

Example 237

5-Bromo-3-[6-(2-dimethylamino-ethylamino)-2-(2-ethoxy-ethyl)2H-pyrazolo[3,4-d]pyrimidin-4-yl]-1,3-dihydro-indol-2-one

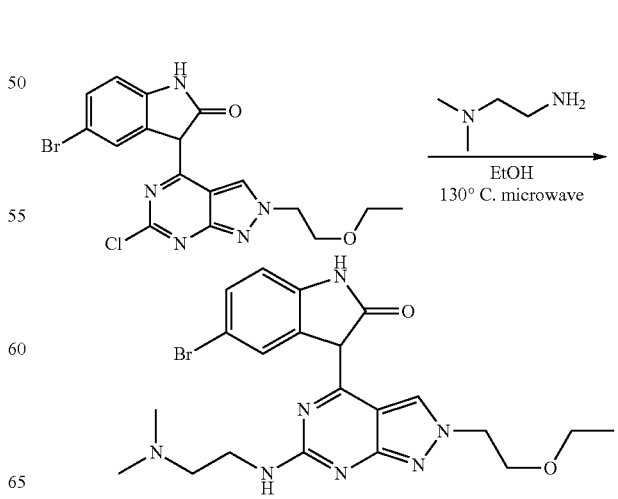

Using the procedure outlined for Example 212, Example 236 (30 mg, 0.0687 mmol) and N,N-dimethylaminoethylamine (60.5 μL, 0.687 mmol) were heated in 1 mL EtOH at 130° C. in microwave for 10 min. Upon cooling, the product precipitated in the reaction tube. The resulting solid was filtered and pumped dry to afford 24 mg (71%) of a yellow solid. Example 237: mp 247-251° C.; MS (ES$^+$ calculated: 488.39; found: 489.4 M+H). HPLC (94%) purity, retention time 3.410 minutes—Method C); $^1$H NMR (400 MHz, DMSO-d$_6$) δ 9.99 (s, 1H), 9.44 (s, 1H), 8.63 (s, 1H), 7.02 (d, 1H), 6.67 (d, 1H), 4.31 (t, 2H), 3.76 (m, 2H), 3.61 (br s, 1H), 3.42 (m), 2.33 (s, 2H) 2.18 (s, 1H), 0.86 (m, 9H).

Example 238

5-Bromo-3-[2-(2-ethoxy-ethyl)-6-((S)-2-hydroxy-propylamno)-2H-pyrazolo[3,4-d]pyrimidin-4-yl]-1,3-dihydro-indol-2-one

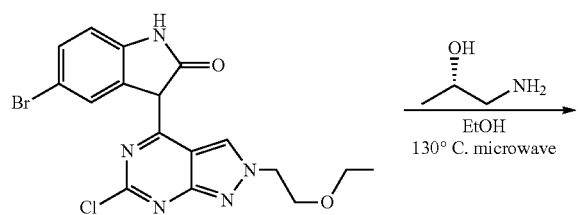

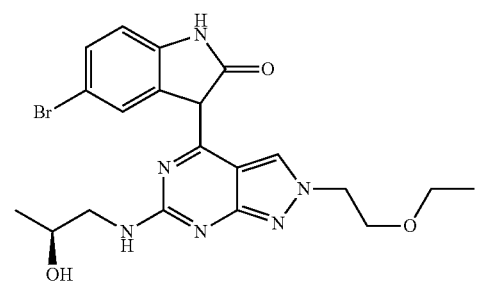

Using the procedure outlined for Example 212, Example 236 (30 mg, 0.0687 mmol) and (S)-(+)-1-amino-2-propanol (54 μL, 0.687 mmol) were heated in 1 mL EtOH at 130° C. in microwave for 10 min. Upon cooling, the product precipitated in the reaction tube. The resulting solid was filtered and pumped dry to afford 26 mg (80%) of a yellow solid. Example 238: mp 297-299° C.; MS (ES$^+$ calculated: 475.35; found: 475.2 M+H). HPLC (94%) purity, retention time 2.785 minutes—Method C); $^1$H NMR (400 MHz, DMSO-d$_6$) δ 10.00 (s, 1H), 9.44 (s, 1H), 8.61 (s, 1H), 7.00 (d, 1H), 6.67 (d, 1H), 4.97 (br s, 1H), 4.31 (t, 2H), 3.76 (m, 2H), 3.61 (br s, 1H), 3.43 (m), 1.22 (d, 3H), 1.07 (m).

Example 239

5-Bromo-3-[2-(2-ethoxy-ethyl)-6-((R)-2-hydroxy-propylamino)-2H-pyrazolo[3,4-d]pyrimidin-4-yl]-1,3-dihydro-indol-2-one

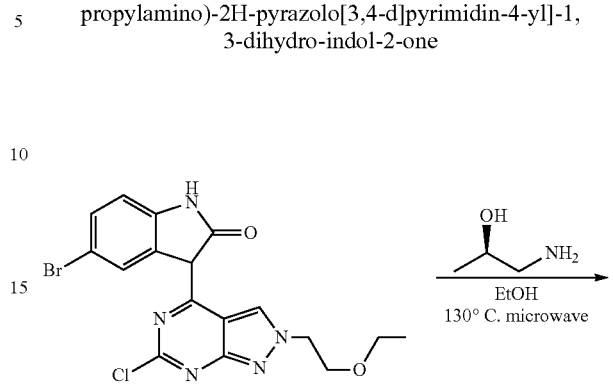

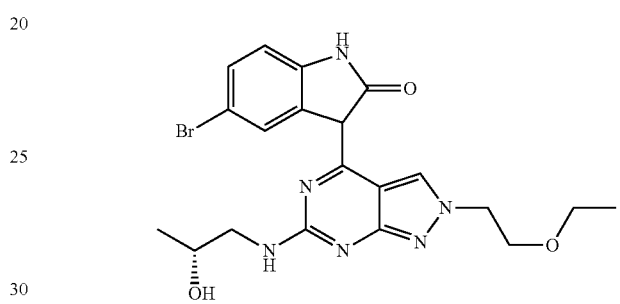

Using the procedure outlined for Example 212, Example 236 (30 mg, 0.0687 mmol) and (R)-(−)-1-amino-2-propanol (54 μL, 0.687 mmol) were heated in 1 mL EtOH at 130° C. in microwave for 10 min. Upon cooling, the product precipitated in the reaction tube. The resulting solid was filtered and pumped dry to afford 28 mg (86%) of a yellow solid. Example 239: mp 298-300° C.; MS (ES$^+$ calculated: 475.35; found: 475.2 M+H). HPLC (95%) purity, retention time 2.783 minutes—Method C); $^1$H NMR (400 MHz, DMSO-d$_6$) δ 10.00 (s, 1H), 9.44 (s, 1H), 8.61 (s, 1H), 7.00 (d, 1H), 6.67 (d, 1H), 4.97 (br s, 1H), 4.31 (t, 2H), 3.76 (m, 2H), 3.61 (br s, 1H), 3.43 (m), 1.22 (d, 3H), 1.07 (m).

Example 240

5-Bromo-3-[2-(2-ethoxy-ethyl)-6-(2-morpholin-4-yl-ethylamino)-2H-pyrazolo[3,4-d]pyrimidin-4-yl]-1,3-dihydro-indol-2-one

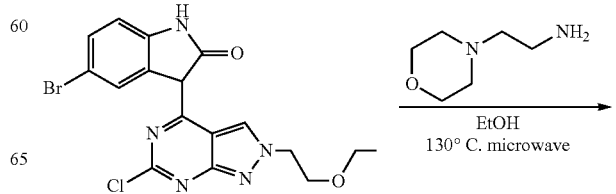

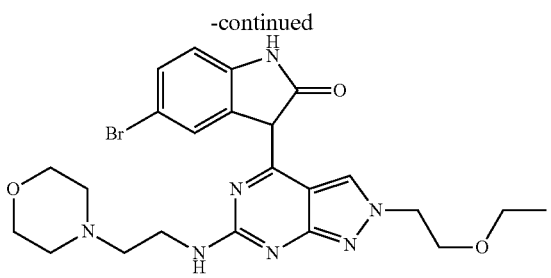

Using the procedure outlined for Example 212, Example 236 (30 mg, 0.0737 mmol) and N-(2-aminoethyl)morpholine (90 μL, 0.737 mmol) were heated in 1 mL EtOH at 130° C. in microwave for 10 min. Upon cooling, the product precipitated in the reaction tube. The resulting solid was filtered and pumped dry to afford 29 mg (80%) of a yellow solid. Example 240: mp 276-278° C.; MS (ES+ calculated: 530.43; found: 530.61 M+H). HPLC (96%) purity, retention time 2.757 minutes—Method C); $^1$H NMR (400 MHz, DMSO-$d_6$) δ 10.00 (s, 1H), 9.45 (s, 1H), 8.53 (s, 1H), 7.00 (d, 1H), 6.87 (m, 1H), 6.66 (d, J=8 Hz, 1H), 4.32 (t, J=7 Hz, 2H), 3.77 (t, 1H), 3.64 (m, 8H), 2.66 (m, 2H), 1.83 (m, 4H), 1.07 (m, 3H).

The following Examples 241-254 in Table 4 were prepared according to procedures disclosed herein including using methods generally known to one skilled in the art.

TABLE 4

| Example | R² | X |
|---|---|---|
| 241 | H | —NH—CH₂-4-Pyridyl |
| 242 | H | —NH—(CH₂)₂-2-pyridyl |
| 243 | H | —NH—CH₂—CH═CH₂ |
| 244 | H | —NH—CH₂—CH(CH₃)₂ |
| 245 | H | —NH—CH(CH₃)₂ |
| 246 | CF₃ | —NH—CH₂-4-pyridyl |
| 247 | CF₃ | —NH—(CH₂)₂-2-pyridyl |
| 248 | CF₃ | —NH—CH₂—CH═CH₂ |
| 249 | CF₃ | —NH—CH₂—CH(CH₃)₂ |
| 250 | CF₃ | —NH—CH(CH₃)₂ |
| 251 | CF₃ | —NH—(CH₂)₂—N(CH₃)₂ |
| 252 | CF₃ | —NH—(CH₂)₂—NH₂*HCl |
| 253 | CF₃ | —NH—(CH₂)₃—NHCH₃*HCl |
| 254 | CF₃ | —NH—(CH₂)₃—NH₂*HCl |

Example 241

3-{2-Cyclopentyl-6-[(pyridin-4-ylmethyl)-amino]-2H-pyrazolo[3,4-d]pyrimidin-4-yl}-1,3-dihydro-indol-2-one A mixture of Example 152 (40 mg, 0.11 mmol), in 4-aminomethylpyridine (119 mg, 1.1 mmol) and 2-methoxyethanol (2 mL) were heated to 130° C. for 5 h. The reaction was concentrated. The Example was purified via a flash silica gel column eluting with 5% to 10% methanol/methylene chloride. The most pure fractions were concentrated, treated with ethyl ether and filtered to give 23 mg (50%) of Example 241. Example 241: $^1$HNMR (400 MHz, DMSO-$d_6$) δ 13.9 (s, 1H), 10.7 (s, 1H), 8.6 (m, 2H), 8.4 (m, 1H), 7.8 (m, 1H), 7.3 (m, 2H), 7.0 (m, 2H), 6.9 (m, 1H), 5.0 (m, 1H), 4.8 (m, 1H), 4.6 (d, 2H), 1.6-2.2 (m, 8H); MS (m/e) 426 (M+1); HPLC (95%) purity, retention time 3.472 minutes—Method C; mp 198-200° C.

Example 242

3-[2-Cyclopentyl-6-(2-pyridin-2-yl-ethylamino)-2H-pyrazolo[3,4-d]pyrimidin-4-yl]-1,3-dihydro-indol-2-one Examples 242 was synthesized in a similar manner to Example 241 as disclosed herein using the appropriate starting materials. Example 242: $^1$HNMR (400 MHz, DMSO-$d_6$) δ 13.7 (s, 1H), 10.7 (s, 1H), 8.8 (s, 1H), 8.6 (m, 1H), 7.8 (m, 3H), 7.3 (m, 1H), 7.2 (m, 1H), 7.0 (m, 1H), 5.8 (s, 2H), 5.0 (m, 1H), 3.7 (m, 2H), 3.1 (m, 2H), 1.6-2.2 (m, 8H); MS (m/e) 440 (M+1); HPLC (99%) purity, retention time 3.397 minutes—Method C; mp 246-248° C.

Example 243

3-(6-Allylamino-2-cyclopentyl-2H-pyrazolo[3,4-d]pyrimidin-4-yl)-1,3-dihydro-indol-2-one Examples 243 was synthesized in a similar manner to Example 241 as disclosed herein using the appropriate starting materials. Example 243: $^1$HNMR (400 MHz, DMSO-$d_6$) δ 13.8 (s, 1H), 10.7 (s, 1H), 8.8 (s, 1H), 7.9 (m, 1H), 7.7 (m, 1H), 6.7-7.0 (m, 4H), 5.9-6.1 (m, 1H), 5.0-5.3 (m, 2H), 3.8 (m, 2H), 1.6-2.2 (m, 8H); MS (m/e) 375 (M+1); HPLC (99%) purity, retention time 4.082 minutes—Method C; mp>300° C.

Example 244

3-(2-Cyclopentyl-6-isobutylamino-2H-pyrazolo[3,4-d]pyrimidin-4-yl)-1,3-dihydro-indol-2-one Examples 244 was synthesized in a similar manner to Example 241 as disclosed herein using the appropriate starting materials. Example 244: $^1$HNMR (400 MHz, DMSO-$d_6$) δ 13.7 (s, 1H), 10.7 (s, 1H), 8.7 (s, 1H), 7.7 (m, 2H), 6.7-7.1 (m, 4H), 5.0 (m, 1H), 3.1 (m, 2H), 1.6-2.2 (m, 8H), 1.0 (m, 6H); MS (m/e) 391 (M+1); HPLC (95%) purity, retention time 4.469 minutes—Method C; mp 280-282° C.

Example 245

3-(2-Cyclopentyl-6-isopropylamino-2H-pyrazolo[3,4-d]pyrimidin-4-yl)-1,3-dihydro-indol-2-one Examples 245 was synthesized in a similar manner to Example 241 as disclosed herein using the appropriate starting materials. Example 245: $^1$HNMR (400 MHz, DMSO-$d_6$) δ 13.6 (s, 1H), 10.7 (s, 1H), 8.7 (s, 1H), 7.7 (d, 1H), 7.5 (d, 1H), 6.7-7.1 (m, 3H), 5.0 (m, 1H), 4.1 (m, 1H), 1.6-2.2 (m, 8H), 1.2 (m, 6H); MS (m/e) 377 (M+1); HPLC (92%) purity, retention time 4.124 minutes—Method C; mp 303-305° C.

Example 246

3-{2-Cyclopentyl-6-[(pyridin-4-ylmethyl)-amino]-2H-pyrazolo[3,4-d]pyrimidin-4-yl}-5-trifluoromethyl-1,3-dihydro-indol-2-one

A mixture of Example 153 (40 mg, 0.095 mmol), in 4-Aminomethylpyridine (103 mg, 0.95 mmol) and 2-methoxyethanol (2 mL) were heated to 130° C. for 5 h. The reaction was concentrated. The Example was purified via a flash silica gel column eluting with 5% methanol/methylene chloride. The most pure fractions were concentrated, treated with ethyl ether and filtered to give 6 mg (13%) of Example 246. Example 246: $^1$HNMR (400 MHz, DMSO-$d_6$) δ 11.7 (s, 1H), 10.3 (s, 1H), 9.5 (s, 1H), 8.5 (m, 3H), 7.5 (m, 1H), 7.3 (m, 2H), 7.1 (m, 1H), 6.8 (d, 1H), 4.8 (m, 3H), 1.6-2.2 (m, 8H); MS (m/e) 494 (M+1); HPLC (94%) purity, retention time 3.979 minutes—Method C; mp>300° C.

Example 247

3-[2-Cyclopentyl-6-(2-pyridin-2-yl-ethylamino)-2H-pyrazolo[3,4-d]pyrimidin-4-yl]-5-trifluoromethyl-1,3-dihydro-indol-2-one

Example 247 was synthesized in a similar manner to Example 246 as disclosed herein using the appropriate starting materials. Example 247: $^1$HNMR (400 MHz, DMSO-$d_6$) δ 11.4 (s, 1H), 10.3 (s, 1H), 9.5 (s, 1H), 8.7 (s, 1H), 8.5 (d, 1H), 7.7 (m, 1H), 7.2-7.4 (m, 3H), 6.8-7.0 (m, 2H), 4.8 (m, 1H), 3.9 (m, 2H), 3.2 (t, 2H), 1.6-2.2 (m, 8H); MS (m/e) 508 (M+1); HPLC (97%) purity, retention time 4.140 minutes—Method C; mp>300° C.

Example 248

3-(6-Allylamino-2-cyclopentyl-2H-pyrazolo[3,4-d]pyrimidin-4-yl)-5-trifluoromethyl-1,3-dihydro-indol-2-one

Example 248 was synthesized in a similar manner to Example 246 as disclosed herein using the appropriate starting materials. Example 248: $^1$HNMR (400 MHz, DMSO-$d_6$) δ 11.6 (s, 1H), 10.3 (s, 1H), 9.5 (s, 1H), 8.7 (s, 1H), 7.2 (d, 1H), 7.1 (m, 1H), 6.9 (m, 1H), 6.0 (m, 1H), 5.3 (d, 1H), 5.1 (d, 1H), 4.8 (m, 1H), 4.2 (s, 2H), 1.6-2.2 (m, 8H); MS (m/e) 443 (M+1); HPLC (99%) purity, retention time 4.965 minutes—Method C; mp>300° C.

Example 249

3-(2-Cyclopentyl-6-isobutylamino-2H-pyrazolo[3,4-d]pyrimidin-4-yl)-5-trifluoromethyl-1,3-dihydro-indol-2-one

Example 249 was synthesized in a similar manner to Example 246 as disclosed herein using the appropriate starting materials. Example 249: $^1$HNMR (400 MHz, DMSO-$d_6$) δ 11.2 (s, 1H), 10.3 (s, 1H), 9.5 (s, 1H), 8.7 (s, 1H), 7.2 (d, 1H), 6.9 (d, 1H), 6.8 (m, 1H), 4.8 (m, 1H), 3.4 (m, 2H), 1.6-2.2 (m, 8H), 0.9 (d, 6H); MS (m/e) 459 (M+1); HPLC (99%) purity, retention time 5.305 minutes—Method C; mp 282-285° C.

Example 250

3-(2-Cyclopentyl-6-isopropylamino-2H-pyrazolo[3,4-d]pyrimidin-4-yl)-5-trifluoromethyl-1,3-dihydro-indol-2-one

Example 250 was synthesized in a similar manner to Example 246 as disclosed herein using the appropriate starting materials. Example 250: $^1$HNMR (400 MHz, DMSO-$d_6$) δ 11.1 (s, 1H), 10.3 (s, 1H), 9.5 (s, 1H), 8.7 (s, 1H), 7.2 (d, 1H), 6.9 (d, 1H), 6.7 (m, 1H), 4.8 (m, 1H), 4.4 (m, 1H), 1.6-2.2 (m, 8H), 1.3 (d, 6H); MS (m/e) 445 (M+1); HPLC (97%) purity, retention time 4.973 minutes—Method C; mp 299-301° C.

Example 251

3-[2-Cyclopentyl-6-(2-dimethylamino-ethylamino)-2H-pyrazolo[3,4-d]pyrimidin-4-yl]-5-trifluoromethyl-1,3-dihydro-indol-2-one

Example 251 was synthesized in a similar manner to Example 246 as disclosed herein using the appropriate starting materials. Example 251: $^1$HNMR (400 MHz, DMSO-$d_6$) δ 10.3 (s, 1H), 9.5 (s, 1H), 8.7 (s, 1H), 7.2 (d, 1H), 6.9 (d, 1H), 4.8 (m, 1H), 3.4 (m, 2H), 2.9 (t, 2H), 2.4 (t, 2H), 2.2 (s, 6H), 1.6-2.2 (m, 8H); MS (m/e) 474 (M+1); HPLC (91%) purity, retention time 4.076 minutes—Method C; mp 211-213° C.

Example 252

3-[6-(2-Amino-ethylamino)-2-cyclopentyl-2H-pyrazolo[3,4-d]pyrimidin-4-yl]-5-trifluoromethyl-1,3-dihydroindol-2-one hydrochloride salt

A mixture of Example 153 (63 mg, 0.15 mmol), N-BOC-ethylenediamine (0.24 gm, 1.5 mmol), and ethanol (1 mL) were heated in a microwave at 130° C. for 10 minutes. The reaction was cooled to room temperature and a precipitate formed. The solid was filtered, washed with ethanol and ethyl ether to give 56 mg (68%) of the intermediate. Next, the material was stirred in 4N HCl in 1,4-dioxane (2 mL). After 1 hour the reaction was concentrated. The solid was treated with ether and filtered to give 35 mg (70%) of Example 252. Example 252: $^1$HNMR (400 MHz, DMSO-$d_6$) δ 12.0 (s, 1H), 10.3 (s, 1H), 9.5 (s, 1H), 8.6 (s, 1H), 8.0 (m, 2H), 7.4 (m, 2H), 6.9 (m, 1H), 4.8 (m, 1H), 3.7 (m, 2H), 3.2 (m, 2H), 1.6-2.2 (m, 8H); MS (m/e) 446 (M+1); HPLC (99%) purity, retention time 3.917 minutes—Method C; mp 290-293° C.

Example 253

3-[2-Cyclopentyl-6-(3-methylamino-propylamino)-2H-pyrazolo [3,4-d]pyrimidin-4-yl]-5-trifluoromethyl-1,3-dihydro-indol-2-one hydrochloride salt

Example 253 was synthesized in a similar manner to Example 252 as disclosed herein using the appropriate starting materials. Example 253: $^1$HNMR (400 MHz, DMSO-$d_6$) δ 11.8 (bs, 1H), 10.3 (bs, 1H), 9.5 (bs, 1H), 8.8 (s, 1H), 8.7 (m, 1H), 7.4 (m, 1H), 7.2 (m, 1H), 6.9 (m, 1H), 4.8 (m, 1H), 3.6 (m, 2H), 3.0 (m, 4H), 1.6-2.2 (m, 11H); MS (m/e) 475 (M+1); HPLC (99%) purity, retention time 3.977 minutes—Method C; mp 260-262° C.

Example 254

3-[6-(3-Amino-propylamino)-2-cyclopentyl-2H-pyrazolo[3,4-d]pyrimidin-4-yl]-5-trifluoromethyl-1,3-dihydro-indol-2-one hydrochloride salt Example 254 was synthesized in a similar manner to Example 252 as disclosed herein using the appropriate starting materials. Example 254: $^1$HNMR (400 MHz, DMSO-d$_6$) δ 11.9 (bs, 1H), 10.3 (bs, 1H), 9.5 (bs, 1H), 8.8 (s, 1H), 8.1 (m, 2H), 7.7 (m, 1H), 7.3 (m, 1H), 6.9 (m, 1H), 4.8 (m, 1H), 3.6 (m, 2H), 3.0 (m, 4H), 1.6-2.2 (m, 8H); MS (m/e) 460 (M+1); HPLC (97%) purity, retention time 3.850 minutes—Method C; mp 304-306° C.

Compound 255 and 256

5-Amino-1-isobutyl-1H-pyrazole-4-carbonitrile

3-Amino-1-isobutyl-1H-pyrazole-4-carbonitrile

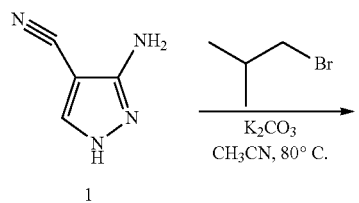

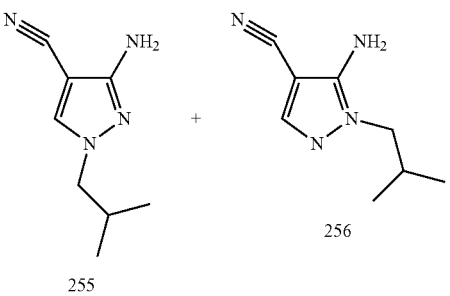

3-Amino-4-pyrazolecarbonitrile 1 (Aldrich, 24.0 g, 0.222 mole), 1-bromo-2-methyl-propane (Lancaster, 36.48 g, 0.266 mole) and anhydrous potassium carbonate (Acros, 36.8 g, 0.266 mole) were suspended in 240 mL reagent grade acetonitrile and heated at 80° C. under nitrogen for 22 hours. LC/MS indicated 1 remained. Therefore, added an additional 3 mL (0.027 mole) 1-bromo-2-methylpropane and 4.25 g (0.031 mole) K$_2$CO$_3$. After 24 hours, the reaction was filtered and the filtrate concentrated in vacuo. The solid was stirred in 250 mL of water for 3.5 hours at room temp. The solid was filtered, washed with 50 mL diethyl ether, and dried to yield 16.28 g (45%) of a tan powder which was seen by $^1$H NMR to contain a mixture of 255 and 256 in approximately a 2:1 ratio. This mixture was used without further purification. Mixture of 255 and 256: mp 91.3-106; MS (ES$^+$ calculated: 164.21; found: 165.28 M+H). HPLC (99% purity, retention times 6.920 and 7.086 minutes—Method B); $^1$H NMR (400 MHz, DMSO-d$_6$) δ 8.05 and 7.51 (s, 1H), 6.50 and 5.49 (s, 2H), 3.68 (t, 2H), 2.05 (m, 1H), 0.82 and 0.81 (d, 6H).

Compound 257 and 258

5-Amino-1-isobutyl-1H-pyrazole-4-carboxylic acid amide

3-Amino-1-isobutyl-1H-pyrazole-4-carboxylic acid amide

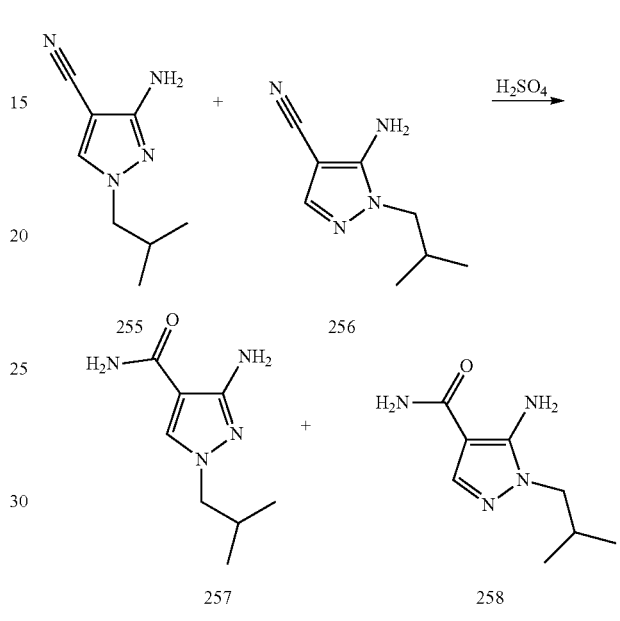

To concentrated sulfuric acid (Fisher, 48 mL) at 0° C. was added 229 and 230 (5.89 g, 36.0 mmol) in small portions. The reaction was allowed to warm to room temperature and was stirred over 4.25 hours. The viscous reaction was added slowly (violent) to 240 mL concentrated ammonium hydroxide solution (Fisher) over 25 minutes. Added 300 mL of water to the mixture and extracted with EtOAc, dried over MgSO$_4$, filtered, and concentrated in vacuo to afford 5.48 g (84%) of an off-white solid which was seen by $^1$H NMR to contain a mixture of 257 and 258 in approximately a 2:1 ratio. Mixture of 257 and 258: mp 154-157.8° C.; MS (ES$^+$ calculated: 182.23; found: 183.23 M+H). HPLC (99% purity, retention time 6.498 minutes—Method B); $^1$H NMR (400 MHz, DMSO-d$_6$) δ 7.84 and 7.61 (s, 1H), 7.10 (br s, 1H), 6.70 (br s, 1H), 6.14 and 5.31 (s, 1H), 3.64 (m, 2H), 2.05 (m, 1H), 0.83 (d, 6H).

Compound 259

2-Isobutyl-2H-pyrazolo[3,4-d]pyrimidine-4,6-diol

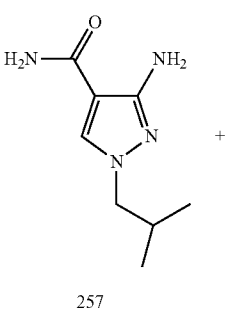

-continued

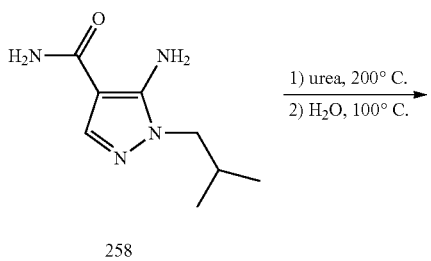

258

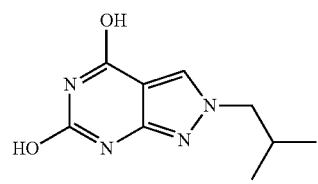

259

Heated 1.575 g (8.64 mmol) and 4.725 g (78.7 mmol) urea at 200° C. in a selade tube for 3.5 hours in a sealed tube. The mixture was cooled to 100° C., and 34 mL water was added. The mixture was refluxed at 100° C. for 20 hours. The reaction was cooled to room temperature, additional water was added, and the product was extrated using ethyl acetate. The organic layer was dried with MgSO$_4$, filtered, and conc. in vacuo to give 989 mg (55%) of a white solid which was seen by $^1$H NMR to contain only 259: mp 327.5-330° C.; MS (ES$^+$ calculated: 208.22; found: 209.25 M+H). HPLC (99% purity, retention time 5.631 minutes—Method B); $^1$H NMR (400 MHz, DMSO-d$_6$) δ 11.32 (s, 1H), 10.64 (s, 1H), 8.32 (s, 1H), 3.90 (d, 2H), 2.12 (m, 1H), 0.84 (d, 6H).

Compound 260

4,6-Dichloro-2-isobutyl-2H-pyrazolo[3,4-d]pyrimidine

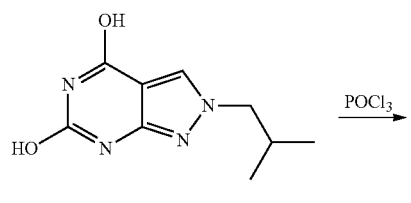

259

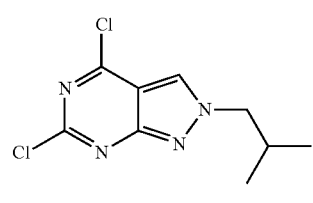

260

Compound 259 (500 mg, 2.4 mmol) was dissolved in phosphorus oxychloride (Acros, 8 mL) and the mixture was refluxed under argon at 110° C. for 29.5 hours. Excess phosphorus oxychloride was removed in vacuo and ice then water was added to the dark orange syrup. Next, 10N NaOH was added until the pH equaled 14. The product was then extracted with methylene chloride, dried over MgSO$_4$, filtered and conc. in vacuo. afford a white solid which was purified by flash chromatography on silica gel eluting with 500:11 dichloromethane:methanol to afford 388 mg (25%) of a white solid. Compound 260: MS (ES$^+$ calculated: 245.11; found: 245.40 M). HPLC (99%) purity, retention time 10.794 minutes—Method B); $^1$H NMR (400 MHz, DMSO-d$_6$) δ 9.05 (s, 1H), 4.34 (d, 2H), 2.33 (m, 1H), 0.90 (d, 6H).

Example 261

5-Chloro-3-(6-chloro-2-isobutyl-2H-pyrazolo[3,4-d]pyrimidin-4-yl)-1,3-dihydro-indol-2-one

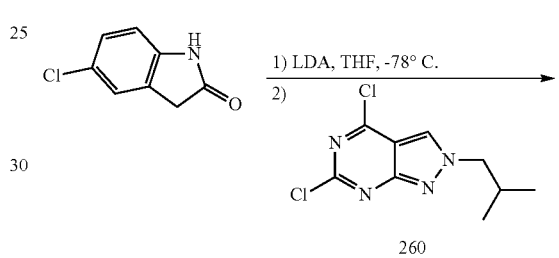

260

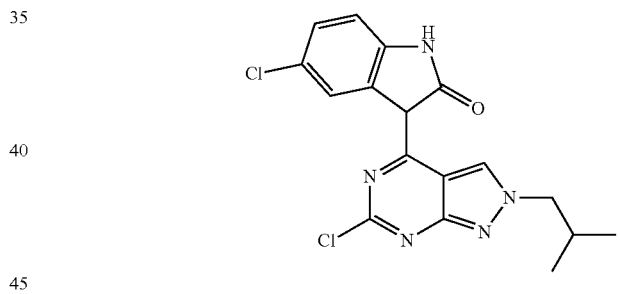

261

To 5-cyanooxindole (CombiBlocks, 238 mg, 1.42 mmol) in 7.0 mL anhydrous THF under argon at −78° C. was added lithium diisopropylamine (Acros, 1.42 mL of a 2.0M solution in THF/heptane, 2.84 mmol). The solution was stirred for fifteen minutes at which point compound 260 (348 mg, 1.42 mmol) was added. The reaction was stirred for fifteen minutes, external cooling was removed, and the reaction was allowed to warm to room temperature. After 2.75 hours the solution was quenched with water. The reaction was concentrated in vacuo and the residue was purified by flash chromatography on silica gel eluting with 99:1 dichloromethane:methanol to afford 125 mg of Example 261 as an orange solid: mp 284° C. (dec); MS (ES$^+$ calculated: 376.25; found: 376.62 M). HPLC (95%) purity, retention time 13.170 minutes—Method B); $^1$H NMR (400 MHz, DMSO-d$_6$) δ 10.53 (br s, 1H), 9.28 (s, 1H), 8.09 (s, 1H), 7.06 (d, 1H), 6.84 (d, 1H), 4.15 (d, 2H), 3.33 (br s, 1H), 2.21 (m, 1H), 0.90 (d, 6H).

Example 262

5-Bromo-3-(6-chloro-2-isobutyl-2H-pyrazolo[3,4-d]pyrimidin-4-yl)-1,3-dihydro-indol-2-one

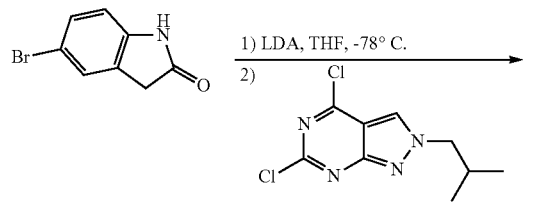

262

To 5-bromooxindole (CombiBlocks, 216 mg, 1.02 mmol) in 7.0 mL anhydrous THF under argon at −78° C. was added lithium diisopropylamine (Acros, 1.02 mL of a 2.0M solution in THF/heptane, 2.04 mmol) over 4 minutes. The solution was stirred for thirty minutes at which point a solution of compound 260 (250 mg, 1.02 mmol) in 3.13 mL dry THF was added over 3 minutes. The reaction was stirred for twenty-three minutes, the external cooling was removed, and the reaction was permitted to warm to room temperature. After 3 hours the solution was quenched with water. The reaction was concentrated in vacuo and the residue was purified by flash chromatography on silica gel eluting with 98:2 then 95:5 dichloromethane:methanol to afford Example 262 as a burnt orange solid in two separate lots totaling 183 mg (43%): m.p. 295° C. (decomp.); MS (ES+ calculated: 420.70; found: 421.94 M+H). HPLC (89% purity, retention time 13.399 minutes—Method B); $^1$H NMR (400 MHz, DMSO-$d_6$): δ 10.49 (br s, 1H), 9.29 (br s, 1H), 8.26 (br s, 1H), 7.18 (d, 1H), 6.79 (d, 1H), 4.14 (d, 2H), 3.49 (br s, 1H), 2.20 (m, 1H), 0.89 (d, 6H).

Example 263

5-Bromo-3-[2-isobutyl-6-(2-methoxy-ethylamino)-2H-pyrazolo[3,4-d]pyrimidin-4-yl]-1,3-dihydro-indol-2-one

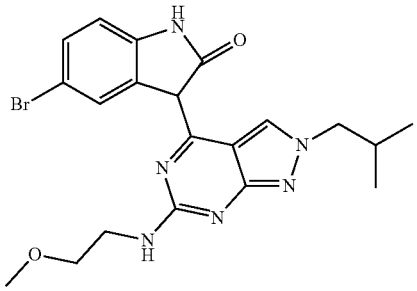 [SMILES: COCCNc1nc(C2C(=O)Nc3ccc(Br)cc32)c2cn(CC(C)C)nc2n1]

m.p. 294-296.8° C.; MS (ES+ calculated: 459.35; found: 459.67 M+H). HPLC (99% purity, retention time 10.803 minutes—Method B); $^1$H NMR (400 MHz, DMSO-$d_6$): δ 11.23 (br s, 1H), 9.99 (s, 1H), 9.40 (s, 1H), 8.49 (s, 1H), 7.01 (d, 1H), 6.68 (d, 1H), 3.99 (d, 2H), 3.66 (m, 4H), 3.48 (m, 1H), 3.38 (s, 3H), 2.17 (m, 1H), 0.88 (d, 6H).

Example 264

5-Bromo-3-[2-isobutyl-6-(2-morpholin-4-yl-ethylamino)-2H-pyrazolo[3,4-d]pyrimidin-4-yl]-1,3-dihydro-indol-2-one

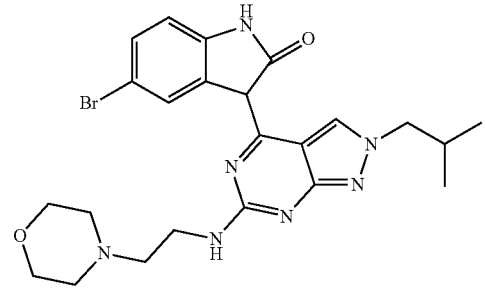 [SMILES: CC(C)Cn1cc2c(C3C(=O)Nc4ccc(Br)cc43)nc(NCCN3CCOCC3)nc2n1]

m.p. 282-287° C.; MS (ES+ calculated: 514.43; found: 514.63 M+H). HPLC (99% purity, retention time 9.976 minutes—Method B); $^1$H NMR (400 MHz, DMSO-$d_6$): δ 11.62 (br s, 1H), 9.98 (s, 1H), 9.40 (s, 1H), 8.53 (s, 1H), 7.00 (d, 1H), 6.67 (d, 1H), 3.99 (d, 2H), 3.64 (m, 6H), 3.29 (m, 1H), 2.66 (t, 2H), 2.45 (m, 4H), 2.16 (m, 1H), 0.88 (d, 6H).

Example 265

5-Bromo-3-[2-isobutyl-6-(3-morpholin-4-yl-propylamino)-2H-pyrazolo[3,4-d]pyrimidin-4-yl]-1,3-dihydro-indol-2-one

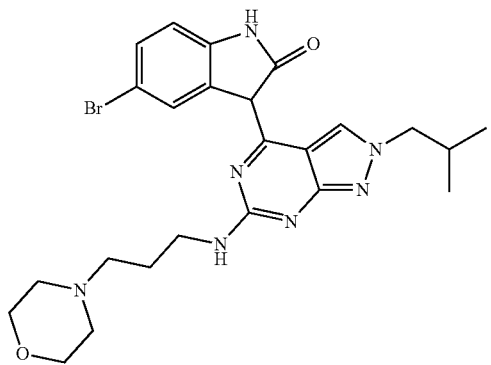 [SMILES: CC(C)Cn1cc2c(C3C(=O)Nc4ccc(Br)cc43)nc(NCCCN3CCOCC3)nc2n1]

m.p. 271-274° C.; MS (ES⁺ calculated: 528.46; found: 528.58 M+H). HPLC (99% purity, retention time 9.547 minutes—Method B); ¹H NMR (400 MHz, DMSO-d₆): δ 11.40 (br s, 1H), 9.97 (s, 1H), 9.40 (s, 1H), 8.55 (s, 1H), 7.00 (d, 1H), 6.67 (d, 1H), 3.99 (d, 2H), 3.57 (m, 6H), 3.29 (s, 1H), 2.38 (s, 6H), 2.16 (m, 1H), 1.84 (m, 2H), 0.88 (d, 6H).

Example 267

5-Bromo-3-[2-isobutyl-6-(3-methylamino-propylamino)-2H-pyrazolo[3,4-d]pyrimidin-4-yl]-1,3-dihydro-indol-2-one

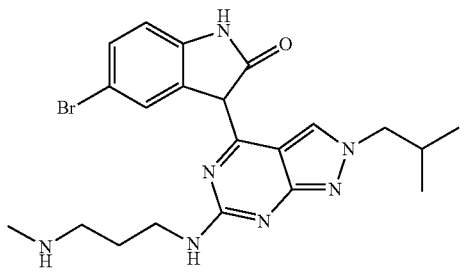 [SMILES: CNCCCNc1nc(C2C(=O)Nc3ccc(Br)cc32)c2cn(CC(C)C)nc2n1]

m.p. 240-259° C.; MS (ES⁺ calculated (free base)-472.39; found: 472.60 M+H). HPLC (99% purity, retention time 9.265 minutes—Method B); ¹H NMR (400 MHz, DMSO-d₆): δ10.11 (br s, 1H), 9.32 (br s, 1H), 8.83 (br s, 2H), 8.48 (br s, 1H), 7.50 (br s, 1H), 7.09 (br s, 1H), 6.77 (br s, 1H), 4.04 (br s, 2H), 3.56 (br s, 2H), 3.02 (br s, 1H), 2.55 (t, 3H), 2.19 (m, 1H), 2.03 (br s, 2H), 0.89 (d, 6H).

Example 268

5-Bromo-3-[6-(2-dimethylamino-ethylamino)-2-isobutyl-2H-pyrazolo[3,4-d]pyrimidin-4-yl]-1,3-dihydro-indol-2-one

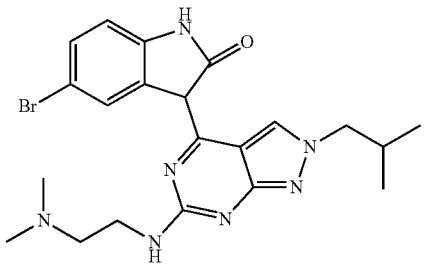 [SMILES: CC(C)Cn1cc2c(C3C(=O)Nc4ccc(Br)cc43)nc(NCCN(C)C)nc2n1]

m.p. 261-264.5° C.; MS (ES⁺ calculated: 472.39; found: 472.64 M+H). HPLC (99% purity, retention time 9.577 minutes—Method B); ¹H NMR (400 MHz, DMSO-d₆): δ 9.97 (s, 1H), 9.40 (s, 1H), 8.51 (s, 1H), 6.99 (d, 1H), 6.83 (br s 1H), 6.67 (d, 1H), 3.97 (d, 2H), 3.59 (s, 2H), 3.28 (m, 2H), 2.61 (s, 1H), 2.27 (s, 6H), 2.15 (s, 1H), 0.89 (d, 6H).

Example 269

5-Bromo-3-[6-(3-dimethylamino-propylamino)-2-isobutyl-2H-pyrazolo[3,4-d]pyrimidin-4-yl]-1,3-dihydro-indol-2-one

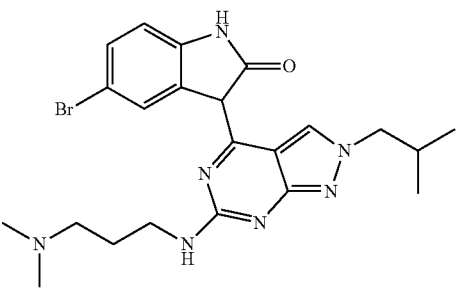 [SMILES: CC(C)Cn1cc2c(C3C(=O)Nc4ccc(Br)cc43)nc(NCCCN(C)C)nc2n1]

m.p. 250.5-254° C.; MS (ES⁺ calculated: 486.42; found: 486.62 M+H). HPLC (99% purity, retention time 9.427 minutes—Method B); ¹H NMR (400 MHz, DMSO-d₆): δ 9.92 (s, 1H), 9.40 (s, 1H), 8.54 (s, 1H), 7.16 (m, 1H), 6.98 (d, 1H), 6.66 (d, 1H), 3.99 (d, 2H), 3.50 (br s, 2H), 3.31 (br s, 2H), 2.24 (s, 6H), 2.20 (m, 2H), 1.82 (m, 2H), 0.88 (d, 6H).

Example 270

5-Chloro-3-[6-(2-dimethylamino-ethylamino)-2-isobutyl-2H-pyrazolo[3,4-d]pyrimidin-4-yl]-1,3-dihydro-indol-2-one

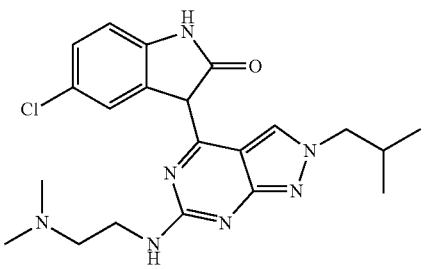 [SMILES: CC(C)Cn1cc2c(C3C(=O)Nc4ccc(Cl)cc43)nc(NCCN(C)C)nc2n1]

m.p. 264-265.5° C.; MS (ES⁺ calculated: 427.94; found: 428.45 M+H). HPLC (96% purity, retention time 9.183 minutes—Method B); ¹H NMR (400 MHz, DMSO-d₆): δ 9.89 (s, 1H), 9.40 (s, 1H), 8.38 (s, 1H), 6.83 (d, 1H), 6.76 (m, 1H), 6.70 (d, 1H), 3.98 (d, 2H), 3.57 (br s, 2H), 3.27 (m, 2H), 2.59 (s, 1H), 2.26 (s, 6H), 2.20 (s, 1H), 0.88 (d, 6H).

Example 271

5-Chloro-3-[2-isobutyl-6-(3-morpholin-4-yl-propylamino)-2H-pyrazolo[3,4-d]pyrimidin-4-yl]-1,3-dihydro-indol-2-one

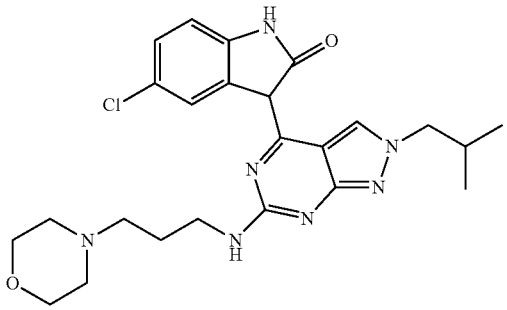 [SMILES: CC(C)Cn1cc2c(C3C(=O)Nc4ccc(Cl)cc43)nc(NCCCN3CCOCC3)nc2n1]

m.p. 263-265.5° C.; MS (ES$^+$ calculated: 484.01 found: 484.44 M+H). HPLC (99% purity, retention time 9.391 minutes—Method B); $^1$H NMR (400 MHz, DMSO-d$_6$): δ 11.35 (br s, 1H), 9.95 (s, 1H), 9.41 (s, 1H), 8.40 (s, 1H), 6.88 (dd, 1H), 6.71 (d, 1H), 3.99 (d, 2H), 3.60 (s, 4H), 3.32 (m, 1H), 2.50 (m, 6H), 2.45 (t, 2H), 2.17 (s, 1H), 1.83 (m, 2H), 0.88 (d, 6H).

Example 272

5-Chloro-3-[2-isobutyl-6-(2-methoxy-ethylamino)-2H-pyrazolo[3,4-d]pyrimidin-4-yl]-1,3-dihydro-indol-2-one

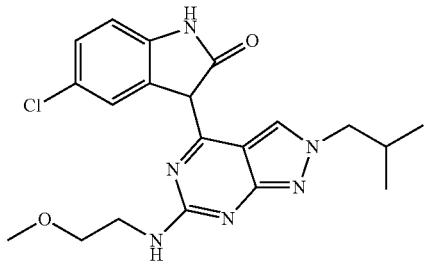 [SMILES: COCCNc1nc(C2C(=O)Nc3ccc(Cl)cc32)c2cn(CC(C)C)nc2n1]

m.p. 286-289° C.; MS (ES$^+$ calculated: 414.90; found: 415.48 M+H). HPLC (99% purity, retention time 10.583 minutes—Method B); $^1$H NMR (400 MHz, DMSO-d$_6$): δ 11.22 (br s, 1H), 9.98 (s, 1H), 9.41 (s, 1H), 8.34 (s, 1H), 6.91 (d, 1H), 6.71 (d, 1H), 3.99 (d, 2H), 3.67 (s, 2H), 3.64 (d, 2H), 3.48 (m, 1H), 3.33 (s, 3H), 2.17 (m, 1H), 0.88 (d, 6H).

Example 273

5-Chloro-3-(6-chloro-2-isobutyl-2H-pyrazolo[3,4-d]pyrimidin-4-yl)-1,3-dihydro-indol-2-one

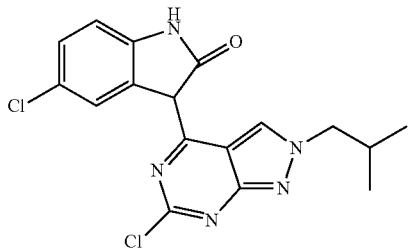 [SMILES: CC(C)Cn1cc2c(C3C(=O)Nc4ccc(Cl)cc43)nc(Cl)nc2n1]

m.p. 284 (decomp.)° C.; MS (ES$^+$ calculated: 376.25; found: 376.62 M+H). HPLC (95% purity, retention time 13.170 minutes—Method B); $^1$H NMR (400 MHz, DMSO-d$_6$): δ 10.53 (br s, 1H), 9.28 (br s, 1H), 8.09 (br s, 1H), 4.15 (d, 2H), 3.33 (br s, 1H), 2.21 (m, 1H), 0.89 (d, 6H).

Example 275

3-{6-[(1-Butyl-piperidin-4-ylmethyl)-amino]-2-cyclopentyl-2H-pyrazolo[3,4-d]pyrimidin-4-yl}-5-chloro-1,3-dihydro-indol-2-one

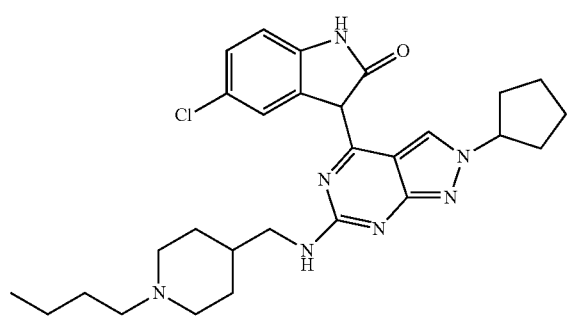 [SMILES: CCCCN1CCC(CNc2nc(C3C(=O)Nc4ccc(Cl)cc43)c3cn(C4CCCC4)nc3n2)CC1]

m.p. 83-201° C.; MS (ES$^+$ calculated: 522.10; found: 522.47 M+H). HPLC (95% purity, retention time 10.638 minutes—Method B); $^1$H NMR (400 MHz, DMSO-d$_6$): δ 9.93 (br s, 1H), 9.49 (br s, 1H), 8.37 (br s, 1H), 6.90 (m, 1H), 6.86 (d, 1H), 6.71 (d, 1H), 4.78 (s, 1H), 3.49-3.17 (m, 3H), 2.96-2.71 (m, 3H), 2.25 (s, 2H), 2.12 (s, 2H), 1.96 (s, 2H), 1.85-1.57 (m, 7H), 1.38-1.10 (m, 6H).

Example 276

N-{2-[4(5-Chloro-2-oxo-2,3-dihydro-1H-indol-3-yl)-2-cyclopentyl-2H-pyrazolo[3,4-d]pyrimidin-6-ylamino]-ethyl}-acetamide

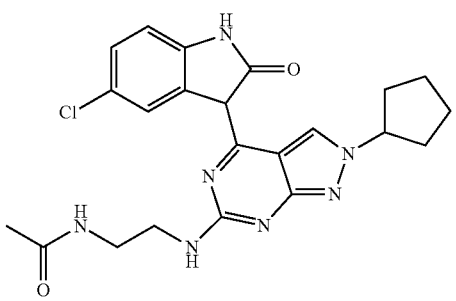 [SMILES: CC(=O)NCCNc1nc(C2C(=O)Nc3ccc(Cl)cc32)c2cn(C3CCCC3)nc2n1]

m.p. 209-226° C.; MS (ES$^+$ calculated: 453.94; found: 454.52 M+H). HPLC (93.5% purity, retention time 10.332 minutes—Method B); $^1$H NMR (400 MHz, DMSO-d$_6$): δ 11.46 (br s), 10.81 (s), 9.96 (s), 9.49 (s), 8.67 (s), 8.35 (s), 8.01-7.83 (m, 5H), 7.04-6.72 (m, 2H), 5.01 (m), 4.80 (m), 3.55 (s, 1H), 3.37 (m, 1H), 3.07 (m, 4H), 2.13 (s, 1H), 1.95 (s, 1H), 1.82 (s, 7H).

Example 277

5-Chloro-3-[2-cyclopentyl-6-(2-methyoxy-ethylamino)-2H-pyrazolo[3,4-d]pyrimidin-4-yl]-1,3-dihydro-indol-2-one

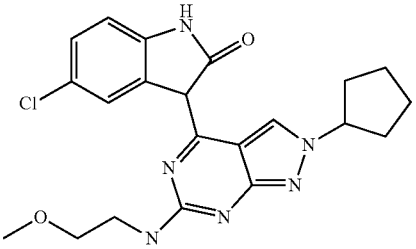 [SMILES: COCCNc1nc(C2C(=O)Nc3ccc(Cl)cc32)c2cn(C3CCCC3)nc2n1]

m.p. 249-259° C.; MS (ES$^+$ calculated: 426.91; found: 427.46 M+H). HPLC (98.5% purity, retention time 11.161 minutes—Method B); $^1$H NMR (400 MHz, DMSO-d$_6$): δ 11.37 (br s, 1H), 9.97 (s, 1H), 9.49 (s, 1H), 6.88 (dd, 1H), 6.71 (d, 1H), 5.00 and 4.80 (m, 1H), 3.68-3.62 (m, 2H), 3.52-3.43 (m, 2H), 3.32 (s, 3H), 2.97 (t, 1H), 2.13 (m, 2H), 1.96 (m, 2H), 1.82 (m, 2H), 1.69 (m, 2H).

Example 278

5-Chloro-3-[2-cyclopentyl-6-(3-morpholin-4-yl-propylamino)-2H-pyrazolo[3,4-d]pyrimidin-4-yl]-1,3-dihydro-indole-2-one

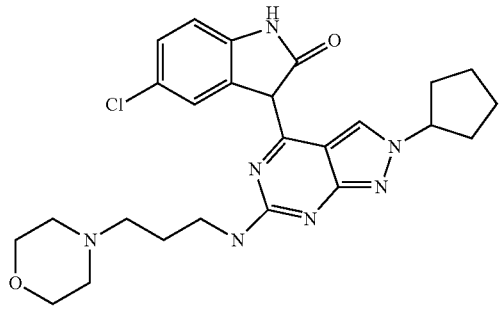 [SMILES: O=C1Nc2ccc(Cl)cc2C1c1nc(NCCCN2CCOCC2)nc2nn(C3CCCC3)cc12]

m.p. 250-254.5° C.; MS (ES$^+$ calculated: 496.02; found: 496.44 M+H). HPLC (99% purity, retention time 9.988 minutes—Method B); $^1$H NMR (400 MHz, DMSO-d$_6$): δ 9.93 (s, 1H), 9.48 (s, 1H), 8.39 (s, 1H), 6.98 (dd, 1H), 6.86 (d, 1H), 6.70 (d, 1H), 4.80 (m, 1H), 3.61 (m, 4H), 3.50 (m, 1H), 3.29 (m, 2H), 2.45 (t, 1H), 2.37 (m, 5H), 2.13 (m, 2H), 1.95 (m, 2H), 1.83 (m, 4H), 1.71 (m, 2H).

Example 279

5-Chloro-3-[2-cyclopentyl-6-(2-pyridin-3-yl-ethylamino)-2H-pyrazolo[3,4-d]pyrimidin-4-yl]-1,3-dihydro-indol-2-one

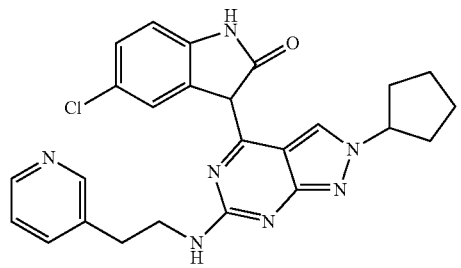 [SMILES: O=C1Nc2ccc(Cl)cc2C1c1nc(NCCc2cccnc2)nc2nn(C3CCCC3)cc12]

m.p. 277-281° C.; MS (ES$^+$ calculated: 473.97; found: 474.37 M+H). HPLC (99% purity, retention time 9.571 minutes—Method B); $^1$H NMR (400 MHz, DMSO-d$_6$): δ 11.39 (br s, 1H), 9.98 (s, 1H), 9.50 (s, 1H), 8.51 (m, 1H), 8.42 (m, 2H), 7.72 (m, 1H), 7.33 (m, 1H), 6.99 (dd, 1H), 6.80 (dd, 1H), 4.82 (m, 1H), 3.78 (m, 2H), 3.57 (m, 0.5H), 3.30 (m, 2H), 3.02 (m, 0.5H), 2.13 (m, 2H), 1.95 (m, 2H), 1.82 (m, 2H), 1.68 (m, 2H).

Example 280

5-Chloro-3-(2-cyclopentyl-6-isobutylamino-2H-pyrazolo[3,4-d]pyrimidin-4-yl)-1,3-dihydro-indol-2-one

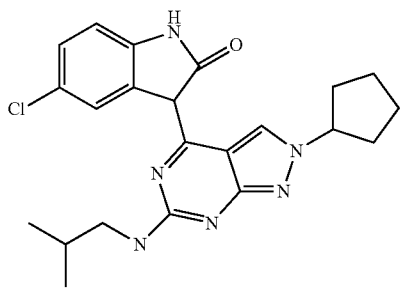 [SMILES: CC(C)CNc1nc(C2C(=O)Nc3ccc(Cl)cc32)c2cn(C3CCCC3)nc2n1]

m.p. 282-286° C.; MS (ES$^+$ calculated: 424.94; found: 425.45 M+H). HPLC (99% purity, retention time 12.303 minutes—Method B); $^1$H NMR (400 MHz, DMSO-d$_6$): δ 11.20 (br s, 1H), 9.96 (s, 1H), 9.49 (s, 1H), 8.42 (s, 1H), 3.35 (m, 1H), 2.13 (m, 2H), 2.02 (m, 4H), 1.82 (m, 2H), 1.68 (m, 2H).

Compound 281 and 282

3-Amino-1-pentyl-1H-pyrazole-4-carbonitrile

5-Amino-1-pentyl-1H-pyrazole-4-carbonitrile

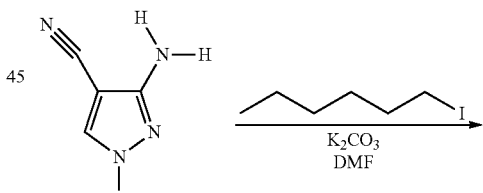

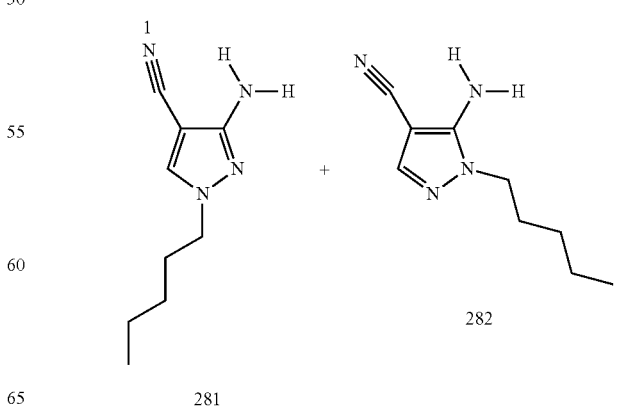

3-Amino-4-pyrazolecarbonitrile 1 (Acros, 15 g, 0.138 mol), pentyliodide (Acros, 24.45 ml, 0.187 mol) and anhydrous potassium carbonate (Fisher, 25.88 g, 0.187 mol) were suspended in 100 mL anhydrous DMF and heated at 80° C. under nitrogen overnight. HPLC analysis (Method D) showed starting material still present. An additional 9 ml (69 mmol) of pethyliodide and 9.5 g (69 mmol) $K_2CO_3$ were added to the reaction and heating continued for 5 more hours. The reaction was permitted to cool and the DMF was removed on a rotary evaporator. Water was added (100 mL) and the organics were extracted with dichloromethane (3×100 mL). The combined dichloromethane fractions were washed with water (50 mL) and brine (50 mL) and were dried (magnesium sulfate). Concentration of the organics afforded orange solid which contained both pentyl isomers and residual DMF by NMR analysis (27.65 g, greater than theoretical yield). This was carried on crude. HPLC (1 peak, 63%) elutes at 9.5 minutes (Method D). $^1$H NMR (400 MHz, DMSO-$d_6$) δ 7.87 (s, 1H), 7.60 (s, 1H), 6.15 (s, 1H), 5.33 (s, 2H), 3.80 (t, J=7, 2H), 1.68 (m, 2H), 1.25 (m, 4H) 0.75 (t, J=7, 3H).

Compound 283 and 284

3-Amino-1-pentyl-1H-pyrazole-4-caroboxylic acid amide

5-Amino-1-pentyl-1H-pyrazole-4-carboxylic acid amide

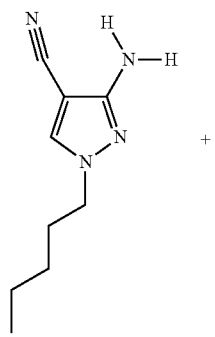

281

+

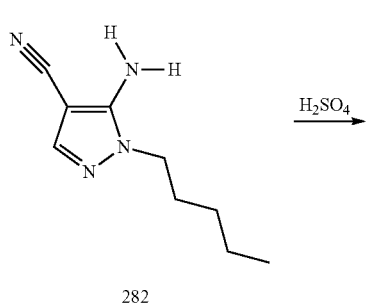

282

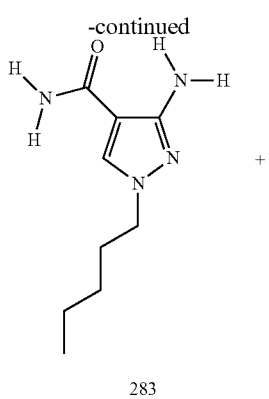

283

+

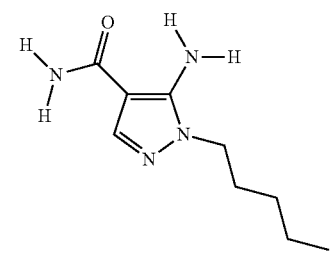

284

To 4 ml conc. $H_2SO_4$ at 0° C., was added 1.6 g (8.9 mmol) of the crude mixture (Example 254 and Compound 255) from the above alkylation reaction. The reaction was allowed to stir and warm to room temperature. After 4 h stirring, the entire solid had been dissolved. The thick, acid solution was added dropwise to stirring, ice cold NH$_4$OH (aq). The resulting white precipitate (1.23 g, 70%), as a mixture of the two isomers, was collected via vacuum filtration, washed with water and dried in vacuo. $^1$H NMR (400 MHz, DMSO-$d_6$) δ 7.82 (s, 1H), 7.58 (s, 1H), 7.15 (br s, 2H), 6.65 (br s, 2H), 5.32 (s, 1H), 3.80 (t, J=7 Hz, 2H), 1.68 (m, 2H), 1.25 (m, 4H), 0.75 (t, J=7 Hz, 3H).

Compound 285

2-Pentyl-2H-pyrazole[3,4-d]pyrimidine-4,6-diol

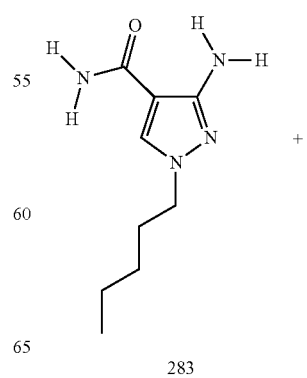

+

283

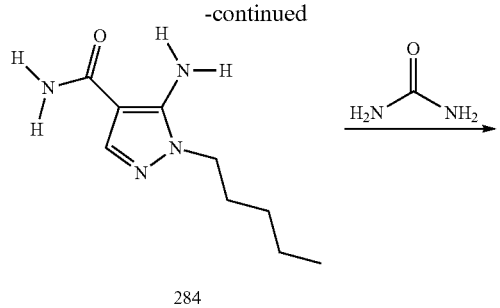

284

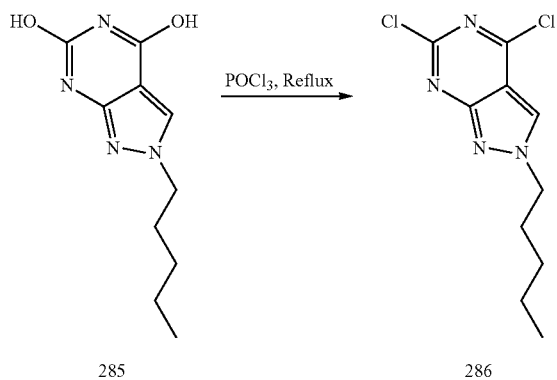 [SMILES: CCCCCn1cc2c(O)nc(O)nc2n1 ; CCCCCn1cc2c(Cl)nc(Cl)nc2n1]

285

In a sealed tube 539 mg (2.75 mmol) of the mixture of isomers (Compound 283 and Compound 284) from the above reaction and 1.65 g (27.5 mmol) urea were combined and heated to 180° C. The solids became an off white liquid and then returned to solid at approximately 3 h of heating. The reaction was cooled to 130° C. and 10 ml water added. The aqueous solution was refluxed overnight, cooled to room temperature in the morning, and filtered. Only the desired isomer was collected as a white solid (177 mg, 29%). HPLC (87%) elutes at 7.88 min. (Method B). $^1$H NMR (400 MHz, DMSO-$d_6$) δ 11.35 (s, 1H), 11.65 (s, 1H), 8.35 (s, 1H), 4.10 (t, J=7 Hz, 2H), 1.80 (m, 2H), 1.25 (m, 4H), 0.75 (t, J=7 Hz, 3H).

Compound 286

4,6-Dichloro-2-pentyl-2H-pyrazolo[3,4-d]pyrimidine

To 30 ml POCl$_3$, was added 1.12 g compound 285 prepared as above. The solution was refluxed for 5 h and monitored by removing aliquots, quenching them into saturated NaHCO$_3$ and extracting with ether. The POCl$_3$ was first removed via rotary evaporation and subsequent high vacuum for approximately 1 h. The resulting dark syrup was quenched into stirring ice water and the aqueous solution made basic with 5% NaOH. The solution was transferred to a reparatory funnel and extracted with 3×50 ml portions of ether. The combined ether was dried over MgSO$_4$, filtered and evaporated to a white to off white solid (900 mg, 69%). HPLC (99%) elutes at 11.78 min. (Method B). $^1$H NMR (400 MHz, DMSO-$d_6$) δ 9.05 (s, 1H), 4.55 (t, J=7 Hz, 2H), 1.90 (m, 2H), 1.28 (m, 4H), 0.9 (t, J=7 Hz, 3H).

Example 287

3-(6-Chloro-2-pentyl-2H-pyrazolo[3,4-d]pyrimidin-4-yl)-5-trifluoromethyl-1,3-dihydro-indol-2-one

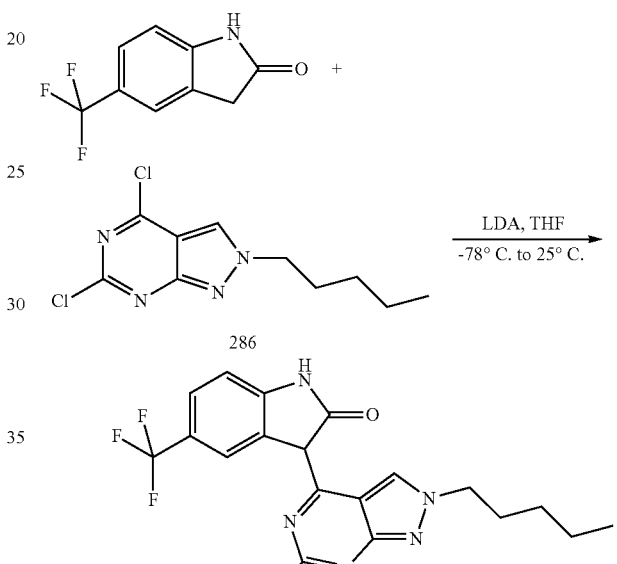

To a stirring solution of 5-trifluoromethyloxindole (300 mg, 1.49 mmol) and THF (5 mL), in 50 mL flask at −78° C. was added LDA (1.86 mL, 3.73 mmol). After the reaction was stirred for 45 min, a solution of compound 286 prepared above (402 mg, 1.55 mmol) in THF (3 mL×2) was added and continued to stir for 1 h at −78° C. The reaction was allowed to warm to room temperature and stirred for additional 2 h. It was quenched with saturated NH$_4$Cl (10 mL). The resulting precipitate was filtered, washed with water, and dried under house vacuum at 50° C. overnight to give 587 mg (93%) of the desired product as a light yellow solid: mp=267° C. dec., $^1$H NMR (400 MHz, DMSO-$d_6$) δ 11.45 (br s, 1H), 9.35 (s, 1H), 8.55 (s, 1H), 8.35 (m, 1H), 7.25 (s, 1H), 7.15 (s, 1H), 7.05 (s, 1H), 4.25 (t, J=7 Hz, 2H), 1.82 (m, 2H), 1.30 (m, 4H), 0.85 (t, J=7 Hz, 3H); MS m/e 424 (M+1), HPLC (99% purity, retention time 13.71 minutes, method B)

General Procedure for Aminations Using Microwave—

In a CEM 10 ml disposable microwave tube equipped with a stir bar, was placed 75 mg (0.18 mmol) of the oxidolepyrazolopyrimidine prepared above and 2 ml EtOH. To the tube was added 10 eq. of the corresponding amine and the tube heated to 130° C. for 10 min in the microwave reactor. The resulting solid was filtered and washed with ether and dried in vacuo. If no solid was formed, the EtOH was evaporated and the resulting solid triturated with ether, filtered and dried in vacuo.

Example 288

3-[6-(2-Amino-ethylamino)-2-pentyl-2H-pyrazolo[3,4-d]pyrimidin-4-yl]-5-trifluoromethyl-1,3-dihydro-indol-2-one

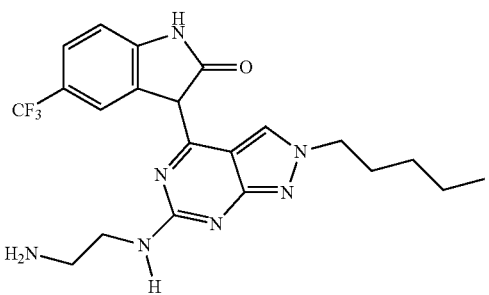 [SMILES: CCCCCn1cc2c(C3C(=O)Nc4ccc(C(F)(F)F)cc43)nc(NCCN)nc2n1]

Yellow solid (37 mg, 46%): mp=192° C. dec., $^1$H NMR (400 MHz, DMSO-d$_6$) δ 10.08 (br s, 1H), 9.40 (s, 1H), 7.10 (d, J=5 Hz, 1H), 6.80 (d, J=5 Hz, 1H), 4.15 (t, J=7 Hz, 2H), 3.7-3.0 (br m, 4H), 1.82 (m, 2H), 1.25 (m, 4H), 0.85 (t, J=7 Hz, 3H); MS m/e 448 (M+1), HPLC (80% purity, retention time 9.66 minutes, method B).

Example 289

3-[6-(3-Amino-propylamino)-2-pentyl-2H-pyrazolo[3,4-d]pyrimidin-4-yl]-5-trifluoromethyl-1,3-dihydro-indol-2-one

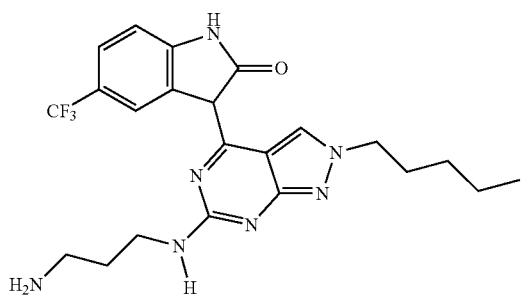 [SMILES: CCCCCn1cc2c(C3C(=O)Nc4ccc(C(F)(F)F)cc43)nc(NCCCN)nc2n1]

Yellow solid (15 mg, 16%): mp=235° C. dec., $^1$H NMR (400 MHz, DMSO-d$_6$) δ 9.97 (br s, 1H), 9.40 (s, 1H), 8.70 (s, 1H), 7.10 (d, J=5 Hz, 1H), 6.80 (d, J=5 Hz, 1H), 4.15 (m, 2H), 3.50 (m, 2H), 2.80 (m, 4H), 1.82 (m, 4H), 1.25 (m, 4H), 0.85 (t, J=7 Hz, 3H); MS m/e 462 (M+1), HPLC (80% purity, retention time 9.48 minutes, method B).

Example 290

3-[6-(3-Morpholin-4-yl-propylamino)-2-pentyl-2H-pyrazolo[3,4-d]pyrimidin-4-yl]-5-trifluoromethyl-1,3-dihydro-indol-2-one

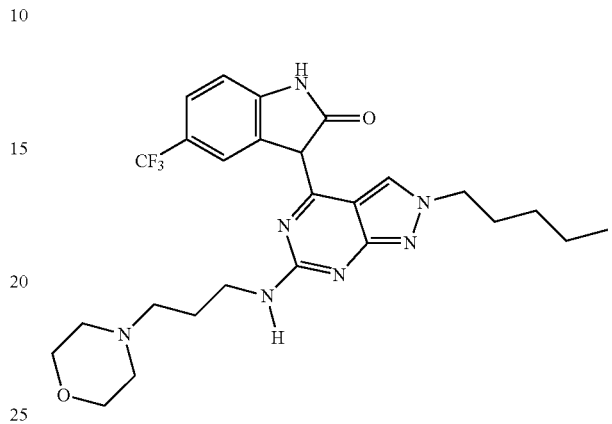

Yellow-brown solid (81 mg, 85%): mp=230° C. dec., $^1$H NMR (400 MHz, DMSO-d$_6$) δ 10.30 (s, 1H), 9.40 (s, 1H), 8.70 (s, 1H), 7.10 (d, J=5 Hz, 1H), 6.80 (d, J=5 Hz, 1H), 4.15 (m, 2H), 3.30 (m, 2H), 2.80 (m, 4H), 1.82 (m, 4H), 1.25 (m, 4H), 0.85 (t, J=7 Hz, 3H); MS m/e 532 (M+1), HPLC (93% purity, retention time 10.10 minutes, method B).

Example 291

3-(6-Chloro-2-pentyl-2H-pyrazolo[3,4-d]pyrimidin-4-yl)-2-oxo-2,3-dihydro-1H-indole-5-carbonitrile

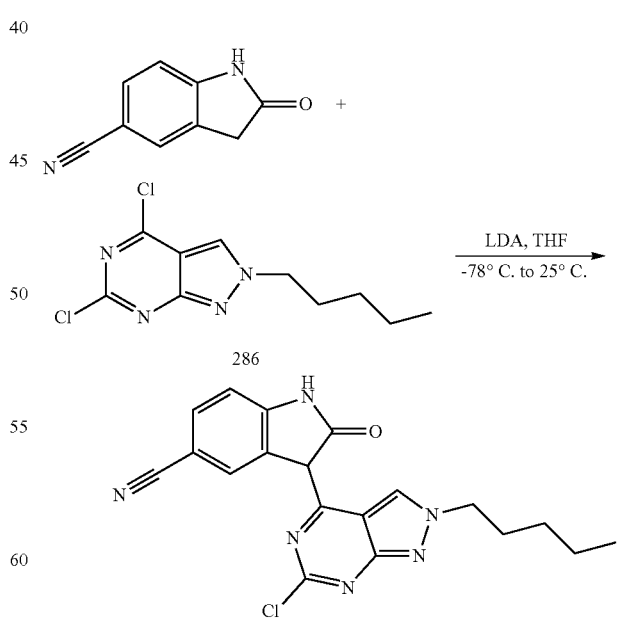

To a stirring solution of 5-cyanoloxindole (166 mg, 1.05 mmol) and THF (2 mL) in 50 mL flask at −78° C. was added LDA (1.31 mL, 2.62 mmol). After the reaction was stirred for 45 min, a solution of compound 286 prepared above (290 mg, 1.11 mmol) in THF (1 mL×2) was added and continued to stir for 1 h at −78° C. The reaction was allowed to warm to room temperature and stirred for additional 2 h. It was quenched with saturated NH₄Cl (10 mL). The resulting precipitate was filtered, washed with water, and dried under house vacuum at 50° C. overnight to give 115 mg (29%) of the desired product as a light yellow solid: mp=254° C. dec., $^1$H NMR (400 MHz, DMSO-$d_6$) δ 10.28 (br s, 1H), 9.45 (s, 1H), 8.55 (s, 1H), 7.25 (d, J=7 Hz, 1H), 6.85 (d, J=7 Hz, 1H), 4.25 (t, J=7 Hz, 2H), 1.82 (m, 2H), 1.25 (m, 4H), 0.85 (t, J=7 Hz, 3H); MS m/e 381 (M+1), HPLC (97% purity, retention time 11.71 minutes, method B)

General Procedure for Aminations in Radley's Tube—

In a Radley's Tube equipped with a stir bar, was placed 50 mg (0.18 mmol) of the 5-cyano oxidolepyrazolopyrimidine prepared above and 2 ml 2-methoxyethanol. To the tube was added 10 eq. of the corresponding amine and the tube heated to 130° C. and the reaction followed by LC/MS. When reaction was complete, the solvent was removed via Speedi-Vac overnight. The resulting solid suspended in MeOH, filtered, washed with ether and dried in vacuo.

Example 292

2-Oxo-3-{2-pentyl-6-[(pyridin-4-ylmethyl)-amino]-2H-pyrazolo [3,4-d]pyrimidin-4-yl}-2,3-dihydro-1H-indole-5-carbonitrile

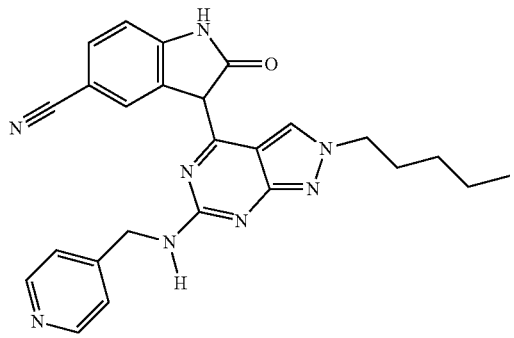 [SMILES: CCCCCn1cc2c(C3C(=O)Nc4ccc(C#N)cc43)nc(NCc3ccncc3)nc2n1]

Yellow solid (39 mg, 65%): mp=288-290° C. dec., $^1$H NMR (400 MHz, DMSO-$d_6$) δ 11.85 (br, s, 1H), 10.40 (s, 1H), 9.40 (s, 1H), 8.50 (d, J=8 Hz, 2H), 8.50 (d, J=8 Hz, 2H), 7.10 (d, J=5 Hz, 1H), 6.80 (d, J=5 Hz, 1H), 4.80 (m, 2H), 2.80 (m, 4H), 1.82 (m, 4H), 1.25 (m, 4H), 0.85 (t, J=7 Hz, 3H); MS m/e 453 (M+1), HPLC (98% purity, retention time 7.91 minutes, method B).

Example 293

3-(6-Allylamino-2-pentyl-2H-pyrazolo[3,4-d]pyrimidin-4-yl)-2-oxo-2,3-dihydro-1H-indole-5-carbonitrile

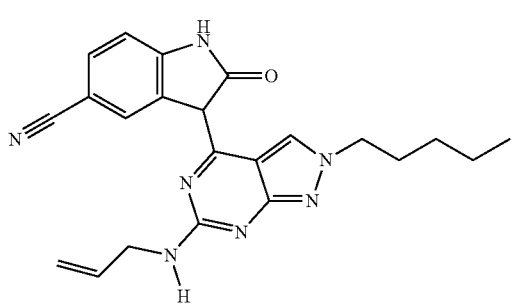 [SMILES: C=CCNc1nc(C2C(=O)Nc3ccc(C#N)cc32)c2cn(CCCCC)nc2n1]

Yellow solid (18 mg, 65%): mp=265° C. dec., $^1$H NMR (400 MHz, DMSO-$d_6$) δ 11.55 (br s, 1H), 10.40 (s, 1H), 9.40 (s, 1H), 8.50 (br s, 2H), 8.50 (d, J=8 Hz, 2H), 7.30 (d, J=10 Hz, 1H), 6.80 (d, J=10 Hz, 1H), 6.00 (m, 1H), 5.30 (d, J=7 Hz, 1H), 5.15 (d, J=7 Hz, 1H), 4.80 (m, 2H), 2.80 (m, 4H), 1.82 (m, 4H), 1.25 (m, 4H), 0.85 (t, J=7 Hz, 3H); MS m/e 402 (M+1), HPLC (99% purity, retention time 9.93 minutes, method B).

Example 294

3-(6-Methylamino-2-pentyl-2H-pyrazolo [3,4-d]pyrimidin-4-yl)-2-oxo-2,3-dihydro-1H-indole-5-carbonitrile

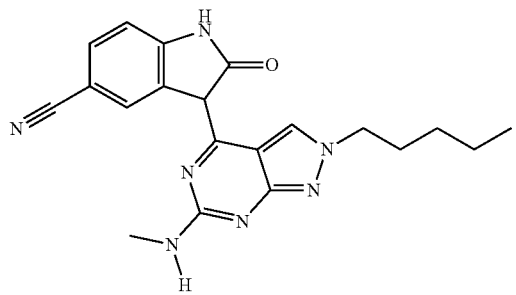 [SMILES: CCCCCn1cc2c(C3C(=O)Nc4ccc(C#N)cc43)nc(NC)nc2n1]

Yellow solid (32 mg, 65%): mp=>310° C., $^1$H NMR (400 MHz, DMSO-$d_6$) δ 11.75 (s, 1H), 10.40 (s, 1H), 9.40 (s, 1H), 8.75 (s, 1H), 7.30 (d, J=10 Hz, 1H), 6.80 (d, J=10 Hz, 1H), 4.80 (m, 2H), 3.0 (s, 3H), 1.82 (m, 4H), 1.25 (m, 4H), 0.85 (t, J=7 Hz, 3H); MS m/e 376 (M+1), HPLC (95% purity, retention time 8.81 minutes, method B).

Example 295

3-(6-Isopropylamino-2-pentyl-2H-pyrazolo[3,4-d]pyrimidin-4-yl)-2-oxo-2,3-dihydro-1H-indole-5-carbonitrile

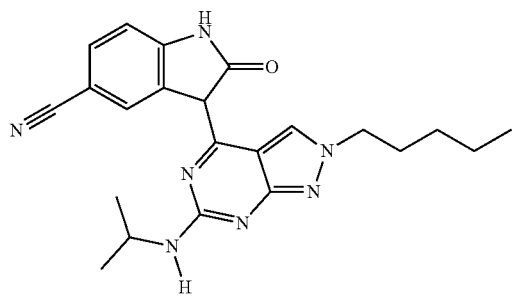 [SMILES: CCCCCn1cc2c(C3C(=O)Nc4ccc(C#N)cc43)nc(NC(C)C)nc2n1]

Yellow solid (11 mg, 20%): mp=199° C. dec., $^1$H NMR (400 MHz, DMSO-$d_6$) δ 10.40 (s, 1H), 9.40 (s, 1H), 8.75 (s, 1H), 7.30 (d, J=10 Hz, 1H), 6.80 (d, =10 Hz, 1H), 4.80 (m, 5H), 1.82 (m, 4H), 1.25 (m, 7H), 0.85 (t, J=7 Hz, 3H); MS m/e 404 (M+1), HPLC (95% purity, retention time 9.97 minutes, method B).

Scheme 6

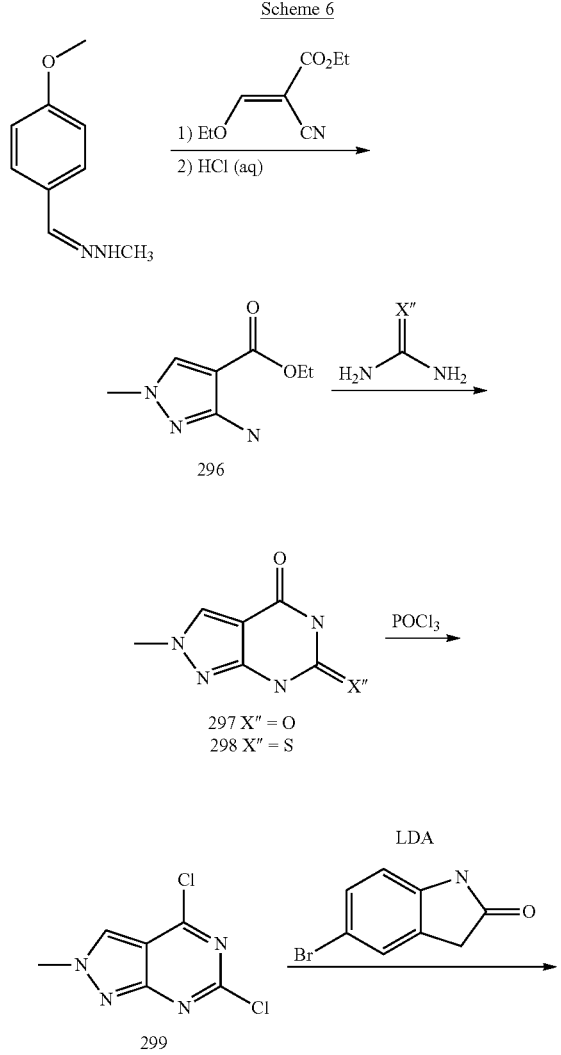

Compound 296

3-Amino-1-methyl-1H-pyrazole-4-carboxylic acid ethyl ester

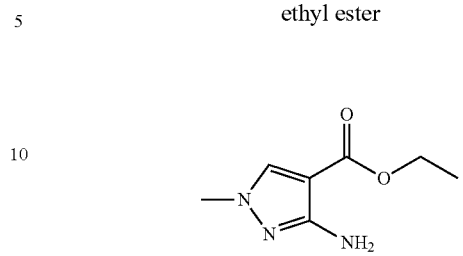

Methylhydrazine (5.90 g, 128 mmol) and p-anisaldehyde (17.43 g, 128 mmol) were refluxed in 100 mL dry benzene employing a Dean-Start trap to remove water. After 24 hours the organics were concentrated and the reaction was reconstituted by the addition of 50 mL anhydrous benzene. Ethyl ethoxymethylenecyanoacetate (21.65 g, 128 mmol) in 50 mL anhydrous benzene was added dropwise and the mixture was refluxed for one hour. The reaction was concentrated and the remaining organics were triturated with ethanol to afford a solid after filtering. To this solid was added approximately 100 mL ethanol and 17 mL concentrated hydrochloric acid. The mixture was stirred ½ hour at 80° C. at which point the reaction became homogeneous. The reaction was concentrated and the product obtained was triturated with approximately 500 mL boiling ethyl ether for one hour to remove anisaldehyde. The suspended solid was filtered off and dissolved in chloroform (approximately 250 mL). The chloroform solution was washed with saturated sodium bicarbonate solution and was dried (magnesium sulfate) and concentrated to afford 19.66 g (91%) of a peach solid Compound 296 which was used in succeeding steps without purification.

Compound 297

2-Methyl-2,7-dihydropyrazolo[3,4-d]pyrimidine-4,6-dione

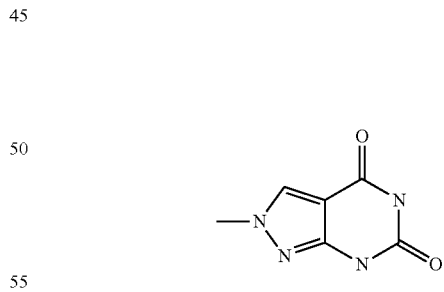

Compound 296 (2 g, 11.8 mmol) was melted at 200° C. with 6 g urea (large excess) for two hours. The reaction was permitted to cool to 40° C. and 20 mL water was added. The mixture was then boiled for 1 hour and stirred at room temperature overnight. Filtration and drying in vacuo afforded 1.86 g (95%) of a white solid. Compound 297: mp>300° C.; MS (ES$^+$ calculated: 166.14; found: 167.24 M+H). HPLC (100% purity, retention time 2.103 minutes—Method A); $^1$H NMR (400 MHz, DMSO-d$^6$): δ 11.34 (br s, 1H), 10.66 (br s, 1H), 8.27 (s, 1H), 3.82 (s, 3H).

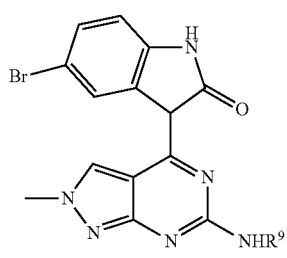

Compound 298

2-Methyl-6-thioxo-2,5,6,7-tetrahydropyrazolo[3,4-d]pyrimidin-4-one

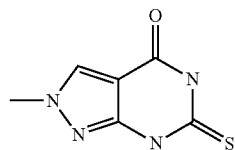

Compound 296 (2 g, 11.8 mmol) was melted at 200° C. with 6 g thiourea (large excess) for two hours. The reaction was permitted to cool to 40° C. and 50 mL water was added. The mixture was then boiled overnight. Filtration and drying in vacuo afforded 1.06 g (49%) of a white solid. Compound 298: mp>300° C.; MS (ES+ calculated: 182.20; found: 183.18 M+H). HPLC (100% purity, retention time 5.328 minutes—Method D); $^1$H NMR (400 MHz, DMSO-d$^6$): δ 13.05 (br s, 1H), 12.86 (br s, 1H), 8.70 (s, 1H), 3.88 (s, 3H).

Compound 299

4,6-Dichloro-2-methyl-2H-pyrazolo[3,4-d]pyrimidine

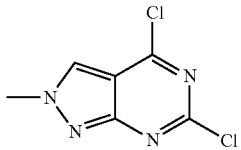

Compound 297 (1.04 g, 5.7 mmol) was refluxed under argon with 50 mL phosphorous oxychloride for 24 hours. Following introduction of a pipette for analysis, the suspension became homogeneous after approximately an hour. Following homogeneity the reaction was refluxed an additional hour. Excess phosphorus oxychloride was then scrupulously removed in vacuo (high vacuum). Ice was added and the mixture neutralized to basic by addition of 10N sodium hydroxide solution. A yellow solid was removed by filtration and dried in vacuo to afford 0.76 g (66%). Compound 299: MS (ES+ calculated: 203.03; found: 203.19 M+H). HPLC (67% purity—pdt decomposes on hplc column, retention time 6.895 minutes—Method A); $^1$H NMR (400 MHz, DMSO-d$^6$): δ 9.02 (s, 1H), 4.23 (s, 3H).

Example 300

5-Bromo-3-(6-chloro-2-methyl-2H-pyrazolo[3,4-d]pyrimidin-4-yl)-1,3-dihydro-indol-2-one

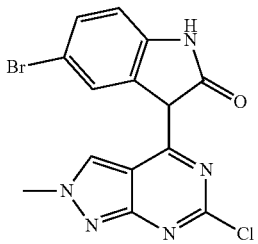 [SMILES: Cn1cc2c(C3C(=O)Nc4ccc(Br)cc43)nc(Cl)nc2n1]

To 5-bromooxindole (212 mg, 1.0 mmol) in 5 mL anhydrous tetrahydrofuran at −78° C. under argon was added lithium diisopropylamide (1.05 mL of a 2.0M solution in THF/hexane, 2.1 mmol) dropwise. The solution was stirred ten minutes and Compound 299 (202 mg, 1.0 mmol) was added in one portion. The reaction was permitted to warm to room temperature at which point 2 mL of N-methylpyrrolidinone was added to promote homogeneity. Dissolution occurred and the reaction was stirred for 90 minutes. The reaction was concentrated and residual solvent was removed via lyophilization. The resulting organics were applied to silica gel and eluted (gradient from 1 to 10% methanol:dichloromethane) to afford 275 mg (73%) of an orange solid. Example 300: mp>300° C.; MS (ES+ calculated: 378.62; found: 380.02 M+H). HPLC (78% purity, retention time 11.002 minutes—Method B); $^1$H NMR (400 MHz, DMSO-d$^6$): δ 10.47 (br s, 1H), 9.26 (br s, 1H), 8.25 (br s, 1H), 7.14 (m, 1H), 6.77 (m, 1H), 4.04 (s, 3H), 3.40 (m, 1H).

Example 301

3-(6-Allylamino-2-methyl-2H-pyrazolo[3,4-d]pyrimidin-4-yl)-5-bromo-1,3-dihydro-indol-2-one

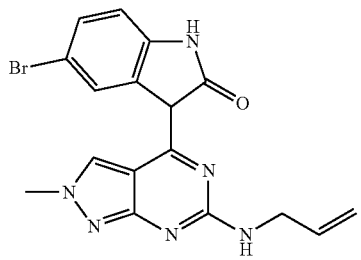 [SMILES: C=CCNc1nc(C2C(=O)Nc3ccc(Br)cc32)c2cn(C)nc2n1]

Example 300 (30 mg, 0.08 mmol), allylamine (46 mg, 0.90 mmol) and methoxyethanol (2 mL) were combined and heated in a sealed tube at 130° C. overnight. The reaction was concentrated to afford a solid which was triturated with 1 mL methanol. Filtration and drying afforded 19 mg (60%) of a yellow solid. Example 301: mp 336-340° C.; MS (ES+ calculated: 399.25; found: 400.77 M+H). HPLC (96% purity, retention time 9.036 minutes—Method B); $^1$H NMR (400 MHz, DMSO-d$^6$): δ 11.35 (s, 1H), 9.99 (s, 1H), 9.38 (s, 1H), 8.52 (s, 1H), 6.99 (d, J=8 Hz, 1H), 6.65 (d, J=8 Hz, 1H), 6.05 n(m, 1H), 5.31 (d, J=17 Hz, 1H), 5.16 (d, J=10 Hz, 1H), 4.15 (m, 2H), 4.01 (m, 1H), 3.92 (s, 3H).

Example 302

5-Bromo-3-{2-methyl-6-[(pyridin-4-ylmethyl)-amino]-2H-pyrazolo[3,4-d]pyrimidin-4-yl}-1,3-dihydro-indol-2-one

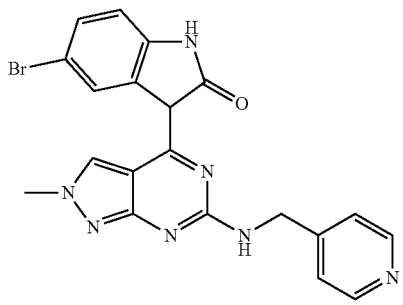 [SMILES: Cn1cc2c(C3C(=O)Nc4ccc(Br)cc43)nc(NCc3ccncc3)nc2n1]

Example 302 was prepared as a gum from the reaction of Example 300 and 4-aminomethylpyridine. Yield: 12 mg (33%). Example 302: MS (ES+ calculated: 450.30; found: 451.79 M+H). HPLC (93% purity, retention time 7.220 minutes—Method B); $^1$H NMR (400 MHz, DMSO-d$^6$): δ 11.50

(br s, 1H), 9.99 (s, 1H), 9.39 (s, 1H), 8.50 (s, 1H), 67.60-7.17 (m, 4H), 6.90 (m, 1H), 6.62 (m, 1H), 64.10-3.90 (m, 3H), 3.92 (s, 3H).

Example 303

3-[6-(2-Amino-ethylamino)-2-methyl-2H-pyrazolo [3,4-d]pyrimidin-4-yl]-5-bromo-1,3-dihydro-indol-2-one

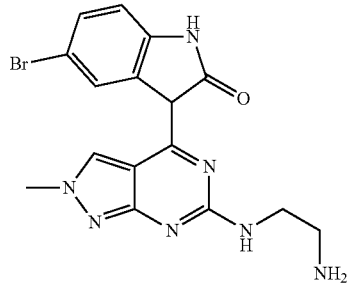 [SMILES: Cn1cc2c(C3C(=O)Nc4ccc(Br)cc43)nc(NCCN)nc2n1]

Example 303 was prepared by reacting Example 300 and ethylenediamine. Yield: 19 mg (59%). Example 303: mp 260-2° C.; MS (ES⁺ calculated: 402.26; found: 403.79 M+H). HPLC (86% purity, retention time 7.036 minutes—Method B); ¹H NMR (400 MHz, DMSO-d⁶): δ 9.56 (br s, 1H), 9.37 (br s, 1H), 8.55 (br s, 1H), 6.79 (m, 1H), 6.57 (m, 1H), 6.43 (br s, 1H), 3.88 (s, 3H), 3.60-3.20 (m, 7H).

Example 304

5-Bromo-3-[6-(2-(S)-hydroxypropylamino)-2-methyl-2H-pyrazolo [3,4-d]pyrimidin-4-yl]-1,3-dihydro-indol-2-one

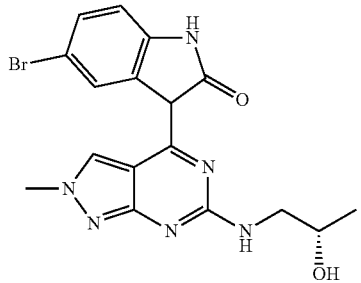 [SMILES: C[C@H](O)CNc1nc(C2C(=O)Nc3ccc(Br)cc32)c2cn(C)nc2n1]

Example 304 was prepared from the reaction of Example 300 and (S)-2-hydroxy-1-aminopropane. Yield: 16 mg (48%). Example 304: mp 338-40° C.; MS (ES⁺ calculated: 417.27; found: 418.72 M+H). HPLC (97% purity, retention time 7.743 minutes—Method B); ¹H NMR (400 MHz, DMSO-d⁶): δ 10.00 (s, 1H), 9.37 (s, 1H), 8.50 (s, 1H), 7.00 (d, J=8 Hz, 1H), 6.67 (d, J=8 Hz, 1H), 3.91 (s, 3H), 3.70-3.20 (m, 4H), 1.22 (m, 3H).

Example 305

5-Bromo-3-[2-methyl-6-(2-pyridin-3-yl-ethylamino)-2H-pyrazolo [3,4-d]pyrimidin-4-yl]-1,3-dihydro-indol-2-one

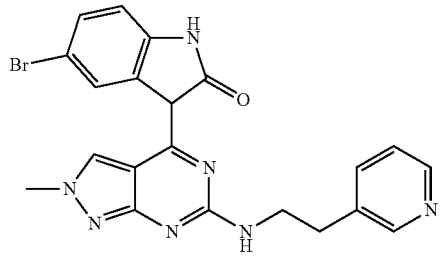 [SMILES: Cn1cc2c(C3C(=O)Nc4ccc(Br)cc43)nc(NCCc3cccnc3)nc2n1]

Example 300 (30 mg, 0.08 mmol) and 3-(2' aminoethyl) pyridine (98 mg, 0.80 mmol) in 2 mL ethanol was subjected to reaction at 130° C. in a microwave for ten minutes. On cooling a mustard brown solid was collected by filtration. It was washed with ethanol and dried in vacuo to afford 24 mg (65%). Example 305: mp 314-7° C.; MS (ES⁺ calculated: 464.33; found: 465.78 M+H). HPLC (96% purity, retention time 7.201 minutes—Method B); ¹H NMR (400 MHz, DMSO-d⁶): δ 9.89 (s, 1H), 9.36 (s, 1H), 8.60-8.40 (m, 3H), 7.72 (m, 1H), 7.32 (m, 1H), 6.94 (d, J=8 Hz, 1H), 6.80 (br s, 1H), 6.64 (d, J=8 Hz, 1H), 3.90 (s, 3H), 3.85-2.80 (m, 5H).

Example 306

5-Bromo-3-[2-methyl-6-(3-methylamino-propylamino)-2H-pyrazolo [3,4-d]pyrimidin-4-yl]-1,3-dihydro-indol-2-one

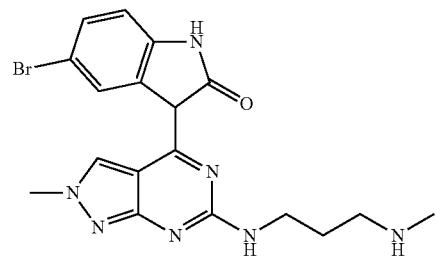 [SMILES: CNCCCNc1nc(C2C(=O)Nc3ccc(Br)cc32)c2cn(C)nc2n1]

In a similar fashion to Example 305, BOC protected Example 306 was prepared from the reaction of Example 300 and N-(3-aminopropyl)-N-methylcarbamic acid-t-butyl ester. The product obtained by filtration from the ethanolic solution was taken up into 4 mL 4N hydrochloric acid:dioxane and stirred at room temperature for one hour. The reaction was concentrated and the solid was triturated with ethyl ether to afford after filtering 17 mg (46%) of a yellow solid—isolated as the hydrochloride salt. mp 271-273° C.; MS (ES⁺ calculated: 430.31; found: 431.91 M+H). HPLC (92% purity, retention time 8.228 minutes—Method D); ¹H NMR (400 MHz, DMSO-d⁶): δ 10.10 (br s, 1H), 9.34 (br s, 1H), 8.64 (br s, 1H), 7.27 (br s, 1H), 7.04 (m, 1H), 6.72 (m, 1H), 3.95 (s, 3H), 3.38 (d, J=7 Hz, 3H), 3.78-1.80 (m, 9H).

Example 307

5-Bromo-3-[6-(3-dimethylamino-propylamino)-2-methyl-2H-pyrazolo[3,4-d]pyrimidin-4-yl]-1,3-dihydro-indol-2-one

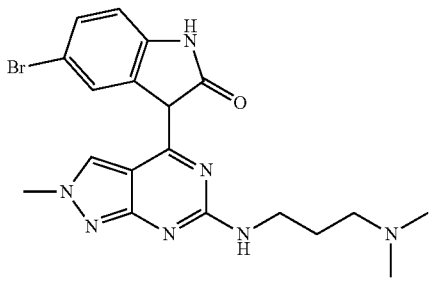 [SMILES: CN(C)CCCNc1nc(C2C(=O)Nc3ccc(Br)cc32)c2cn(C)nc2n1]

In a similar manner as for the preparation Example 305, Example 307 was prepared from the reaction of 300 and N,N-dimethylpropylenediamine in ethanol to afford 10 mg (28%) of a yellow solid. Example 307: mp 310-12° C. (dec); MS (ES+ calculated: 444.34; found: 445.88 M+H). HPLC (97% purity, retention time 7.155 minutes—Method B); $^1$H NMR (400 MHz, DMSO-d$^6$): δ 9.93 (s, 1H), 9.37 (s, 1H), 8.54 (s, 1H), 7.00 (br s, 1H), 6.97 (d, J=8 Hz, 1H), 6.65 (d, J=8 Hz, 1H), 3.91 (s, 3H), 3.50 (m, 2H), 2.47 (m, 2H), 2.23 (s, 6H), 1.81 (m, 2H).

Example 308

3-(6-Chloro-2-propyl-2H-pyrazolo[3,4-d]pyrimidin-4-yl)-5-methyl-1,3-dihydroindol-2-one

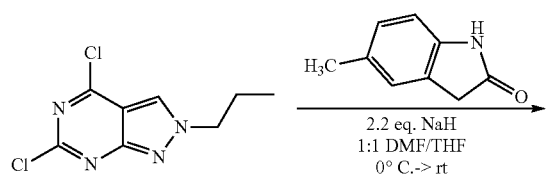

A solution of 5-methyloxindole (147 mg, 1.0 mmol) and compound 105 (231 mg, 1.0 mmol) in 2 mL dry THF and 2 mL dry DMF was cooled to 0° C., and a dispersion of 60% NaH in mineral oil (80 mg, 2.0 mmol) was added. After the hydrogen evolution ceased, the reaction mixture was allowed to warm to rt. The reaction mixture was stirred under N$_2$ for 2 days. The dark yellow homogeneous reaction was quenched with sat. NH$_4$Cl, and a yellow precipitate formed. The precipitate was washed with water, and the product allowed to air dry. The crude product was then suspended in diethyl ether, and the yellow solid recovered by filtration affording 272 mg (80%) of the product: mp 275-80° C. $^1$H NMR (400 MHz, TFA-d): δ 9.68 (s, 1H), 8.41 (br. s, 1H), 8.09 (d, J=7.8 Hz, 1H), 8.02 (d, J=7.8 Hz, 1H), 5.33 (q, J=6.3 Hz, 2H), 3.30 (s, 3H), 2.97 (dq, J=6.3, 7.1 Hz), 1.93 (t, J=7.1 Hz).

Example 309

3-[6-(2-Dimethylamino-ethylamino)-2-propyl-2H-pyrazolo[3,4-d]pyrimidin-4-yl]-5-methyl-1,3-dihydro-indol-2-one

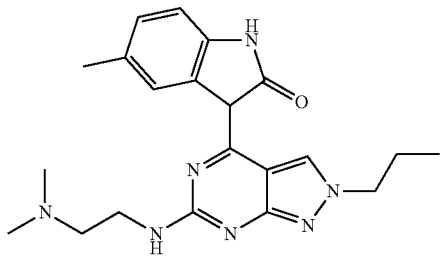 [SMILES: CCCn1cc2c(C3C(=O)Nc4ccc(C)cc43)nc(NCCN(C)C)nc2n1]

Using microwave procedure as described previously, the homogeneous reaction mixture was triturated with hexanes to precipitate the product from solution. Filtration and ether wash provided the product (15 mg, 33% yield) as a yellow solid; mp 255-7° C. $^1$H NMR (400 MHz, TFA-d): δ 8.83 (s, 1H), 7.66 (s, 1H), 7.34 (d, J=8.3 Hz, 1H), 7.22 (d, J=7.8 Hz, 1H), 4.48 (m, 2H), 4.36 (q, J=7.1 Hz, 2H), 3.94 (m, 2H), 3.30 (s, 6H), 2.55 (s, 3H), 2.19 (dt, J=7.1, 7.1 Hz, 2H), 1.20 (t, J=7.1 Hz, 3H).

Example 310

3-[6-(3-Methoxy-propylamino)-2-propyl-2H-pyrazolo[3,4-d]pryrimidin-4-yl]-5-methyl-1,3-dihydro-indol-2-one

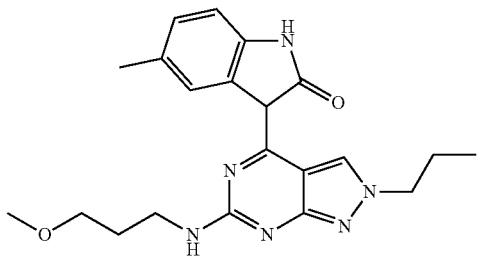 [SMILES: CCCn1cc2c(C3C(=O)Nc4ccc(C)cc43)nc(NCCCOC)nc2n1]

Using microwave procedure as described for Example 309, the yellow precipitate was recovered by filtration, and the solid washed with water to provide the product (25 mg, 54%); mp 286-8° C. $^1$H NMR (400 MHz, TFA-d): δ 8.75 (s, 1H), 7.59 (br. s, 1H), 7.26 (d, J=7.6 Hz, 1H), 7.16 (m, 1H), 4.41 (t, J=7.1 Hz, 2H), 3.95 (t, J=6.6 Hz, 2H), 3.87 (m, 2H), 3.65 (s, 3H), 2.48 (s, 3H), 2.33 (m, 2H), 2.11 (dt, J=6.8, 7.4 Hz, 2H), 1.12 (t, J=7.3 Hz, 3H).

Scheme 7

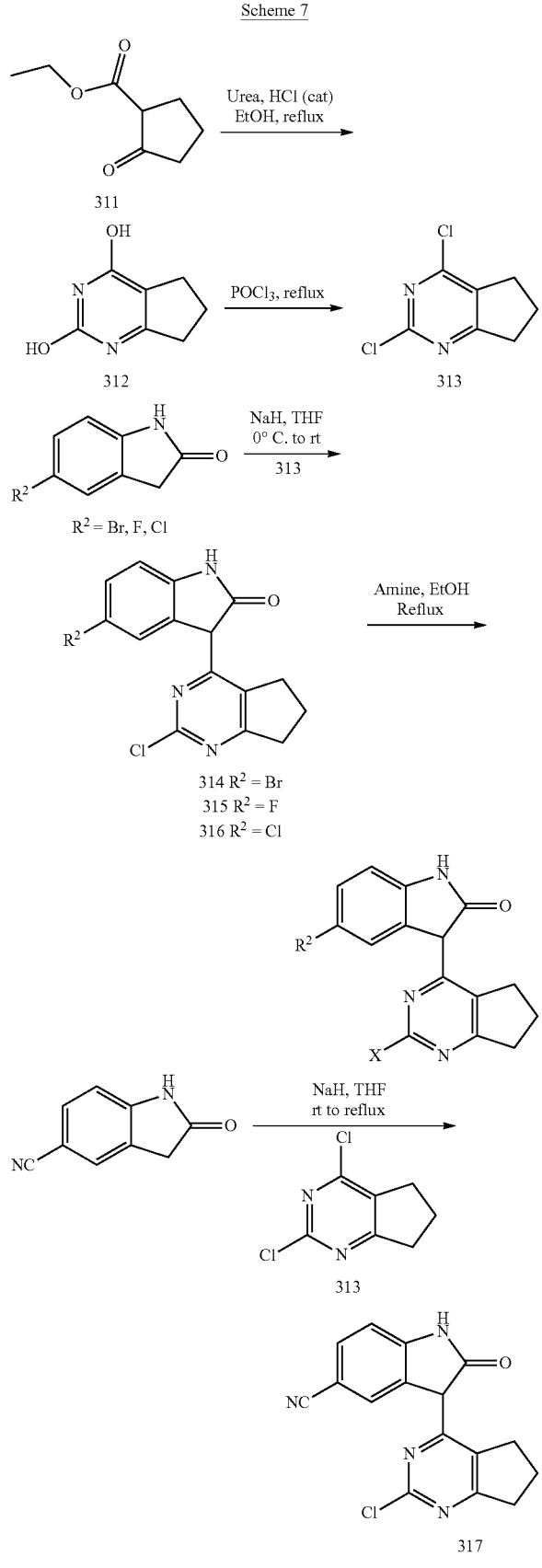

R² = Br, F, Cl

314 R² = Br
315 R² = F
316 R² = Cl

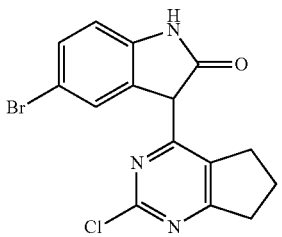

Compound 312

6,7-Dihydro-5H-cyclopentapyrimidine-2,4-diol

To a 100 mL of flask was added ethyl 2-oxocyclopentanecarboxylate 311 (10 mL, 67.2 mmol), urea (6.07 g, 101 mmol), ethanol (20 mL) and concentrated HCl (1 mL). After the mixture was heated to reflux for 2 h, it was cooled to room temp. The ethanol was decanted and remain white crystalline was heated to reflux in 5% NaOH solution (25 mL) for 30 min. The reaction was cooled to room temp and the precipitate was collected by filtration. It was washed with water and dried to give 6.77 g (66%) of the title compound 312. Compound 312: $^1$H NMR (400 MHz, DMSO-$d_6$) δ 11.03 (s, 1H), 10.72 (s, 1H), 2.63 (m, 2H), 2.44 (m, 2H), 1.98-1.91 (m, 2H); MS (m/e) 153 (M+1).

Compound 313

2,4-Dichloro-6,7-dihyro-5H-cyclopentapyrimidine

To a 100 mL flask was added compound 312 (3.00 g, 19.7 mmol) and POCl$_3$ (15 mL). The reaction mixture was heated to reflux for 5 h. After cooled to room temp, the reaction was concentrated in vacuo. The gummy residue was quenched with ice-water and the resulted precipitation was collected by filtration. It was washed with water and dried to give 3.10 g (83%) of the title compound 313. Compound 313: $^1$H NMR (400 MHz, DMSO-$d_6$) δ 3.03 (m, 2H), 2.93 (m, 2H), 2.17-2.09 (m, 2H); MS (m/e) 190 (M+1).

Example 314

5-Bromo-3-(2-chloro-6,7-dihydro-5H-cyclopentapyrimidin-4-yl)-1,3-dihydro-indol-2-one To a stirring mixture of NaH (480 mg, 12.0 mmol) in THF (20 mL) at 0° C. was added 5-bromooxindole (1.00 g, 4.72 mmol) in portion. Additional THF (5 mL×3) was used to make sure all the oxindole was added into the reaction flask. After stirred for 50 min, a solution of compound 313 (892 mg, 4.72 mmol) in THF (5 mL×3) was added. The reaction was continued stir for 1 h at 0° C. and 2.5 h at room temp. A saturated NH$_4$Cl solution (50 mL) was added into the reaction and the mixture was extracted with EtOAc (50 mL×3). The combined organic extracts was washed with brine and concentrated. The residue was triturated with MeOH and dried to give 1.27 g (74%) of the title Example 314. Example 314: $^1$H NMR (400 MHz, DMSO-$d_6$) δ 10.83 (s, 1H), 7.43 (m, 1H), 7.27 (s, 1H), 6.87 (m, 1H), 5.11 (s, 1H), 3.02-2.76 (m, 4H), 2.13-2.03 (m, 2H); MS (m/e) 365 (M+1), 366 (M+2).

Example 315

3-(2-Chloro-6,7-dihydro-5H-cyclopentapyrimidin-4-yl)-5-fluoro-1,3-dihydro-indol-2-one

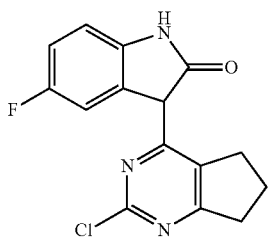 [SMILES: O=C1Nc2ccc(F)cc2C1c1nc(Cl)nc2c1CCC2]

Experimental data: $^1$H NMR (400 MHz, DMSO-$d_6$) δ 10.74 (s, 1H), 7.11-6.89 (m, 3H), 5.09 (s, 1H), 3.00-2.73 (m, 4H), 2.12-2.03 (m, 2H); MS (m/e) 304 (M+1).

Example 316

5-Chloro-3-(2-chloro-6,7-dihydro-5H-cyclopentapyrimidin-4-yl)-1,3-dihydro-inodol-2-one

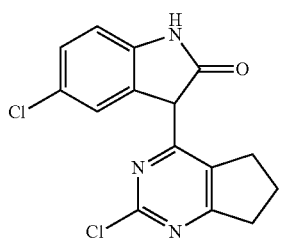

Experimental data: $^1$H NMR (400 MHz, DMSO-$d_6$) δ 10.82 (s, 1H), 7.30 (m, 1H), 7.16 (m, 1H), 6.92 (m, 1H), 5.10 (s, 1H), 3.02-2.76 (m, 4H), 2.10 (m, 2H); MS (m/e) 320 (M+1).

Example 317

3-(2-Chloro-6,7-dihydro-5H-cyclopentapyrimidin-4-yl)-2-oxo-2,3-dihydro-1H-indole-5-carbonitrile

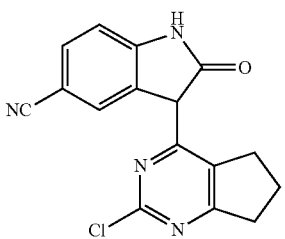 [SMILES: N#Cc1ccc2c(c1)C(c1nc(Cl)nc3c1CCC3)C(=O)N2]

To mixture of 5-cyanooxindole (1.00 g, 6.32 mmol) and NaH (650 mg, 16.3 mmol) was added THF (20 mL). After the reaction mixture was stirred for 45 min at rt, a solution of 313 (1.20 g, 6.32 mmol) in THF (10 mL) was added. The reaction was heated to reflux for 2 h, and was cooled to room temp. Water (30 mL) was slowly added to the reaction, and was acidified to pH ~3 with concentrated HCl. The resulting precipitate was collected by filtration. It was washed with water, MeOH, and dried to give 1.31 g (67%) of the desired Example 317. $^1$HNMR (400 MHz, DMSO-$d_6$) δ 11.18 (s, 1H), 7.73 (m, 1H), 7.57 (s. 1H), 7.06 (m, 1H), 5.17 (s, 1H), 3.01 (m, 2H), 2.83 (m, 2H), 2.10 (m, 2H); MS (m/e) 311 (M+1).

The following Examples 318-354 in Table 5 were prepared according to procedures disclosed herein including using methods generally known to one skilled in the art.

TABLE 5

| Example | R² | X |
|---|---|---|
| 318 | F | morpholine-CH₂CH₂-NH |
| 319 | F | EtO-CH₂CH₂-NH |
| 320 | F | 4-pyridyl-CH₂-NH |
| 321 | F | 3-pyridyl-CH₂-NH |
| 322 | F | 2-pyridyl-CH₂-NH |
| 323 | Cl | (CH₃)₂N-CH₂CH₂-NH |
| 324 | Cl | morpholine-CH₂CH₂-NH |
| 325 | Cl | EtO-CH₂CH₂-NH |
| 326 | Cl | 4-pyridyl-CH₂-NH |
| 327 | Cl | 3-pyridyl-CH₂-NH |

TABLE 5-continued
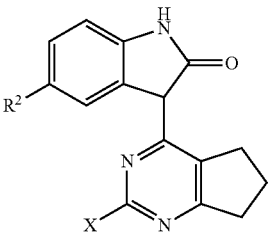
| Example | R² | X |
|---|---|---|
| 328 | Cl | 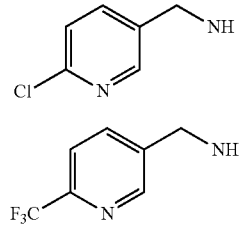 |
| 329 | Cl | 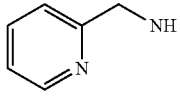 |
| 330 | Cl | 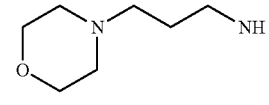 |
| 331 | Br | 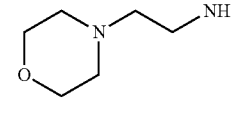 |
| 332 | Br | 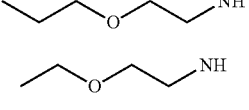 |
| 333 | Br | 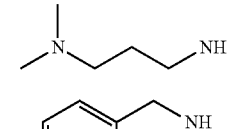 |
| 334 | Br | 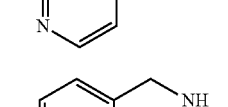 |
| 335 | Br | 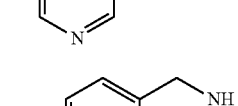 |
| 336 | Br | 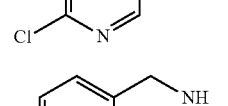 |
| 337 | Br | 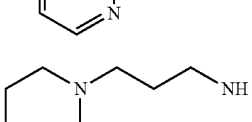 |
| 338 | Br | 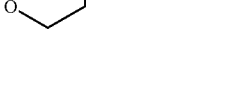 |
| 339 | Br |  |
| 340 | CN | 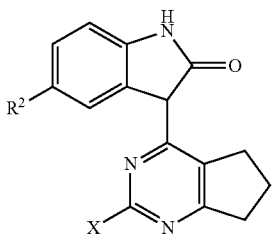 |
TABLE 5-continued
| Example | R² | X |
|---|---|---|
| 341 | CN | 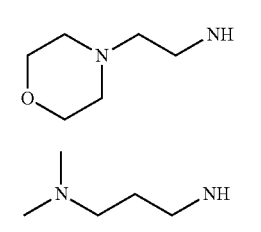 |
| 342 | CN | 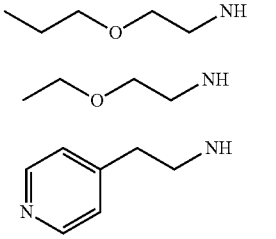 |
| 343 | CN | 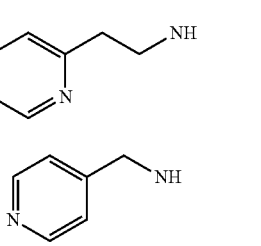 |
| 344 | CN | 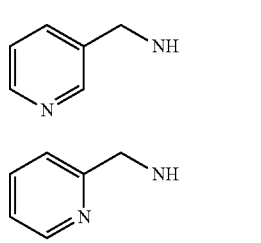 |
| 345 | CN | 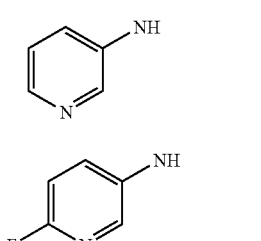 |
| 346 | CN | 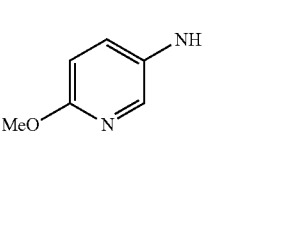 |
| 347 | CN |  |
| 348 | CN | |
| 349 | CN | |
| 350 | CN | |
| 351 | CN | |
| 352 | CN | |

TABLE 5-continued

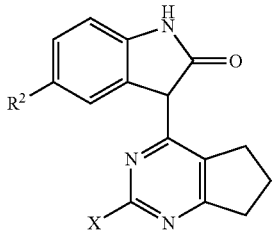

| Example | R² | X |
|---|---|---|
| 353 | CN | *N-methylpiperazinyl* |
| 354 | CN | *piperazinyl* |

Example 318

5-Fluoro-3-[2-(2-morpholin-4-ylethylamino)-6,7-dihydro-5H-cyclopentapyrimidin-4-yl]-1,3-dihydro-indol-2-one ¹H NMR (400 MHz, DMSO-$d_6$) δ 15.41 (s, 1H), 10.54 (s, 1H), 7.99 (s, 1H), 7.38 (m, 1H), 6.80 (m, 1H), 6.65 (m, 1H), 3.58 (m, 4H), 3.43 (m, 2H), 3.21 (m, 2H), 2.69 (m, 2H), 2.50 (m, 2H), 2.42 (m, 4H), 2.02 (m, 2H); MS (m/e) 398 (M+1).

Example 319

3-[2-(2-Ethoxy-ethylamino)-6,7-dihydro-5H-cyclopentapyrimidin-4-yl]-5-fluoro-1,3-dihydro-indol-2-one ¹H NMR (400 MHz, DMSO-$d_6$) δ 15.41 (s, 1H), 10.53 (s, 1H), 8.16 (s, 1H), 7.38 (m, 1H), 6.79 (m, 1H), 6.66 (m, 1H), 3.53 (m, 1H), 3.47 (m, 4H), 3.21 (m, 2H), 2.69 (m, 2H), 2.02 (m, 2H), 1.11 (m, 3H); MS (m/e) 357 (M+1).

Example 320

5-Fluoro-3-{2-[(pyridin-4-ylmethyl)-amino]-6,7-dihydro-5H-cyclopentapyrimidin-4-yl}-1,3-dihydro-indol-2-one ¹H NMR (400 MHz, DMSO-$d_6$) δ 15.63 (s, 1H), 10.59 (s, 1H), 8.70 (s, 1H), 8.51 (m, 2H), 7.39 (m, 1H), 7.33 (m, 2H), 6.80 (m, 1H), 6.66 (m, 1H), 4.57 (m, 2H), 3.22 (m, 2H), 2.67 (m, 2H), 2.01 (m, 2H); MS (m/e) 376 (M+1).

Example 321

5-Fluoro-3-{2-[(pyridin-3-ylmethyl)-amino]-6,7-dihydro-5H-cyclopentapyrimidin-4-yl}-1,3-dihydro-indol-2-one ¹H NMR (400 MHz, DMSO-$d_6$) δ 15.60 (s, 1H), 10.56 (s, 1H), 8.66 (m, 1H), 8.59 (s, 1H), 8.47 (m, 1H), 7.76 (m, 1H), 7.38 (m, 2H), 6.79 (m, 1H), 6.66 (m, 1H), 4.56 (d, 2H), 3.22 (m, 2H), 2.70 (m, 2H), 2.02 (m, 2H); MS (m/e) 376 (M+1).

Example 322

5-Fluoro-3-{2-[(pyridin-2-ylmethyl)-amino]-6,7-dihydro-5H-cyclopentapyrimidin-4-yl}-1,3-dihydro-indol-2-one ¹H NMR (400 MHz, DMSO-$d_6$) δ 15.58 (s, 1H), 10.55 (s, 1H), 8.67 (s, 1H), 8.52 (m, 1H), 7.76 (m, 1H), 7.37 (m, 2H), 7.27 (m, 1H), 6.80 (m, 1H), 6.66 (m, 1H), 4.65 (m, 2H), 3.21 (m, 2H), 2.67 (m, 2H), 2.01 (m, 2H); MS (m/e/) 376 (M+1).

Example 323

5-Chloro-3-[2-(2-dimethylamino-ethylamino)-6,7-dihydro-5H-cyclopentapyrimidin-4-yl]-1,3-dihydro-indol-2-one ¹H NMR (400 MHz, DMSO-$d_6$) δ 10.60 (s, 1H), 7.97 (s, 1H), 7.60 (m, 1H), 6.84 (m, 2H), 3.41 (m, 2H), 3.18 (m, 2H), 2.69 (m, 2H), 2.45 (m, 2H), 2.20 (s, 6H), 2.02 (m, 2H); MS (m/e) 372 (M+1).

Example 324

5-Chloro-3-[2-(2-morpholin-4-yl-ethylamino)-6,7-dihydro-5H-cyclopentapyrimidin-4-yl]-1,3-dihydro-indol-2-one ¹H NMR (400 MHz, DMSO-$d_6$) δ 15.33 (s, 1H), 10.65 (s, 1H), 8.02 (s, 1H), 7.59 (s, 1H), 6.85 (m, 2H), 3.57 (m, 4H), 3.43 (m, 2H), 3.19 (m, 2H), 2.69 (m, 2H), 2.50 (m, 2H), 2.43 (m, 4H), 2.03 (m, 2H); MS (m/e) 414 (M+1).

Example 325

5-Chloro-3-[2-(2-ethoxy-ethylamino)-6,7-dihydro-5H-cyclopentapyrimidin-4-yl]-1,3-dihydro-indol-2-one ¹H NMR (400 MHz, DMSO-$d_6$) δ 15.29 (s, 1H), 10.63 (s, 1H), 8.19 (s, 1H), 7.59 (s, 1H), 6.85 (m, 2H), 3.53 (m, 2H), 3.46 (m, 4H), 3.19 (m, 2H), 2.70 (m, 2H), 2.03 (m, 2H), 1.11 (m, 3H); MS (m/e) 373 (M+1).

Example 326

5-Chloro-3-{2-[(pyridin-4-ylmethyl)-amino]-6,7-dihydro-5H-cyclopentapyrimidin-4-yl}-1,3-dihydro-indol-2-one ¹H NMR (400 MHz, DMSO-$d_6$) δ 15.54 (s, 1H), 10.70 (s, 1H), 8.73 (s, 1H), 8.51 (m, 2H), 7.61 (s, 1H), 7.34 (m, 2H), 6.85 (m, 2H), 4.57 (m, 2H), 3.20 (m, 2H), 2.68 (m, 2H), 2.02 (m, 2H); MS (m/e) 392 (M+1).

Example 327

5-Chloro-3-{2-[(pyridin-3-ylmethyl)-amino]-6,7-dihydro-5H-cyclopentapyrimidin-4-yl}-1,3-dihydro-indol-2-one ¹H NMR (400 MHz, DMSO-$d_6$) δ 15.49 (s, 1H), 10.69 (s, 1H), 8.70 (s, 1H), 8.59 (m, 1H), 8.47 (m, 1H), 7.76 (m, 1H), 7.60 (s, 1H), 7.37 (m, 1H), 6.85 (m, 2H), 4.56 (m, 2H), 3.20 (m, 2H), 2.70 (m, 2H), 2.03 (m, 2H); MS (m/e) 392 (M+1).

Example 328

5-Chloro-3-{2-[(6-chloro-pyridin-3-ylmethyl)-amino]-6,7-dihydro-5H-cyclopentapyrimidin-4-yl}-1,3-dihydro-indol-2-one $^1$H NMR (400 MHz, DMSO-d$_6$) δ 15.52 (s, 1H), 10.71 (s, 1H), 8.68 (m, 1H), 8.42 (m, 1H), 7.84 (m, 1H), 7.60 (s, 1H), 7.49 (m, 1H), 6.85 (m, 2H), 4.55 (m, 2H), 3.20 (m, 2H), 2.70 (m, 2H), 2.03 (m, 2H); MS (m/e) 426 (M+1).

Example 329

5-Chloro-3-{2-[(6-trifluoromethyl-pyridin-3-ylmethyl)-amino]-6,7-dihydro-5H-cyclopentapyrimidin-4-yl}-1,3-dihydro-indol-2-one $^1$H NMR (400 MHz, DMSO-d$_6$) δ 15.57 (s, 1H), 10.72 (s, 1H), 8.78 (s, 2H), 8.04 (m, 1H), 7.88 (m, 1H), 7.61 (m, 1H), 6.86 (m, 2H), 6.67 (m, 2H), 3.20 (m, 2H), 2.70 (m, 2H), 2.02 (m, 2H); MS (m/e) 460 (M+1).

Example 330

5-Chloro-3-{2-[(pyridin-2-ylmethyl)-amino]-6,7-dihydro-5H-cyclopentapyrimidin-4-yl}-1,3-dihydro-indol-2-one $^1$H NMR (400 MHz, DMSO-d$_6$) δ 15.46 (s, 1H), 10.66 (s, 1H), 8.70 (s, 1H), 8.52 (m, 1H), 7.76 (m, 1H), 7.59 (s, 1H), 7.36 (m, 1H), 7.26 (m, 1H), 6.85 (m, 2H), 4.64 (m, 2H), 3.19 (m, 2H), 2.67 (m, 2H), 2.02 (m, 2H); MS (m/e) 392 (M+1).

Example 331

5-Bromo-3-[2-(3-morpholin-4-yl-propylamino)-6,7-dihydro-5H-cyclopentapyrimidin-4-yl]-1,3-dihydro-indol-2-one $^1$H NMR (400 MHz, DMSO-d$_6$) δ 15.35 (s, 1H), 10.65 (s, 1H), 8.12 (s, 1H), 7.74 (s, 1H), 6.98 (m, 1H), 6.79 (m, 1H), 3.56 (m, 4H), 3.35 (m, 2H), 3.18 (m, 2H), 2.69 (m, 2H), 2.36 (m, 6H), 2.03 (m, 2H), 1.72 (m, 2H); MS (m/e) 472 (M).

Example 332

5-Bromo-3-[2-(2-morpholin-4-yl-ethylamino)-6,7-dihydro-5H-cyclopentapyrimidin-4-yl]-1,3-dihydro-indol-2-one $^1$H NMR (400 MHz, DMSO-d$_6$) δ 15.30 (s, 1H), 10.66 (s, 1H), 8.02 (s, 1H), 7.73 (s, 1H), 6.98 (m, 1H), 6.81 (m, 1H), 3.57 (m, 4H), 3.43 (m, 2H), 3.17 (m, 2H), 2.70 (m, 2H), 2.50 (m, 2H), 2.43 (m, 4H), 2.03 (m, 2H); MS (m/e) 458 (M).

Example 333

5-Bromo-3-[2-(2-propoxy-ethylamino)-6,7-dihydro-5H-cyclopentapyrimidin-4-yl]-1,3-dihydro-indol-2-one $^1$H NMR (400 MHz, DMSO-d$_6$) δ 15.26 (s, 1H), 10.64 (s, 1H), 8.18 (s, 1H), 7.72 (s, 1H), 6.98 (m, 1H), 6.80 (m, 1H), 3.52 (m, 2H), 3.48 (m, 2H), 3.37 (m, 2H), 3.17 (m, 2H), 2.70 (m, 2H), 2.03 (m, 2H), 1.50 (m, 2H), 0.85 (m, 3H); MS (m/e) 431 (M).

Example 334

5-Bromo-3-[2-(2-ethoxy-ethylamino)-6,7-dihydro-5H-cyclopentapyrimidin-4-yl]-1,3-dihydro-indol-2-one $^1$H NMR (400 MHz, DMSO-d$_6$) δ 15.24 (s, 1H), 10.65 (s, 1H), 8.20 (s, 1H), 7.72 (s, 1H), 6.98 (m, 1H), 6.80 (m, 1H), 3.52 (m, 2H), 3.46 (m, 4H), 3.17 (m, 2H), 2.70 (m, 2H), 2.03 (m, 2H), 1.11 (m, 3H); MS (m/e) 417 (M).

Example 335

5-Bromo-3-[2-(3-dimethylamino-propylamino)-6,7-dihydro-5H-cyclopentapyrimidin-4-yl]-1,3-dihydro-indol-2-one H NMR (400 MHz, DMSO-d$_6$) δ 15.23 (s, 1H), 10.60 (s, 1H), 8.06 (s, 1H), 7.75 (s, 1H), 6.96 (m, 1H), 6.78 (m, 1H), 3.32 (m, 2H), 3.17 (m, 2H), 2.69 (m, 2H), 2.30 (m, 2H), 2.14 (s, 6H), 2.02 (m, 2H), 1.70 (m, 2H); MS (m/e) 430 (M).

Example 336

5-Bromo-3-{2-[(pyridin-4-ylmethyl)-amino]-6,7-dihydro-5H-cyclopentapyrimidin-4-yl}-1,3-dihydro-indol-2-one $^1$H NMR (400 MHz, DMSO-d$_6$) δ 15.55 (s, 1H), 10.72 (s, 1H), 8.74 (m, 1H), 8.51 (m, 2H), 7.74 (s, 1H), 7.34 (m, 2H), 7.00 (m, 1H), 6.80 (m, 1H), 4.57 (m, 2H), 3.18 (m, 2H), 2.68 (m, 2H), 2.02 (m, 2H); MS (m/e) 436 (M).

Example 337

5-Bromo-3-{2-[(pyridin-3-ylmethyl)-amino]-6,7-dihydro-5H-cyclopentapyrimidin-4-yl}-1,3-dihydro-indol-2-one $^1$H NMR (400 MHz, DMSO-d$_6$) δ 15.44 (s, 1H), 10.67 (s, 1H), 8.70 (s, 1H), 8.52 (m, 1H), 7.76 (m, 1H), 7.73 (s, 1H), 7.36 (m, 1H), 7.27 (m, 1H), 6.99 (m, 1H), 6.80 (m, 1H), 4.64 (m, 2H), 3.18 (m, 2H), 2.67 (m, 2H), 2.02 (m, 2H); MS (m/e) 436 (M).

Example 338

5-Bromo-3-{2-[(6-chloro-pyridin-3-ylmethyl)-amino]-6,7-dihydro-5H-cyclopentapyrimidin-4-yl}-1,3-dihydro-indol-2-one $^1$H NMR (400 MHz, DMSO-d$_6$) δ 15.49 (s, 1H), 10.71 (s, 1H), 8.68 (m, 1H), 8.41 (m, 1H), 7.84 (m, 1H), 7.74 (s, 1H), 7.49 (m, 1H), 6.99 (m, 1H), 6.80 (m, 1H), 4.55 (m, 2H), 3.18 (m, 2H), 2.70 (m, 2H), 2.03 (m, 2H); MS (m/e) 470 (M).

Example 339

5-Bromo-3-{2-[(pyridin-2-ylmethyl)-amino]-6,7-dihydro-5H-cyclopentapyrimidin-4-yl}-1,3-dihydro-indol-2-one $^1$H NMR (400 MHz, DMSO-d$_6$) δ 15.46 (s, 1H), 10.68 (s, 1H), 8.70 (s, 1H), 8.59 (m, 1H), 8.46 (m, 1H), 7.76 (m, 2H), 7.36 (m, 1H), 6.98 (m, 1H), 6.79 (m, 1H), 4.56 (m, 2H), 3.18 (m, 2H), 2.70 (m, 2H), 2.03 (m, 2H); MS (m/e) 436 (M).

Example 340

3-[2-(3-Morpholin-4-yl-propylamino)-6,7-dihydro-5H-cyclopentapyrimidin-4-yl]-2-oxo-2,3-dihydro-1H-indole-5-carbonitrile $^1$H NMR (400 MHz, DMSO-d$_6$) δ 15.13 (s, 1H), 11.02 (s, 1H), 8.21 (s, 1H), 7.89 (s, 1H), 7.25 (m, 1H), 6.97 (m, 1H), 3.57 (m, 4H), 3.35 (m, 2H), 3.22 (m, 2H), 2.71 (m, 2H), 2.36 (m, 6H), 2.04 (m, 2H), 1.73 (m, 2H); MS (m/e) 419 (M+1).

Example 341

3-[2-(2-Morpholin-4-yl-ethylamino)-6,7-dihydro-5H-cyclopentapyrimidin-4-yl]-2-oxo-2,3-dihydro-1H-indole-5-carbonitrile $^1$H NMR (400 MHz, DMSO-d$_6$) δ 15.04 (s, 1H), 11.03 (s, 1H), 8.12 (s, 1H), 7.87 (s, 1H), 7.25 (m, 1H), 6.97 (m, 1H), 3.57 (m, 4H), 3.45 (m, 2H), 3.21 (m, 2H), 2.72 (m, 2H), 2.51 (m, 2H), 2.43 (m, 4H), 2.04 (m, 2H); MS (m/e) 405 (M+1).

Example 342

3-[2-(3-Dimethylamino-propylamino)-6,7-dihydro-5H-cyclopentapyrimidin-4-yl]-2-oxo-2,3-dihydro-1H-indole-5-carbonitrile $^1$H NMR (400 MHz, DMSO-d$_6$) δ 14.90 (s, 1H), 10.89 (s, 1H), 7.92 (s, 1H), 7.22 (m, 1H), 6.95 (m, 1H), 3.34 (m, 2H), 3.20 (m, 3H), 2.71 (m, 2H), 2.35 (m, 2H), 2.18 (s, 6H), 2.02 (m, 2H), 1.72 (m, 2H); MS (m/e) 377 (M+1).

Example 343

2-Oxo-3-[2-(2-propoxy-ethylamino)-6,7-dihydro-5H-cyclopentapyrimidin-4-yl]-2,3-dihydro-1H-indole-5-carbonitrile $^1$H NMR (400 MHz, DMSO-d$_6$) δ 15.02 (s, 1H), 11.01 (s, 1H), 8.28 (s, 1H), 7.87 (s, 1H), 7.26 (m, 1H), 6.98 (m, 1H), 3.53 (m, 2H), 3.49 (m, 2H), 3.37 (m, 2H), 3.22 (m, 2H), 2.72 (m, 2H), 2.04 (m, 2H), 1.50 (m, 2H), 0.85 (m, 3H); MS (m/e) 378 (M+1).

Example 344

3-[2-(2-Ethoxy-ethylamino)-6,7-dihydro-5H-cyclopentapyrimidin-4-yl]-2-oxo-2,3-dihydro-1H-indole-5-carbonitrile $^1$H NMR (400 MHz, DMSO-d$_6$) δ 14.99 (s, 1H), 11.01 (s, 1H), 8.30 (s, 1H), 7.87 (s, 1H), 7.26 (m, 1H), 6.98 (m, 1H), 3.53 (m, 2H), 3.47 (m, 4H), 3.22 (m, 2H), 2.72 (m, 2H), 2.05 (m, 2H), 1.12 (m, 3H); MS (m/e) 364 (M+1).

Example 345

2-Oxo-3-[2-(2-pyridin-4-yl-ethylamino)-6,7-dihydro-5H-cyclopentapyrimidin-4-yl]-2,3-dihydro-1H-indole-5-carbonitrile $^1$H NMR (400 MHz, DMSO-d$_6$) δ 11.08 (s, 1H), 8.48 (m, 2H), 8.33 (s, 1H), 7.89 (s, 1H), 7.32 (m, 2H), 7.26 (m, 1H), 6.98 (m, 1H), 3.60 (m, 2H), 3.23 (m, 2H), 2.92 (m, 2H), 2.72 (m, 2H), 2.04 (m, 2H); MS (m/e) 397 (M+1).

Example 346

2-Oxo-3-[2-(2-pyridin-2-yl-ethylamino)-6,7-dihydro-5H-cyclopentapyrimidin-4-yl]-2,3-dihydro-1H-indole-5-carbonitrile $^1$H NMR (400 MHz, DMSO-d$_6$) δ 11.05 (s, 1H), 8.50 (m, 1H), 8.31 (s, 1H), 7.88 (s, 1H), 7.72 (m, 1H), 7.33 (m, 1H), 7.24 (m, 2H), 6.99 (m, 1H), 3.70 (m, 2H), 3.23 (m, 2H), 3.05 (m, 2H), 2.72 (m, 2H), 2.05 (m, 2H); MS (m/e) 397 (M+1).

Example 347

2-Oxo-3-{2-[(pyridin-4-ylmethyl)-amino]-6,7-dihydro-5H-cyclopentapyrimidin-4-yl}-2,3-dihydro-1H-indole-5-carbonitrile $^1$H NMR (400 MHz, DMSO-d$_6$) δ 15.30 (s, 1H), 11.09 (s, 1H), 8.83 (s, 1H), 8.51 (m, 2H), 7.89 (s, 1H), 7.34 (m, 2H), 7.27 (m, 1H), 6.99 (m, 1H), 4.59 (m, 2H), 3.23 (m, 2H), 2.70 (m, 2H), 2.04 (m, 2H); MS (m/e) 383 (M+1).

Example 348

2-Oxo-3-{2-[(pyridin-3-ylmethyl)-amino]-6,7-dihydro-5H-cyclopentapyrimidin-4-yl}-2,3-dihydro-1H-indole-5-carbonitrile $^1$H NMR (400 MHz, DMSO-d$_6$) δ 15.26 (s, 1H), 11.06 (s, 1H), 8.79 (s, 1H), 8.59 (m, 1H), 8.47 (m, 1H), 7.90 (s, 1H), 7.77 (m, 1H), 7.37 (m, 1H), 7.26 (m, 1H), 6.97 (m, 1H), 4.58 (m, 2H), 3.22 (m, 2H), 2.72 (m, 2H), 2.04 (m, 2H); MS (m/e) 383 (M+1).

Example 349

2-Oxo-3-{2-[(pyridin-2-ylmethyl)-amino]-6,7-dihydro-5H-cyclopentapyrimidin-4-yl}-2,3-dihydro-1H-indole-5-carbonitrile $^1$H NMR (400 MHz, DMSO-d$_6$) δ 15.17 (s, 1H), 11.05 (s, 1H), 8.80 (s, 1H), 8.52 (m, 1H), 7.88 (s, 1H), 7.76 (m, 1H), 7.37 (m, 1H), 7.28 (m, 2H), 6.98 (m, 1H), 4.65 (m, 2H), 3.22 (m, 2H), 2.70 (m, 2H), 2.03 (m, 2H); MS (m/e) 383 (M+1).

Example 350

2-Oxo-3-[2-(pyridin-3-ylamino)-6,7-dihydro-5H-cyclopentapyrimidin-4-yl]-2,3-dihydro-1H-indole-5-carbonitrile $^1$H NMR (400 MHz, DMSO-d$_6$) δ 10.46 (s, 1H), 9.27 (s, 1H), 9.09 (s, 1H), 8.12 (s, 1H), 7.86 (m, 2H), 7.15 (m, 1H), 6.99 (m, 1H), 6.86 (m, 2H), 3.20 (m, 2H), 2.93 (m, 2H), 2.07 (m, 2H); MS (m/e) 369 (M+1).

Example 351

3-[2-(6-Fluoro-pyridin-3-ylamino)-6,7-dihydro-5H-cyclopentapyrimidin-4-yl]-2-oxo-2,3-dihydro-1H-indole-5-carbonitrile $^1$H NMR (400 MHz, DMSO-d$_6$) δ 15.40 (s, 1H), 11.10 (s, 1H), 9.68 (s, 1H), 8.39 (s, 1H), 7.96 (s, 1H), 7.73 (m, 1H), 7.57 (s, 1H), 7.06 (m, 1H), 2.89 (m, 2H), 2.80 (m, 2H), 2.07 (m, 2H); MS (m/e) 387 (M+1).

Example 352

3-[2-(6-Methoxy-pyridin-3-ylamino)-6,7-dihydro-5H-cyclopentapyrimidin-4-yl]-2-oxo-2,3-dihydro-1H-indole-5-carbonitrile $^1$H NMR (400 MHz, DMSO-$d_6$) δ 15.39 (s, 1H), 11.12 (s, 1H), 10.15 (s, 1H), 8.33 (m, 1H), 7.93 (s, 1H), 7.88 (m, 1H), 7.56 (s, 1H), 7.28 (m, 1H), 6.85 (m, 1H), 3.86 (s, 3H), 3.26 (m, 2H), 2.76 (m, 2H), 2.08 (m, 2H); MS (m/e) 399 (M+1).

Example 353

3-[2-(4-Methyl-piperazin-1-yl)-6,7-dihydro-5H-cyclopentapyrimidin-4-yl]-2-oxo-2,3-dihydro-1H-indole-5-carbonitrile $^1$H NMR (400 MHz, DMSO-$d_6$) δ 11.08 (s, 1H), 7.97 (s, 1H), 7.26 (s, 1H), 7.01 (s, 1H), 3.71 (s, 3H), 3.29 (m, 4H), 2.74 (m, 2H), 2.50 (m, 2H), 2.26 (m, 4H), 2.05 (m, 2H); MS (m/e) 375 (M+1).

Example 354

2-Oxo-3-(2-piperazin-1-yl-6,7-dihydro-5H-cyclopentapyrimidin-4-yl)-2,3-dihydro-1H-indole-5-carbonitrile $^1$H NMR (400 MHz, DMSO-$d_6$) δ 10.22 (s, 1H), 7.98 (s, 1H), 7.03 (m, 1H), 6.83 (m, 1H), 3.80 (m, 4H), 3.14 (m, 2H), 3.01 (m, 4H), 2.67 (m, 2H), 1.94 (m, 2H); MS (m/e) 361 (M+1).

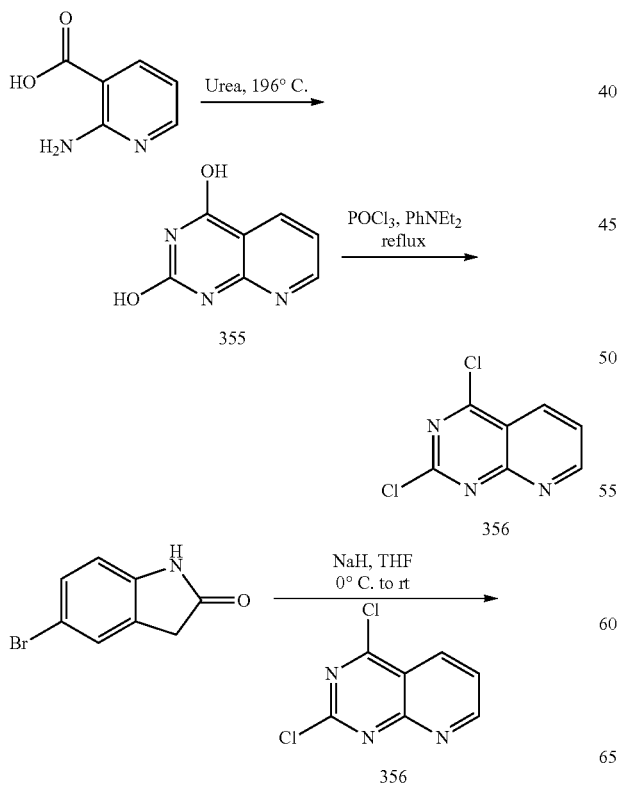

Scheme 8

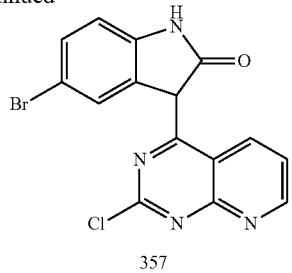

357

Compound 355

Pyrido[2,3-d]pyrimidine-2,4-diol

A mixture of 2-aminonicotinic acid (5.00 g, 36.2 mmol) and urea (10.9 g, 181 mmol) in a 100 mL flask was heated to 195° C. for 1.5 h. After the reaction was cooled to room temp, NaOH (1.45 g, 36.2 mmol) and water (50 mL) was added. The mixture was heated to reflux for 1 h and cooled to room temp. The reaction solution was acidified to pH 4, the resulting precipitate was collected by filtration. It was washed with water and dried to give 4.49 g (76%) the title Compound 355. $^1$H NMR (400 MHz, DMSO-$d_6$) δ 11.66 (s, 1H), 11.45 (s, 1H), 8.60 (m, 1H), 8.26 (m, 1H), 7.24 (m, 1H).

Compound 356

2,4-Dichloro-pyrido[2,3-d]pyrimidine

To a 100 mL flask was added Compound 355 (500 mg, 3.06 mmol), N,N-diethylaniline (1 mL), and POCl$_3$ (10 mL). The reaction mixture was heated to reflux for 5.5 h. After cooled to room temp, the reaction was concentrated in vacuo. The residue was quenched with ice-water (50 mL) and was immediately extracted with CHCl$_3$ (50 mL×3). The combined organic extracts was washed with water (50 mL), dried (MgSO$_4$), filtered and concentrated to give crude the title Compound 356. The material was used for next step without purification.

Example 357

5-Bromo-3-(2-chloro-pyrido[2,3-d]pyrimidin-4-yl)-1,3-dihydro-indol-2-one

To a stirring mixture of NaH (260 mg, 6.50 mmol) in THF (20 mL) at 0° C. was added 5-bromooxindole (551 g, 2.60 mmol) in portion. Additional THF (5 mL×2) was used to make sure all the oxindole was added into the reaction flask. After stirred for 1 h, a solution of crude compound 356 in THF (5 mL×3) was added. The reaction was continued stir for 1 h at 0° C. and 24 h at room temp. A saturated NH$_4$Cl solution (30 mL) was added into the reaction and the resulted red precipitate was collected by filtration. It was dried to give 361 mg (37%) the title Example 357. $^1$H NMR (400 MHz, DMSO-d₆) δ 10.41 (s, 1H), 10.11 (s, 1H), 8.61 (m, 1H), 8.50 (s, 1H), 7.47 (m, 1H), 7.18 (m, 1H), 6.73 (m, 1H); MS (m/e) 376 (M+1).

Example 358

5-Bromo-3-[6-(2-(R)-hydroxy-propylamino)-2-methyl-2H-pyrazolo [3,4-d]pyrimidin-4-yl]-1,3-dihydroindol-2-one

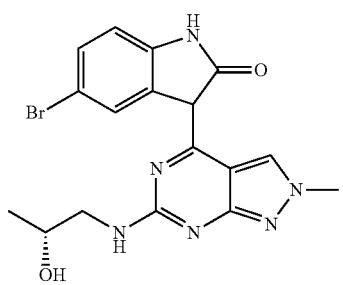 [SMILES: C[C@@H](O)CNc1nc(C2C(=O)Nc3ccc(Br)cc32)c2cn(C)nc2n1]

Example 300 (30 mg, 0.079 mmol) and (R)-(−)-1-amino-2-propanol (62 µL, 0.79 mmol) were heated in 1 mL EtOH at 130° C. in microwave for 10 min. Upon cooling, the product precipitated in the reaction tube. The resulting solid was filtered and pumped dry to afford 22 mg (67%) of a bright yellow solid. mp 298-301° C.; MS (ES⁺ calculated: 417.27; found: 417.61, 418.73 M+H). HPLC (91%) purity, retention time 2.484 minutes—Method C); ¹H NMR (400 MHz, TFA) δ 8.75 (s, 1H), 8.4 (s, 1H), 7.55 (br d, 1H), 7.1 (br s, 1H), 4.5 (m, 1H), 4.2 (s, 2H), 3.8 (m, 1H), 3.7 (m, 1H), 1.6 (d, 2H).

Example 359

5-Bromo-3-[6-(2-dimethylamino-ethylamino)-2-methyl-2H-pyrazolo[3,4-d]pyrimidin-4-yl]-1,3-dihydro-indol-2-one

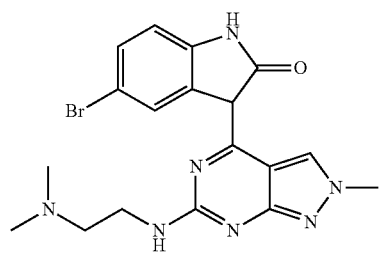

Example 300 (30 mg, 0.079 mmol) and N,N-dimethylaminoethylamine (69 mg, 0.79 mmol) were heated in 1 mL EtOH at 130° C. in microwave for 10 min. Upon cooling, the product precipitated in the reaction tube. The resulting solid was filtered and pumped dry to afford 14 mg (41%) of a brown solid. mp 279-289° C.; MS (ES⁺ calculated: 430.31; found: 430.67, 431.82 M+H). HPLC (88%) purity, retention time 2.375 minutes—Method C); ¹H NMR (400 MHz, TFA) δ 8.81 (s, 1H), 7.96 (s, 1H), 7.62 (d, J=9 Hz, 1H) 7.24 (d, J=8 Hz, 1H), 4.37 (m, 2H), 4.31 (s, 3H), 3.94 (m, 3H), 3.30 (s, 6H), 3.26 (s, 1H).

Example 360

5-Bromo-3-[2-methyl-6-(2-methylamino-ethylamino)-2H-pyrazolo[3,4-d]pyrimidin-4-yl]-1,3-dihydro-indol-2-one hydrochloride salt

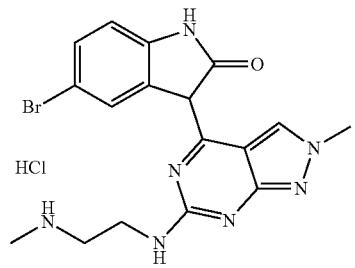

Example 300 (40 mg, 0.106 mmol) and N-(3-aminoethyl)-N-methyl carbamic acid t-butyl ester (184 mg, 1.06 mmol) were heated in 1 mL EtOH at 130° C. in microwave for 10 min. Upon cooling, the product precipitated in the reaction tube. The resulting solid was filtered and pumped dry before stirring in 5 mL of 4N HCl/dioxane for 1 h at RT. The reaction mixture was pumped dry, triturated in ether and filtered to afford 19 mg (40%) of a yellow solid. mp 269-272° C.; MS (ES⁺ calculated: 416.28; found: 416.58, 417.79 M+H). HPLC (88%) purity, retention time 2.357 minutes—Method C); ¹H NMR (400 MHz, TFA) δ 8.74 (s, 1H), 7.89 (s, 1H), 7.54 (d, J=8 Hz, 1H), 7.17 (d, J=8 Hz, 1H), 4.32 (m, 1H), 4.25 (s, 4H), 4.07 (m, 1H), 3.85 (m, 3H), 3.11 (br s, 2H), 3.07 (s, 1H).

Example 361

5-Bromo-3-{2-propyl-6-[((S)-1-pyrrolidin-2-ylmethyl)-amino]-2H-pyrazolo[3,4-d]pyrimidin-4-yl}-1,3-dihydro-indol-2-one

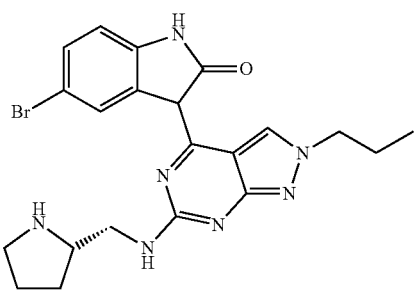

Example 188 (30 mg, 0.0737 mmol) and (S)-(+)-2-(aminomethyl)pyrrolidine (79 µL, 0.737 mmol) were heated in 1 mL EtOH at 130° C. in microwave for 10 min. Upon cooling, the product precipitated in the reaction tube. The resulting solid was filtered and pumped dry to afford 15 mg (43%) of a yellow solid. mp 286-293° C.; MS (ES⁺ calculated: 470.38; found: 470.65, 471.81 M+H). HPLC (97%) purity, retention time 3.66 minutes—Method C); ¹H NMR (400 MHz, DMSO-d₆) δ 9.57 (s, 1H), 9.39 (s, 1H), 8.57 (s, 1H), 7.85 (br s, 4H), 6.80 (d, J=8 Hz, 1H), 6.59 (d, J=8 Hz, 1H), 4.18 (m, 1H), 4.09 (t, J=7 Hz, 2H), 3.86 (m, 1H), 3.74 (m, 1H), 3.07 (d, J=12 Hz, 1H), 2.94 (m, 1H), 2.14 (m, 1H), 2.01 (m, 1H), 1.98 (m, 1H), 1.85 (m, 3H), 0.85 (t, J=8 Hz, 3H).

Example 362

5-Bromo-3-[2-propyl-64(S)-pyrrolidin-3-ylamino)-2H-pyrazolo[3,4-d]pyrimidin-4-yl]-1,3-dihydro-indol-2-one

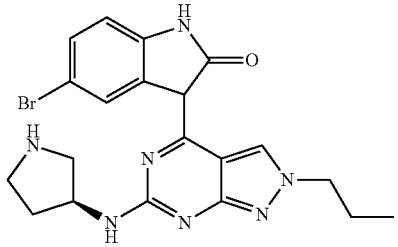 [SMILES: CCCn1cc2c(C3C(=O)Nc4ccc(Br)cc43)nc(N[C@H]3CCNC3)nc2n1]

Example 188 (40 mg, 0.0983 mmol) and (S)-(−)-3-aminopyrrolidine (87 μL, 0.983 mmol) were heated in 1 mL EtOH at 130° C. in microwave for 10 min. Upon cooling, the product precipitated in the reaction tube. The resulting solid was filtered and pumped dry to afford 44 mg (98%) of a yellow solid. mp 315-320° C.; MS (ES+ calculated: 456.35; found: 456.63, 457.79 M+H). HPLC (99%) purity, retention time 3.40 minutes—Method C); $^1$H NMR (400 MHz, DMSO-$d_6$) δ 9.70 (s, 1H), 9.40 (s, 1H), 8.55 (s, 1H), 6.86 (d, J=8 Hz, 1H), 6.61 (d, J=8 Hz, 1H), 5.9 (br s, 2H), 4.11 (t, J=7 Hz, 2H), 3.77 (br s, 2H), 3.70 (br s, 2H), 3.43 (m, 2H), 2.18 (m, 1H), 1.86 (m, 4H), 1.07 (m, 2H), 0.85 (t, J=7 Hz, 3H).

Example 363

5-Bromo-3-[2-propyl-64(R)-pyrrolidin-3-ylamino)-2H-pyrazolo [3,4-d]pyrimidin-4-yl]-1,3-dihydro-indol-2-one

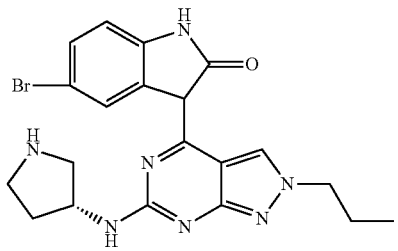 [SMILES: CCCn1cc2c(C3C(=O)Nc4ccc(Br)cc43)nc(N[C@@H]3CCNC3)nc2n1]

Example 188 (45 mg, 0.11 mmol) and (R)-(+)-3-aminopyrrolidine (96 μL, 1.1 mmol) were heated in 1 mL EtOH at 130° C. in microwave for 10 min. Upon cooling, the product precipitated in the reaction tube. The resulting solid was filtered and pumped dry to afford 46 mg (92%) of a yellow solid. mp 314-320° C.; MS (ES+ calculated: 456.35; found: 456.63, 457.78 M+H). HPLC (96%) purity, retention time 3.389 minutes—Method C); $^1$H NMR (400 MHz, DMSO-$d_6$) δ 9.71 (s, 1H), 9.40 (s, 1H), 8.55 (s, 1H), 6.87 (d, J=8 Hz, 1H), 6.62 (d, J=8 Hz, 1H), 4.11 (t, J=7 Hz, 2H), 3.77 (br s, 2H), 3.70 (br s, 2H), 3.43 (m, 2H), 2.18 (m, 1H), 1.86 (m, 4H), 0.85 (t, J=7 Hz, 3H).

Example 364

5-Bromo-3-[6-((S)-2,3-dihydroxy-propylamino)-2-propyl-2H-pyrazolo [3,4-d]pyrimidin-4-yl]-1,3-dihydro-indol-2-one

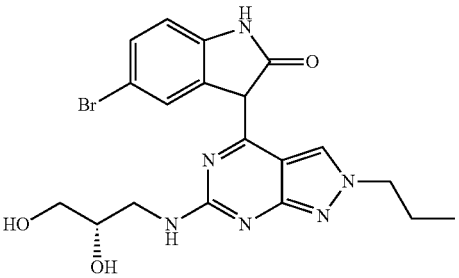 [SMILES: CCCn1cc2c(C3C(=O)Nc4ccc(Br)cc43)nc(NC[C@H](O)CO)nc2n1]

Example 188 (40 mg, 0.0983 mmol) and (S)-(−)-3-amino-1,2-propanediol (89 mg, 0.983 mmol) were heated in 1 mL EtOH at 130° C. in microwave for 10 min. Upon cooling, the product precipitated in the reaction tube. The resulting solid was filtered and pumped dry to afford 28 mg (62%) of a yellow solid. mp 295-297° C.; MS (ES+ calculated: 461.32; found: 461.64, 462.71 M+H). HPLC (93%) purity, retention time 3.517 minutes—Method C); $^1$HNMR (400 MHz, TFA) δ 8.74 (s, 1H), 7.90 (s, 1H), 7.53 (d, J=8 Hz, 1H), 7.17 (d, J=8 Hz, 1H), 4.52 (m, 1H), 4.44 (m, 2H), 4.18 (m, 2H), 3.99 (m, 2H), 2.12 (q, J=7 Hz, 2H), 1.36 (m, 1H), 1.12 (t, J=7 Hz, 3H).

Example 365

5-Bromo-3-[6-(2-methylamino-ethylamino)-2-propyl-2H-pyrazolo [3,4-d]pyrimidin-4-yl]-1,3-dihydro-indol-2-one hydrochloride salt

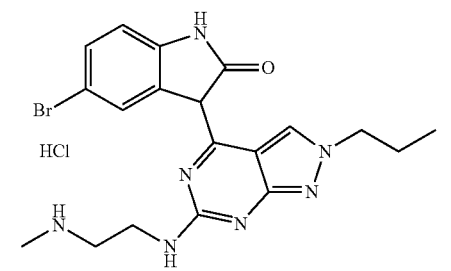 [SMILES: CCCn1cc2c(C3C(=O)Nc4ccc(Br)cc43)nc(NCCNC)nc2n1 ; Cl]

Example 188 (50 mg, 0.123 mmol) and N-(3-aminoethyl)-N-methyl carbamic acid t-butyl ester (214 mg, 1.23 mmol) were heated in 1 mL EtOH at 130° C. in microwave for 10 min. Upon cooling, the product precipitated in the reaction tube. The resulting solid was filtered and pumped dry before stirring in 5 mL of 4N HCl/dioxane for 1 h at r.t. The reaction mixture was pumped dry, triturated in ether and filtered to afford 38 mg (65%) of a yellow solid. mp 269-271° C.; MS (ES+ calculated: 444.34; found: 444.63, 445.75 M+H). HPLC (95%) purity, retention time 3.937 minutes—Method C); $^1$H NMR (400 MHz, TFA) δ 8.73 (s, 1H), 7.89 (s, 1H), 7.54 (d, J=8 Hz, 1H), 7.17 (d, J=8 Hz, 1H), 4.4 (m, 2H), 4.31 (br s, 2H), 4.07 (m, 1H), 3.85 (m, 3H), 3.10 (br s, 2H), 2.12 (m, 2H), 1.13 (t, J=7 Hz, 3H).

Example 366

5-Bromo-3-(2-propyl-6-{[(R)-1-(tetrahydro-furan-2-yl)methyl]-amino}-2H-pyrazolo[3,4-d]pyrimidin-4-yl)-1,3-dihydro-indol-2-one

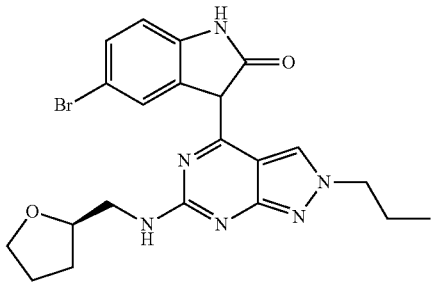 [SMILES: CCCn1cc2c(C3C(=O)Nc4ccc(Br)cc43)nc(NC[C@H]3CCCO3)nc2n1]

Example 188 (40 mg, 0.0983 mmol) and (R)-(−)-tetrahydrofurfurylamine (101 μL, 0.983 mmol) were heated in 1 mL EtOH at 130° C. in microwave for 10 min. Upon cooling, the product precipitated in the reaction tube. The resulting solid was filtered and pumped dry to afford 26 mg (56%) of a yellow solid. mp 309-312° C.; MS (ES$^+$ calculated: 471.36; found: 471.66, 472.78 M+H). HPLC (98%) purity, retention time 11.134 minutes—Method B); $^1$H NMR (400 MHz, TFA) δ 8.74 (s, 1H), 7.90 (s, 1H), 7.53 (d, J=8, 1H), 7.19 (br d, 1H), 4.62 (br s, 1H), 4.44 (t, J=7, 2H), 4.19 (t, J=7, 2H), 3.91 (br d, 1H), 3.77 (m, 1H), 2.44 (m, 1H), 2.4-1.9 (m, 5H), 1.13 (t, J=7, 3H).

Example 367

5-Bromo-3-(2-propyl-6-{[(S)-1-(tetrahydro-furan-2-yl)methyl]-amino}-2H-pyrazolo [3,4-d]pyrimidin-4-yl)-1,3-dihydro-indol-2-one

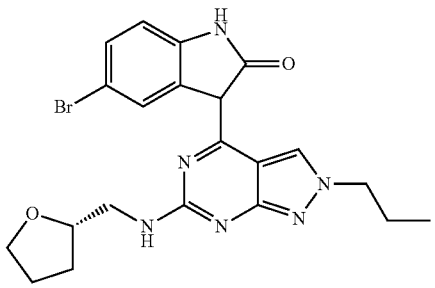 [SMILES: CCCn1cc2c(C3C(=O)Nc4ccc(Br)cc43)nc(NC[C@@H]3CCCO3)nc2n1]

Example 188 (40 mg, 0.0983 mmol) and (S)-(+)-tetrahydrofurfurylamine (101 μL, 0.983 mmol) were heated in 1 mL EtOH at 130° C. in microwave for 10 min. Upon cooling, the product precipitated in the reaction tube. The resulting solid was filtered and pumped dry to afford 32 mg (69%) of a yellow solid. mp 309-312° C.; MS (ES$^+$ calculated: 471.36; found: 471.63, 472.78 M+H). HPLC (98%) purity, retention time 4.738 minutes—Method C); $^1$H NMR (400 MHz, TFA) δ 8.74 (s, 1H), 7.90 (s, 1H), 7.53 (d, J=8, 1H), 7.19 (br d, 1H), 4.62 (br s, 1H), 4.44 (t, J=7, 2H), 4.19 (t, J=7, 2H), 3.91 (br d, 1H), 3.77 (m, 1H), 2.44 (m, 1H), 2.4-1.9 (m, 5H), 1.13 (t, J=7, 3H).

Example 368

5-Bromo-3-[6-((R)-2,3-dihydroxy-propylamino)-2-propyl-2H-pyrazolo[3,4-d]pyrimidin-4-yl]-1,3-dihydro-indol-2-one

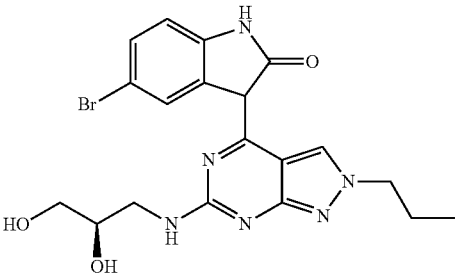

Example 188 (40 mg, 0.0983 mmol) and (R)-(+)-3-amino-1,2-propanediol (89 mg, 0.983 mmol) were heated in 1 mL EtOH at 130° C. in microwave for 10 min. Upon cooling, the product precipitated in the reaction tube. The resulting solid was filtered and pumped dry to afford 32 mg (71%) of a yellow solid. mp 293-296° C.; MS (ES$^+$ calculated: 461.32; found: 461.60, 462.75 M+H). HPLC (93%) purity, retention time 9.155 minutes—Method B); $^1$H NMR (400 MHz, TFA) δ 8.74 (s, 1H), 7.90 (s, 1H), 7.53 (d, J=8 Hz, 1H), 7.17 (d, J=8 Hz, 1H), 4.52 (m, 1H), 4.44 (m, 2H), 4.18 (m, 2H), 3.99 (m, 2H), 2.12 (q, J=7 Hz, 2H), 1.36 (m, 1H), 1.12 (t, J=7 Hz, 3H).

Example 369

3-[6-(2-(R)-Amino-propylamino)-2-propyl-2H-pyrazolo[3,4-d]pyrimidin-4-yl]-5-bromo-1,3-dihydro-indol-2-one

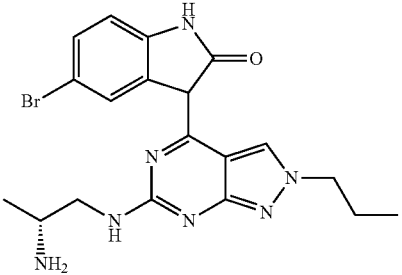 [SMILES: CCCn1cc2c(C3C(=O)Nc4ccc(Br)cc43)nc(NC[C@@H](C)N)nc2n1]

(R)-(+)-1,2-diaminopropane dihydrochloride (144 mg, 0.983 mmol) was stirred with triethylamine in 2 mL EtOH. Once homogeneous Example 188 (40 mg, 0.0983 mmol) was added and the reaction was heated at 130° C. in microwave for 10 min. The resulting reaction mixture was concentrated onto silica gel and flash columned (10% MeOH/1% NH$_4$OH in CH$_2$Cl$_2$). The resulting fractions were concentrated to afford 13 mg (30%) of a yellow solid. mp 247-250° C.; MS (ES$^+$ calculated: 444.34; found:444.65, 445.76M+H). HPLC (100%) purity, retention time 11.643 minutes—Method B); $^1$H NMR (400 MHz, TFA) δ 8.74 (s, 1H), 7.90 (s, 1H), 7.56 (d, J=8 Hz, 1H), 7.17 (d, J=8 Hz, 1H), 4.44 (m, 2H), 4.23 (br s, 1H), 4.12 (br s, 2H), 2.12 (m, 2H), 1.72 (m, 3H), 1.13 (t, J=7 Hz, 3H).

The following Examples 270-379 in Table 6 were prepared according to procedures disclosed herein including using methods generally known to one skilled in the art.

TABLE 6

| Example # | R² | X |
|---|---|---|
| 370 | Br | —NH—(CH₂)₂—N(CH₃)₂ |
| 371 | Br | —NH—(CH₂)₃—N(CH₃)₂ |
| 372 | Br | —(S)—NH—CH₂—CH(OH)CH₃ |
| 373 | Br | —(R)—NH—CH₂—CH(OH)CH₃ |
| 374 | Cl | —(S)—NH—CH₂—CH(OH)CH₃ |
| 375 | Cl | —(R)—NH—CH₂—CH(OH)CH₃ |
| 376 | Cl | —NH—(CH₂)₂—N(CH₃)₂ |
| 377 | Cl | —NH—(CH₂)₃—N(CH₃)₂ |
| 378 | Br | —NH—(CH₂)₂—NHCH₃*HCl |
| 379 | Br | —NH—(CH₂)₃—NHCH₃*HCl |

Example 370

5-Bromo-3-[2-cyclopentyl-6-(2-dimethylamino-ethylamino)-2H-pyrazolo [3,4-d]pyrimidin-4-yl]-1,3-dihydro-indol-2-one A mixture of 5-Bromo-3-(6-chloro-2-cyclopentyl-2-H-pyrazolo[3,4-d]pyrimidin-4-yl)-1,3-dihydro-indol-2-one (30 mg, 0.07 mmol) (Example 182), N,N-dimethylethylenediamine (61 mg, 0.7 mmol) and ethanol (2 mL) were heated to 130° C. in a microwave for 10 minutes. The reaction was concentrated, treated with ethyl ether and filtered to give 15 mg (44%) of Example 370. Example 370: ¹HNMR (400 MHz, TFA-d) δ 8.8 (s, 1H), 8.0 (s, 1H), 7.6 (d, 1H), 7.3 (d, 1H), 5.1 (m, 1H), 4.4 (m, 2H), 4.0 (m, 3H), 3.3-3.4 (m, 6H), 2.0-2.7 (m, 8H); MS (m/e) 484 (M+1); HPLC (87%) purity, retention time 3.052 minutes—Method C; mp 190-192° C.

Example 371

5-Bromo-3-[2-cyclopentyl-6-(3-dimethylamino-propylamino)-2H-pyrazolo [3,4-d]pyrimidin-4-yl]-1,3-dihydro-indol-2-one Example 371 was synthesized in a similar manner to Example 370 using the appropriate starting materials. Example 371: ¹HNMR (400 MHz, TFA-d) δ 8.9 (s, 1H), 8.1 (s, 1H), 7.7 (d, 1H), 7.4 (d, 1H), 5.2 (m, 1H), 4.1 (m, 2H), 3.7-3.8 (m, 5H), 3.3 (m, 6H), 2.1-2.8 (m, 8H); MS (m/e) 498 (M+1); HPLC (90%) purity, retention time 3.042 minutes—Method C; mp 198-200° C.

Example 372

5-Bromo-3-[2-cyclopentyl-64(S)-2-hydroxy-propylamino)-2H-pyrazolo [3,4-d]pyrimidin-4-yl]-1,3-dihydro-indol-2-one Example 372 was synthesized in a similar manner to Example 370 using the appropriate starting materials. Example 372: ¹HNMR (400 MHz, TFA-d) δ 8.8 (s, 1H), 8.0 (s, 1H), 7.6 (m, 1H), 7.3 (m, 1H), 5.1 (m, 1H), 4.4 (m, 1H), 3.9 (m, 1H), 3.8 (m, 1H), 2.0-2.7 (m, 8H), 1.6 (d, 3H); MS (m/e) 471 (M+1); HPLC (99%) purity, retention time 3.237 minutes—Method C; mp>300° C.

Example 373

5-Bromo-3-[2-cyclopentyl-64(R)-2-hydroxy-propylamino)-2H-pyrazolo [3,4-d]pyrimidin-4-yl]-1,3-dihydro-indol-2-one Example 373 was synthesized in a similar manner to Example 370 using the appropriate starting materials. Example 373: ¹HNMR (400 MHz, TFA-d) δ 8.8 (s, 1H), 8.0 (s, 1H), 7.6 (m, 1H), 7.3 (m, 1H), 5.1 (m, 1H), 4.4 (m, 1H), 3.9 (m, 1H), 3.8 (m, 1H), 2.0-2.7 (m, 8H), 1.6 (d, 3H); MS (m/e) 471 (M+1); HPLC (99%) purity, retention time 3.238 minutes—Method C; mp>300° C.

Example 374

5-Chloro-3-[2-cyclopentyl-64(S)-2-hydroxy-propylamino)-2H-pyrazolo [3,4-d]pyrimidin-4-yl]-1,3-dihydro-indol-2-one Example 374 was synthesized in a similar manner to Example 370 using Example 113A and the appropriate starting materials. Example 374: ¹HNMR (400 MHz, TFA-d) δ 8.8 (s, 1H), 7.7 (s, 1H), 7.3 (m, 1H), 7.2 (m, 1H), 5.0 (m, 1H), 4.3 (m, 1H), 3.8 (m, 1H), 3.7 (m, 1H), 2.0-2.7 (m, 8H), 1.6 (d, 3H); MS (m/e) 427 (M+1); HPLC (99%) purity, retention time 3.169 minutes—Method C; mp>300° C.

Example 375

5-Chloro-3-[2-cyclopentyl-64(R)-2-hydroxy-propylamino)-2H-pyrazolo [3,4-d]pyrimidin-4-yl]-1,3-dihydro-indol-2-one Example 375 was synthesized in a similar manner to Example 370 using Example 113A and the appropriate starting materials. Example 375: ¹HNMR (400 MHz, TFA-d) δ 8.8 (s, 1H), 7.7 (s, 1H), 7.3 (m, 1H), 7.2 (m, 1H), 5.0 (m, 1H), 4.3 (m, 1H), 3.8 (m, 1H), 3.7 (m, 1H), 2.0-2.7 (m, 8H), 1.6 (d, 3H); MS (m/e) 427 (M+1); HPLC (99%) purity, retention time 3.167 minutes—Method C; mp>300° C.

Example 376

5-Chloro-3-[2-cyclopentyl-6-(2-dimethylamino-ethylamino)-2H-pyrazolo [3,4-d]pyrimidin-4-yl]-1,3-dihydro-indol-2-one Example 376 was synthesized in a similar manner to Example 370 using Example 113A and the appropriate starting materials. Example 376: ¹HNMR (400 MHz, TFA-d) δ 8.8 (s, 1H), 7.8 (s, 1H), 7.6 (d, 1H), 7.3 (d, 1H), 5.1 (m, 1H), 4.4 (m, 2H), 4.0 (m, 3H), 3.3-3.4 (m, 6H), 2.0-2.7 (m, 8H); MS (m/e) 440 (M+1); HPLC (95%) purity, retention time 2.994 minutes—Method C; mp 145-148° C.

Example 377

5-Chloro-3-[2-cyclopentyl-6-(3-dimethylamino-propylamino)-2H-pyrazolo [3,4-d]pyrimidin-4-yl]-1,3-dihydro-indol-2-one Example 377 was synthesized in a similar manner to Example 370 using Example 113A and the appropriate starting materials. Example 377: ¹H NMR (400 MHz, TFA-d) δ 8.9 (s, 1H), 8.1 (s, 1H), 7.7 (d, 1H), 7.4 (d, 1H), 5.2 (m, 1H), 4.1 (m, 2H), 3.8 (m, 3H), 3.3 (m, 8H), 2.1-2.8 (m, 8H); MS (m/e) 454 (M+1); HPLC (99%) purity, retention time 2.986 minutes—Method C; mp 176-179° C.

Example 378

5-Bromo-3-[2-cyclopentyl-6-(2-methylamino-ethylamino)-2H-pyrazolo [3,4-d]pyrimidin-4-yl]-1,3-dihydro-indol-2-one hydrochloride salt A mixture of 5-Bromo-3-(6-chloro-2-cyclopentyl-2-H-pyrazolo[3,4-d]pyrimidin-4-yl)-1,3-dihydro-indol-2-one (50 mg, 0.115 mmol) (Example 182), N'-BOC-N'-methylethylenediamine (200 mg, 1.15 mmol) and ethanol (2 mL) were heated to 130° C. in a microwave for 10 minutes. The reaction was concentrated, treated with ethyl ether and filtered to give 36 mg (55%) of the product. The product was dissolved in 4N HCl in dioxane (3 mL) and stirred at rt for 1 hr. The reaction was concentrated, treated with acetone and filtered. The solid was washed with acetone, ethyl ether and pumped dry to give 9 mg (28%) of Example 378. Example 378: ¹H NMR (400 MHz, TFA-d) δ 8.9 (s, 1H), 8.1 (s, 1H), 7.7 (d, 1H), 7.4 (d, 1H), 5.1 (m, 1H), 4.3 (m, 2H), 4.0 (m, 4H), 3.1 (m, 3H), 2.1-2.8 (m, 8H); MS (m/e) 470 (M+1); HPLC (99%) purity, retention time 3.040 minutes—Method C; mp 201-204° C.

Example 379

5-Bromo-3-[2-cyclopentyl-6-(3-methylamino-propylamino)-2H-pyrazolo[3,4-d]pyrimidin-4-yl]-1,3-dihydro-indol-2-one hydrochloride salt Example 379 was synthesized in a similar manner to Example 378 using the appropriate starting materials. Example 379: ¹H NMR (400 MHz, TFA-d) δ 8.9 (s, 1H), 8.1 (s, 1H), 7.7 (d, 1H), 7.4 (d, 1H), 5.1 (m, 1H), 4.3 (m, 2H), 3.5 (m, 8H), 2.1-2.8 (m, 8H); MS (m/e) 484 (M+1); HPLC (99%) purity, retention time 3.003 minutes—Method C; mp 208-211° C.

Scheme 9 discloses a general procedure for the preparation of compounds of the invention wherein $R^6$ is an alkyl group.

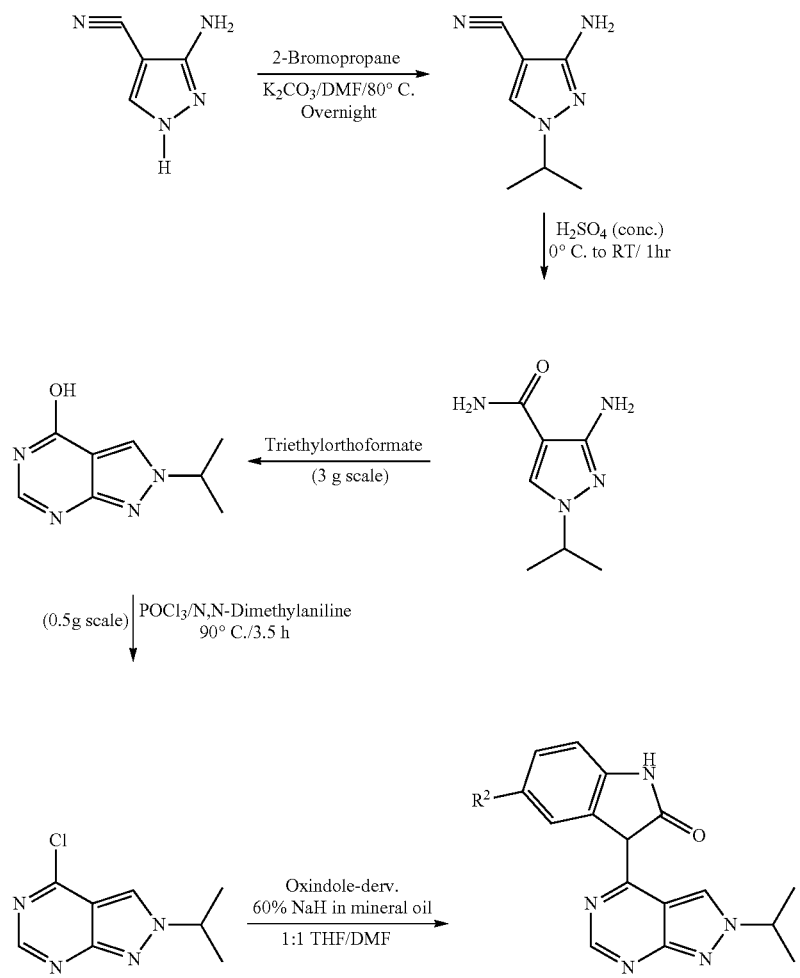

Example 380

5-Bromo-3-(2-isopropyl-2H-pyrazolo[3,4-d]pyrimidin-4-yl)-1,3-dihydro-indol-2-one Example 380 was synthesized in using the general procedure of Scheme 9, wherein $R^2$=Br, and the appropriate starting materials. Example 380: $^1$HNMR (400 MHz, TFA-d) δ 9.1 (s, 1H), 8.8 (s, 1H), 7.9 (s, 1H), 7.6 (d, 1H), 7.2 (d, 1H), 5.0 (m, 1H), 1.8 (m, 6H); MS (m/e) 373 (M+1); HPLC (99%) purity retention time 3.298 minutes—Method C; mp>300° C.

Example 381

5-Chloro-3-(2-isopropyl-2H-pyrazolo[3,4-d]pyrimidin-4-yl)-1,3-dihydro-indol-2-one Example 381 was synthesized in using the general procedure of Scheme 9, wherein $R^2$=Cl, and the appropriate starting materials. Example 381: $^1$HNMR (400 MHz, TFA-d) δ 9.1 (s, 1H), 8.9 (s, 1H), 7.8 (s, 1H), 7.4 (d, 1H), 7.3 (d, 1H), 5.0 (m, 1H), 1.8 (m, 6H); MS (m/e) 328 (M+1); HPLC (99%) purity retention time 3.189 minutes—Method C; mp>300° C.

Example 382

3-(2-Isopropyl-2H-pyrazolo[3,4-d]pyrimidin-4-yl)-2-oxo-2,3-dihydro-1H-indole-5-carbonitrile Example 382 was synthesized in using the general procedure of Scheme 9, wherein $R^2$=CN, and the appropriate starting materials. Example 382: $^1$HNMR (400 MHz, TFA-d) δ 10.3 (s, 1H), 9.0 (s, 1H), 8.3 (s, 1H), 7.9 (d, 1H), 7.5 (d, 1H), 5.0 (m, 1H), 1.8 (m, 6H); MS (m/e) 319 (M+1); HPLC (99%) purity retention time 3.189 minutes—Method C; mp>300° C.

Example 383

5-Bromo-3-fluoro-3-(2-propyl-2H-pyrazolo[3,4-d]pyrimidin-4-yl)-1,3-dihydroindol-2-one

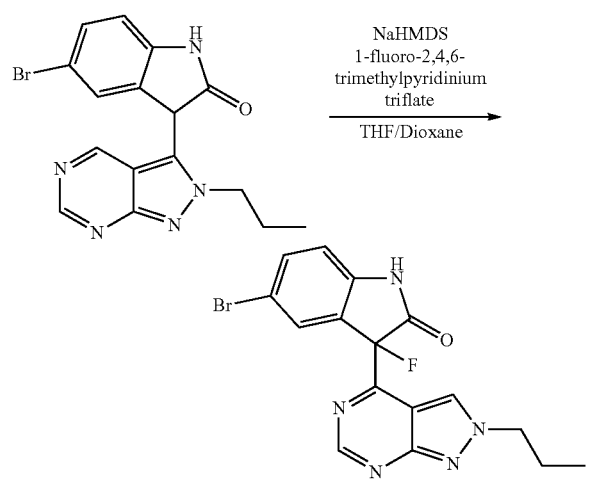

To a solution of Example 97 (85 mg, 0.23 mmol) in a mixture of THF/dioxane (1:1. 12.8 mL) was added a 1M solution of sodium bis(trimethylsilyl)amide (0.23 ml) at –40° C. followed by addition of 1-fluoro-2,4,6-trimethylpyridinium triflate (67 mg, 0.23 mmol). The reaction was allowed to warm to room temperature where it stirred overnight. The reaction was heated to ~50° C. for 4 h then quenched with ammonium chloride. The reaction was concentrated in vacuo and purified prep HPLC on a Rainin Dynamax system with a Higgins Analytical Clipeus 10 μm C18 column (250×20 mm). Example 383: $^1$HNMR (400 MHz, DMSO-$d_6$) δ 0.91 (s, 3H), 2.02 (m, 2H), 4.54 (m, 2H), 6.98 (d, 1H), 7.53 (s, 1H), 7.61 (d, 1H), 8.85 (s, 1H), 9.03 (s, 1H), 11.2 (s, 1H); MS (m/e) 391 (M+1); HPLC (91%) purity retention time 3.87 minutes—Method F; mp 184-186° C.

HPLC Methods:

Wavelengths monitored included 254, 290 and/or 215 nm

Method A: Flow rate: 1.6 mL/min, gradient over 15 minutes from 10 to 50% [acetonitrile (0.1% TFA added):water (0.1% TFA added)] ramping with a gradient from 50% to 100% acetonitrile:water from 15 to 20 minutes, column: 5 micron Zorbax RX-C8 (4.6×150 mm).

Method B: Flow rate 1.6 mL/min, gradient over 20 minutes from 10 to 100% [acetonitrile (0.1% TFA added):water (0.1% TFA added)], column: 5 micron Zorbax RX-C8 (4.6×150 mm).

Method C: Flow rate 2.4 mL/min, gradient over 8 minutes at 30° C. from 10 to 100% [acetonitrile (0.1% TFA added):water (0.1% TFA added)], column: 3.5 micron Zorbax SB-C18 (4.6×75 mm).

Method D: Flow rate 1.6 mL/min, 100% water (0.1% TFA added) for 1 minute, gradient over 15 minutes from 0 to 100% [acetonitrile (0.1% TFA added):water] 100% acetonitrile for 4 minutes, column: 5 micron Zorbax RX-C8 (4.6×150 mm).

Method E: Flow rate 1.6 mL/min, 10-100% Acetonitrile/water (both with 0.1% TFA) over 7 minutes.

Method F: Flow rate 1.6 mL/min, 10-100% Acetonitrile/water (both with 0.1% TFA) over 8 minutes.

It is noted that NMRs of some oxindole containing products (particularly in the N-2 series) are very complicated due to possible restricted rotational isomerism as well as possible tautomeric forms—signal positions only and no integrations are given for the N-2 series due to inability to assign protons.

Utility

The present invention relates to novel substituted heterobicyclic pyrimidine compounds, in particular substituted pyrazolopyrimidine oxindoles, that act as inhibitors of glycogen synthase kinase 3 and/or cyclin dependant kinase 5, and their use in the treatment of chronic neurodegenerative diseases, neurotraumatic diseases, depression and/or diabetes. Compounds of the present invention are well suited as inhibitors of GSK-3β activity and/or CDK5 activity. Representative compounds of the invention have exhibited good in vitro potency against GSK-3β kinase and/or CDK5 kinase. Table 7 below provides data related to several example compounds of the invention with respect to, for example, ability to inhibit GSK-3β activity and/or CDK5 activity. Accordingly, the compounds of the present invention are expected to be useful in the prevention and/or treatment of conditions mediated by GSK-3β activity and/or CDK5 activity.

Cloning, Expression and Purification of CDK5/GST-p25

Two recombinant baculoviral constructs were created, one encoding for human CDK5 and the other encoding for human p25 with an amino-terminal glutathione-S-transferase (GST) tag. PCR amplification of full-length CDK5 was performed utilizing human brain cDNA as a template and Pfu Turbo polymerase (Strategene). The PCR product from this reaction was subcloned into the baculoviral expression vector pFAST-BAC1 (Gibco/BRL). The final construct, encoding for full-length human CDK5 (base pairs 25-903 of GenBank Accession #NM_004935), is 292 amino acids long with a predicted MW of 33.3 kDa.

For p25, the active truncated form of p35, amino acids 108-307 were PCR-amplified from human fetal brain cDNA (Clontech QUICK-Clone cDNA) using the Advantage 2 PCR system (Clontech). The PCR product was subcloned into the baculoviral transfer vector pFBGSTP (an engineered derivative of the baculoviral transfer vector pFASTBAC1). The final baculoviral construct encodes for base pairs 419-1021 of GenBank Accession #NM_003885, with an amino-terminal GST tag. The expressed GST-p25 is 444 amino acids long with a predicted MW of 50.3 kDa.

The CDK5/GST-p25 complex was generated by coexpression. Sf21 cells were cultured in TNM-FHS media at a density of $1.5 \times 10^6$ cells/mL and infected with each recombinant virus at MOI values of 5 (for CDK5) and 10 (for GST-p25). The cells were harvested 40 h after infection. For purification, the 100,000×g supernatant solution was used. Expression was confirmed by running samples on SDS-PAGE, followed by immunoblot analysis utilizing antibodies against CDK5 (anti-CDK5 (268-283); Calbiochem #219449) and p35 (Santa Cruz #sc820). The CDK5/GST-p25 complex was purified by glutathione affinity chromatography.

Inhibition of CDK5/GST-p25 Kinase Activity

Compounds were tested for their ability to inhibit the kinase activity of recombinant baculoviral CDK5/GST-p25 using an enzyme-linked immunosorbent assay (ELISA) with time-resolved fluorescence (TRF) readout. Briefly, each 384-well FluoroNunc Maxisorp plate (Cat # 460372) plate was coated with 50 μl/well of 50 μg/ml substrate solution (recombinant GST-Rb(773-928)) in Tris-buffered saline (TBS). The CDK5/GST-p25 assay mixture (total volume=50 μl/well) consisting of 20 mM HEPES (pH 7.2), 10 μM ATP, 10 mM $MgCl_2$, 5 mM EGTA, 25 mM β-glycerophosphate, 0.05% BSA, 2.5% DMSO, and various concentrations of test compound were then added to the assay plate. Enzyme (2 ng/ml CDK5/GST-p25) was added and the reaction was allowed to proceed at 37° C. for 20 minutes. Detection of the phosphorylated product was performed by adding 50 μl/well of phospho-Rb (Ser-780) antibody (Cell Signaling # 9307) diluted 1:10,000 in antibody dilution buffer (0.1% BSA in TBST). After 1-hour incubation at 37° C., 50 μl/well of Eu-Nl labelled anti-rabbit antibody (Wallac # AD0105; 1:50,000 in antibody dilution buffer) was added. Incubation at 37° C. then proceeded for 1 hour, followed by addition of 50 μl enhancement solution (Wallac #1244-105). The plate was gently agitated and after a few minutes, the fluorescence of the resulting solution was measured using a Multilabel Reader (Victor2 Model # 1420-018 or Envision Model # 2100). Inhibition data were analyzed using ActivityBase and $IC_{50}$ curves were generated using XLFit 3.0.5.

Cloning, Expression and Purification of $His_6$-GSK-3β

Full-length GSK-3β was amplified from a sequence-verified I.M.A.G.E. EST acquired from Research Genetics (Invitrogen, Clone ID# CSODB003YJ02). The final sequence-verified cDNA contained the coding region for a $NH_2$-terminal tag, which encoded for 6 histidines and then eight vector-encoded amino acids prior to the start of GSK3β, which contained by # 43-1342 of Genbank Accession # NM_002093, encoding amino acids #2-419. The predicted molecular weight of the tagged, 435 amino acid, full-length protein is 48.5 kDa. The major structural element of this protein is the kinase domain, which is from amino acids #56-340. Recombinant baculoviral DNA was prepared by transposition in *E. coli* (BAC-TO-BAC system: Invitrogen) and the virus generated and amplified in Sf21 insect cells. A suspension culture of Sf21 cells was infected at an MOI of 0.7 and cell density of $1.5 \times 10^6$ cells/mL in Excell 420 serum-free media (JRH BioScience) and harvested 65 h after infection. The 100,000×g supernatant solution was used for purification. Expression was confirmed by running samples on SDS-PAGE, followed by immunoblot analysis utilizing both a Penta-HIS antibody (Qiagen #34660) and a GSK-3α/GSK-3β antibody (Calbiochem #368662, data not shown). The $His_6$-tagged protein was purified to in one step by Ni-NTA affinity chromatography.

Inhibition of $His_6$-GSK-3β Kinase Activity

Inhibitory effects of compounds on baculoviral GSK-3β kinase activity were evaluated using an ELISA-based format in a 384-well FluoroNunc Maxisorp plate (Cat # 460372) with a time-resolved fluorescence readout. Briefly, each plate was coated with 50 μl/well of 20 μg/ml substrate solution (recombinant GST-Rb) in Tris-buffered saline (TBS). The GSK-3β assay mixture (total volume=50 μl/well) consisting of 50 mM HEPES (pH 7.2), 20 μM ATP, 10 mM $MgCl_2$, 5 mM EGTA, 25 mM β-glycerophosphate, 0.05% BSA, 2.5% DMSO, and various concentrations of test compound were then added to the assay plate. Enzyme (200 ng/ml $His_6$-GSK-3β) was then added and the reaction was allowed to proceed at 37° C. for 30 minutes. Detection of the phosphorylated product was performed by adding 50 μl/well of phospho-Rb (Ser-780) antibody (Cell Signaling # 9307) diluted 1:10,000 in antibody dilution buffer (0.1% BSA in TBST). After 1-hour incubation at 37° C., 50 μl/well of Eu-N1 labelled anti-rabbit antibody (Wallac # AD0105; 1:50,000 in antibody dilution buffer) was added. Incubation at 37° C. then proceeded for 1 hour, followed by addition of 50 μl enhancement solution (Wallac #1244-105). The plate was gently agitated and after a few minutes, the fluorescence of the resulting solution was measured using a Multilabel Reader (Victor2 Model # 1420-018 or Envision Model 2100). Inhibition data were analyzed using ActivityBase and $IC_{50}$ curves were generated using XLFit 3.0.5.

Compound Activity

Using the assays disclosed herein the following Table 7 demonstrates the utility of compounds of the invention for tau kinase inhibition. Compounds of the present invention are considered active if their $IC_{50}$ values are less than 50 uM. In the following Table, for the inhibition of CDK5, compounds of the present invention with a "+" are less than 10000 nM; compounds of the present invention with a "++" are less than 3000 nM; and compounds of the present invention with a "+++" are less than 300 nM in $IC_{50}$ for CDK5 inhibition. In the following Table, for the inhibition of GSK3β, compounds of the present invention with a "+" are less than 10000 nM; compounds of the present invention with a "++" are less than 3000 nM; and compounds of the present invention with a "+++" are less than 300 nM in $IC_{50}$ for GSK3β inhibition. Where ">+" occurs activity was greater than the limits of the assay. Where no $IC_{50}$ value is represented, data has yet to be determined.

TABLE 7

| Example | CDK5 $IC_{50}$ (nM) | GSK3β $IC_{50}$ (nM) |
|---|---|---|
| 30 | +++ | +++ |
| 31 | +++ | +++ |
| 32 | ++ | >3000 |
| 33 | +++ | +++ |
| 34 | +++ | +++ |
| 35 | >3000 | ++ |
| 36 | +++ | +++ |
| 37 | ++ | ++ |

TABLE 7-continued

| Example | CDK5 IC$_{50}$ (nM) | GSK3β IC$_{50}$ (nM) |
|---|---|---|
| 38 | >+ | >+ |
| 39 | +++ | ++ |
| 40 | +++ | ++ |
| 41 | ++ | ++ |
| 42 | ++ | ++ |
| 43 | ++ | ++ |
| 44 | >+ | >+ |
| 45 | +++ | +++ |
| 46 | +++ | +++ |
| 47 | ++ | ++ |
| 48 | ++ | +++ |
| 49 | +++ | +++ |
| 50 | ++ | ++ |
| 51 | >3000 | |
| 52 | ++ | ++ |
| 53 | >+ | ++ |
| 54 | >3000 | >+ |
| 55 | >+ | ++ |
| 56 | >+ | >+ |
| 57 | >+ | ++ |
| 58 | >+ | >3000 |
| 59 | >+ | ++ |
| 60 | >+ | >+ |
| 61 | >+ | >+ |
| 62 | >+ | >3000 |
| 63 | >+ | ++ |
| 64 | >+ | >+ |
| 65 | >+ | >+ |
| 66 | >+ | >3000 |
| 67 | >+ | >+ |
| 68 | >+ | >+ |
| 69 | >3000 | >+ |
| 70 | >+ | >+ |
| 71 | >+ | >+ |
| 72 | >+ | >+ |
| 73 | >+ | >+ |
| 74 | >+ | >+ |
| 75 | >+ | >+ |
| 76 | +++ | ++ |
| 82 | +++ | ++ |
| 83 | +++ | ++ |
| 84 | +++ | ++ |
| 85 | +++ | >3000 |
| 86 | +++ | >+ |
| 89 | +++ | +++ |
| 90 | +++ | ++ |
| 93 | >+ | >+ |
| 94 | >+ | >+ |
| 95 | >3000 | >+ |
| 96 | +++ | +++ |
| 97 | +++ | +++ |
| 98 | +++ | +++ |
| 99 | +++ | 62% @10 μM |
| 100 | +++ | ++ |
| 108 | +++ | >+ |
| 109 | +++ | +++ |
| 111 | +++ | +++ |
| 113 | >+ | +++ |
| 114 | +++ | +++ |
| 115 | +++ | +++ |
| 116 | | +++ |
| 117 | + | +++ |
| 118 | ++ | +++ |
| 119 | ++ | +++ |
| 120 | >+ | +++ |
| 121 | >+ | +++ |
| 122 | >+ | +++ |
| 123 | +++ | +++ |
| 124 | ++ | +++ |
| 125 | >+ | +++ |
| 126 | +++ | +++ |
| 127 | >+ | +++ |
| 128 | >+ | +++ |
| 129 | >+ | +++ |
| 130 | >+ | +++ |
| 131 | >+ | +++ |
| 132 | >+ | +++ |
| 133 | +++ | +++ |
| 134 | >3000 | +++ |
| 135 | >+ | +++ |
| 136 | >3000 | +++ |
| 137 | >+ | +++ |
| 138 | ++ | +++ |
| 139 | +++ | +++ |
| 140 | >+ | +++ |
| 141 | >+ | +++ |
| 142 | | |
| 143 | >+ | +++ |
| 144 | >+ | +++ |
| 148 | >+ | >+ |
| 149 | +++ | +++ |
| 150 | 76% @10 μM | +++ |
| 151 | +++ | +++ |
| 152 | >+ | >+ |
| 153 | >+ | >3000 |
| 154 | 68% @10 μM | ++ |
| 155 | >1000 | ++ |
| 156 | +++ | +++ |
| 157 | >3000 | ++ |
| 158 | >3000 | ++ |
| 159 | >+ | >+ |
| 160 | >+ | +++ |
| 161 | 68% @10 μM | +++ |
| 162 | >1000 | +++ |
| 163 | ++ | +++ |
| 164 | >+ | +++ |
| 165 | +++ | +++ |
| 166 | 41% @10 μM | +++ |
| 167 | >3000 | +++ |
| 168 | +++ | +++ |
| 169 | >+ | +++ |
| 170 | ++ | +++ |
| 171 | +++ | +++ |
| 172 | >+ | +++ |
| 173 | +++ | +++ |
| 174 | +++ | +++ |
| 175 | +++ | +++ |
| 176 | +++ | +++ |
| 177 | +++ | +++ |
| 178 | ++ | +++ |
| 179 | ++ | +++ |
| 180 | +++ | +++ |
| 181 | 70% @10 μM | +++ |
| 182 | >+ | >3000 |
| 183 | | |
| 184 | +++ | +++ |
| 185 | +++ | +++ |
| 186 | +++ | +++ |
| 187 | +++ | +++ |
| 188 | >+ | >3000 |
| 189 | +++ | +++ |
| 190 | +++ | +++ |
| 191 | +++ | +++ |
| 192 | +++ | +++ |
| 193 | +++ | +++ |
| 194 | +++ | +++ |
| 195 | +++ | +++ |
| 196 | +++ | +++ |
| 197 | +++ | +++ |
| 198 | +++ | +++ |
| 199 | +++ | +++ |
| 200 | +++ | +++ |
| 201 | +++ | +++ |
| 202 | +++ | +++ |
| 203 | +++ | +++ |
| 204 | ++ | >3000 |
| 205 | >3000 | >+ |
| 211 | >+ | >+ |
| 212 | +++ | +++ |
| 213 | +++ | +++ |
| 214 | +++ | +++ |
| 215 | ++ | ++ |
| 216 | ++ | ++ |
| 217 | +++ | +++ |
| 218 | +++ | +++ |
| 219 | +++ | +++ |

TABLE 7-continued

| Example | CDK5 IC$_{50}$ (nM) | GSK3β IC$_{50}$ (nM) |
|---|---|---|
| 225 | >+ | +++ |
| 226 | +++ | +++ |
| 227 | +++ | +++ |
| 228 | +++ | +++ |
| 229 | ++ | ++ |
| 230 | +++ | +++ |
| 231 | +++ | +++ |
| 232 | +++ | +++ |
| 233 | +++ | +++ |
| 234 | +++ | +++ |
| 235 | +++ | +++ |
| 236 | >+ | >+ |
| 237 | +++ | +++ |
| 238 | +++ | +++ |
| 239 | +++ | +++ |
| 240 | +++ | +++ |
| 241 | ++ | +++ |
| 242 | 43% @10 μM | ++ |
| 243 | 63% @10 μM | >1000 |
| 244 | >+ | >1000 |
| 245 | >+ | >3000 |
| 246 | >3000 | +++ |
| 247 | >+ | +++ |
| 248 | >+ | +++ |
| 249 | >+ | 52% @10 μM |
| 250 | >+ | +++ |
| 251 | >3000 | +++ |
| 252 | ++ | +++ |
| 253 | ++ | +++ |
| 254 | ++ | +++ |
| 261 | >+ | >3000 |
| 262 | >+ | >3000 |
| 263 | +++ | +++ |
| 264 | +++ | +++ |
| 265 | +++ | +++ |
| 267 | +++ | +++ |
| 268 | +++ | +++ |
| 269 | +++ | +++ |
| 270 | ++ | +++ |
| 271 | +++ | +++ |
| 272 | +++ | +++ |
| 273 | >+ | >3000 |
| 275 | >+ | +++ |
| 276 | ++ | +++ |
| 277 | +++ | +++ |
| 278 | ++ | +++ |
| 279 | ++ | +++ |
| 280 | >+ | +++ |
| 287 |  |  |
| 288 | ++ | +++ |
| 289 | +++ | +++ |
| 290 | 73% @10 μM | +++ |
| 291 | >3000 | ++ |
| 292 | +++ | +++ |
| 293 | +++ | +++ |
| 294 | 73% @10 μM | 70% @10 μM |
| 295 | +++ | +++ |
| 300 |  |  |
| 301 | +++ | +++ |
| 302 | +++ | +++ |
| 303 | +++ | ++ |
| 304 | +++ | +++ |
| 305 | +++ | +++ |
| 306 | +++ | ++ |
| 307 | ++ | ++ |
| 309 | ++ | ++ |
| 310 | ++ | ++ |
| 314 | >+ | >+ |
| 315 | >+ | >+ |
| 316 | >+ | >+ |
| 317 | >+ | >+ |
| 318 | >+ | >+ |
| 319 | >+ | >+ |
| 320 | >3000 | >3000 |
| 321 | >3000 | >3000 |
| 322 | >3000 | >+ |
| 323 | >+ | >+ |
| 324 | >3000 | >3000 |
| 325 | >+ | >+ |
| 326 | >+ | ++ |
| 327 | >3000 | ++ |
| 328 | >+ | >+ |
| 329 | >+ | >+ |
| 330 | >+ | >+ |
| 331 | >+ | ++ |
| 332 | >3000 | ++ |
| 333 | >+ | >+ |
| 334 | >+ | >+ |
| 335 | >3000 | >3000 |
| 336 | >+ | >3000 |
| 337 | ++ | ++ |
| 338 | >3000 | >+ |
| 339 | >+ | >+ |
| 340 | ++ | ++ |
| 341 | ++ | ++ |
| 342 | ++ | ++ |
| 343 | >+ | >+ |
| 344 | ++ | 69% @10 μM |
| 345 | >+ | 67% @10 μM |
| 346 | ++ | ++ |
| 347 | ++ | ++ |
| 348 | +++ | ++ |
| 349 | +++ | ++ |
| 350 | >3000 | ++ |
| 351 | >+ | >+ |
| 352 | >+ | >+ |
| 353 | >+ | ++ |
| 354 | +++ | ++ |
| 357 |  |  |
| 358 | +++ | +++ |
| 359 | ++ | ++ |
| 360 | ++ | ++ |
| 361 | >3000 | +++ |
| 362 | >3000 | ++ |
| 363 | ++ | ++ |
| 364 | +++ | +++ |
| 365 | ++ | +++ |
| 366 | +++ | +++ |
| 367 | +++ | +++ |
| 368 | +++ | +++ |
| 369 | ++ | +++ |
| 370 | >3000 | +++ |
| 371 | >3000 | +++ |
| 372 | 77% @10 μM | +++ |
| 373 | 67% @10 μM | +++ |
| 374 | 56% @10 μM | +++ |
| 375 | 62% @10 μM | +++ |
| 376 | >+ | ++ |
| 377 | >+ | ++ |
| 378 | >3000 | ++ |
| 379 | >3000 | +++ |
| 380 |  |  |
| 381 | +++ | ++ |
| 382 | +++ | ++ |

Accordingly, these results demonstrate that compounds of the present invention exhibit inhibitory activity against GSK3β kinase and/or CDK5 kinase.

References

1. Bacon, Edward R.; Singh, Baldev; Lesher, George Y. 6-(heterocyclyl)pyrazolo[3,4-d]pyrimidin-4-one phosphodiesterase inhibitors. (1994), U.S. Pat. No. 5,294,612 A.
2. Herling, Andreas; Maguire, Martin P.; Spada, Alfred P.; Myers, Michael R.; Choi-Sledeski, Yong Mi; Pauls, Heinz W.; Ewing, William R. Adenosine analogues for the treatment of insulin resistance syndrome and diabetes. (2001), Ep Appl. 1 258 247 A1
3. Chu, I. Lynch, B.M. Synthesis and Biological evaluation of Xanthine Oxidase Inhibitors. Pyrazolo[3,4-d]pyrimidines and Pyrazolo[3,4-b]pyridines. *J Med. Chem.* 1975, 18, 161-165.

Pharmaceutical Formulations and Dosage Forms

When employed as pharmaceuticals, the compounds of Formula (I) can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more of the compounds of Formula (I) above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like.

In therapeutic applications, compositions can be administered to a patient already suffering from a disease in an amount sufficient to cure or at least partially arrest the symptoms of the disease and its complications. An amount adequate to accomplish this is referred to as "therapeutically effective amount." Effective doses will depend on the disease condition being treated as well as by the judgement of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present invention also includes pharmaceutical kits useful, for example, in the treatment or prevention of inflammatory diseases, which comprise one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Various modifications of the invention, in addition to those described herein, will be apparent to those skilled in the art from the foregoing description. Such modifications are also intended to fall within the scope of the appended claims. Each reference cited in the present application, including patents, published patent applications, and journal articles, is incorporated herein by reference in its entirety.

As those skilled in the art will appreciate, numerous changes and modifications may be made to the embodiments of the invention without departing from the spirit of the invention. It is intended that all such variations fall within the scope of the invention.

What is claimed is:

1. A compound of Formula (I):

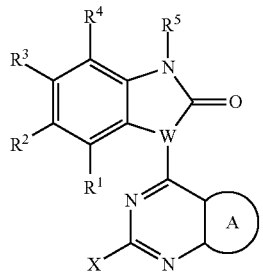

(I)

or a stereoisomeric form, a mixture of stereoisomeric forms, a tautomeric form, or a pharmaceutically acceptable salt form thereof, wherein:
W is CH or N;
ring A is

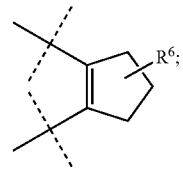

$R^1$, $R^2$, $R^3$, and $R^4$ at each occurrence are independently selected from H, halo, $-OR^{11}$, $-NO_2$, $-CN$, $-CF_3$, $-CHF_2$, $C_2$-$C_4$ alkenyl, $C_2$-$C_4$ alkynyl, $C_1$-$C_4$ haloalkyl, $-NR^{13}R^{14}$, $-NHOR^{13a}$, $-C(=O)R^{15}$, $-C(=O)OR^{15}$, $-OC(=O)R^{15}$, $-C(=O)NR^{13}R^{14}$, $-NR^{13a}C(=O)R^{15}$, $-NR^{13a}CO_2R^{15}$, $-OC(=O)NR^{13}R^{14}$, $-NR^{13a}C(=S)R^{15}$, $-SR^{15}$, $-S(=O)R^{15}$, $-S(=O)_2R^{15}$, $-S(=O)_2NR^{13}R^{14}$, and $C_1$-$C_4$ alkyl substituted with 0-1 $R^{19}$;

$R^5$ is H or $C_1$-$C_6$ alkyl;
$R^6$ is selected from H;
  $C_1$-$C_6$ alkyl substituted by 0-2 $R^{22}$;
  $C_2$-$C_6$ alkenyl substituted by 0-2 $R^{22}$;
  $C_2$-$C_6$ alkynyl substituted by 0-2 $R^{22}$; and
  $C_3$-$C_7$ cycloalkyl substituted by 0-3 $R^{22}$;

X is selected from H, $-NR^9R^{10}$, halo, $OR^{12}$, $-NO_2$, $-CN$, $-CF_3$, $-CHF_2$, $C_1$-$C_4$ alkyl, $C_2$-$C_4$ alkenyl, $C_2$-$C_4$ alkynyl, $C_1$-$C_4$ haloalkyl, $-CH_2NR^9R^{10}$, $-CH_2OR^{12}$, $-NHOR^{16}$, $-C(=O)R^{18}$, $-C(=O)OR^{18}$, $-OC(=O)R^{18}$, $-C(=O)NR^9R^{10}$, $-NR^{16}C(=O)R^{18}$, $-NR^{16}CO_2R^{18}$, $-OC(=O)NR^9R^{10}$, $-NR^{16}C(=S)R^{18}$, $-SR^{18}$, $-S(=O)R^{18}$, $-S(=O)_2R^{18}$, $-S(=O)_2NR^9R^{10}$, and $-NR^{16}S(=O)_2R^{18}$;

$R^9$ and $R^{10}$ at each occurrence are each independently selected from H, $-NH_2$;
  $C_1$-$C_6$ alkyl substituted by 0-1 $R^{19}$;
  $C_2$-$C_6$ alkenyl substituted by 0-1 $R^{19}$;
  $C_2$-$C_6$ alkynyl substituted by 0-1 $R^{19}$;
  $C_6$-$C_{10}$ aryl substituted by 0-5 $R^{19}$;
  $C_3$-$C_7$ carbocyclyl substituted by 0-5 $R^{19}$;
  5 to 14 membered heterocyclyl group substituted by 0-5 $R^{19}$, wherein said heterocyclyl group comprises one, two, or three heteroatoms selected from N, O, and S; and
  5 to 14 membered heteroaryl group substituted by 0-5 $R^{19}$, wherein said heteroaryl group comprises one, two, or three heteroatoms selected from N, O, and S;
alternatively, $R^9$ and $R^{10}$, together with the nitrogen to which they are attached, form a 3-7 membered heterocyclic ring, wherein said 3-7 membered heterocyclic ring contains a nitrogen atom and optionally a second atom selected from N, O, S, S(=O), and S(=O)$_2$, wherein said 3-7 membered heterocyclic ring is substituted with 0-1 $R^{17}$;

$R^{11}$ at each occurrence is independently selected from H, $C_1$-$C_4$ alkyl, and $C_1$-$C_4$ haloalkyl;

$R^{12}$ at each occurrence is independently selected from H, $C_1$-$C_4$ haloalkyl and $C_1$-$C_4$ alkyl substituted with 0-1 $R^{19}$;

$R^{13}$ and $R^{14}$, at each occurrence, are independently selected from H, $C_1$-$C_4$ alkyl substituted with 0-3 $R^{30}$; and $C_6$-$C_{10}$ aryl substituted with 0-5 $R^{30}$;

$R^{13a}$ at each occurrence is independently selected from H, $C_1$-$C_4$ alkyl, and $C_6$-$C_{10}$ aryl;

$R^{15}$ at each occurrence is independently selected from H,
  $C_1$-$C_6$ alkyl substituted by 0-1 $R^{30}$;
  $C_2$-$C_6$ alkenyl substituted by 0-1 $R^{30}$;
  $C_2$-$C_6$ alkynyl substituted by 0-1 $R^{30}$;
  $C_6$-$C_{10}$ aryl substituted by 0-5 $R^{30}$;
  $C_3$-$C_7$ carbocyclyl substituted by 0-5 $R^{30}$; and
  5 to 14 membered heterocyclyl group substituted by 0-5 $R^{30}$, wherein said heterocyclyl group comprises one, two, or three heteroatoms selected from N, O, and S;
  5 to 14 membered heteroaryl group substituted by 0-5 $R^{30}$, wherein said heteroaryl group comprises one, two, or three heteroatoms selected from N, O, and S;
$R^{16}$ at each occurrence is independently selected from H and $C_1$-$C_4$ alkyl;
$R^{17}$ is H, —$NR^{23}R^{24}$, halo, —$NO_2$, —CN, —$CF_3$, $C_1$-$C_4$ haloalkyl, —NHOH, $OR^{25}$, $C(=O)R^{25}$, $C(=O)OR^{25}$, $OC(=O)R^{25}$, $C(=O)NR^{23}R^{24}$, $NR^{23a}C(=O)R^{25}$, $NR^{23a}CO_2R^{25}$, $OC(=O)NR^{23}R^{24}$, $NR^{23a}C(=S)R^{25}$, $SR^{25}$, $S(=O)R^{25}$, $S(=O)_2R^{25}$, $S(=O)_2NR^{23}R^{24}$, —$NR^{23a}S(=O)_2R^{25}$, or $C_1$-$C_4$ alkyl substituted by 0-1 $R^{19}$;
$R^{18}$ at each occurrence is independently selected from H;
  $C_1$-$C_6$ alkyl substituted by 0-1 $R^{30}$;
  $C_2$-$C_6$ alkenyl substituted by 0-1 $R^{30}$;
  $C_2$-$C_6$ alkynyl substituted by 0-1 $R^{30}$;
  $C_6$-$C_{10}$ aryl substituted by 0-5 $R^{30}$;
  $C_3$-$C_7$ carbocyclyl substituted by 0-5 $R^{30}$; and
  5 to 14 membered heterocyclyl group substituted by 0-5 $R^{30}$, wherein said heterocyclyl group comprises one, two, or three heteroatoms selected from N, O, and S;
  5 to 14 membered heteroaryl group substituted by 0-5 $R^{30}$, wherein said heteroaryl group comprises one, two, or three heteroatoms selected from N, O, and S;
$R^{19}$ at each occurrence is independently selected from H, —$NR^{23}R^{24}$, halo, —$NO_2$, —CN, —$CF_3$, $C_1$-$C_4$ haloalkyl, —NHOH, $OR^{25}$, $C(=O)R^{25}$, $C(=O)OR^{25}$, $OC(=O)R^{25}$, $C(=O)NR^{23}R^{24}$, $NR^{23a}C(=O)R^{25}$, $NR^{23a}CO_2R^{25}$, $OC(=O)NR^{23}R^{24}$, $NR^{23a}C(=S)R^{25}$, $SR^{25}$, $S(=O)R^{25}$, $S(=O)_2R^{25}$, $S(=O)_2NR^{23}R^{24}$, —$NR^{23a}S(=O)_2R^{25}$,
  $C_1$-$C_4$ alkyl substituted by 0-1 $R^{30}$;
  $C_2$-$C_4$ alkenyl substituted by 0-1 $R^{30}$;
  $C_2$-$C_4$ alkynyl substituted by 0-1 $R^{30}$;
  $C_6$-$C_{10}$ aryl substituted by 0-5 $R^{30}$;
  $C_3$-$C_7$ carbocyclyl substituted by 0-5 $R^{30}$;
  5 to 14 membered heterocyclyl group substituted by 0-5 $R^{30}$, wherein said heterocyclyl group comprises one, two, or three heteroatoms selected from N, O, and S; and
  5 to 14 membered heteroaryl group substituted by 0-5 $R^{30}$, wherein said heteroaryl group comprises one, two, or three heteroatoms selected from N, O, and S;
$R^{22}$ is H, —$NR^{23}R^{24}$, —$N_3$, halo, —$NO_2$, —CN, —$CF_3$, $C_1$-$C_4$ alkyl, $C_2$-$C_4$ alkenyl, $C_2$-$C_4$ alkynyl, $C_1$-$C_4$ haloalkyl, $C_3$-$C_7$ carbocyclyl, phenyl, —NHOH, $OR^{25}$, —$CH_2OR^{25}$, $C(=O)R^{25}$, $C(=O)OR^{25}$, $OC(=O)R^{25}$, $C(=O)NR^{23}R^{24}$, $NR^{23a}C(=O)R^{25}$, $NR^{23a}CO_2R^{25}$, $OC(=O)NR^{23}R^{24}$, $NR^{23a}C(=S)R^{25}$, $SR^{25}$, $S(=O)R^{25}$, $S(=O)_2R^{25}$, $S(=O)_2NR^{23}R^{24}$, or —$NR^{23a}S(=O)_2R^{25}$;
$R^{23}$ and $R^{24}$ at each occurrence are each independently selected from H or $C_1$-$C_6$ alkyl;
alternatively, $R^{23}$ and $R^{24}$, together with the nitrogen to which they are attached, form a 3-7 membered heterocyclic ring, wherein said 3-7 membered heterocyclic ring contains a nitrogen atom and optionally a second atom selected from N, O and S; wherein said 3-7 membered heterocyclic ring is substituted with 0-1 $C_1$-$C_4$ alkyl;
$R^{23a}$ at each occurrence is each independently selected from H or $C_1$-$C_4$ alkyl;
$R^{25}$ at each occurrence is each independently selected from H or $C_1$-$C_6$ alkyl; and
$R^{30}$ is H, F, Cl, Br, —$CF_3$, $C_1$-$C_6$ alkyl, and $C_1$-$C_6$ alkoxy.

2. The compound of claim 1 wherein $R^1$, $R^2$, $R^3$, and $R^4$ at each occurrence are independently selected from H, halo, —$OR^{11}$, —$NO_2$, —CN, and —$CF_3$.

3. The compound of claim 1 wherein $R^1$, $R^3$, and $R^4$ are each H and $R^2$ is selected from H, F, Cl, Br, —$OCH_3$, —$NO_2$, —CN, and —$CF_3$.

4. The compound of claim 1 wherein X is H, —$NR^9R^{10}$, halo, $C_1$-$C_4$ alkyl, or $OR^{12}$.

5. The compound of claim 1 wherein X is —$NR^9R^{10}$.

6. The compound of claim 1 of Formula (II):

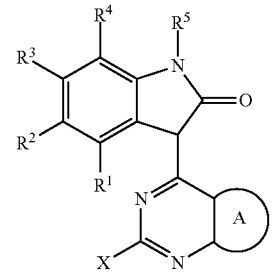

(II)

or a stereoisomeric form, a mixture of stereoisomeric forms, a tautomeric form, or a pharmaceutically acceptable salt form thereof,
wherein:
ring A is

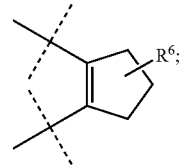

$R^1$, $R^2$, $R^3$, and $R^4$ at each occurrence are independently selected from
H, halo, —$OR^{11}$, —$NO_2$, —CN, —$CF_3$, —$CHF_2$, $C_2$-$C_4$ alkenyl, $C_2$-$C_4$ alkynyl, $C_1$-$C_4$ haloalkyl, and $C_1$-$C_4$ alkyl;
$R^5$ is H or $C_1$-$C_6$ alkyl;
$R^6$ is selected from H;
  $C_1$-$C_6$ alkyl substituted by 0-2 $R^{22}$;
  $C_2$-$C_6$ alkenyl substituted by 0-2 $R^{22}$;
  $C_2$-$C_6$ alkynyl substituted by 0-2 $R^{22}$; and
  $C_3$-$C_7$ cycloalkyl substituted by 0-2 $R^{22}$;
X is H, —$NR^9R^{10}$, halo, $OR^{12}$, $C_1$-$C_4$ alkyl, or $C_2$-$C_4$ alkenyl;
$R^9$ and $R^{10}$ at each occurrence are each independently selected from H, —$NH_2$;
  $C_1$-$C_6$ alkyl substituted by 0-1 $R^{19}$;
  $C_2$-$C_6$ alkenyl substituted by 0-1 $R^{19}$;
  $C_2$-$C_6$ alkynyl substituted by 0-1 $R^{19}$;
  $C_6$-$C_{10}$ aryl substituted by 0-5 $R^{19}$;

$C_3$-$C_7$ carbocyclyl substituted by 0-5 $R^{19}$;
5 to 14 membered heterocyclyl group substituted by 0-5 $R^{19}$, wherein said heterocyclyl group comprises one, two, or three heteroatoms selected from N, O, and S; and
5 to 14 membered heteroaryl group substituted by 0-5 $R^{19}$, wherein said heteroaryl group comprises one, two, or three heteroatoms selected from N, O, and S;

alternatively, $R^9$ and $R^{10}$, together with the nitrogen to which they are attached, form a 3-7 membered heterocyclic ring, wherein said 3-7 membered heterocyclic ring contains a nitrogen atom and optionally a second atom selected from N, O, S, S(=O), and S(=O)$_2$, wherein said 3-7 membered heterocyclic ring is substituted with 0-1 $R^{17}$;

$R^{11}$ at each occurrence is independently selected from H, $C_1$-$C_4$ alkyl, and $C_1$-$C_4$ haloalkyl;

$R^{12}$ at each occurrence is independently selected from H, $C_1$-$C_4$ haloalkyl and $C_1$-$C_4$ alkyl substituted with 0-1 $R^{19}$;

$R^{17}$ is H or $C_1$-$C_4$ alkyl substituted by 0-1 $R^{19}$;

$R^{19}$ at each occurrence is independently selected from H, —NR$^{23}$R$^{24}$, halo, —NO$_2$, —CN, —CF$_3$, $C_1$-$C_4$ haloalkyl, —NHOH, OR$^{25}$, C(=O)R$^{25}$, C(=O)OR$^{25}$, OC(=O)R$^{25}$, C(=O)NR$^{23}$R$^{24}$, NR$^{23a}$C(=O)R$^{25}$, NR$^{23a}$CO$_2$R$^{25}$, OC(=O)NR$^{23}$R$^{24}$, NR$^{23a}$C(=S)R$^{25}$, SR$^{25}$, S(=O)R$^{25}$, S(=O)$_2$R$^{25}$; S(=O)$_2$NR$^{23}$R$^{24}$, —NR$^{23a}$S(=O)$_2$R$^{25}$, $C_1$-$C_4$ alkyl substituted by 0-1 $R^{30}$;
$C_2$-$C_4$ alkenyl substituted by 0-1 $R^{30}$;
$C_2$-$C_4$ alkynyl substituted by 0-1 $R^{30}$;
$C_6$-$C_{10}$ aryl substituted by 0-5 $R^{30}$;
$C_3$-$C_7$ carbocyclyl substituted by 0-5 $R^{30}$;
5 to 14 membered heterocyclyl group substituted by 0-5 $R^{30}$, wherein said heterocyclyl group comprises one, two, or three heteroatoms selected from N, O, and S; and
5 to 14 membered heteroaryl group substituted by 0-5 $R^{30}$, wherein said heteroaryl group comprises one, two, or three heteroatoms selected from N, O, and S;

$R^{22}$ is H, —NR$^{23}$R$^{24}$, —N$_3$, halo, —NO$_2$, —CN, —CF$_3$, $C_1$-$C_4$ alkyl, $C_2$-$C_4$ alkenyl, $C_2$-$C_4$ alkynyl, $C_1$-$C_4$ haloalkyl, $C_3$-$C_7$ carbocyclyl, phenyl, —NHOH, OR$^{25}$, —CH$_2$OR$^{25}$, C(=O)R$^{25}$, C(=O)OR$^{25}$, OC(=O)R$^{25}$, C(=O)NR$^{23}$R$^{24}$, NR$^{23a}$C(=O)R$^{25}$, NR$^{23a}$CO$_2$R$^{25}$, OC(=O)NR$^{23}$R$^{24}$, NR$^{23a}$C(=S)R$^{25}$, SR$^{25}$, S(=O)R$^{25}$, S(=O)$_2$R$^{25}$; S(=O)$_2$NR$^{23}$R$^{24}$, or —NR$^{23a}$S(=O)$_2$R$^{25}$;

$R^{23}$ and $R^{24}$ at each occurrence are each independently selected from H or $C_1$-$C_6$ alkyl;
alternatively, $R^{23}$ and $R^{24}$, together with the nitrogen to which they are attached, form a 3-7 membered heterocyclic ring, wherein said 3-7 membered heterocyclic ring contains a nitrogen atom and optionally a second atom selected from N, O and S, wherein said 3-7 membered heterocyclic ring is substituted with 0-1 $C_1$-$C_4$ alkyl;

$R^{23a}$ at each occurrence is each independently selected from H or $C_1$-$C_4$ alkyl;

$R^{25}$ at each occurrence is each independently selected from H or $C_1$-$C_6$ alkyl; and $R^{30}$ is H, F, Cl, Br, —CF$_3$, $C_1$-$C_6$ alkyl, and $C_1$-$C_6$ alkoxy.

7. The compound of claim 6 wherein $R^1$, $R^2$, $R^3$, and $R^4$ at each occurrence are independently selected from H, F, Cl, Br, —OCH$_3$, —NO$_2$, —CN, and —CF$_3$.

8. The compound of claim 6 wherein $R^1$, $R^3$, and $R^4$ are each H and $R^2$ is selected from H, F, Cl, Br, —OCH$_3$, —NO$_2$, —CN, and —CF$_3$.

9. The compound of claim 6 wherein X is —NR$^9$R$^{10}$.

10. The compound of claim 6 wherein $R^6$ is cyclopentyl.

11. The compound of claim 1 of Formula (III):

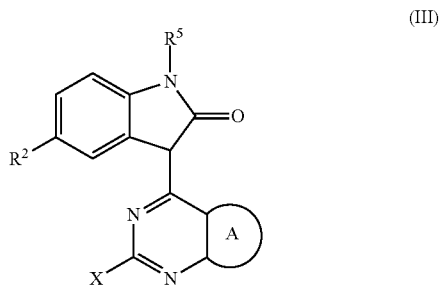

(III)

or a stereoisomeric form, a mixture of stereoisomeric forms, a tautomeric form, or a pharmaceutically acceptable salt form thereof,
wherein:
ring A is

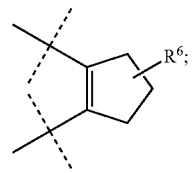

$R^2$ is selected from
H, halo, —OR$^{11}$, —NO$_2$, —CN, —CF$_3$, —CHF$_2$, $C_2$-$C_4$ alkenyl, $C_2$-$C_4$ alkynyl, $C_1$-$C_4$ haloalkyl, and $C_1$-$C_4$ alkyl;

$R^5$ is H or methyl;

$R^6$ is selected from H;
$C_1$-$C_6$ alkyl substituted by 0-2 $R^{22}$;
$C_2$-$C_6$ alkenyl substituted by 0-2 $R^{22}$;
$C_2$-$C_6$ alkynyl substituted by 0-2 $R^{22}$; and
$C_3$-$C_7$ cycloalkyl substituted by 0-2 $R^{22}$;

X is H, —NR$^9$R$^{10}$, halo, OR$^{12}$, $C_1$-$C_4$ alkyl, or $C_2$-$C_4$ alkenyl;

$R^9$ and $R^{10}$ at each occurrence are each independently selected from H, —NH$_2$;
$C_1$-$C_6$ alkyl substituted by 0-1 $R^{19}$;
$C_2$-$C_6$ alkenyl substituted by 0-1 $R^{19}$;
$C_2$-$C_6$ alkynyl substituted by 0-1 $R^{19}$;
$C_6$-$C_{10}$ aryl substituted by 0-5 $R^{19}$;
$C_3$-$C_7$ carbocyclyl substituted by 0-51e;
5 to 14 membered heterocyclyl group substituted by 0-5, wherein said heterocyclyl group comprises one, two, or three heteroatoms selected from N, O, and S; and
5 to 14 membered heteroaryl group substituted by 0-5 $R^{19}$, wherein said heteroaryl group comprises one, two, or three heteroatoms selected from N, O, and S;

alternatively, $R^9$ and $R^{10}$, together with the nitrogen to which they are attached, form a 3-7 membered heterocyclic ring, wherein said 3-7 membered heterocyclic ring contains a nitrogen atom and optionally a second atom selected from N, O, S, S(=O), and S(=O)$_2$, wherein said 3-7 membered heterocyclic ring is substituted with 0-1 $R^{17}$;

R¹¹ at each occurrence is independently selected from H, $C_1$-$C_4$ alkyl, and $C_1$-$C_4$ haloalkyl;

R¹² at each occurrence is independently selected from H, $C_1$-$C_4$ haloalkyl and $C_1$-$C_4$ alkyl substituted with 0-1 R¹⁹;

R¹⁷ is H or $C_1$-$C_4$ alkyl substituted by 0-1 R¹⁹;

R¹⁹ at each occurrence is independently selected from H, —NR²³R²⁴, halo, —NO₂, —CN, —CF₃, $C_1$-$C_4$ haloalkyl, —NHOH, OR²⁵, C(═O)R²⁵, C(═O)OR²⁵, OC(═O)R²⁵, C(═O)NR²³R²⁴, NHC(═O)R²⁵, NHCO₂R²⁵, OC(═O)NR²³R²⁴, NHC(═S)R²⁵, SR²⁵, S(═O)R²⁵, S(═O)₂R²⁵; S(═O)₂NR²³R²⁴, —NHS(═O)₂R²⁵, $C_1$-$C_4$ alkyl substituted by 0-1 R³⁰;
$C_2$-$C_4$ alkenyl substituted by 0-1 R³⁰;
$C_2$-$C_4$ alkynyl substituted by 0-1 R³⁰;
$C_6$-$C_{10}$ aryl substituted by 0-5 R³⁰;
$C_3$-$C_7$ carbocyclyl substituted by 0-5 R³⁰;
5 to 14 membered heterocyclyl group substituted by 0-5 R³⁰, wherein said heterocyclyl group comprises one, two, or three heteroatoms selected from N, O, and S; and
5 to 14 membered heteroaryl group substituted by 0-5 R³⁰, wherein said heteroaryl group comprises one, two, or three heteroatoms selected from N, O, and S;

R²² is H, —NR²³R²⁴, —N₃, halo, —NO₂, —CN, —CF₃, $C_1$-$C_4$ alkyl, $C_2$-$C_4$ alkenyl, $C_2$-$C_4$ alkynyl, $C_1$-$C_4$ haloalkyl, $C_3$-$C_7$ carbocyclyl, phenyl, —NHOH, OR²⁵, C(═O)R²⁵, C(═O)OR²⁵, OC(═O)R²⁵, C(═O)NR²³R²⁴, NHC(═O)R²⁵, NHCO₂R²⁵, OC(═O)NR²³R²⁴, NHC(═S)R²⁵, SR²⁵, S(═O)R²⁵, S(═O)₂R²⁵; S(═O)₂NR²³R²⁴, or —NHS(═O)₂R²⁵;

R²³ and R²⁴ at each occurrence are each independently selected from H or $C_1$-$C_4$ alkyl;

R²⁵ at each occurrence is each independently selected from H or $C_1$-$C_4$ alkyl; and R³⁰ is H, F, Cl, Br, —CF₃, $C_1$-$C_4$ alkyl, and $C_1$-$C_4$ alkoxy.

12. The compound of claim 11 wherein R⁶ is cyclobutyl, cyclopentyl, or cyclohexyl.

13. The compound of claim 11 wherein R⁶ is cyclopentyl.

14. The compound of claim 11 wherein X is —NR⁹R¹⁰.

15. The compound of claim 11 wherein R⁶ is cyclopentyl and X is —NR⁹R¹⁰.

16. The compound of claim 1 of Formula (II)

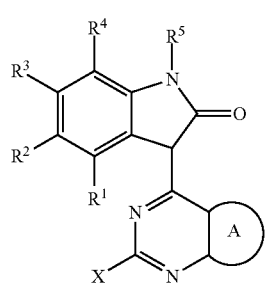

(II)

or a stereoisomeric form, a mixture of stereoisomeric forms, a tautomeric form, or a pharmaceutically acceptable salt form thereof, wherein:
ring A is

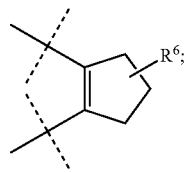

R¹, R², R³, and R⁴ at each occurrence are independently selected from H, F, Cl, Br, —OCH₃, —NO₂, —CN, and —CF₃;

R⁵ is H;

R⁶ is selected from H, methyl, ethyl, n-propyl, i-propyl, n-butyl, i-butyl, n-pentyl, i-pentyl, allyl, cyclopentyl, cyclohexyl,
—CH₂CH₂OCH₃, —CH₂CH₂OCH₂CH₃, —CH₂CH₂CH₂N₃, and —CH₂CH₂CH₂NHCH₃;

X is selected from H, Cl, methyl, ethyl, propyl, butyl,
—OH; —OCH₂CH₂N(CH₃)₂; —OCH₂CH₂(pyrid-3-yl);
—NHCH₃; —NHCH₂CH₃; —NHCH(CH₃)₂; —NHCH₂CH₂CH₂CH₃; —NHCH₂CH(CH₃)₂;
—NHCH₂CH₂CF₃; —NHCH═CH₂;
—NHCH₂CH═CH₂;
—NHCH₂CH₂N(CH₃)₂; —N(CH₃)CH₂CH₂N(CH₃)₂;
—NHCH₂CH₂CH₂N(CH₃)₂;
—NHCH₂CH₂CH₂NH(CH₃);
—NHCH₂CH₂NH₂; —NHCH₂CH₂CH₂NH₂; —N(H)CH₂CH(NH₂)CH₃;
—N(CH₃)CH₂CH₂N(CH₂CH₃)₂; —NHNH₂;
—NHCH₂CH₂NHC(═O)CH₃;
—N(CH₂CH₂OCH₃)₂; —N(H)CH₂CH₂OCH₃; —N(H)CH₂CH₂CH₂OCH₃;
—N(H)CH₂CH₂OCH₂CH₃; —N(H)CH₂CH₂OCH₂CH₂CH₃;
—N(CH₂CH₂OH)₂; —N(H)CH₂CH(OH)CH₃; —N(H)CH₂CH(OH)CH₂CH₃;
—NH(pyrid-3-yl); —NH(4-F-pyrid-3-yl); —NH(4-MeO-pyrid-3-yl); piperazin-1-yl;

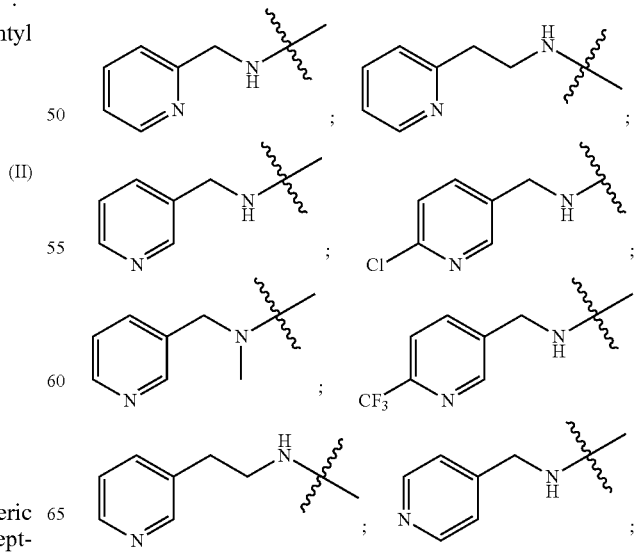

-continued

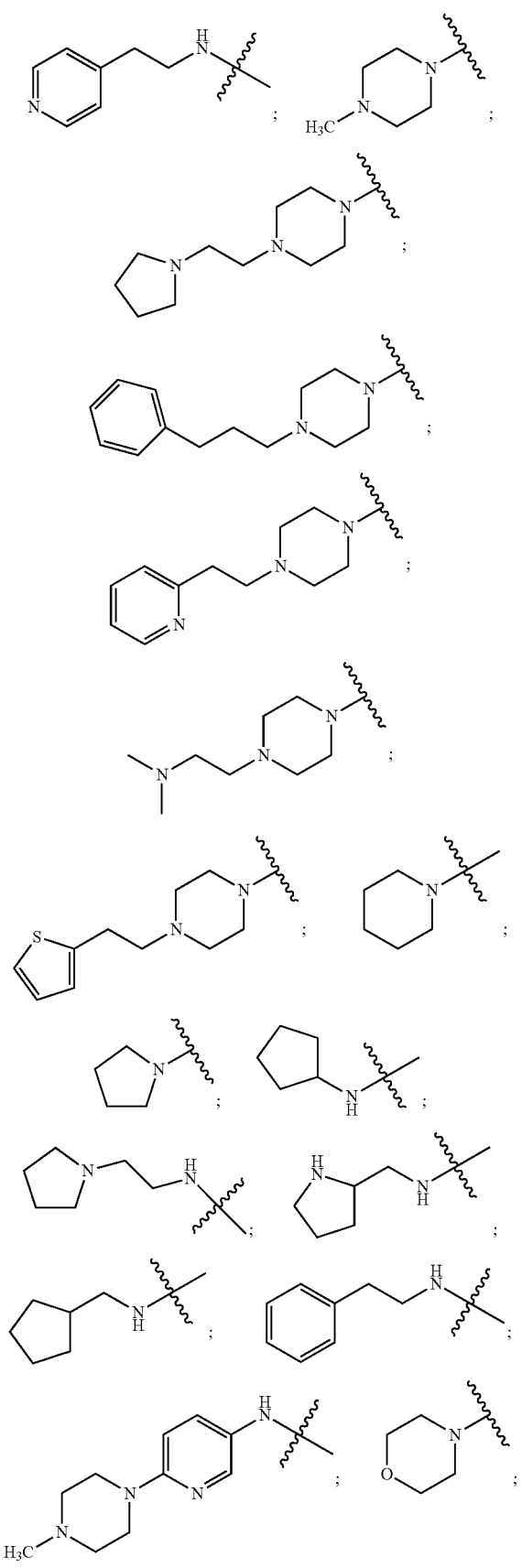

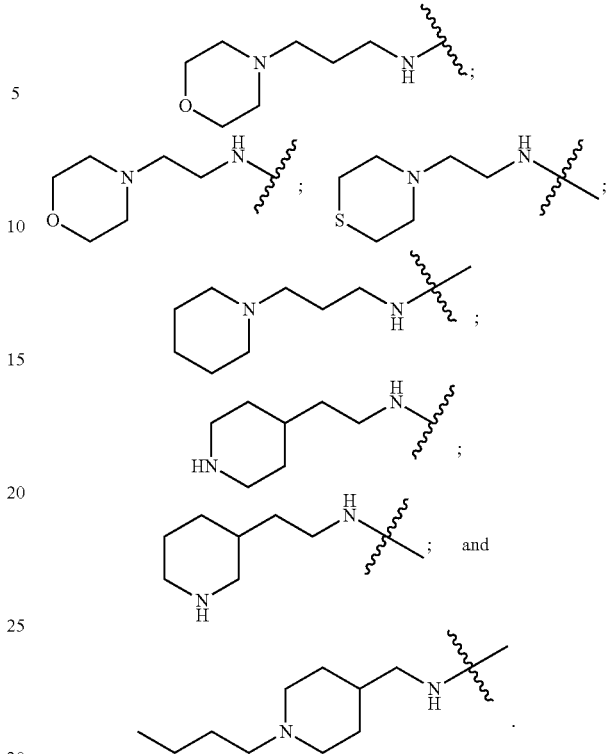

17. A compound which is:
5-Bromo-3-(2-chloro-6,7-dihydro-5H-cyclopentapyrimidin-4-yl)-1,3-dihydro-indol-2-one;
3-(2-Chloro-6,7-dihydro-5H-cyclopentapyrimidin-4-yl)-5-fluoro-1,3-dihydro-indol-2-one;
5-Chloro-3-(2-chloro-6,7-dihydro-5H-cyclopentapyrimidin-4-yl)-1,3-dihydro-inodol-2-one;
3-(2-Chloro-6,7-dihydro-5H-cyclopentapyrimidin-4-yl)-2-oxo-2,3-dihydro-1H-indole-5-carbonitrile;
5-Fluoro-3-[2-(2-morpholin-4-ylethylamino)-6,7-dihydro-5H-cyclopentapyrimidin-4-yl]-1,3-dihydro-indol-2-one;
3-[2-(2-Ethoxy-ethylamino)-6,7-dihydro-5H-cyclopentapyrimidin-4-yl]-5-fluoro-1,3-dihydro-indol-2-one;
5-Fluoro-3-{2-[(pyridin-4-ylmethyl)-amino]-6,7-dihydro-5H-cyclopentapyrimidin-4-yl}-1,3-dihydro-indol-2-one;
5-Fluoro-3-{2-[(pyridin-3-ylmethyl)-amino]-6,7-dihydro-5H-cyclopentapyrimidin-4-yl}-1,3-dihydro-indol-2-one;
5-Fluoro-3-{2-[(pyridin-2-ylmethyl)-amino]-6,7-dihydro-5H-cyclopentapyrimidin-4-yl}-1,3-dihydro-indol-2-one;
5-Chloro-3-[2-(2-dimethylamino-ethylamino)-6,7-dihydro-5H-cyclopentapyrimidin-4-yl]-1,3-dihydro-indol-2-one;
5-Chloro-3-[2-(2-morpholin-4-yl-ethylamino)-6,7-dihydro-5H-cyclopentapyrimidin-4-yl]-1,3-dihydro-indol-2-one;
5-Chloro-3-[2-(2-ethoxy-ethylamino)-6,7-dihydro-5H-cyclopentapyrimidin-4-yl]-1,3-dihydro-indol-2-one;
5-Chloro-3-{2-[(pyridin-4-ylmethyl)-amino]-6,7-dihydro-5H-cyclopentapyrimidin-4-yl}-1,3-dihydro-indol-2-one;
5-Chloro-3-{2-[(pyridin-3-ylmethyl)-amino]-6,7-dihydro-5H-cyclopentapyrimidin-4-yl}-1,3-dihydro-indol-2-one;

5-Chloro-3-{2-[(6-chloro-pyridin-3-ylmethyl)-amino]-6,7-dihydro-5H-cyclopentapyrimidin-4-yl}-1,3-dihydro-indol-2-one;

5-Chloro-3-{2-[(6-trifluoromethyl-pyridin-3-ylmethyl)-amino]-6,7-dihydro-5H-cyclopentapyrimidin-4-yl}-1,3-dihydro-indol-2-one;

5-Chloro-3-{2-[(pyridin-2-ylmethyl)-amino]-6,7-dihydro-5H-cyclopentapyrimidin-4-yl}-1,3-dihydro-indol-2-one;

5-Bromo-3-[2-(3-morpholin-4-yl-propylamino)-6,7-dihydro-5H-cyclopentapyrimidin-4-yl]-1,3-dihydro-indol-2-one;

5-Bromo-3-[2-(2-morpholin-4-yl-ethylamino)-6,7-dihydro-5H-cyclopentapyrimidin-4-yl]-1,3-dihydro-indol-2-one;

5-Bromo-3-[2-(2-propoxy-ethylamino)-6,7-dihydro-5H-cyclopentapyrimidin-4-yl]-1,3-dihydro-indol-2-one;

5-Bromo-3-[2-(2-ethoxy-ethylamino)-6,7-dihydro-5H-cyclopentapyrimidin-4-yl]-1,3-dihydro-indol-2-one;

5-Bromo-3-[2-(3-dimethylamino-propylamino)-6,7-dihydro-5H-cyclopentapyrimidin-4-yl]-1,3-dihydro-indol-2-one;

5-Bromo-3-{2-[(pyridin-4-ylmethyl)-amino]-6,7-dihydro-5H-cyclopentapyrimidin-4-yl}-1,3-dihydro-indol-2-one;

5-Bromo-3-{2-[(pyridin-3-ylmethyl)-amino]-6,7-dihydro-5H-cyclopentapyrimidin-4-yl}-1,3-dihydro-indol-2-one;

5-Bromo-3-{2-[(6-chloro-pyridin-3-ylmethyl)-amino]-6,7-dihydro-5H-cyclopentapyrimidin-4-yl}-1,3-dihydro-indol-2-one;

5-Bromo-3-{2-[(pyridin-2-ylmethyl)-amino]-6,7-dihydro-5H-cyclopentapyrimidin-4-yl}-1,3-dihydro-indol-2-one;

3-[2-(3-Morpholin-4-yl-propylamino)-6,7-dihydro-5H-cyclopentapyrimidin-4-yl]-2-oxo-2,3-dihydro-1H-indole-5-carbonitrile;

3-[2-(2-Morpholin-4-yl-ethylamino)-6,7-dihydro-5H-cyclopentapyrimidin-4-yl]-2-oxo-2,3-dihydro-1H-indole-5-carbonitrile;

3-[2-(3-Dimethylamino-propylamino)-6,7-dihydro-5H-cyclopentapyrimidin-4-yl]-2-oxo-2,3-dihydro-1H-indole-5-carbonitrile;

2-Oxo-3-[2-(2-propoxy-ethylamino)-6,7-dihydro-5H-cyclopentapyrimidin-4-yl]-2,3-dihydro-1H-indole-5-carbonitrile;

3-[2-(2-Ethoxy-ethylamino)-6,7-dihydro-5H-cyclopentapyrimidin-4-yl]-2-oxo-2,3-dihydro-1H-indole-5-carbonitrile;

2-Oxo-3-[2-(2-pyridin-4-yl-ethylamino)-6,7-dihydro-5H-cyclopentapyrimidin-4-yl]-2,3-dihydro-1H-indole-5-carbonitrile;

2-Oxo-3-[2-(2-pyridin-2-yl-ethylamino)-6,7-dihydro-5H-cyclopentapyrimidin-4-yl]-2,3-dihydro-1H-indole-5-carbonitrile;

2-Oxo-3-{2-[(pyridin-4-ylmethyl)-amino]-6,7-dihydro-5H-cyclopentapyrimidin-4-yl}-2,3-dihydro-1H-indole-5-carbonitrile;

2-Oxo-3-{2-[(pyridin-3-ylmethyl)-amino]-6,7-dihydro-5H-cyclopentapyrimidin-4-yl}-2,3-dihydro-1H-indole-5-carbonitrile;

2-Oxo-3-{2-[(pyridin-2-ylmethyl)-amino]-6,7-dihydro-5H-cyclopentapyrimidin-4-yl}-2,3-dihydro-1H-indole-5-carbonitrile;

2-Oxo-3-[2-(pyridin-3-ylamino)-6,7-dihydro-5H-cyclopentapyrimidin-4-yl]-2,3-dihydro-1H-indole-5-carbonitrile;

3-[2-(6-Fluoro-pyridin-3-ylamino)-6,7-dihydro-5H-cyclopentapyrimidin-4-yl]-2-oxo-2,3-dihydro-1H-indole-5-carbonitrile;

3-[2-(6-Methoxy-pyridin-3-ylamino)-6,7-dihydro-5H-cyclopentapyrimidin-4-yl]-2-oxo-2,3-dihydro-1H-indole-5-carbonitrile;

3-[2-(4-Methyl-piperazin-1-yl)-6,7-dihydro-5H-cyclopentapyrimidin-4-yl]-2-oxo-2,3-dihydro-1H-indole-5-carbonitrile;

2-Oxo-3-(2-piperazin-1-yl-6,7-dihydro-5H-cyclopentapyrimidin-4-yl)-2,3-dihydro-1H-indole-5-carbonitrile;

or a pharmaceutically acceptable salt thereof.

18. A pharmaceutical composition comprising a compound of claim 1 and one or more pharmaceutically acceptable excipients.

* * * * *